US012677849B2

(12) United States Patent
Markosyan et al.

(10) Patent No.: US 12,677,849 B2
(45) Date of Patent: *Jul. 14, 2026

(54) HIGH-PURITY STEVIOL GLYCOSIDES

(71) Applicant: PURECIRCLE SDN BHD, Kuala Lumpur (MY)

(72) Inventors: Avetik Markosyan, Kuala Lumpur (MY); Indra Prakash, Alpharetta, GA (US); Cyrille Jarrin, Muret (FR); Aurélien Badie, Labège (FR); Robert Ter Halle, Baziege (FR); Cynthia Curran, Atlanta, GA (US); Daniel Auriol, Roques (FR)

(73) Assignee: PureCircle Sdn. Bhd., Negeri Sembilan (MY)

( * ) Notice: Subject to any disclaimer, the term of this patent is extended or adjusted under 35 U.S.C. 154(b) by 195 days.

This patent is subject to a terminal disclaimer.

(21) Appl. No.: 18/155,002

(22) Filed: Jan. 16, 2023

(65) Prior Publication Data

US 2023/0413865 A1      Dec. 28, 2023

Related U.S. Application Data

(63) Continuation of application No. 15/512,711, filed as application No. PCT/US2015/046354 on Aug. 21, 2015, now Pat. No. 11,653,679, and a continuation-in-part of application No. PCT/US2015/045906, filed on Aug. 19, 2015.

(60) Provisional application No. 62/118,132, filed on Feb. 19, 2015, provisional application No. 62/062,288, filed on Oct. 10, 2014, provisional application No. 62/097,387, filed on Dec. 29, 2014, provisional application No. 62/061,359, filed on Oct. 8, 2014, provisional application No. 62/185,964, filed on Jun. 29, 2015, provisional application No. 62/052,544, filed on Sep. 19, 2014, provisional application No. 62/082,446, filed on Nov. 20, 2014, provisional application No. 62/064,830, filed on Oct. 16, 2014.

(51) Int. Cl.
| | |
|---|---|
| *A23L 2/60* | (2006.01) |
| *A23L 27/30* | (2016.01) |
| *C07H 1/06* | (2006.01) |
| *C07H 15/256* | (2006.01) |
| *C12P 19/18* | (2006.01) |
| *C12P 19/56* | (2006.01) |

(52) U.S. Cl.
CPC ................ *A23L 2/60* (2013.01); *A23L 27/36* (2016.08); *C07H 1/06* (2013.01); *C07H 15/256* (2013.01); *C12P 19/18* (2013.01); *C12P 19/56* (2013.01); *C12Y 204/01* (2013.01); *C12Y 302/01021* (2013.01); *A23V 2002/00* (2013.01); *Y02P 20/582* (2015.11)

(58) Field of Classification Search
CPC .......... A23L 2/60; C07H 1/06; C07H 15/256; C12P 19/18; C12P 19/56; C12Y 204/01; C12Y 302/01021; A23V 2002/00; Y02P 20/582
See application file for complete search history.

(56) References Cited

U.S. PATENT DOCUMENTS

| | | | |
|---|---|---|---|
| 9,243,273 B2 | 1/2016 | Markosyan et al. | |
| 9,562,251 B2 | 2/2017 | Kishore et al. | |
| 9,752,174 B2 | 9/2017 | Markosyan et al. | |
| 10,392,644 B2 | 8/2019 | Kishore et al. | |
| 11,653,679 B2 * | 5/2023 | Markosyan .......... | C12Y 204/01 435/74 |
| 2014/0271996 A1 | 9/2014 | Prakash et al. | |
| 2014/0357588 A1 | 12/2014 | Markosyan et al. | |

FOREIGN PATENT DOCUMENTS

| | | |
|---|---|---|
| CN | 103179850 | 6/2013 |
| CN | 103974628 | 8/2014 |
| WO | 2010038911 | 4/2010 |
| WO | 2013022989 | 2/2013 |
| WO | 2013102793 A2 | 7/2013 |
| WO | 2013/110673 | 8/2013 |
| WO | 2013/176738 | 11/2013 |
| WO | 2014/122227 | 8/2014 |
| WO | 2014/146089 | 9/2014 |
| WO | 2014/146135 | 9/2014 |
| WO | 2014/193934 | 12/2014 |
| WO | 2015/171555 | 11/2015 |
| WO | 2017218888 A1 | 12/2017 |
| WO | 2018031955 A2 | 2/2018 |

(Continued)

OTHER PUBLICATIONS

Kisselev L., Polypeptide release factors in prokaryotes and eukaryotes: same function, different structure. Structure, 2002, vol. 10: 8-9. (Year: 2002).*

(Continued)

*Primary Examiner* — Iqbal H Chowdhury

(57) ABSTRACT

Methods of preparing highly purified steviol glycosides, particularly rebaudiosides A, D and M are described. The methods include utilizing recombinant microorganisms for converting various staring compositions to target steviol glycosides. In addition, novel steviol glycosides reb D2, reb M2, and reb I are disclosed, as are methods of preparing the same. The highly purified rebaudiosides are useful as non-caloric sweetener in edible and chewable compositions such as any beverages, confectioneries, bakery products, cookies, and chewing gums.

6 Claims, 148 Drawing Sheets

Specification includes a Sequence Listing.

(56) References Cited

FOREIGN PATENT DOCUMENTS

WO       2018164747  A1      9/2018
WO       2019006244  A1      1/2019

OTHER PUBLICATIONS

Noguchi et al., cDNA cloning of glycosyltransferases from Chinese wolfberry (*Lycium barbarum* L.) fruits and enzymatic synthesis of a catechin glucoside using a recombinant enzyme (UGT73A10) Journal of Molecular Catalysis B: Enzymatic 55 (2008) 84-92.

Whisstock et al., Quaterly reviews of Biophysics, 2003, "Prediction of protein function from protein sequence and structure", 36(3): 307-340.

Witkowski et al., Conversion of a beta-ketoacyl synthase to a malonyl decarboxylase by replacement of the active-site cysteine with glutamine, Biochemistry, Sep. 7, 1999, 38(36), 11643-11650.

Yang et al., Base substitution mutations in uridine-diphosphate-dependent glycosyltransferase 76G1 of Stevia rebaudiana causes the low levels of rebaudioside A: Mutations in UGT76G1, a key gene of steviol glycosides synthesis, Plant Physiology and Biochemistry 80 (2014); 220-225, Epub Apr. 23, 2014.

Dian Spakman, How to broaden the applicability of the high potency sweeteners steviol glycosides: from enzymatic glycosylation to recombinant production. University of Groningen, GBB, p. 1-21, 2014.

Okamoto, et al., Purification and some properties of a Glucosidase from Flavobacterium johnsonae, Biosci Biotechnol, Biochem 64(2), 333-340, 2000.

Prakash, I et al. "Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita" Biomolecules, vol. 4, Mar. 31, 2014, pp. 374-389; p. 385, paragraph [5].

Masaya Ohta et al, "Characterization of Novel Steviol Glycosides from Leaves of Stevia rebaudiana Morita", Oyo Toshitsu Kagaku—Journal of Applied Glycoscience., JP, (Aug. 17, 2010), vol. 57, No. 3, doi:10.5458/iag.57.199, ISSN 1340-3494, pp. 199-209, XP055121080 [X] 13 * p. 204; table 4 * [Y] 14-17.

* cited by examiner

FIG. 2

HPLC Chromatogram of Standard Rebaudioside M

Current Chromatogram (s)

DAD1 A, Sig=210,4 Ref=260,100 (REBXPC000106.D)

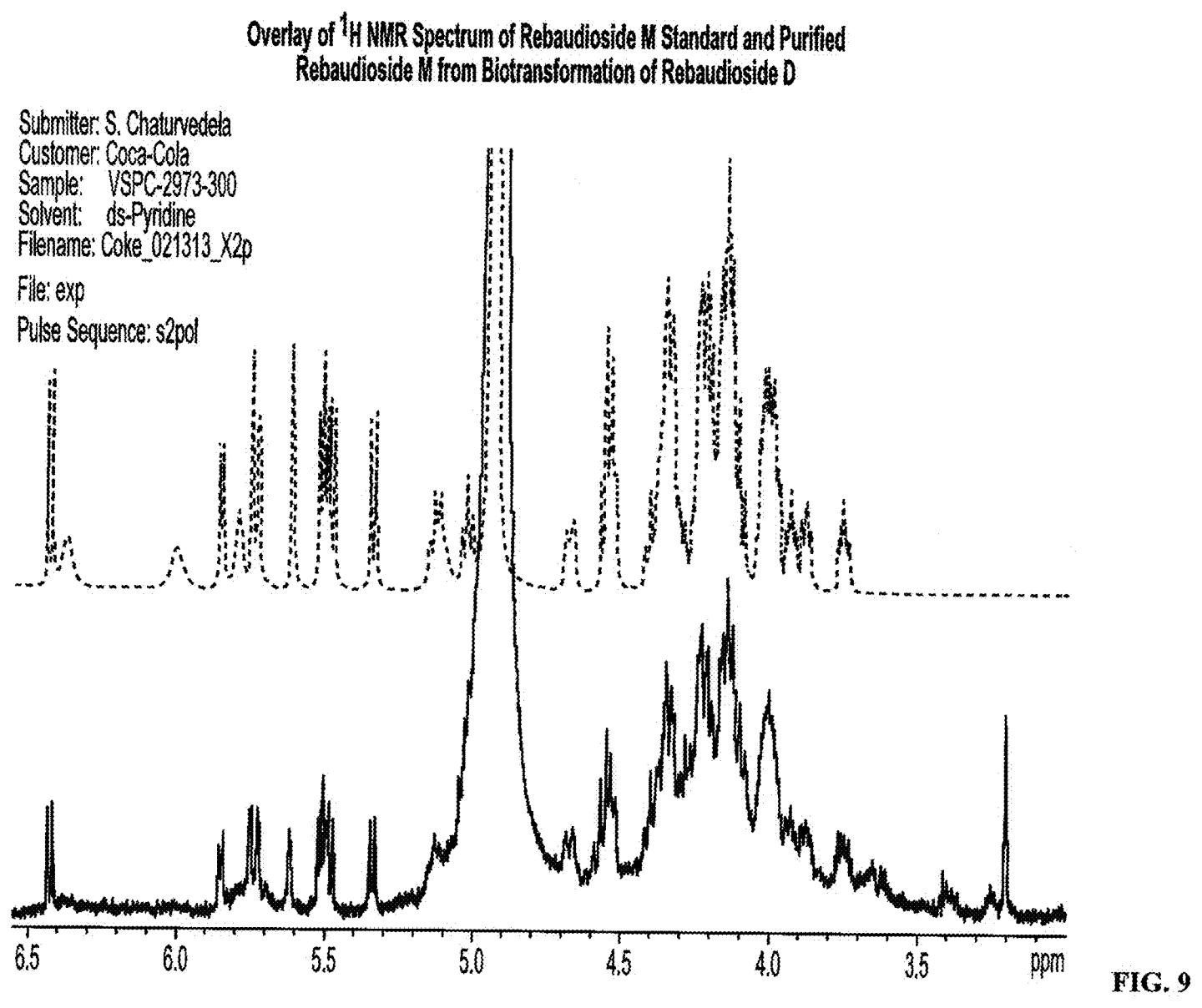

Overlay of $^{1}$H NMR Spectrum of Rebaudioside M Standard and Purified Rebaudioside M from Biotransformation of Rebaudioside D Submitter: S. Chaturvedela
Customer: Coca-Cola
Sample: VSPC-2973-300
Solvent: d5-Pyridine
Filename: Coke_021313_X2p File: exp
Pulse Sequence: s2pol

FIG. 9

The signal at m/z 1313.52652 is consistent with the sodium adduct of a species with molecular formula $C_{58}H_{98}O_{33}$ (+0.658 ppm).
Sample was dissolved in methanol and eluted in 2:2:1 methanol:acetonitrile:water.

Current Data Parameters
NAME                KPD-B-17
EXPNO               11
PROCNO              2

F2 - Acquisition Parameters
Date_               20130814
Time                10.52
INSTRUM             spect
PROBHD    mm PABBI  1H-BB
PULPROG             zg30
TD                  65536
SOLVENT             Pyr
NS                  128
DS                  2
SWH                 10330.578 Hz
FIDRES              0.157632 Hz
AQ                  3.1719909 sec
RG                  256
DW                  48.400 usec
DE                  6.00 usec
TE                  300.0 K
D1                  1.00000000 sec
TD0                 1

======== CHANNEL f1 ========
NUC1                1H
P1                  2.97 usec
PL1                 -2.80 dB
PL1W                21.05972290 W
SFO1                500.2204504 MHz F2 - Processing parameters
SI                  32768
SF                  500.2199792 MHz
WDW                 EM
SSB         0
LB                  0.30 Hz
GB          0
PC                  1.00

FROM
FIG. 14A

FIG. 14B

FROM

Current Data Parameters

| NAME | KPD-B-17 |
|---|---|
| EXPNO | 59 |
| PROCNO | 14 |

F2 - Acquisition Parameters

| Date_ | 20130905 |
|---|---|
| Time | 18.55 |
| INSTRUM | spect |
| PROBHD | mm PABBI 1H-BB |
| PULPROG | zgpg30 |
| TD | 65536 |
| SOLVENT | Pyr |
| NS | 295992 |
| DS | 4 |
| SWH | 30030.029 Hz |
| FIDRES | 0.458222 Hz |
| AQ | 1.0911911 sec |
| RG | 2048 |
| DW | 16.650 usec |
| DE | 6.00 usec |
| TE | 300.0 K |
| D1 | 0.50000000 sec |
| D11 | 0.03000000 sec |
| TD0 | 1 |

======== CHANNEL f1 ========

| NUC1 | 13C |
|---|---|
| P1 | 14.50 usec |
| PL1 | -3.00 dB |
| PL1W | 125.29680634 W |
| SFO1 | 125.7929971 MHz |

TO

FROM

Current Data Parameters
NAME                KPD-B-17
EXPNO                     59
PROCNO                    14

F2 - Acquisition Parameters
Date_              20130905
Time                  18.55
INSTRUM               spect
PROBHD    mm PABBI   1H-BB
PULPROG              zgpg30
TD                    65536
SOLVENT                 Pyr
NS                   295992
DS                        4
SWH           30030.029 Hz
FIDRES         0.458222 Hz
AQ           1.0911911 sec
RG                     2048
DW            16.650 usec
DE              6.00 usec
TE               300.0 K
D1         0.50000000 sec
D11        0.03000000 sec
TD0                       1

======== CHANNEL f1 ========
NUC1                    13C
P1             14.50 usec
PL1              -3.00 dB
PL1W        125.29680634 W
SFO1       125.7929971 MHz

TO

FROM

FROM

======== CHANNEL f2 ========
CPDPRG[2                    waltz16
NUC2                          18
PCPD2                    80.00 usec
PL2                        -2.80 dB
PL12                      25.81 dB
PL13                     120.00 dB
PL2W              21.05972290 W
PL12W              0.02900366 W
PL13W        0 W
SFO2            500.2220009 MHz F2 - Processing parameters
SI                          32768
SF              125.7803247 MHz
WDW                          EM
SSB          0
LB                         1.00 Hz
GB           0
PC                           1.00

TO

AMRI, 21 Corporate Circle
location: 13
ARN: 20133237
Lot: MAU-D-111-8
Project: 8417
User: kdevkota

FROM

Current Data Parameters
NAME                    KPD-B-17
EXPNO                         12
PROCNO                         2

F2 - Acquisition Parameters
Date_                   20130814
Time                       16.08
INSTRUM                    spect
PROBHD          mm PABBI 1H-BB
PULPROG             cosygpqf-45
TD                          2048
SOLVENT                      Pyr
NS                            32
DS                             8
SWH                 6666.667 Hz
FIDRES             3.255208 Hz
AQ                0.1536750 sec
RG                          2048
DW                  75.000 usec
DE                    6.00 usec
TE                      300.0 K
D0             0.00000300 sec
D1             1.48689198 sec
D13            0.00000400 sec
D16            0.00010000 sec
IN0            0.00015000 sec
P0                    1.49 usec ======== CHANNEL f1 ========
NUC1                         1H
P1                    2.97 usec
PL1                   -2.80 dB
PL1W           21.05972290 W
SFO1         500.2230074 MHz

TO

TO

AMRI: 21 Corporate Circle
location: 13
ARN: 20133237
Lot: MAU-D-111-8
Project: 8417
User: kdevkota

FROM

| | |
|---|---|
| NAME | KPD-B-17 |
| EXPNO | 13 |
| PROCNO | 4 |
| Date_ | 20130814 |
| Time_ | 23.54 |
| INSTRUM | spect |
| PROBHD | mm PABBI 1H-BB |
| PULPROG | hsqcedetgp |
| TD | 1024 |
| SOLVENT | Pyr |
| NS | 256 |
| DS | 16 |
| SWH | 5000.000 Hz |
| FIDRES | 4.882813 Hz |
| AQ | 0.1025500 sec |
| RG | 20642.5 |
| DW | 100.000 usec |
| DE | 6.00 usec |
| TE | 300.0 K |
| CNST2 | 145.0000000 |
| D0 | 0.00000300 sec |
| D1 | 1.53706869 sec |
| D4 | 0.00172414 sec |
| D11 | 0.03000000 sec |
| D13 | 0.00000400 sec |
| D16 | 0.00010000 sec |
| D21 | 0.00344800 sec |
| IN0 | 0.00001985 sec |
| ZGOPTNS | |

======== CHANNEL f1 ========

| | |
|---|---|
| NUC1 | 1H |
| P1 | 2.97 usec |
| P2 | 5.94 usec |
| P28 | 2000.00 usec |
| PL1 | -2.80 dB |
| PL1W | 21.05972290 W |
| SFO1 | 500.2225011 MHz |

TO

FROM

FROM

======= CHANNEL f2 =======
CPDPRG2          garp
NUC2             13C
P3               14.50 usec
P4               29.00 usec
PCPD2            70.00 usec
PL2              -3.00 dB
PL12             10.67 dB
PL2W             125.29680634 W
PL12W            5.38195419 W
SFO2             125.7929970 MHz ====== GRADIENT CHANNEL =====
GPNAM1           SINE.100
GPNAM2           SINE.100
GPZ1             80.00 %
GPZ2             20.10 %
P16              1000.00 usec
NDO              2
TD               256
SFO1             125.793 MHz
FIDRES           98.275780 Hz
SW               200.000 ppm
FnMODE           Echo-Antiecho
SI               1024
SF               500.2199769 MHz
WDW              QSINE
SSB              2
LB               0.00 Hz
GB               0
PC               1.00
SI               1024
MC2              echo-antiecho
SF               125.7803393 MHz
WDW              QSINE
SSB              2
LB               0.00 Hz
GB               0

TO FIG. 19B

AMRI; 21 Corporate Circle
location: 13
ARN: 20133237
Lot: MAU-D-111-8
Project: 8417
User: kdewkota Current Data Parameters
NAME                         KPD-B-17
EXPNO                             12
PROCNO                         11

F2 - Acquisition Parameters
Date_                         20130816
Time_                          8.10
INSTRUM                   spect
PROBHD      mm PABBI   1H-BB
PULPROG        hmbogp12ndgf
TD                              4096
SOLVENT                    Pyr
NS                              394
DS                              16
SWH                 5000.000 Hz
FIDRES             1.220703 Hz
AQ                0.9097000 sec
RG                   20642.3
DW               100.000 usec
DE                  6.00 usec
TE                   300.0 K
CNST6          119.0000000
CNST7          180.0000000
CNST13           7.6500001
D0             0.00000300 sec
D1             3.00000000 sec
D6             0.06501950 sec
D16           0.00010000 sec
IN0            0.00001730 sec ======== CHANNEL f1 ========
NUC1                      1H
P1                   2.97 usec
P2                   5.94 usec
PL1                -2.80 dB
PL1W        21.05972290 W
SFO1        500.2225011 MHz ======== CHANNEL f2 ========
NUC2                   10C
P3                  14.30 usec
PL2               -3.00 dB
PL2W     123.29690634 W
SFO2      123.7936259 MHz

FROM
FIG. 19A

FROM

===== GRADIENT CHANNEL =====

| | |
|---|---|
| GPNAM[1] | SINE.100 |
| GPNAM[2] | SINE.100 |
| GPNAM[3] | SINE.100 |
| GPNAM[4] | SINE.100 |
| GPNAM[5] | SINE.100 |
| GPNAM[6] | SINE.100 |
| GPL1 | 50.00 % |
| GPL2 | 30.00 % |
| GPL3 | 40.10 % |
| GPL4 | 15.00 % |
| GPL5 | -10.00 % |
| GPL6 | -5.00 % |
| P16 | 1000.00 usec |

F1 - Acquisition parameters

| | |
|---|---|
| TD | 256 |
| SFO1 | 125.7936 MHz |
| FIDRES | 113.017708 Hz |
| SW | 230.000 ppm |
| FnMODE | QF |

F2 - Processing parameters

| | |
|---|---|
| SI | 2048 |
| SF | 300.2199780 MHz |
| WDW | SINE |
| SSB | 0 |
| LB | 0 Hz |
| GB | 0 |
| PC | 1.00 |

F1 - Processing parameters

| | |
|---|---|
| SI | 1024 |
| MC2 | QF |
| ST | 125.7803215 MHz |
| WDW | SINE |
| SSB | 0 |
| LB | 0 Hz |
| GB | 0 |

FROM

TO

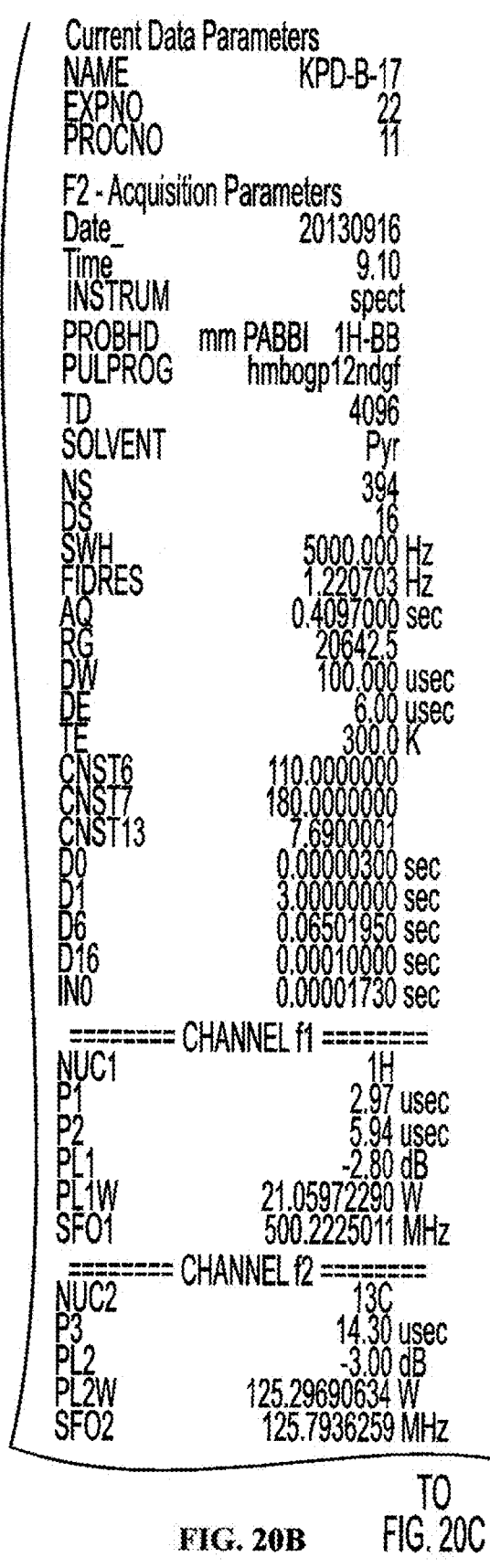

Current Data Parameters
NAME                KPD-B-17
EXPNO                     22
PROCNO                    11

F2 - Acquisition Parameters
Date_              20130916
Time_                   9.10
INSTRUM               spect
PROBHD    mm PABBI  1H-BB
PULPROG       hmbogp12ndgf
TD                      4096
SOLVENT                  Pyr
NS                       394
DS                        16
SWH             5000.000 Hz
FIDRES          1.220703 Hz
AQ            0.4097000 sec
RG                   20642.5
DW             100.000 usec
DE                6.00 usec
TE                  300.0 K
CNST6        110.0000000
CNST7        180.0000000
CNST13          7.6900001
D0           0.00000300 sec
D1           3.00000000 sec
D6           0.06501950 sec
D16          0.00010000 sec
IN0          0.00001730 sec ======== CHANNEL f1 ========
NUC1                      1H
P1                2.97 usec
P2                5.94 usec
PL1                -2.80 dB
PL1W        21.05972290 W
SFO1        500.2225011 MHz ======== CHANNEL f2 ========
NUC2                     13C
P3               14.30 usec
PL2                -3.00 dB
PL2W       125.29690634 W
SFO2        125.7936259 MHz

FROM
FIG. 20A

FROM

FROM

```
====== GRADIENT CHANNEL ======
GPNAM[1]              SINE.100
GPNAM[2]              SINE.100
GPNAM[3]              SINE.100
GPNAM[4]              SINE.100
GPNAM[5]              SINE.100
GPNAM[6]              SINE.100
GPL1                   50.00 %
GPL2                   30.00 %
GPL3                   40.10 %
GPL4                   15.00 %
GPL5                  -10.00 %
GPL6                   -5.00 %
P16                 1000.00 usec F1 - Acquisition parameters
TD                        256
SFO1             125.7936 MHz
FIDRES          113.017708 Hz
DW                230.000 ppm
FnMODE                     QF F2 - Processing parameters
SI                       2048
SF            300.2199780 MHz
WDW                      SINE
SSB          0
LB           0 Hz
GB           0
PC                       1.00

F1 - Processing parameters
SI                       1024
MC2                        QF
SF            125.7803215 MHz
WDW                      SINE
SSB          0
LB           0 Hz
GB           0
```

FROM

Current Data Parameters
NAME                KPD-B-21
EXPNO                     10
PROCNO                     2

F2 - Acquisition Parameters
Date_              20130821
Time_                 18.03
INSTRUM               spect
PROBHD  mm PABBI 1H-BB
PULPROG               zg30
TD                    65536
SOLVENT                 D20
NS                       32
DS                        2
SWH            10330.578 Hz
FIDRES          0.157632 Hz
AQ             3.1719909 sec
RG                    228.1
DH                48.400 usec
DE                 6.00 usec
TE                   300.0 K
D1           1.00000000 sec
TD0                       1

======== CHANNEL f1 ========
NUC1                     1H
P1                  2.97 usec
PL1                 -2.80 dB
PL1W          21.05972290 W
SFO1         500.2230885 MHz F2 - Processing Parameters
SI                    32768
SF           500.2199536 MHz
WDW                      EM
SSB          0
LB                   0.30 Hz
GB           0
PC                     1.00

TO

AMRI: 21 Corporate Circle
location: 13
ARN: 20133235
Lot: KPD-B-21 (MAU-D-111-4)
Project: 8417
User: kdevkota

FROM
FIG. 24A

Current Data Parameters
Name                    KPD-B-21
EXPNO                        11
PROCNO                        2

F2 - Acquisition Parameters
Date_                  20130821
Time                      18.14
INSTRUM                   spect
PROBHD          mm PABBI 1H-BB
PULPROG           cosygpqf-45
TD                        2048
SOLVENT                    D20
NS                          16
DS                           8
SWH               6666.667 Hz
FIDRES            3.255208 Hz
AQ               0.1536750 sec
RG                      3649.1
DW                  75.000 usec
DE                    6.00 usec
TE                    300.0 k
D0               0.00000300 sec
D1               1.48689198 sec
D13              0.000004000 sec
D16              0.00010000 sec
IN0              0.00015000 sec
P0                    1.49 usec
======== CHANNEL f1 ========
NUC1                        1H
P1                    2.97 usec
PL1                  -2.80 dB
PLW1            21.05972290 W
SFO1           500.2230074 MHz

FROM
FIG. 24B

FROM
FIG. 24A

===== GRADIENT CHANNEL =====
GPNAM (1)          SINE.100
GPNAM (2)          SINE.100
GP21                  10.00  %
GP22                  10.00  %
P16                 1000.00  usec F1 - Acquisition parameters
TD                      512
SFO1                500.223  MHz
FIDRES            13.020833  Hz
SW                   13.327  ppm
FnMODE                   QF F2 - Processing parameters
SI                     1024
SF             500.2199513  MHz
WDW                    SINE
SSB        0
LB         0 Hz
GB         0
PC                     1.00

F1 - Processing parameters
SI                     1024
MC2                     QF
SF             500.2199509  MHz
WDW                    SINE
SSB        0
LB         0 Hz
GB         0

AMRI 21 Corporate Circle
location: 13
ARN: 20133235
Lot: KPD-B-21 (MAU-D-111-4)
Project: 8417
User: kdevkota

| | | |
|---|---|---|
| Name | KPD-B-21 | |
| EXPNO | 13 | |
| PROCNO | 8 | |
| Date_ | 20130822 | |
| Time | 7.59 | |
| INSTRUM | spect | |
| PROBHD | mm | PABBI 1H-BB |
| PULPROG | hsqcedstgp | |
| TD | 1024 | |
| SOLVENT | D20 | |
| NS | 256 | |
| DS | 16 | |
| SWH | 5000.000 | HZ |
| FIDRES | 4.882813 | Hz |
| AQ | 0.1025500 | sec |
| RG | 20642.5 | |
| DW | 100.00 | usec |
| DE | 6.00 | usec |
| TE | 300.0 K | K |
| CNST2 | 145.0000000 | |
| D0 | 0.00000300 | sec |
| D1 | 1.53706896 | sec |
| D4 | 0.00172414 | sec |
| D11 | 0.03000000 | sec |
| D13 | 0.00000400 | sec |
| D16 | 0.00010000 | sec |
| D21 | 0.00344800 | sec |
| INO | 0.00001985 | sec |
| ZGOPTNS | | |

======== CHANNEL f1 ========

| | | |
|---|---|---|
| NUC1 | 1H | |
| P1 | 2.97 | usec |
| P2 | 5.94 | usec |
| P28 | 2000.00 | usec |
| PL1 | -2.80 | dB |
| PL1W | 21.05972290 | W |
| SFO1 | 500.2225011 | MHz |

FROM
FIG. 25A

FROM
FIG. 25B

======== CHANNEL f2 ========

| | |
|---|---|
| CPDPRG2 | garp |
| NUC2 | 13C |
| P3 | 14.50 usec |
| P4 | 29.00 usec |
| PCPD2 | 70.00 usec |
| PL2 | -3.00 dB |
| PL12 | 10.67 dB |
| PL2W | 125.29680634 W |
| PL12W | 5.38195419 W |
| SFO2 | 125.7929970 MHz |

===== GRADIENT CHANNEL =====

| | |
|---|---|
| GPNAM1 | SINE.100 |
| GPNAM2 | SINE.100 |
| GP21 | 80.00 % |
| GP22 | 20.10 % |
| P15 | 1000.00 usec |
| NDO | 2 |
| TD | 208 |
| SFO1 | 125.793 MHz |
| FIDRES | 120.954803 Hz |
| SW | 200.000 |
| FnMODE | Echo-Antiecho |
| SI | 1024 |
| SF | 500.2199536 MHz |
| WDW | QSINE |
| SSB | 2 |
| LB | 0.00 Hz |
| GB | 0 |
| PC | 1.00 |
| SI | 1024 |
| MC2 | echo-antiecho |
| SF | 125.7800518 MHz |
| WDW | QSINE |
| SSB | 2 |
| LB | 0.00 Hz |
| GB | 0 |

FROM
FIG. 25A

```
Current Date Parameters
NAME              KPD-B-21
EXPNO                    14
PROCNO                   11

F2 - Acquisition Parameters
Date_             20130823
Time                 16.33
INSTRUM              spect
PROBHD       mm PABBI 1H-BB
PULPROG       hnbogp12ndqf
TD                    4096
SOLVENT                D20
NS                     384
DS                      16
SWH            5000.000  Hz
FIDRES         1.220703  Hz
AQ            0.4097000  sec
RG               20992.5
DW              100.00  usec
DE                6.00  usec
TE               300.0  K
CNST6        110.0000000
CNST7        100.0000000
CNST13         7.6900001
D0           0.00000300  sec
D1           3.00000000  sec
D6           0.06301930  sec
D16          0.00010000  sec
INO          0.00001730  sec
```

FROM
FIG. 26A

FROM

FROM

======= CHANNEL f1 =======

| NUC1 | 1H | |
| P1 | 2.97 | usec |
| P2 | 5.94 | usec |
| PL1 | -2.80 | dB |
| PL1W | 21.05972290 W | W |
| SFO1 | 500.2225011 MHz | MHz |

======= CHANNEL f2 =======

| NUC2 | 13c | |
| P3 | 14.50 | usec |
| PL2 | -3.00 | dB |
| PL2W | 125.29680634 | W |
| STO2 | 125.7936259 | MHz |

===== GRADIENT CHANNEL =====

| GPNAM [1] | SINE.100 | |
| GPNAM [2] | SINE.100 | |
| GPNAM [3] | SINE.100 | |
| GPNAM [4] | SINE.100 | |
| GPNAM [5] | SINE.100 | |
| GPNAM [6] | SINE.100 | |
| GPL1 | 50.00 | % |
| GPL2 | 30.00 | % |
| GPL3 | 40.10 | % |
| GPL4 | 15.00 | % |
| GPL5 | -10.00 | % |
| GPL6 | -5.00 | % |
| P15 | 1000.00 | usec |

TO

FROM
FIG. 26C

FROM
FIG. 26A

F1 - Acquisition parameters
FD                    235
SFO1         125.7936 MHz
FIDRES    123.117163 Hz
SW            230.000 ppm
FnMODE              QF F2 - Processing parameters
SI                     2044
SF       300.2199330 MHz
WDW                  SINE
SSB        0
LB         0 Hz
GB         0
PC                     1.00

F1 - Processing parameters
SI                     1024
MC2                     QF
SF        125.7800514 MHz
WDW                  SINE
SSB        0
LB         0Hz
GB         0

AMRI, 21 Corporate Circle
location: 13
ARN: 20133235
Lot: KPD-B-21 (MAU-D-111-4)
Project: 8417
User: kdevkota Current Date Parameters
NAME KPD-B-21
EXPNO 14
PROCNO 11

F2 - Acquisition Parameters
Date_ 20130823
Time 16.33
INSTRUM spect
PROBHD mm PABBI 1H-BB
PULPROG bnbogp12ndqf
ID 4096
SOLVENT D20
NS 389
DS 16
SWX 5000.000 Hz
FIDRES 1.220703 Hz
AQ 0.4097000 sec
RG 20662.5
DW 100.00 usec
DE 6.00 usec
TE 300.0 K
CNST6 110.0000000
CNST7 190.0000000
CNST13 7.6900001
D0 0.00000300 sec
D1 3.00000000 sec
D6 0.06501950 sec
D16 0.00010000 sec
INO 0.00001730 sec

FROM
FIG. 27A

FROM

```
======== CHANNEL f1 ========

NUC1              1H
P1                2.97  usec
P2                3.94  usec
PL1               -2.80  dB
PL1W          21.03972290  W
SFO1          500.2225011  MHz ======== CHANNEL f2 ========

NUC2              13c
P3                14.50  usec
PL2               -3.00  dB
PL2W         125.29680634  W
STO2          135.7936259  MHz

===== GRADIENT CHANNEL =====

GPNAM [1]         SINE.100
GPNAM [2]         SINE.100
GPNAM [3]         SINE.100
GPNAM [4]         SINE.100
GPNAM [5]         SINE.100
GPNAM [6]         SINE.100
GPL1              50.00  %
GPL2              30.00  %
GPL3              40.10  %
GPL4              15.00  %
GPL5             -10.00  %
GPL6              -5.00  %
P16             1000.00  usac
```

FROM

TO

FROM
FIG. 27C

FROM
FIG. 27A

F1 - Acquisition parameters
FD                    235
SFO1          123.7936 MHz
FIDRES      123.117165 Hz
SW             230.000 ppm
FnMODE              QF F2 - Processing parameters
SI                   2048
SF         300.2199530 MHz
WDW                 SINE
SSB         0
LB          0Hz
GB          0
PC                   1.00

F1 - Processing parameters
SI                   1024
MC2                  QF
SF         125.7800514 MHz
WDW                 SINE
SSB         0
LB          0Hz
GB          0

FIG. 27D

Figure 35B:
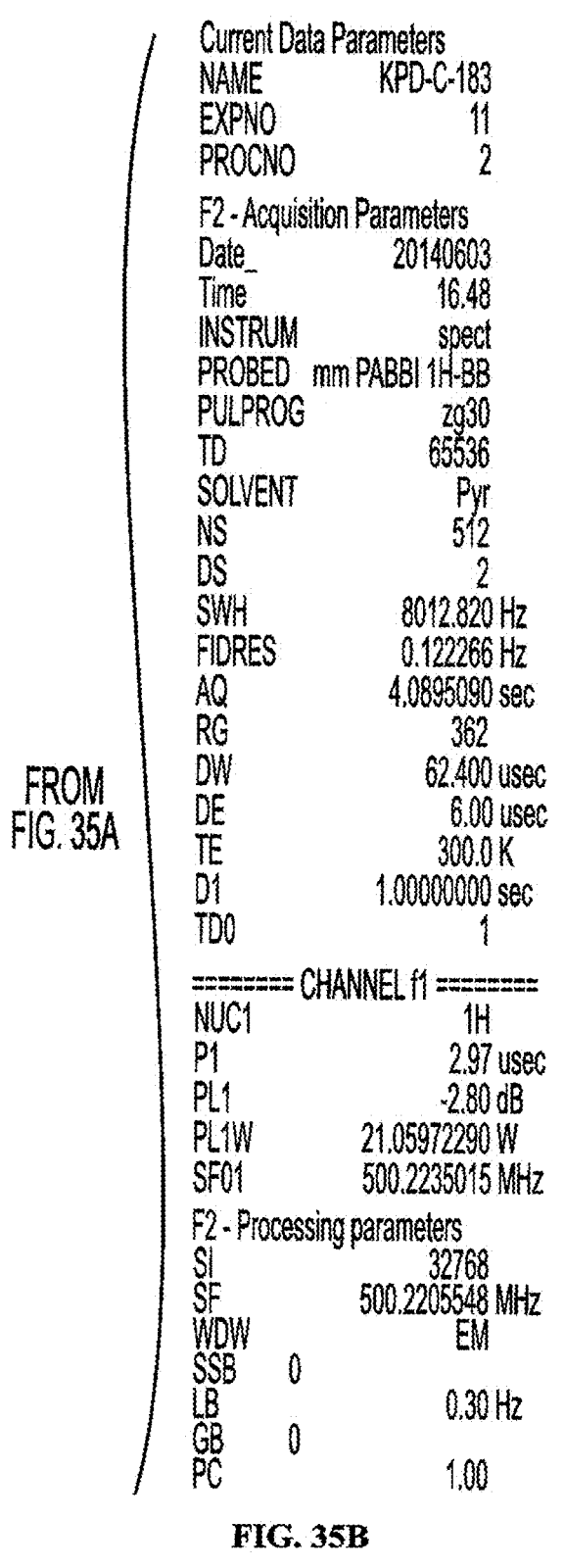

Current Data Parameters
NAME                KPD-C-183
EXPNO                      11
PROCNO                      2

F2 - Acquisition Parameters
Date_                20140603
Time                    16.48
INSTRUM                 spect
PROBED   mm PABBI 1H-BB
PULPROG                  zg30
TD                      65536
SOLVENT                   Pyr
NS                        512
DS                          2
SWH             8012.820 Hz
FIDRES          0.122266 Hz
AQ            4.0895090 sec
RG                        362
DW              62.400 usec
DE               6.00 usec
TE                  300.0 K
D1          1.00000000 sec
TD0                         1

======== CHANNEL f1 ========
NUC1                       1H
P1                  2.97 usec
PL1                   -2.80 dB
PL1W           21.05972290 W
SF01        500.2235015 MHz F2 - Processing parameters
SI                      32768
SF          500.2205548 MHz
WDW                       EM
SSB          0
LB                   0.30 Hz
GB           0
PC                       1.00

FROM FIG. 35A

FROM

Current Data Parameters
NAME                KPD-C-183
EXPNO                     62
PROCNO                     2

F2 - Acquisition Parameters
Date_               20140611
Time                   15.33
INSTRUM                spect
PROBHD    mm PABBI 1H-BB
PULPROG                 zg30
TD                     65536
SOLVENT                  Pyr
NS                       128
DS                         2
SWH              8012.820 Hz
FIDRES          0.122266 Hz
AQ              4.0895090 sec
RG                       362
DW               62.400 usec
DE                6.00 usec
TE                   292.0 K
D1            1.00000000 sec
TD0                        1

======== CHANNEL f1 ========
NUC1                     1H
P1                 3.06 usec
PL1                 -2.80 dB
PL1W          21.05972290 W
SFO1          500.2235015 MHz F2 - Processing parameters
SI                     32768
SF            500.2205483 MHz
WDW                       EM
SSB           0
LB                   0.30 Hz
GB            0
PC                      1.00

FROM

Current Data Parameters
NAME            KPD-C-183
EXPNO                  62
PROCNO                  2

F2 - Acquisition Parameters
Date_            20140611
Time                15.33
INSTRUM             spect
PROBHD    mm PABBI 1H-BB
PULPROG             zg30
TD                  65536
SOLVENT              Pyr
NS                    128
DS                      2
SWH         8012.820 Hz
FIDRES      0.122266 Hz
AQ         4.0895090 sec
RG                    362
DW           62.400 usec
DE             6.00 usec
TE             292.0 K
D1        1.00000000 sec
TD0                     1
======== CHANNEL f1 ========
NUC1                 1H
P1            3.06 usec
PL1           -2.80 dB
PL1W     21.05972290 W
SFO1     500.2235015 MHz F2 - Processing parameters
SI                  32768
SF       500.2205483 MHz
WDW                   EM
SSB          0
LB              0.30 Hz
GB           0
PC                   1.00

TO FIG. 38B

FROM

Current Data Parameters
NAME          KPD_C_183_600_062314
EXPNO              2000
PROCNO                2

F2 - Acquisition Parameters
Date_           20140623
Time               10.09
INSTRUM            spect
PROBHD     5 mm CPTCI 1H-
PULPROG           zgpg30
TD                 50324
SOLVENT              Pyr
NS                139811
DS                     4
SWH         36057.691 Hz
FIDRES      0.716511 Hz
AQ          0.6978261 sec
RG                   912
DW           13.867 usec
DE            31.31 usec
TE              292.0 K
D1        0.50000000 sec
D11       0.03000000 sec
TD0                    1
======== CHANNEL f1 ========
NUC1                 13C
P1           21.10 usec
PL1            4.00 dB
PL1W      29.20000076 W
SFO1      150.9178988 MHz

TO

FROM
FIG. 38B

```
======== CHANNEL f2 ========
CPDPRG[2        waltz16
NUC2            1H
PCPD2           80.00 usec
PL2             2.65 dB
PL12            22.65 dB
PL13            26.56 dB
PL2W            8.55593586 W
PL12W           0.08555937 W
PL13W           0.03477504 W
SFO2            600.1324005 MHz F2 - Processing parameters
SI              65536
SF              150.9027706 MHz
WDW             EM
SSB         0
LB              6.00 Hz
GB          0
PC              1.40
```

FIG. 38C

FROM

Current Data Parameters
NAME          KPD_C_183_600_062314
EXPNO              2000
PROCNO                2

F2 - Acquisition Parameters
Date_            20140623
Time               10.09
INSTRUM            spect
PROBHD    5 mm CPTCI 1H-
PULPROG           zgpg30
TD                 50324
SOLVENT              Pyr
NS                139811
DS                     4
SWH         36057.691 Hz
FIDRES       0.716511 Hz
AQ          0.6978261 sec
RG                   912
DW            13.867 usec
DE             31.31 usec
TE               292.0 K
D1          0.50000000 sec
D11         0.03000000 sec
TD0                    1

TO

FROM
FIG. 39B

======= CHANNEL f1 ========
| | |
|---|---|
| NUC1 | 13C |
| P1 | 21.10 usec |
| PL1 | 4.00 dB |
| PL1W | 29.20000076 W |
| SF01 | 150.9178988 MHz |

======= CHANNEL f2 ========
| | |
|---|---|
| CPDPRG[2 | waltz16 |
| NUC2 | 1H |
| PCPD2 | 80.00 usec |
| PL2 | 2.65 dB |
| PL12 | 22.65 dB |
| PL13 | 26.56 dB |
| PL2W | 8.55593586 W |
| PL12W | 0.08555937 W |
| PL13W | 0.03477504 W |
| SF02 | 600.1324005 MHz |

F2 - Processing parameters
| | |
|---|---|
| SI | 65536 |
| SF | 150.9027706 MHz |
| WDW | EM |
| SSB | 0 |
| LB | 6.00 Hz |
| GB | 0 |
| PC | 1.40 |

AMRI 21 Corporate Circle
location; 9
ARN: 20141941
Lot: CJP-C-178 (1)
Project: 9246
Conc: ~1.0 mg/180 μL
User: kdevkota

FROM

Current Data Parameters

NAME            KPD-C-183
EXPNO                  17
PROCNO                  5

F2 - Acquisition Parameters

Date_            20140628
Time_               15.58
INSTRUM             spect
PROBHD    5 mm BBO  BB-1H
PULPROG      cosygpqf45-FS
TD                   2048
SOLVENT              Pyr
NS                    160
DS                      8
SWH           6009.615 Hz
FIDRES        2.934382 Hz
AQ          0.1704768 sec
RG                   3251
DW            83.200 usec
DE              6.00 usec
TE               292.0 K
D0         0.00000300 sec
D1         1.42954803 sec
D13        0.00000400 sec
D16        0.00010000 sec
IN0        0.00016660 sec ======== CHANNEL f1 ========
NUC1                  1H
P0            6.75 usec
P1           13.50 usec
PL1             0.50 dB
PL1W       13.43232727 W
SF01      500.1327507 MHz

TO

FROM
FIG. 40B

===== GRADIENT CHANNEL =====
GPNAM(1)　　　　SINE.100
GPNAM(2)　　　　SINE.100
GP21　　　　　　10.00 %
GP22　　　　　　10.00 %
P16　　　　　　1000.00 usec F1 - Acquisition parameters
TD　　　　　　　512
SF01　　　　　500.1328 MHz
FIDRES　　　　11.721861 Hz
SW　　　　　　12.000 ppm
FnMODE　　　　　QF F2 - Processing parameters
SI　　　　　　　1024
SF　　　　500.1305487 MHz
WDW　　　　　　SINE
SSB　　　0
LB　　　　0 Hz
GB　　　　0
PC　　　　　　　1.00

F1 - Processing parameters
SI　　　　　　　1024
MC2　　　　　　　QF
SF　　　　500.1305492 MHz
WDW　　　　　　SINE
SSB　　　0
LB　　　　0 Hz
GB　　　　0

FIG. 40C

AMRI, 21 Corporate Circle
location: 13
ARN: 20141941
Lot: CJP-C-178 (1)
Project: 9246
Conc: ~1.0 mg/180 μL
User: kdevkota
2.5 mm probe

TO

FROM

| NAME | KPD-C-183 |
|---|---|
| EXPNO | 63 |
| PROCNO | 4 |
| Date_ | 20140611 |
| Time | 15.51 |
| INSTRUM | spect |
| PROBHD | mm PABBI 1H-BB |
| PULPROG | hsqcadatgp |
| TD | 1024 |
| SOLVENT | Pyr |
| NS | 256 |
| DS | 16 |
| SWH | 6009.615 Hz |
| FIDRES | 5.868765 Hz |
| AQ | 0.0853300 sec |
| RG | 20642.5 |
| DW | 83.200 usec |
| DE | 6.00 usec |
| TE | 292.0 K |
| CNST2 | 145.0000000 |
| D0 | 0.00000300 sec |
| D1 | 1.53706896 sec |
| D4 | 0.00172414 sec |
| D11 | 0.03000000 sec |
| D13 | 0.00000400 sec |
| D16 | 0.00010000 sec |
| D21 | 0.00344800 sec |
| IN0 | 0.00002340 sec |
| ZGOPTNS | |

======= CHANNEL f1 =======

| NUC1 | 1H |
|---|---|
| P1 | 3.06 usec |
| P2 | 6.12 usec |
| P28 | 2000.00 usec |
| PL1 | -2.80 dB |
| PL1W | 21.05972290 W |
| SF01 | 500.2227512 MHz |

TO

FROM
FIG. 41B

======= CHANNEL f2 =======

| | |
|---|---|
| CPDPRG2 | garp |
| NUC2 | 13C |
| P3 | 13.75 usec |
| P4 | 27.50 usec |
| PCPD2 | 70.00 usec |
| PL2 | -2.00 dB |
| PL12 | 12.14 dB |
| PL2W | 99.52679443 W |
| PL12W | 3.83654213 W |
| SFO2 | 125.7898525 MHz |

===== GRADIENT CHANNEL =====

| | |
|---|---|
| GPNAM1 | SINE.100 |
| GPNAM2 | SINE.100 |
| GPZ1 | 80.00 % |
| GPZ2 | 20.10 % |
| P16 | 1000.00 usec |
| ND0 | 2 |
| TD | 170 |
| SFO1 | 125.7899 MHz |
| FIDRES | 125.789856 Hz |
| SW | 170.000 ppm |
| FnMODE | Echo-Antiecho |
| SI | 1024 |
| SF | 500.2205437 MHz |
| WDW | QSINE |
| SSB | 2 |
| LB | 0.00 Hz |
| GB | 0 |
| PC | 1.00 |
| SI | 1024 |
| MC2 | echo-antiecho |
| SF | 125.7805204 MHz |
| WDW | QSINE |
| SSB | 2 |
| LB | 0.00 Hz |
| GB | 0 |

ARN: 20141941
Lot: CJP-C-178 (1)
Project: 9246
Conc: ~1.0 mg/180 μL
Data collected at 800 MHz Current Data Parameters
NAME anri_RPD_C_183_061714_2nd
EPXND 5
PROCNO 1

F2 - Acquisition Parameters
Date_ 20140617
Time 11.29
INSTRUM spect
PROBHD 5 mm CPICI 1H-
PULPROG habcgp12ndqf
TD 4096
SOLVENT Pyr
NS 288
DS 120
SWH 9615.385 Hz
FIDRES 2.347506 Hz
AQ 0.2129920 sec
RG 512
DW 52.000 usec
DE 6.00 usec
TE 292.0 K
CNST6 110.0000000
CNST7 180.0000000
CNST13 7.6900001
D0 0.0000300 sec
D1 2.0000000 sec
D6 0.06301950 sec
D16 0.00019000 sec
IN0 0.00001150 sec

FROM
FIG. 42A

FROM
FIG. 42B

FROM
FIG. 42A

```
======== CHANNEL f1 ========

NUC1                    1H
P1                 7.20 usec
P2                14.40 usec
PL1                  -1.20 dB
PL1W         14.49692039 W
SFO1         000.1444000 MHz ======== CHANNEL f2 ========

NUC2                   13C
P3                12.60 usec
PL2                  -2.30 dB
PL2W        144.61043937 W
SFO2        201.2134035 MHz

====== GRADIENT CHANNEL ====

GPNAM (1)          SINE.100
GPNAM (2)          SINE.100
GPNAM (3)          SINE.100
GPNAM (4)          SINE.100
GPNAM (5)          SINE.100
GPNAM (6)          SINE.100
CPL1                 50.00 %
CPL2                 30.00 %
CPL3                 40.10 %
CPL4                 15.00 %
CPL5                -10.00 %
CPL6                 -5.00 %
P16             1000.00 usec
```

FROM

FROM

F1 - Acquisition parameters
TD                          295
SF01              201.2155 MHz
FIDRES          147.399099 Hz
SW                  216.096 ppm
FnMODE                     QF F2 - Processing parameters
SI                         4096
SF         000.1399717 MHz
WDW                    QSINE
SSB                           2
LB              0 Hz
GB              0
PC                        1.00

F1 - Processing parameters
SI                        1024
MC2                         Qr
SF         201.1932940 MHz
WDW                    QSINE
SSB                           2
LB              0 Hz
GB              0

TO

ARN: 20141941
Lot: CJP-C-178 (1)
Project: 9246
Conc: ~1.0 mg/180 μL
Data collected at 800 MHz Current Data Parameters
NAME  anri_KPD_C_183_001714_2nd
EXPNO                          5
PROCNO                         1

F2 - Acquisition Parameters
Date_                   20140617
Time                       11.29
INSTRUM                    spect
PROBHD     3 mm CPICI 1H-
PULPROG        habcgp12ndqf
TD                          4096
SOLVENT                      Pyr
WS                           288
DS                           128
SWH                  9615.385 Hz
FIDRES               2.347506 Hz
AQ                 0.2129920 sec
RG                           512
DW                   52.000 usec
DE                     6.00 usec
TE                       292.0 K
CNST6            110.0000000
CNST7            180.0000000
CNST13             7.6900001
D0                 0.00000300 sec
D1                 2.00000000 sec
D6                 0.06301950 sec
D16                0.00016000 sec
IN0                0.00001150 sec

FROM
FIG. 43A

FROM
FIG. 43B

FROM
FIG. 43A

======== CHANNEL f1 ========

| NUC1 | 1H |
|------|-----|
| P1 | 7.20 usec |
| P2 | 14.40 usec |
| PL1 | -1.20 dB |
| PL1W | 14.49692059 W |
| SFO1 | 900.1444000 MHz |

======== CHANNEL f2 ========

| NUC2 | 13C |
|------|-----|
| P3 | 12.60 usec |
| PL2 | -2.30 dB |
| PL2M | 199.61043937 W |
| SFO2 | 201.2134005 MHz |

====== GRADIENT CHANNEL =====

| GPNAM (1) | SINE.100 |
|-----------|----------|
| GPNAM (2) | SINE.100 |
| GPNAM (3) | SINE.100 |
| GPNAM (4) | SINE.100 |
| GPNAM (5) | SINE.100 |
| GPNAM (6) | SINE.100 |
| CPL1 | 50.00 % |
| CPL2 | 30.00 % |
| CPL3 | 40.10 % |
| CPL4 | 15.00 % |
| CPL5 | -10.00 % |
| CPL6 | -5.00 % |
| P16 | 1000.00 usec |

FROM

FROM

F1 - Acquisition parameters
TD                              295
SF01                    201.2155 MHz
FIDRES               147.399099 Hz
SW                        216.096 ppm
FnMODE                          QF F2 - Processing parameters
SI                             4096
SF              000.1399717 MHz
WDW                          QSINE
SSB                              2
LB            0 Hz
GB            0
PC                             1.00

F1 - Processing parameters
SI                             1024
MC2                             QF
SF              201.1932940 MHz
WDW                          QSINE
SSB                              2
LB            0 Hz
GB            0

AMRI: 21 Corporate Circle
location: 13
ARN: 20141941
Lot: CJP-C-178(1)
Project: 9246
Conc: ~1.0 mg/180 µL
User: kdevkota
2.5 mm probe

TO

Current Data Parameters
NAME             KPD-C-183
EXPNO                   96
PROCNO                   6

F2 - Acquisition Parameters
Date_            20140626
Time                  8.33
INSTRUM              spect
PROBHD   mm PABBI 1H-BB
PULPROG          noesygpph
TD                    2048
SOLVENT               Pyr
NS                     128
DS                      16
SWH             7374.631 Hz
FIDRES          3.600894 Hz
AQ              0.1389222 sec
RG                     181
DW               67.800 usec
DE                6.00 usec
TE                 292.0 K
D0          0.00006389 sec
D1          2.06184793 sec
D8          0.30000001 sec
D16         0.00010000 sec
IN0         0.00013560 sec ======== CHANNEL f1 ========
NUC1                    1H
P1                3.06 usec
P2                6.12 usec
PL1                -2.80 dB
PL1W        21.05972290 W
SF01       500.2232232 MHz

FROM
FIG. 44A

FROM
FIG. 44B

FROM
FIG. 44A

===== GRADIENT CHANNEL =====
GPNAM(1)          SINE.100
GP21              40.00 %
P16               1000.00 usec F1 - Acquisition parameters
TD                512
SF01              500.2232 MHz
FIDRES            14.406169 Hz
SW                14.745 ppm
FnMODE            TPPI F2 - Processing parameters
SI                1024
SF                500.2205449 MHz
WDW               QSINE
SSB               2
LB        0 Hz
GB        0
PC                1.00

F1 - Processing parameters
SI                1024
MC2               TPPI
SF                500.2205495 MHz
WDW               QSINE
SSB               2
LB        0 Hz
GB        0

AMRI; 21 Corporate Circle
location; 13
ARN: 20141941
Lot: CJP-C-178 (1)
Project: 9246
Conc: ~1.0 mg/180 µL
User: kdevkota
2.5 mm probe

FROM
FIG. 45A

Current Data Parameters
NAME            KPD-C-183
EXPNO                    96
PROCNO                    6

F2 - Acquisition Parameters
Date_            20140626
Time                  8.33
INSTRUM              spect
PROBHD   mm PABBI 1H-BB
PULPROG          noesygpph
TD                    2048
SOLVENT               Pyr
NS                     128
DS                      16
SWH            7374.631 Hz
FIDRES        3.600894 Hz
AQ          0.1389222 sec
RG                     181
DW             67.800 usec
DE              6.00 usec
TE                 292.0 K
D0          0.00006389 sec
D1          2.06184793 sec
D8          0.30000001 sec
D16         0.00010000 sec
IN0         0.00013560 sec ======== CHANNEL f1 ========
NUC1                    1H
P1              3.06 usec
P2              6.12 usec
PL1               -2.80 dB
PL1W        21.05972290 W
SFO1       500.2232232 MHz

FROM
FIG. 45B

FROM
FIG. 45A

===== GRADIENT CHANNEL =====
GPNAM(1)                    SINE.100
GP21                        40.00 %
P16                         1000.00 usec F1 - Acquisition parameters
TD                          512
SF01                        500.2232 MHz
FIDRES                      14.406169 Hz
SW                          14.745 ppm
FnMODE                      TPPI F2 - Processing parameters
SI                          1024
SF                          500.2205449 MHz
WDW                         QSINE
SSB                         2
LB              0 Hz
GB              0
PC                          1.00

F1 - Processing parameters
SI                          1024
MC2                         TPPI
SF                          500.2205495 MHz
WDW                         QSINE
SSB                         2
LB              0 Hz
GB              0

Synthesis of Rebaudioside M from Rebaudioside D/ CAD detection catalyzed by in-vitro produced UGT76G1

| CAD Ch 1 Results | | |
| Compound | Retention time | Integration (area) |
| Rebaudioside D | 5.775 | 3,264,475 |
| Unknown@RT6.986 | 6.986 | 4,110,607 |
| Unknown@RT7.330 | 7.330 | 564,033,104 |
| Unknown@RT7.700 | 7.700 | 328,710,539 |
| Unknown@RT8.158 | 8.158 | 6,344,796 |
| Rebaudioside A | 9.135 | 673,271,863 |
| Unknown@RT9.653 | 9.653 | 616,489,141 |
| Total | | 2,196,224,525 |

Sample : 12400 S129N02 T45h 130712ABA
> gi|87373030 / ACD03249.1
Filename : 130712_12400_004.dat CAD Ch 1
12400 S129N02 T45h 130712ABA
130712_12400_004.dat Retention Time

| CAD Ch 1 Results Compound | Retention time | Integration (area) |
|---|---|---|
| Rebaudioside D | 5.772 | 1,997,401 |
| Unknown@RT6.977 | 6.977 | 3,341,419 |
| Unknown@RT7.252 | 7.252 | 10,576,676 |
| Unknown@RT7.687 | 7.687 | 298,862,034 |
| Rebaudioside A | 9.117 | 675,210,845 |
| Unknown@RT9.639 | 9.639 | 874,680,345 |
| Total | | 1,864,668,720 |

Sample : 12400 S129N04 T45h 130712ABA
> gi460409128 / XP_004249992.1
Filename : 130712_12400_006.dat CAD Ch 1
12400 S129N04 T45h 130712ABA
130712_12400_006.dat

| CAD Ch 1 Results | | |
|---|---|---|
| Compound | Retention time | Integration (area) |
| Unknown@RT4.526 | 4.526 | 89,809,997 |
| Rebaudioside D | 5.777 | 217,830,913 |
| Rebaudioside UNK | 6.711 | 192,129,243 |
| Unknown@RT6.986 | 6.986 | 10,241,417 |
| Unknown@RT7.331 | 7.331 | 41,195,765 |
| Unknown@RT7.701 | 7.701 | 310,640,254 |
| Unknown@RT8.162 | 8.162 | 7,950,609 |
| Rebaudioside A | 9.137 | 304,611,760 |
| Unknown@RT9.656 | 9.656 | 863,496,704 |
| Total | | 2,037,906,662 |

FIG. 55C

Samples :
1) 12400 <u>S129N04</u> T45h 130712ABA
> gi460409128 / XP_004249992.1
2) MLD1 *Stevia rebaudiana* Bertoni extract

LCMS SIM 1,291

Reb M

Unk@RT3.55

MLD1

S129N04
reaction mixture

| MSD SIM 1,291 Results | |
|---|---|
| Compound | MW |
| Unknown@RT3.550 | 1,291 |
| Rebaudioside *M* | 1,291 |

TO FIG. 59A-2

FROM FIG. 59A-1

| CAD Ch 1 Results Compound | Retention time | Integration (area) |
|---|---|---|
| Unknown @RT4.27 | 4.270 | 45,634,692 |
| Rebaudiosie E | 5.398 | 215,079,800 |
| Unknown @RT6.79 | 6.790 | 11,0326,212 |
| Unknown @RT7.32 | 7.320 | 33,855,010 |
| Unknown @RT7.69 | 7.689 | 271,186,269 |
| Unknown @RT8.18 | 8.178 | 6,003,490 |
| Unknown @RT8.78 | 8.779 | 20,739,231 |
| Stevioside | 9.201 | 114,734,548 |
| Unknown@RT9.65 | 9.648 | 779,225,521 |
| Total | | 1,596,784,773 |

FROM FIG. 59B-1

| CAD Ch 1 Results Compound | Retention time | Integration (area) |
|---|---|---|
| Unknown @RT3.84 | 3.841 | 16,182,482 |
| Unknown @RT4.25 | 4.255 | 20,078,830 |
| Unknown @RT4.91 | 4.910 | 27,630,795 |
| Rebaudioside E | 5.389 | 203,768,956 |
| Unknown @RT5.75 | 5.751 | 8,018,638 |
| Unknown @RT6.82 | 6.817 | 200,959,602 |
| Unknown @RT7.31 | 7.310 | 370188401 |
| Unknown @RT7.68 | 7.680 | 294,963,186 |
| Stevioside | 9.186 | 101,729,292 |
| Unknown @RT9.63 | 9.635 | 727,903,255 |
| Total | | 1,971,423,437 |

FIG. 59B-2

FROM FIG. 60A-1

| CAD Ch 1 Results | | |
|---|---|---|
| Compound | Retention time | Integration (area) |
| Rebaudiosie E | 5.499 | 135,984,743 |
| Unknown @RT7.03 | 7.027 | 54,448,761 |
| Unknown @RT7.30 | 7.302 | 41,308,528 |
| Unknown @RT7.68 | 7.682 | 283,852,603 |
| Unknown @RT8.14 | 8.145 | 5,484,731 |
| Unknown @RT8.74 | 8.742 | 290,946,055 |
| Stevioside | 9.178 | 8,774,098 |
| Unknown @RT9.64 | 9.637 | 761,299,117 |
| Unknown @RT10.54 | 10.542 | 18,276,224 |
| Rubusoside | 11.233 | 155,492,389 |
| Total | | 1,755,867,249 |

FROM FIG. 60B-1

| CAD Ch 1 Results | | |
| --- | --- | --- |
| Compound | Retention time | Integration (area) |
| Unknown @RT5.14 | 5.138 | 5,555,472 |
| Rebaudioside E | 5.505 | 278,529,547 |
| Unknown @RT6.64 | 6.643 | 23,812,633 |
| Unknown @RT7.01 | 7.012 | 84,543,823 |
| Unknown @RT7.31 | 7.315 | 283,724,517 |
| Unknown @RT7.69 | 7.687 | 264,400,008 |
| Unknown @RT8.78 | 8.767 | 188,634,123 |
| Stevioside | 9.193 | 9,365,107 |
| Unknown @RT9.64 | 9.643 | 700,878,865 |
| Rubusoside | 11.238 | 102,484,386 |
| Totals | | 1,941,928,481 |

FIG. 60B-2

FROM FIG. 61A

| CAD Ch 1 Results | | |
| --- | --- | --- |
| Compound | Retention time | Integration (area) |
| Unknown @RT4.53 | 4.530 | 55,894,278 |
| Rebaudioside D | 5.788 | 461,768,318 |
| Unknown @RT6.71 | 6.713 | 7,942,480 |
| Unknown @RT6.99 | 6.993 | 11,192,896 |
| Unknown @RT7.33 | 7.327 | 120,255,606 |
| Unknown @RT7.70 | 7.700 | 38,994,186 |
| Rebaudioside A | 9.140 | 137,037,966 |
| Unknown @RT9.65 | 9.652 | 314,468,535 |
| Total | | 1,147,554,265 |

FIG. 61B

FROM FIG. 63A-1

| CAD Ch 1 Results Compound | Retention time | Integration (area) |
|---|---|---|
| Unknown @4.27 | 4.270 | 101,580,340 |
| Unknown @4.88 | 4.884 | 2,979,482 |
| Rebaudioside E | 5.397 | 13,747,837 |
| Unknown @6.80 | 6.796 | 378,936,196 |
| Unknown @7.32 | 7.319 | 54,838,779 |
| Unknown @7.69 | 7.693 | 291,189,747 |
| Unknown @8.78 | 8.784 | 21,079,018 |
| Stevioside | 9.200 | 50,143,248 |
| Unknown @9.65 | 9.650 | 888,211,556 |
| Unknown @10.70 | 10.697 | 5,878,160 |
| Totals | | 1,808,584,363 |

FIG. 63A-2

SAMPLE : 12400 S151N17 T5h 130927ABA
Gene references: UGTLB (BAG80557.1)
Filename : 130927_12400_084.dat CAD Ch1
— 12400 S151N17 T5h 130927ABA
130927_12400_084.dat Retention Time 5.491
7.010
7.295
7.677
8.728
9.630
11.227

Minutes pA 300
200
100
0

TO FIG. 63B-2

FROM FIG. 63B-1

| CAD Ch 1 Results Compound | Retention time | Integration (area) |
|---|---|---|
| Rebaudioside E | 5.491 | 21921232 |
| Unknown @7.01 | 7.010 | 9764063 |
| Unknown @7.29 | 7.295 | 12510947 |
| Unknown @7.68 | 7.677 | 283386906 |
| Unknown @8.73 | 8.728 | 402240506 |
| Unknown @9.63 | 9.630 | 878990745 |
| Rubusoside | 11.227 | 176000085 |
| Totals | | 1784814484 |

FIG. 63B-2

FROM FIG. 63C-1

| CAD Ch 1 Results Compound | Retention time | Integration (area) |
|---|---|---|
| Unknown @4.42 | 4.522 | 137,916,950 |
| Unknown @4.90 | 4.903 | 2,015,271 |
| Rebaudioside D | 5.762 | 59,876,764 |
| Unknown @6.69 | 6.689 | 364,185,331 |
| Unknown @6.97 | 6.973 | 26,368,965 |
| Unknown @7.32 | 7.318 | 110,284,197 |
| Unknown @7.69 | 7.689 | 294,579,799 |
| Unknown @8.29 | 8.293 | 7,867,452 |
| Unknown @8.78 | 8.779 | 15,928,550 |
| Rebausioside A | 9.118 | 165,602,247 |
| Unknown @9.64 | 9.642 | 868,327,712 |
| Totals | | 2,052,953,238 |

FIG. 63C-2

FROM FIG. 64A

| CAD Ch 1 Results Compound | Retention time | Integration (area) |
|---|---|---|
| Rebaudioside D | 5.750 | 112,094,430 |
| Unknown @6.23 | 6.235 | 17,886,043 |
| Rebaudioside M | 6.700 | 616,583,935 |
| Rebaudioside A | 9.095 | 11,183,884 |
| Unknown @10.27 | 10.272 | 62,863,156 |
| Unknown @11.31 | 11.310 | 35,839,478 |
| Total | | 856,450,926 |

FIG. 64B

FROM FIG. 65A

| CAD Ch 1 Results Compound | Retention time | Integration (area) |
|---|---|---|
| Unknown @4.50 | 4.500 | 75,046,986 |
| Rebaudioside D | 5.731 | 223,409,643 |
| Unknown @6.66 | 6.658 | 228,651,278 |
| Rebaudioside A | 9.084 | 404,642,305 |
| Unknown @10.08 | 10.079 | 43,992,253 |
| Unknown @11.21 | 11.211 | 29,776,761 |
| Unknown @11.90 | 11.905 | 2,185,316 |
| Total | | 1,007,704,542 |

FIG. 65B

SEQUENCE LISTING

```
Sequence total quantity: 13
SEQ ID NO: 1              moltype = DNA   length = 1397
FEATURE                  Location/Qualifiers
source                   1..1397
                         mol_type = genomic DNA
                         organism = Stevia rebaudiana
SEQUENCE: 1
ccatggccca tatggaaaac aaaaccgaaa ccaccgttcg tcgtcgtcgc cgtattattc    60
tgtttccggt tccgtttcag ggtcatatta atccgattct gcagctggca aatgtgctgt   120
atagcaaagg ttttagcatt accatttttc ataccaattt taacaaaccg aaaaccagca   180
attatccgca ttttacccct cgctttattc tggataatga tccgcaggat gaacgcatta   240
gcaatctgcc gacacatggt ccgctggcag gtatgcgtat tccgattatt aacgaacatg   300
gtgcagatga actgcgtcgt gaactggaac tgctgatgct ggcaagcgaa gaagatgaag   360
aagttagctg tctgattacc gatgcactgt ggtattttgc acagagcgtt gcagatagcc   420
tgaatctgcg tcgtctggtt ctgatgacca gcagcctgtt taactttcat gcacatgtta   480
gcctgccgca gtttgatgaa ctgggttatc tggatccgga tgataaaacc cgtctggaag   540
aacaggcaag cggttttccg atgctgaaag tgaaagatat caaaagcgcc tatagcaatt   600
ggcagattct gaaagaaatt ctgggcaaaa tgattaaaca gaccaaagca agcagcggtg   660
ttatttggaa tagctttaaa gaactggaag aaagcgaact ggaaaccgtg attcgtgaaa   720
ttccggcacc gagctttctg attccgctgc cgaaacatct gaccgcaagc agcagcagcc   780
tgctggatca tgatcgtacc gtttttcagt ggctggatca gcagcctccg agcagcgttc   840
tgtatgttag ctttggtagc accagcgaag ttgatgaaaa agattttctg gaaattgccc   900
gtggtctggt tgatagcaaa cagagctttc tgtgggttgc tcgtccgggt tttgttaaag   960
gtagcacctg ggttgaaccg ctgccggatg gttttctggg tgaacgtggt cgtattgtta  1020
aatgggttcc gcagcaagaa gttctggcac acggcgcaat tggtgcattt tggacccata  1080
gcggttggaa tagcaccctg gaaagcgttt gtgaaggtgt tccgatgatt tttagcgatt  1140
ttggtctgga tcagccgctg aatgcacgtt atatgagtga tgttctgaaa gtgggtgtgt  1200
atctggaaaa tggttgggaa cgtggtgaaa ttgcaaatgc aattcgtcgt gttatggtgg  1260
atgaagaagg tgaatatatt cgtcagaatg cccgtgttct gaaacagaaa gcagatgtta  1320
gcctgatgaa aggtggtagc agctatgaaa gcctggaaag tctggttagc tatattagca  1380
gcctgtaata actcgag                                                 1397

SEQ ID NO: 2              moltype = DNA   length = 1442
FEATURE                  Location/Qualifiers
source                   1..1442
                         mol_type = genomic DNA
                         organism = Stevia rebaudiana
SEQUENCE: 2
ccatggcaca tatggcaacc agcgatagca ttgttgatga tcgtaaacag ctgcatgttg    60
caacctttcc gtggctggca tttggtcata ttctgccgta tctgcagctg agcaaactga   120
ttgcagaaaa aggtcataaa gtgagctttc tgagcaccac ccgtaatatt cagcgtctga   180
gcagccatat tagtccgctg attaatgttg ttcagctgac cctgcctcgt gttcaagaac   240
tgccggaaga tgccgaagca accaccgatg ttcatccgga agatattccg tatctgaaaa   300
aagcaagtga tggtctgcag ccggaagtta cccgttttct ggaacagcat agtccggatt   360
ggatcatcta tgattatacc cattattggc tgccgagcat tgcagcaagc ctgggtatta   420
gccgtgcaca ttttagcgtt accaccccgt gggcaattgc atatatgggt ccgagcgcag   480
atgcaatgat taatggtagt gatggtcgta ccaccgttga agatctgacc accctccga   540
aatggtttcc gtttccgacc aaagtttgtt ggcgtaaaca tgatctggca cgtctggttc   600
cgtataaagc accgggtatt agtgatggtt atcgtatggg tctggttctg aaaggtagcg   660
attgtctgct gagcaaatgc tatcatgaat ttggcacca gtggctgccg ctgctggaaa   720
ccctgcatca ggttccggtt gttccggtgg tctgctgcc tccggaagtt ccgggtgatg   780
aaaaagatga aacctgggtt agcatcaaaa aatggctgga tggtaaacag aaaggtagcg   840
tggtttatgt tgcactgggt agcgaagttc tggttagcca gaccgaagtt gttgaactgg   900
cactgggtct ggaactgagc ggtctgccgt ttgtttgggc atatcgtaaa ccgaaaggtc   960
cggcaaaaag cgatagcgtt gaactgccgg atggtttttgt tgaacgtacc cgtgatcgtg  1020
gtctggtttg gaccagctgg gcacctcagc tgcgtattct gagccatgaa agcgtttgtg  1080
gttttctgac ccattgtggt agcggtagca ttgtggaagg tctgatgtt ggtcatccgc  1140
tgattatgct gccgattttt ggtgatcagc cgctgaatgc acgtctgctg gaagataaac  1200
aggttggtat tgaaattccg cgtaatgaag aagatggttg cctgaccaaa gaaagcgttg  1260
cacgtagcct gcgtagcgtt gttgttgaaa gagaaggcga aatctataaa gccaatgcac  1320
gtgaactgag caaaatctat aatgatacca aagtggaaaa agaatatgtg agccagttcg  1380
tggattatct ggaaaaaaac acccgtgcag ttgccattga tcacgaaagc taatgactcg  1440
ag                                                                 1442

SEQ ID NO: 3              moltype = AA   length = 472
FEATURE                  Location/Qualifiers
source                   1..472
                         mol_type = protein
                         organism = Oryza sativa
```

-continued

```
SEQUENCE: 3
MDDAHSSQSP LHVVIFPWLA FGHLLPCLDL AERLAARGHR VSFVSTPRNL ARLPPVRPEL    60
AELVDLVALP LPRVDGLPDG AEATSDVPFD KFELHRKAFD GLAAPFSAFL DTACAGGKRP   120
DWVLADLMHH WVALASQERG VPCAMILPCS AAVVASSAPP TESSADQREA IVRSMGTAAP   180
SPEAKRATEE FATEGASGVS IMTRYSLTLQ RSKLVAMRSC PELEPGAFTI LTRFYGKPVV   240
PFGLLPPRPD GARGVSKNGK HDAIMQWLDA QPAKSVVYVA LGSEAPMSAD LLRELAHGLD   300
LAGTRFLWAM RKPAGVDADS VLPAGFLGRT GERGLVTTRW APQVSILAHA AVCAFLTHCG   360
WGSVVEGLQF GHPLIMLPIL GDQGPNARIL EGRKLGVAVP RNDEDGSFDR GGVAGAVRAV   420
VVEEEGKTFF ANARKLQEIV ADREREERCI DEFVQHLTSW NELKNNSDGQ YP           472

SEQ ID NO: 4           moltype = AA  length = 502
FEATURE                Location/Qualifiers
source                 1..502
                       mol_type = protein
                       organism = Avena strigosa
SEQUENCE: 4
MAVKDEQQSP LHILLFPFLA PGHLIPIADM AALFASRGVR CTILTTPVNA AIIRSAVDRA    60
NDAFRGSDCP AIDISVVPFP DVGLPPGVEN GNALTSPADR LKFFQAVAEL REPFDRFLAD   120
NHPDAVVSDS FFHWSTDAAA EHGVPRLGFL GSSMFAGSCN ESTLHNNPLE TAADDPDALV   180
SLPGLPHRVE LRRSQMMDPK KRPDHWALLE SVNAADQKSF GEVFNSFHEL EPDYVEHYQT   240
TLGRRTWLVG PVALASKDMA GRGSTSARSP DADSCLRWLD TKQPGSVVYV SFGTLIRFSP   300
AELHELARGL DLSGKNFVWV LGRAGPDSSE WMPQGFADLI TPRGDRGFII RGWAPQMLIL   360
NHRALGGFVT HCGWNSTLES VSAGVPMVTW PRFADQFQNE KLIVEVLKVG VSIGAKDYGS   420
GIENHDVIRG EVIAESIGKL MGSSEESDAI QRKAKDLGAE ARSAVENGGS SYNDVGRLMD   480
ELMARRSSVK VGEDIIPTND GL                                           502

SEQ ID NO: 5           moltype = AA  length = 470
FEATURE                Location/Qualifiers
source                 1..470
                       mol_type = protein
                       organism = Solanum lycopersicum
SEQUENCE: 5
MSPKLHKELF FHSLYKKTRS NHTMATLKVL MFPFLAYGHI SPYLNVAKKL ADRGFLIYFC    60
STPINLKSTI EKIPEKYADS IHLIELHLPE LPQLPPHYHT TNGLPPNLNQ VLQKALKMSK   120
PNFSKILQNL KPDLVIYDIL QRWAKHVANE QNIPAVKLLT SGAAVFSYFF NVLKKPGVEF   180
PPPGIYLRKI EQVRLSEMMS KSDKEKELED DDDDDDLLVD GNMQIMLMST SRTIEAKYID   240
FCTALTNWKV VPVGPPVQDL ITNDVDDMEL IDWLGTKDEN STVFVSFGSE YFLSKEDMEE   300
VAFALELSNV NFIWVARFPK GEERNLEDAL PKGFLERIGE RGRVLDKFAP QPRILNHPST   360
GGFISHCGWN SAMESIDFGV PIIAMPMHLD QPMNARLIVE LGVAVEIVRD DDGKIHRGEI   420
AETLKGVITG KTGEKLRAKV RDISKNLKTI RDEEMDAAAE ELIQLCRNGN             470

SEQ ID NO: 6           moltype = AA  length = 464
FEATURE                Location/Qualifiers
source                 1..464
                       mol_type = protein
                       organism = Oryza sativa
SEQUENCE: 6
MHVVMLPWLA FGHILPFAEF AKRVARQGHR VTLFSTPRNT RRLIDVPPSL AGRIRVVDIP    60
LPRVEHLPEH AEATIDLPSN DLRPYLRRAY DEAFSRELSR LLQETGPSRP DWVLADYAAY   120
WAPAAASRHG VPCAFLSLFG AAALCFFGPA ETLQGRGPYA KTEPAHLTAV PEYVPFPTTV   180
AFRGNEAREL FKPSLIPDES GVSESYRFSQ SIEGCQLVAV RSNQEFEPEW LELLGELYQK   240
PVIPIGMFPP PPPQDVAGHE ETLRWLDRQE PNSVVYAAFG SEVKLTAEQL QRIALGLEAS   300
ELPFIWAFRA PPDAGDGDGL PGGFKERVNG RGVVCRGWVP QVKFLAHASV GGFLTHAGWN   360
SIAEGLANGV RLVLLPLMFE QGLNARQLAE KKVAVEVARD EDDGSFAAND IVDALRRVMV   420
GEEGDEFGVK VKELAKVFGD DEVNDRYVRD FLKCLSEYKM QRQG                   464

SEQ ID NO: 7           moltype = AA  length = 515
FEATURE                Location/Qualifiers
source                 1..515
                       mol_type = protein
                       organism = Arabidopsis lyrata
SEQUENCE: 7
MDDKKEEVMH IAMFPWLAMG HLLPFLRLSK LLAQKGHKIS FISTPRNILR LPKLPSNLSS    60
SITFVSFPLP SISGLPPSSE SSMDVPYNKQ QSLKAAFDLL QPPLTEFLRL SSPDWIIYDY   120
ASHWLPSIAK ELGISKAFFS LFNAATLCFM GPSSSLIEES RSTPEDFTVV PPWVPFKSTI   180
VFRYHEVSRY VEKTDEDVTG VSDSVRFGYT IDGSDAVFVR SCPEFEPEWF SLLQDLYRKP   240
VFPIGFLPPV IEDDDDDTTW VRIKEWLDKQ RVNSVVYVSL GTEASLRREE LTELALGLEK   300
SETPFFWVLR NEPQIPDGFE ERVKGRGMVH VGWVPQVKIL SHESVGGFLT HCGWNSVVEG   360
IGFGKVPIFL PVLNEQGLNT RLLQGKGLGV EVLRDERDGS FGSDSVADSV RLVMIDDAGE   420
EIREKVKLMK GLFGNMDENI RYVDELVGFM RNDESSQLKE EEEEDDCSDD QSSEVSSETD   480
EKELNLDLKE EKRRISVYKS LSSEFDDYVA NEKMG                             515

SEQ ID NO: 8           moltype = AA  length = 772
FEATURE                Location/Qualifiers
source                 1..772
                       mol_type = protein
                       organism = Oryza sativa
SEQUENCE: 8
MHVVICPLLA FGHLLPCLDL AQRLACGHRV SFVSTPRNIS RLPPVRPSLA PLVSFVALPL    60
```

-continued

```
PRVEGLPNGA ESTHNVPHDR PDMVELHLRA FDGLAAPFSE FLGTACADWV MPTSSAPRQT  120
LSSNIHRNSS RPGTPAPSGR LLCPITPHSN TLERAAEKLV RSSRQNARAR SLLAFTSPPL  180
PYRDVFRSLL GLQMGRKQLN IAHETNGRRT GTLPLNLCRW MWKQRRCGKL RPSDVEFNTS  240
RSNEAISPIG ASLVNLQSIQ SPNPRAVLPI ASSGVRAVFI GRARTSTPTP PHAKPARSAA  300
PRAHRPPSSV MDSGYSSSYA AAAGMHVVIC PWLAFGHLLP CLDLAQRLAS RGHRVSFVST  360
PRNISRLPPV RPALAPLVAF VALPLPRVEG LPDGAESTND VPHDRPDMVE LHRRAFDGLA  420
APFSEFLGTA CADWVIVDVF HHWAAAAALE HKVPCAMMLL GSAHMIASIA DRRLERAETE  480
SPAAAGQGRP AAAPTFEVAR MKLIRTKGSS GMSLAERFSL TLSRSSLVVG RSCVEFEPET  540
VPLLSTLRGK PITFLGLMPP LHEGRREDGE DATVRWLDAQ PAKSVVYVAL GSEVPLGVEK  600
VHELALGLEL AGTRFLWALR KPTGVSDADL LPAGFEERTR GRGVVATRWV PQMSILAHAA  660
VGAFLTHCGW NSTIEGLMFG HPLIMLPIFG DQGPNARLIE AKNAGLQVAR NDGDGSFDRE  720
GVAAAIRAVA VEEESSKVFQ AKAKKLQEIV ADMACHERYI DGFIQQLRSY KD          772

SEQ ID NO: 9            moltype = AA   length = 442
FEATURE                 Location/Qualifiers
source                  1..442
                        mol_type = protein
                        organism = Solanum lycopersicum
SEQUENCE: 9
MATNLRVLMF PWLAYGHISP FLNIAKQLAD RGFLIYLCST RINLESIIKK IPEKYADSIH  60
LIELQLPELP ELPPHYHTTN GLPPHLNPTL HKALKMSKPN FSRILQNLKP DLLIYDVLQP  120
WAEHVANEQN IPAGKLLTSC AAVFSYFFSF RKNPGVEFPF PAIHLPEVEK VKIREILAKE  180
PEEGGRLDEG NKQMMLMCTS RTIEAKYIDY CTELCNWKVV PVGPPFQDLI TNDADNKELI  240
DWLGTKHENS TVFVSFGSEY FLSKEDMEEV AFALELSNVN FIWVARFPKG EERNLEDALP  300
KGFLERIGER GRVLDKFAPQ PRILNHPSTG GFISHCGWNS AMESIDFGVP IIAMPIHNDQ  360
PINAKLMVEL GVAVEIVRDD DGKIHRGEIA ETLKSVVTGE TGEILRAKVR EISKNLKSIR  420
DEEMDAVAEE LIQLCRNSNK SK                                            442

SEQ ID NO: 10           moltype = AA   length = 454
FEATURE                 Location/Qualifiers
source                  1..454
                        mol_type = protein
                        organism = Escherichia coli
SEQUENCE: 10
MGTEVTVHKN TLRVLMFPWL AYGHISPFLN VAKKLVDRGF LIYLCSTAIN LKSTIKKIPE  60
KYSDSIQLIE LHLPELPELP PHYHTTNGLP PHLNHTLQKA LKMSKPNFSK ILQNLKPDLV  120
IYDLLQQWAE GVANEQNIPA VKLLTSGAAV LSYFFNLVKK PGVEFPFPAI YLRKNELEKM  180
SELLAQSAKD KEPDGVDPFA DGNMQVMLMS TSRIIEAKYI DYFSGLSNWK VVPVGPPVQD  240
PIADDADEME LIDWLGKKDE NSTVFVSFGS EYFLSKEDRE EIAFGLELSN VNFIWVARFP  300
KGEEQNLEDA LPKGFLERIG DRGRVLDKFA PQPRILNHPS TGGFISHCGW NSVMESVDFG  360
VPIIAMPIHL DQPMNARLIV ELGVAVEIVR DDYGKIHREE IAEILKDVIA GKSGENLKAK  420
MRDISKNLKS IRDEEMDTAA EELIQLCKNS PKLK                              454

SEQ ID NO: 11           moltype = AA   length = 458
FEATURE                 Location/Qualifiers
source                  1..458
                        mol_type = protein
                        organism = Stevia rebaudiana
SEQUENCE: 11
MENKTETTVR RRRRIILFPV PFQGHINPIL QLANVLYSKG FSITIFHTNF NKPKTSNYPH  60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFQWLDQ QPPSSVLYVS FGSTEVDEK DFLEIARGLV   300
DSKQSFLWVV RPGFVKGSTW VEPLPDGFLG ERGRIVKWVP QQEVLAHGAI GAFWTHSGWN  360
STLESVCEGV PMIFSDFGLD QPLNARYMSD VLKVGVYLEN GWERGEIANA IRRVMVDEEG  420
EYIRQNARVL KQKADVSLMK GGSSYESLES LVSYISSL                          458

SEQ ID NO: 12           moltype = AA   length = 470
FEATURE                 Location/Qualifiers
source                  1..470
                        mol_type = protein
                        organism = Solanum lycopersicum
SEQUENCE: 12
MSPKLHKELF FHSLYKKTRS NHTMATLKVL MFPPFLAYGHI SPYLNVAKKL ADRGFLIYFC  60
STPINLKSTI EKIPEKYADS IHLIELHLPE LPQLPPHYHT TNGLPPNLNQ VLQKALKMSK  120
PNFSKILQNL KPDLVIYDIL QRWAKHVANE QNIPAVKLLT SGAAVFSYFF NVLKKPGVEF  180
PPPGIYLRKI EQVRLSEMMS KSDKEKELED DDDDDDLLVD GNMQIMLMST SRTIEAKYID  240
FCTALTNWKV VPVGPPVQDL ITNDVDDMEL IDWLGTKDEN STVFVSFGSE YFLSKEDMEE  300
VAFALELSNV NFIWVARFPK GEERNLEDAL PKGFLERIGE RGRVLDKFAP QPRILNHPST  360
GGFISHCGWN SAMESIDFGV PIIAMPMHLD QPMNARLIVE LGVAVEIVRD DDGKIHRGEI  420
AETLKGVITG KTGEKLRAKV RDISKNLKTI RDEEMDAAAE ELIQLCRNGN             470

SEQ ID NO: 13           moltype = AA   length = 808
FEATURE                 Location/Qualifiers
source                  1..808
                        mol_type = protein
                        organism = Arabidopsis thaliana
SEQUENCE: 13
```

-continued

```
MANAERMITR VHSQRERLNE TLVSERNEVL ALLSRVEAKG KGILQQNQII AEFEALPEQT  60
RKKLEGGPFF DLLKSTQEAI VLPPWVALAV RPRPGVWEYL RVNLHALVVE ELQPAEFLHF  120
KEELVDGVKN GNFTLELDFE PFNASIPRPT LHKYIGNGVD FLNRHLSAKL FHDKESLLPL  180
LKFLRLHSHQ GKNLMLSEKI QNLNTLQHTL RKAEEYLAEL KSETLYEEFE AKFEEIGLER  240
GWGDNAERVL DMIRLLLDLL EAPDPCTLET FLGRVPMVFN VVILSPHGYF AQDNVLGYPD  300
TGGQVVYILD QVRALEIEML QRIKQQGLNI KPRILILTRL LPDAVGTTCG ERLERVYDSE  360
YCDILRVPFR TEKGIVRKWI SRFEVWPYLE TYTEDAAVEL SKELNGKPDL IIGNYSDGNL  420
VASLLAHKLG VTQCTIAHAL EKTKYPDSDI YWKKLDDKYH FSCQFTADIF AMNHTDFIIT  480
STFQEIAGSK ETVGQYESHT AFTLPGLYRV VHGIDVFDPK FNIVSPGADM SIYFPYTEEK  540
RRLTKFHSEI EELLYSDVEN KEHLCVLKDK KKPILFTMAR LDRVKNLSGL VEWYGKNTRL  600
RELANLVVVG GDRRKESKDN EEKAEMKKMY DLIEEYKLNG QFRWISSQMD RVRNGELYRY  660
ICDTKGAFVQ PALYEAFGLT VVEAMTCGLP TFATCKGGPA EIIVHGKSGF HIDPYHGDQA  720
ADTLADFFTK CKEDPSHWDE ISKGGLQRIE EKYTWQIYSQ RLLTLTGVYG FWKHVSNLDR  780
LEARRYLEMF YALKYRPLAQ AVPLAQDD                                   808
```

HIGH-PURITY STEVIOL GLYCOSIDES

CROSS-REFERENCE TO RELATED APPLICATIONS

This application is a continuation of U.S. application Ser. No. 15/512,711, filed on Sep. 27, 2017, and claim priority of U.S. Provisional applications 62/061,359, filed on Oct. 8, 2014, 62/062,288, filed on Oct. 16, 2014, 62/064,630, filed on Oct. 16, 2014, 62/082,446, filed on Nov. 20, 2014, 62/097,387, filed on Nov. 20, 2014, 62/185,964, filed on Jun. 29, 2015, 62/118,132, filed on Feb. 19, 2015, 62/052,544, filed on Sep. 19, 2014, and International patent application PCT/US 2015/045906, filed on Aug. 19, 2015; the contents of which applications are incorporated herein by reference.

JOINT RESEARCH AGREEMENT

The present disclosure was made by or on behalf of the below listed parties to a joint research agreement. The joint research agreement was in effect on or before the date the present disclosure was made and the present disclosure was made as a result of activities undertaken within the scope of the joint research agreement. The parties to the joint research agreement are 1) PURECIRCLE SDN BHD and 2) THE COCA-COLA COMPANY.

REFERENCE TO AN ELECTRONIC SEQUENCE LISTING

The contents of the electronic sequence listing entitled: "6089_SWT_US_CON_Sequence_st26.xml," created on Jan. 10, 2023, having 24 kilobytes of data, and filed concurrently herewith, is herein incorporated by reference in its entirety.

TECHNICAL FIELD

The present invention relates to a biocatalytic process for preparing compositions comprising steviol glycosides, including highly purified steviol glycoside compositions. The present invention also relates to novel steviol glycosides, methods for isolation of the same and uses for the novel steviol glycosides.

BACKGROUND OF THE INVENTION

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling for their intake of carbohydrates.

Steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in *Stevia* leaves, composing approximately 10%-20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%). Other known steviol glycosides include rebaudioside B, C, D, E, F and M, steviolbioside and rubusoside.

Although methods are known for preparing steviol glycosides from *Stevia rebaudiana*, many of these methods are unsuitable for use commercially.

Accordingly, there remains a need for simple, efficient, and economical methods for preparing compositions comprising steviol glycosides, including highly purified steviol glycoside compositions.

Additionally, there remains a need for novel steviol glycosides and methods of preparing and isolating the same.

SUMMARY OF THE INVENTION

The present invention provides a biocatalytic process for preparing a composition comprising a target steviol glycoside by contacting a starting composition comprising an organic substrate with a microorganism and/or biocatalyst, thereby producing a composition comprising a target steviol glycoside.

The starting composition comprises an organic compound. In one embodiment, the starting composition is selected from the group consisting of polyols and various carbohydrates.

The target steviol glycoside can be any steviol glycoside. In one embodiment, the target steviol glycoside is steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N, rebaudioside O or a synthetic steviol glycoside.

In one embodiment, the target steviol glycoside is stevioside.

In another embodiment, the target steviol glycoside is rebaudioside A.

In still another embodiment, the target steviol glycoside is rebaudioside D.

In yet another embodiment, the target steviol glycoside is rebaudioside M The microorganism can be any microorganism comprising at least one biocatalyst suitable for converting the starting composition to target steviol glycosides.

The biocatalysts can be located on the surface and/or inside the microorganism.

The biocatalysts include the steviol biosynthesis enzymes and UDP-glycosyltransferases (UGTs), or their variants, having greater than 75% amino-acid sequence identity.

In one embodiment the steviol biosynthesis enzymes include mevalonate (MVA) pathway enzymes.

In another embodiment the steviol biosynthesis enzymes include non-mevalonate 2-C-methyl-D-erythritol-4-phosphate pathway (MEP/DOXP) enzymes.

In one embodiment the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The UDP-glucosyltransferase can be any UDP-glucosyltransferase capable of adding at least one glucose unit to the steviol and or steviol glycoside substrate to provide the target steviol glycoside.

The microorganism may be any suitable microorganism. In one embodiment, the microorganism may be, for example, *E. coli, Saccharomyces* sp., *Aspergillus* sp., *Pichia* sp., *Bacillus* sp., *Yarrowia* sp. etc. In another embodiment, the UDP-glucosyltransferases are synthesized.

In one embodiment, the UDP-glucosyltransferase is selected from group including UGT74G1, UGT85C2, UGT76G1, UGT91D2 or their variants, having greater than 75% amino-acid sequence identity.

In one embodiment, the UDP-glucosyltransferase is any UDP-glucosyltransferase capable of adding at least one glucose unit to rubusoside to form stevioside. In a particular embodiment, the UDP-glucosyltransferase is UGT91D2 or UGT91D2 variant, having greater than 75% amino-acid sequence identity with UGT91D2.

In one embodiment, the UDP-glucosyltransferase is any UDP-glucosyltransferase capable of adding at least one glucose unit to stevioside to form rebaudioside A. In a particular embodiment, the UDP-glucosyltransferase is UGT76G1 or UGT76G1 variant, having greater than 75% amino-acid sequence identity with UGT76G1.

In another embodiment, the UDP-glucosyltransferase is any UDP-glucosyltransferase capable of adding at least one glucose unit to rebaudioside A to form rebaudioside D. In a particular embodiment, the UDP-glucosyltransferase is UGT91D2 or UGT91D2 variant, having greater than 75% amino-acid sequence identity with UGT91D2.

In yet another embodiment, the UDP-glucosyltransferase is any UDP-glucosyltransferase capable of adding at least one glucose unit to rebaudioside D to form rebaudioside M. In a particular embodiment, the UDP-glucosyltransferase is UGT76G1 or UGT76G1 variant, having greater than 75% amino-acid sequence identity with UGT76G1.

In yet another embodiment, the UDP-glucosyltransferase is any UDP-glucosyltransferase capable of adding at least one glucose unit to rebaudioside I to form rebaudioside M. In a particular embodiment, the UDP-glucosyltransferase is UGTSL or UGTSL variant, having greater than 75% amino-acid sequence identity with UGTSL.

In yet another embodiment, the UDP-glucosyltransferase is any UDP-glucosyltransferase capable of adding at least two glucose units to rebaudioside E to form rebaudioside M. In a particular embodiment, the UDP-glucosyltransferase is UGT76G1 or UGT76G1 variant, having greater than 75% amino-acid sequence identity with UGT76G1.

Optionally, the method of the present invention further comprises recycling UDP to provide UDP-glucose. In one embodiment, the method comprises recycling UDP by providing a recycling catalyst and a recycling substrate, such that the biotransformation of the steviol glycoside substrate to the target steviol glycoside is carried out using catalytic amounts of UDP-glucosyltransferase and UDP-glucose (FIG. 3).

In one embodiment, the recycling catalyst is sucrose synthase.

In one embodiment, the recycling substrate is sucrose.

Optionally, the method of the present invention further comprises purifying the composition comprising the target steviol glycoside. The composition comprising the target steviol glycoside can be purified by any suitable method, such as, for example, crystallization, separation by membranes, centrifugation, extraction, chromatographic separation or a combination of such methods.

In one embodiment, purification produces a composition comprising greater than about 80% by weight of the target steviol glycoside on an anhydrous basis. In another embodiment, purification produces a composition comprising greater than about 90% by weight of the target steviol glycoside. In particular embodiments, the composition comprises greater than about 95% by weight of the target steviol glycoside.

The target steviol glycoside can be in any polymorphic or amorphous form, including hydrates, solvates, anhydrous or combinations thereof.

The present invention also provides consumable products comprising compositions prepared by the disclosed methods. Suitable consumer products include, but are not limited to, food, beverages, pharmaceutical compositions, tobacco products, nutraceutical compositions, oral hygiene compositions, and cosmetic compositions.

The present invention also provides novel steviol glycosides reb D2 and reb M2, which are isomers of reb D and reb M, respectively. In one embodiment, isolated and purified reb D2 is provided. In another embodiment, isolated and purified reb M2 is provided. Reb D2 and reb M2 may also be present in any consumable products disclosed herein. In a particular embodiment, beverages comprising reb D2 and/or reb M2 are provided.

Methods of preparing reb D2 and reb M2 are also provided herein. Both are formed during the biotransformation of reb A to reb D. Reb M2 is believed to form from biotransformation of reb D2 in situ.

Methods of selective hydrolysis of 1,6-β-glucosidic linkages in reb D2 and/or reb M2, by enzyme with β-1,6-glucosidase activity, are also provided herein.

In one embodiment for selective hydrolysis of 1,6-β-glucosidic linkages in reb D2 and/or reb M2, at least one enzyme is selected from the group including, glycosidase (NC-IUBMB EC 3.2.1), glucosidase, glucanase, Isolase (011410; National Enzyme Company, USA), Aromase (GLY0151441; Amano Enzyme, Japan), naringinase (NAH0550102; Amano Enzyme, Japan), cellulase (e.g. Cellulase from *Trichoderma reesei* ATCC 26921; Sigma C2730), cellobiase (e.g. Cellobiase from *Aspergillus niger*, Sigma C6105), Viscozyme L (Sigma V2010), etc.

In one embodiment, the present invention is a method for the preparation of a composition comprising reb D2 comprising: (a) contacting a starting composition comprising reb A with an enzyme capable of transforming reb A to reb D2, UDP-glucose, and optionally UDP-glucose recycling enzymes, to produce a composition comprising reb D2, and (b) isolating the composition comprising reb D2.

In another embodiment, the present invention is a method for the preparation of a composition comprising reb M comprising (a) contacting a starting composition comprising reb D with an enzyme capable of transforming reb D to reb M, UDP-glucose, and optionally UDP-glucose recycling enzymes, to produce a composition comprising reb M, and (b) and isolating the composition comprising reb M.

A further embodiment, the present invention is a method for the preparation of a composition comprising reb M comprising (a) contacting a starting composition comprising reb A with an enzyme capable of transforming reb A to reb D, UDP-glucose, and optionally UDP-glucose recycling enzymes, to produce a composition comprising reb D, (b) optionally, isolating the composition comprising reb D, (c) contacting the composition comprising reb D with an enzyme capable of transforming reb D to reb M, UDP-glucose, and optionally UDP-glucose recycling enzymes to produce a composition comprising reb M, and (d) isolating the composition comprising reb M.

The composition can be further purified to provide reb D or reb M with purities greater than about 95% by weight on a dry basis.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

Figure 2:
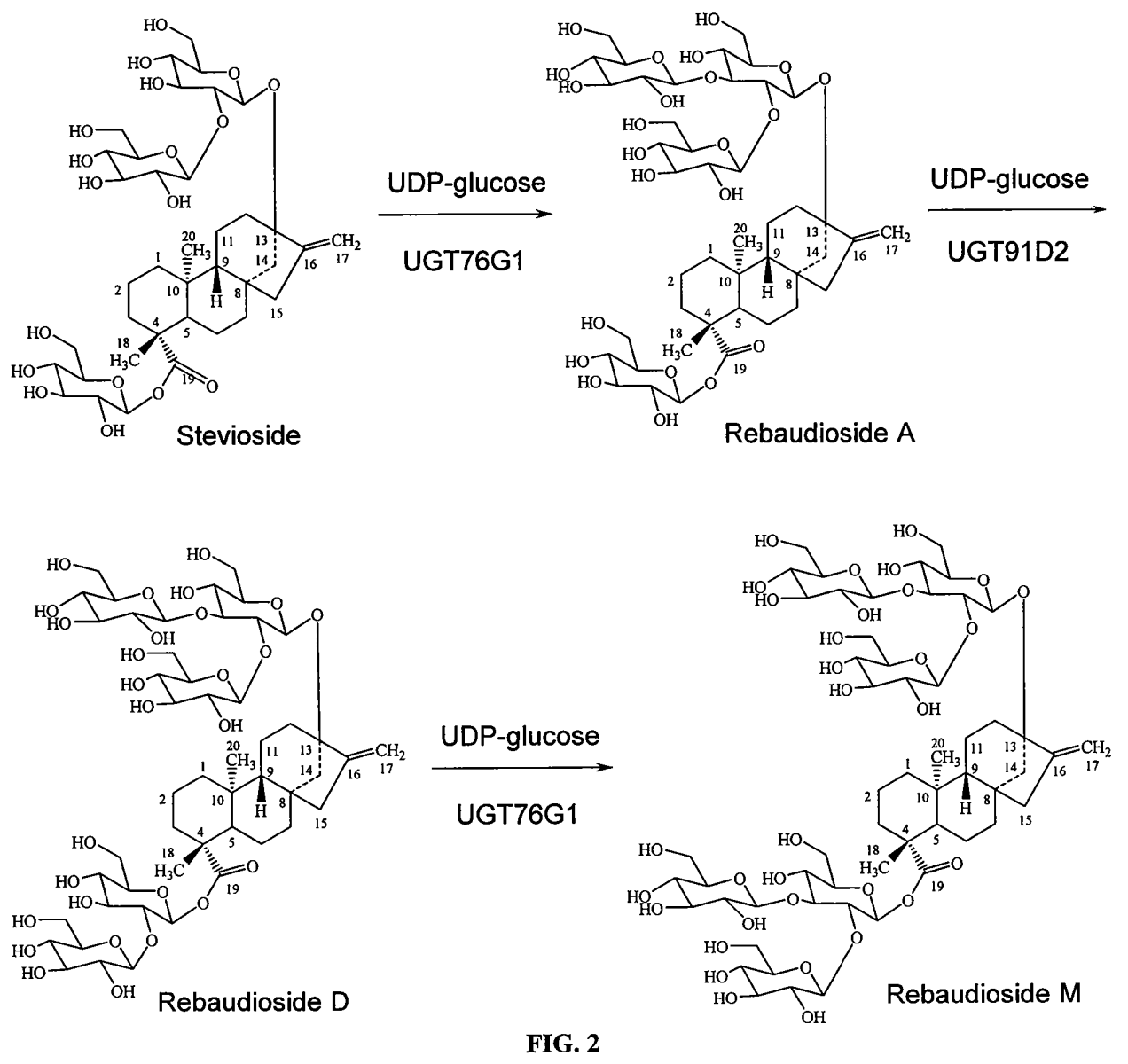

FIG. 2 shows the biocatalytic production of reb M from stevioside.

FIG. 7 shows the HPLC chromatogram of a reb M standard.

FIG. 9 shows an overlay of the $^1$H NMR spectra of a reb M standard and reb M purified following biosynthesis from reb D.

FIGS. 14A-14B show the $^1$H NMR spectrum of reb D2 (500 MHz, pyridine-d$_5$).

FIGS. 24A-24C show the $^1$H-$^1$H COSY spectrum of reb M2 (500 MHz, D20).

FIGS. 25A-25C show the HSQC-DEPT spectrum of reb M2 (500 MHz, D20).

FIGS. 35A-35B show the results of $^1$H NMR as described in Example 47.

FIGS. 44A-44C show the results of NOESY as described Example 47.

FIGS. 45A-45C show the results of NOESY as described Example 47.

FIGS. 55A-55E show HPLC chromatograms showing the HPLC assay results for Example 22.

FIGS. 59A-1-59B-2 show HPLC chromatograms showing the HPLC assay results for Example 28.

FIGS. 60A-1-60B-2 show HPLC chromatograms showing the HPLC assay results for Example 29.

FIGS. 61A-61B show an HPLC chromatogram showing the HPLC assay results for Example 30.

FIGS. 63A-1-63C-2 show HPLC chromatograms showing the HPLC assay results for Example 32.

FIGS. 64A-64B show an HPLC chromatogram showing the HPLC assay results for Example 35.

FIGS. 65A-65B show an HPLC chromatogram showing the HPLC assay results for Example 37

DETAILED DESCRIPTION

Figure 1:
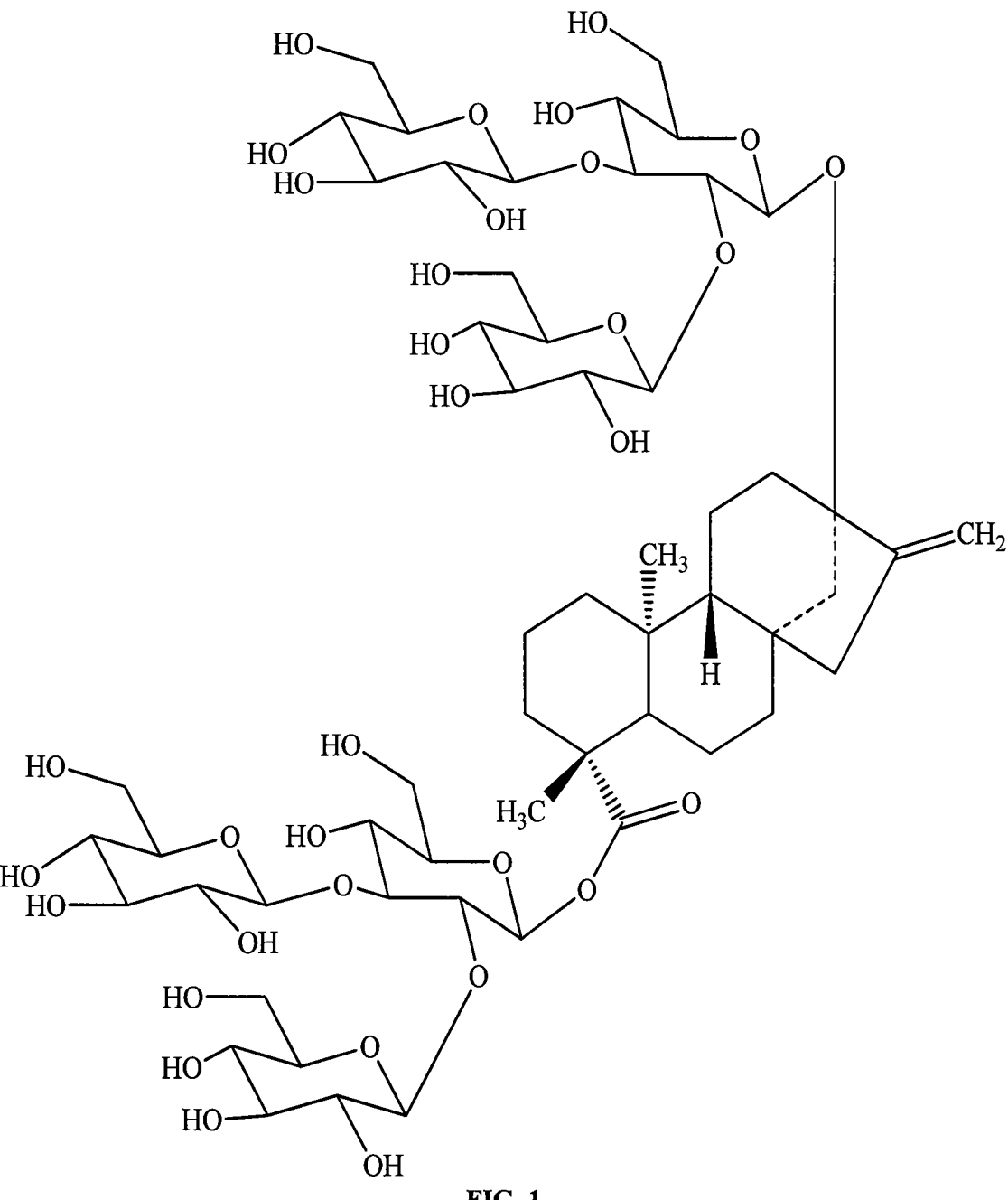
FIG. 1 shows the structure of reb M.

The present invention provides a biocatalytic process for preparing a composition comprising a target steviol glycoside by contacting a starting composition comprising an organic substrate with a microorganism, thereby producing a composition comprising a target steviol glycoside.

One object of the invention is to provide an efficient biocatalytic method for preparing steviol glycosides, particularly stevioside, reb E, reb A, reb D, reb D2, reb M, and reb M2 from various starting compositions.

As used herein, "biocatalysis" or "biocatalytic" refers to the use of natural or genetically engineered biocatalysts, such as cells, protein enzymes, to perform single or multiple step chemical transformations on organic compounds. Biocatalysis include fermentation, biosynthesis and biotransformation processes. Both, isolated enzyme and whole-cell biocatalysis methods are known in the art. Biocatalyst protein enzymes can be naturally occurring or recombinant proteins.

All sequences listed herein, including any nucleic acid or amino acid sequences, include variants having >75%, >80%, >90%, >95%, >96%, >97%, >98%, or >99% sequence identity to the nucleic acid or amino acid sequences described herein.

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside D, rebaudioside M2, rebaudioside D2, rebaudioside N, rebaudioside O, synthetic steviol glycosides, e.g. enzymatically glucosylated steviol glycosides and combinations thereof.

Chemical Structures of Steviol and its Glycosides

| Compound | $R_1$ | $R_2$ |
|---|---|---|
| Steviol | H | H |
| Steviolmonoside | H | β-Glc |
| Steviol monoglucosyl ester | β-Glc | H |
| Rubusoside | β-Glc | β-Glc |
| Steviolbioside | H | β-Glc-β-Glc(2 → 1) |
| Stevioside | β-Glc | β-Glc-β-Glc(2 → 1) |
| Rebaudioside A | β-Glc | β—Glc—β—Glc(2→1), β—Glc(3→1) |
| Rebaudioside D | β-Glc-β-Glc(2 → 1) | β—Glc—β—Glc(2→1), β—Glc(3→1) |

-continued

| Compound | R$_1$ | R$_2$ |
|---|---|---|
| Rebaudioside E | β-Glc-β-Glc(2 → 1) | β-Glc-β-Glc(2 → 1) |
| Rebaudioside M | β—Glc—β—Glc(2→1)<br>\|<br>β—Glc(3→1) | β—Glc—β—Glc(2→1)<br>\|<br>β—Glc(3→1) |

(Glc = glucose)

Starting Composition

As used herein, "starting composition" refers to any composition (generally an aqueous solution) containing one or more organic compound comprising at least one carbon atom.

In one embodiment, the starting composition is selected from the group consisting of polyols and various carbohydrates.

The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced.

The term "carbohydrate" refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

The starting composition may be synthetic or purified (partially or entirely), commercially available or prepared.

In one embodiment, the starting composition is glycerol.

In another embodiment, the starting composition is glucose.

In still another embodiment, the starting composition is sucrose.

In yet another embodiment, the starting composition is starch.

In another embodiment, the starting composition is maltodextrin.

In another embodiment, the starting composition is steviol glycoside(s).

The organic compound(s) of starting composition serve as a substrate(s) for the production of the target steviol glycoside(s), as described herein.

Target Steviol Glycoside

The target steviol glycoside of the present method can be any steviol glycoside that can be prepared by the process disclosed herein. In one embodiment, the target steviol glycoside is selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N or rebaudioside O, or other glycoside of steviol.

In one embodiment, the target steviol glycoside is stevioside. In another embodiment, the target steviol glycoside is reb A. In still another embodiment, the target steviol glycoside is reb E. In yet another embodiment, the target steviol glycoside is reb D. In yet another embodiment, the target steviol glycoside is reb D2. In a further embodiment, the target steviol glycoside is reb M. In a still further another embodiment, the target steviol glycoside is reb M2.

The target steviol glycoside can be in any polymorphic or amorphous form, including hydrates, solvates, anhydrous or combinations thereof.

In one embodiment, the present invention is a biocatalytic process for the production of reb D.

In yet another embodiment, the present invention is a biocatalytic process for the production of reb D2.

In still another embodiment, the present invention is a biocatalytic process for the production of reb M.

In a further embodiment, the present invention is a biocatalytic process for the production of reb M2.

In one embodiment, the present invention is a biocatalytic process for the production of reb I.

In yet another embodiment, the present invention is a biocatalytic process for the production of reb E.

Optionally, the method of the present invention further comprises separating the target steviol glycoside from the starting composition. The target steviol glycoside can be separated by any suitable method, such as, for example, crystallization, separation by membranes, centrifugation, extraction, chromatographic separation or a combination of such methods.

In particular embodiments, the process described herein results in a highly purified target steviol glycoside composition. The term "highly purified", as used herein, refers to a composition having greater than about 80% by weight of the target steviol glycoside on an anhydrous basis. In one embodiment, the highly purified target steviol glycoside composition contains greater than about 90% by weight of the target steviol glycoside on an anhydrous basis, such as, for example, greater than about 91%, greater than about 92%, greater than about 93%, greater than about 94%, greater than about 95%, greater than about 96%, greater than about 97%, greater than about 98% or greater than about 99% target steviol glycoside content on a dry basis.

In one embodiment, when the target steviol glycoside is reb M, the process described herein provides a composition having greater than about 90% reb M content by weight on a dry basis. In another particular embodiment, when the target steviol glycoside is reb M, the process described herein provides a composition comprising greater than about 95% reb M content by weight on a dry basis.

In another embodiment, when the target steviol glycoside is reb M2, the process described herein provides a composition having greater than about 90% reb M2 content by weight on a dry basis. In another particular embodiment, when the target steviol glycoside is reb M2, the process described herein provides a composition comprising greater than about 95% reb M2 content by weight on a dry basis.

In yet another embodiment, when the target steviol glycoside is reb D, the process described herein provides a composition greater than about 90% reb D content by weight on a dry basis. In another particular embodiment, when the target steviol glycoside is reb D, the process described herein provides a composition comprising greater than about 95% reb D content by weight on a dry basis.

In still another embodiment, when the target steviol glycoside is reb D2, the process described herein provides a composition greater than about 90% reb D2 content by weight on a dry basis. In another particular embodiment, when the target steviol glycoside is reb D2, the process described herein provides a composition comprising greater than about 95% reb D2 content by weight on a dry basis.

In a further embodiment, when the target steviol glycoside is reb A, the process described herein provides a composition comprising greater than about 90% reb A content by weight on a dry basis. In another particular embodiment, when the target steviol glycoside is reb A, the process described herein provides a composition comprising greater than about 95% reb A content by weight on a dry basis.

In a still further embodiment, when the target steviol glycoside is reb E, the process described herein provides a composition comprising greater than about 90% reb E content by weight on a dry basis. In another particular embodiment, when the target steviol glycoside is reb E, the process described herein provides a composition comprising greater than about 95% reb E content by weight on a dry basis.

In one embodiment, when the target steviol glycoside is reb I, the process described herein provides a composition comprising greater than about 90% reb I content by weight on a dry basis. In another particular embodiment, when the target steviol glycoside is reb I, the process described herein provides a composition comprising greater than about 95% reb I content by weight on a dry basis.

In yet a further embodiment, when the target steviol glycoside is stevioside, the process described herein provides a composition comprising greater than about 90% stevioside content by weight on a dry basis. In another particular embodiment, when the target steviol glycoside is stevioside, the process described herein provides a composition comprising greater than about 95% stevioside content by weight on a dry basis.

Microorganism

In one embodiment of present invention, a microorganism is contacted with the starting composition to produce a composition comprising the target steviol glycoside. The microorganism can be any microorganism possessing biocatalysts suitable for converting the starting composition to the target steviol glycoside. These biocatalysts are encoded within the microorganism's genome.

In one embodiment the microorganism may be, for example, E. coli, Saccharomyces sp., Aspergillus sp., Pichia sp., Bacillus sp., Yarrowia sp. etc.

The biocatalysts can be located on the surface and/or inside the cell of the microorganism.

The biocatalysts can be separated from the microorganism and used for conversion of starting composition to target steviol glycoside(s). The separation can be achieved by any means known to art, including but not limited to lysis of microbial cells, centrifugation, filtration.

The biocatalysts can be excreted from the microorganism (extracellular enzymes) and used for conversion of starting composition to target steviol glycoside(s).

In one embodiment, the biocatalysts are steviol biosynthesis enzymes and UDP-glycosyltransferases (UGTs), or their variants, having greater than 75% amino-acid sequence identity.

The steviol biosynthesis can be any steviol biosynthesis enzyme, or its variant, having greater than 75% amino-acid sequence identity.

In one embodiment the steviol biosynthesis enzymes include mevalonate (MVA) pathway enzymes, or their variants, having greater than 75% amino-acid sequence identity.

In another embodiment the steviol biosynthesis enzymes include non-mevalonate 2-C-methyl-D-erythritol-4-phosphate pathway (MEP/DOXP) enzymes, or their variants, having greater than 75% amino-acid sequence identity.

In one embodiment, the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase, etc., or their variants, having greater than 75% amino-acid sequence identity.

The UDP-glucosyltransferase can be any UDP-glucosyltransferase capable of adding at least one glucose unit to the steviol and or steviol glycoside substrate to provide the target steviol glycoside.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

In one embodiment the microorganism is in aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment, the medium can also include an organic solvent.

In one embodiment, the UDP-glucosyltransferase is any UDP-glucosyltransferase capable of adding at least one glucose unit to rubusoside, thereby producing stevioside. The UDP-glucosyltransferase may be, for example, UGT91D2 or UGT91D2 variant, having greater than 75% amino-acid sequence identity with UGT91D2.

In another embodiment, the UDP-glucosyltransferase is any UDP-glucosyltransferase capable of adding at least one glucose unit to rubusoside, thereby producing rebaudioside E. The UDP-glucosyltransferase may be, for example, UGTSL2 or UGTSL2 variant, having greater than 75% amino-acid sequence identity with UGTSL2.

In still another embodiment, the UDP-glucosyltransferase is any UDP-glucosyltransferase capable of adding at least one glucose unit to rebaudioside E, thereby producing rebaudioside D. The UDP-glucosyltransferase may be, for example, UGT76G1 or UGT76G1 variant, having greater than 75% amino-acid sequence identity with UGT76G1.

In yet embodiment, the UDP-glucosyltransferase is any UDP-glucosyltransferase capable of adding at least one glucose unit to stevioside, thereby producing rebaudioside A. The UDP-glucosyltransferase may be, for example, UGT76G1 or UGT76G1 variant, having greater than 75% amino-acid sequence identity with UGT76G1.

In a further embodiment, the UDP-glucosyltransferase is any UDP-glucosyltransferase capable of adding at least one glucose unit to rebaudioside A, thereby producing rebaudioside D and/or rebaudioside D2 and/or rebaudioside M2. The UDP-glucosyltransferase may be, for example, UGT91D2 or UGTSL2 or their variant, having greater than 75% amino-acid sequence identity with UGT91D2 or UGTSL2.

In yet another embodiment, the UDP-glucosyltransferase is any UDP-glucosyltransferase capable of adding at least one glucose unit to rebaudioside I to form rebaudioside M In a particular embodiment, the UDP-glucosyltransferase is UGTSL or UGTSL variant, having greater than 75% amino-acid sequence identity with UGTSL.

In yet another embodiment, the UDP-glucosyltransferase is any UDP-glucosyltransferase capable of adding at least two glucose units to rebaudioside E to form rebaudioside M. In a particular embodiment, the UDP-glucosyltransferase is UGT76G1 or UGT76G1 variant, having greater than 75% amino-acid sequence identity with UGT76G1.

In another embodiment, the UDP-glucosyltransferase capable of adding at least one glucose unit to produce target steviol glycoside, has greater than 75% amino-acid sequence identity with at least one enzyme selected from the following listing of GenInfo identifier numbers, preferably from the group presented in Table 1, and more preferably the group presented in Table 2.

| | | | | | |
|---|---|---|---|---|---|
| 397567 | 30680413 | 115480946 | 147798902 | 218193594 | 225443294 |
| 454245 | 32816174 | 116310259 | 147811764 | 218193942 | 225444853 |
| 1359905 | 32816178 | 116310985 | 147827151 | 219885307 | 225449296 |
| 1685003 | 34393978 | 116788066 | 147836230 | 222615927 | 225449700 |
| 1685005 | 37993665 | 116788606 | 147839909 | 222619587 | 225454338 |
| 2191136 | 37993671 | 116789315 | 147846163 | 222623142 | 225454340 |
| 2501497 | 37993675 | 119394507 | 147855977 | 222625633 | 225454342 |
| 2911049 | 39104603 | 119640480 | 148905778 | 222625635 | 225454473 |
| 4218003 | 41469414 | 122209731 | 148905999 | 222636620 | 225454475 |
| 4314356 | 41469452 | 125526997 | 148906835 | 222636621 | 225458362 |
| 13492674 | 42566366 | 125534279 | 148907340 | 222636628 | 225461551 |
| 13492676 | 42570280 | 125534461 | 148908935 | 222636629 | 225461556 |
| 15217773 | 42572855 | 125540090 | 148909182 | 224053242 | 225461558 |
| 15217796 | 44890129 | 125541516 | 148909920 | 224053386 | 225469538 |
| 15223396 | 46806235 | 125545408 | 148910082 | 224055535 | 225469540 |

-continued

| | | | | | |
|---|---|---|---|---|---|
| 15223589 | 50284482 | 125547340 | 148910154 | 224056138 | 226316457 |
| 15227766 | 51090402 | 125547520 | 148910612 | 224056160 | 226492603 |
| 15230017 | 51090594 | 125554547 | 148910769 | 224067918 | 226494221 |
| 15231757 | 52839682 | 125557592 | 156138791 | 224072747 | 226495389 |
| 15234056 | 56550539 | 125557593 | 156138797 | 224080189 | 226495945 |
| 15234195 | 62734263 | 125557608 | 156138799 | 224091845 | 226502400 |
| 15234196 | 62857204 | 125559566 | 156138803 | 224094703 | 226507980 |
| 15238503 | 62857206 | 125563266 | 165972256 | 224100653 | 226531147 |
| 15239523 | 62857210 | 125571055 | 168016721 | 224100657 | 226532094 |
| 15239525 | 62857212 | 125579728 | 171674071 | 224101569 | 238477377 |
| 15239543 | 75265643 | 125588307 | 171906258 | 224103105 | 240254512 |
| 15239937 | 75285934 | 125589492 | 183013901 | 224103633 | 242032615 |
| 15240305 | 75288884 | 125599469 | 183013903 | 224103637 | 242032621 |
| 15240534 | 77550661 | 125601477 | 186478321 | 224109218 | 242038423 |
| 15982889 | 77556148 | 126635837 | 187373030 | 224114583 | 242043290 |
| 18086351 | 82791223 | 126635845 | 187373042 | 224116284 | 242044836 |
| 18418378 | 83778990 | 126635847 | 190692175 | 224120552 | 242051252 |
| 18418380 | 89953335 | 126635863 | 194701936 | 224121288 | 242056217 |
| 18418382 | 110741436 | 126635867 | 195620060 | 224121296 | 242056219 |
| 19743740 | 110743955 | 126635883 | 209954691 | 224121300 | 242056663 |
| 19911201 | 115438196 | 126635887 | 209954719 | 224130358 | 242059339 |
| 20149064 | 115438785 | 133874210 | 209954725 | 224140703 | 242059341 |
| 20260654 | 115441237 | 133874212 | 209954733 | 224143404 | 242060922 |
| 21435782 | 115454819 | 145358033 | 210063105 | 224143406 | 242067411 |
| 21553613 | 115456047 | 147772508 | 210063107 | 224144306 | 242067413 |
| 21593514 | 115457492 | 147776893 | 212275846 | 224285244 | 242076258 |
| 22759895 | 115459312 | 147776894 | 216296854 | 225431707 | 242076396 |
| 23955910 | 115464719 | 147776895 | 217074506 | 225435532 | 242084750 |
| 26452040 | 115471069 | 147786916 | 218185693 | 225436321 | 242091005 |
| 28393204 | 115471071 | 147798900 | 218187075 | 225440041 | 242095206 |
| 30679796 | 115474009 | 147798901 | 218189427 | 225441116 | 242345159 |
| 242345161 | 297724601 | 326492035 | 356523945 | 357140904 | 359486938 |
| 255536859 | 297725463 | 326493430 | 356523957 | 357165849 | 359487055 |
| 255538228 | 297728331 | 326500410 | 356523959 | 357165852 | 359488335 |
| 255541676 | 297738632 | 326506816 | 356523961 | 357168415 | 359488708 |
| 255547075 | 297745347 | 326507826 | 356523963 | 357437837 | 359493630 |
| 255552620 | 297745348 | 326508394 | 356524387 | 357442755 | 359493632 |
| 255552622 | 297795735 | 326509445 | 356524403 | 357442757 | 359493634 |
| 255555343 | 297796253 | 326511261 | 356527181 | 357445729 | 359493636 |
| 255555361 | 297796257 | 326511866 | 356533209 | 357445731 | 359493815 |
| 255555363 | 297796261 | 326512412 | 356533852 | 357445733 | 359495856 |
| 255555365 | 297797587 | 326517673 | 356534718 | 357446799 | 359495858 |
| 255555369 | 297798502 | 326518800 | 356535480 | 357446805 | 359495869 |
| 255555373 | 297799226 | 326521124 | 356542996 | 357452779 | 359495871 |
| 255555377 | 297805988 | 326525567 | 356543136 | 357452781 | 359497638 |
| 255556812 | 297807499 | 326525957 | 356543932 | 357452783 | 359807261 |
| 255556818 | 297809125 | 326526607 | 356549841 | 357452787 | 374256637 |
| 255563008 | 297809127 | 326527141 | 356549843 | 357452789 | 377655465 |
| 255564074 | 297811403 | 326530093 | 356554358 | 357452791 | 378405177 |
| 255564531 | 297820040 | 326534036 | 356554360 | 357452797 | 378829085 |
| 255572878 | 297821483 | 326534312 | 356558606 | 357452799 | 387135070 |
| 255577901 | 297825217 | 332071132 | 356560333 | 357470367 | 387135072 |
| 255583249 | 297832276 | 339715876 | 356560599 | 357472193 | 387135078 |
| 255583253 | 297832280 | 342306012 | 356560749 | 357472195 | 387135092 |
| 255583255 | 297832518 | 342306016 | 356566018 | 357474295 | 387135094 |
| 255585664 | 297832520 | 343457675 | 356566169 | 357474493 | 387135098 |
| 255585666 | 297840825 | 343457677 | 356566173 | 357474497 | 387135100 |
| 255634688 | 297840827 | 350534960 | 356567761 | 357474499 | 387135134 |
| 255644801 | 297847402 | 356498085 | 356574704 | 357490035 | 387135136 |
| 255645821 | 297849372 | 356499771 | 356576401 | 357493567 | 387135174 |
| 255647456 | 300078590 | 356499777 | 356577660 | 357497139 | 387135176 |
| 255648275 | 300669727 | 356499779 | 357114993 | 357497581 | 387135184 |
| 260279126 | 302142947 | 356501328 | 357115447 | 357497671 | 387135186 |
| 260279128 | 302142948 | 356502523 | 357115451 | 357500579 | 387135188 |
| 261343326 | 302142950 | 356503180 | 357115453 | 357504663 | 387135190 |
| 283132367 | 302142951 | 356503184 | 357116080 | 357504691 | 387135192 |
| 283362112 | 302765302 | 356503295 | 357116928 | 357504699 | 387135194 |
| 289188052 | 302796334 | 356504436 | 357117461 | 357504707 | 387135282 |
| 295841350 | 302811470 | 356504523 | 357117829 | 357505859 | 387135284 |
| 296088529 | 302821107 | 356504765 | 357117839 | 357510851 | 387135294 |
| 296090415 | 302821679 | 356511113 | 357125059 | 357516975 | 387135298 |
| 296090524 | 319759260 | 356515120 | 357126015 | 359477003 | 387135300 |
| 296090526 | 319759266 | 356517088 | 357134488 | 359477998 | 387135302 |
| 297599503 | 320148814 | 356520732 | 357135657 | 359478043 | 387135304 |
| 297601531 | 326489963 | 356522586 | 357138503 | 359478286 | 387135312 |
| 297611791 | 326490273 | 356522588 | 357139683 | 359484299 | 387135314 |
| 297722841 | 326491131 | 356522590 | 357139683 | 359486936 | 387135316 |
| 387135318 | 449440433 | 460376293 | 460413408 | 462423864 | 475546199 |
| 387135320 | 449445896 | 460378310 | 460416351 | 470101924 | 475556485 |

-continued

| | | | | | |
|---|---|---|---|---|---|
| 387135322 | 449446454 | 460380744 | 462394387 | 470102280 | 475559699 |
| 387135324 | 449447657 | 460381726 | 462394433 | 470102858 | 475578293 |
| 387135326 | 449449002 | 460382093 | 462394557 | 470104211 | 475591753 |
| 387135328 | 449449004 | 460382095 | 462395646 | 470104264 | 475593742 |
| 388493506 | 449449006 | 460382754 | 462395678 | 470104266 | 475612072 |
| 388495496 | 449451379 | 460384935 | 462396388 | 470106317 | 475622476 |
| 388498446 | 449451589 | 460384937 | 462396389 | 470106357 | 475622507 |
| 388499220 | 449451591 | 460385076 | 462396419 | 470115448 | 475623787 |
| 388502176 | 449451593 | 460385872 | 462396542 | 470130404 | 482550481 |
| 388517521 | 449453712 | 460386018 | 462397507 | 470131550 | 482550499 |
| 388519407 | 449453714 | 460389217 | 462399998 | 470136482 | 482550740 |
| 388521413 | 449453716 | 460394872 | 462400798 | 470136484 | 482550999 |
| 388827901 | 449453732 | 460396139 | 462401217 | 470136488 | 482552352 |
| 388827903 | 449457075 | 460397862 | 462402118 | 470136492 | 482554970 |
| 388827907 | 449467555 | 460397864 | 462402237 | 470137933 | 482555336 |
| 388827909 | 449468742 | 460398541 | 462402284 | 470137937 | 482555478 |
| 388827913 | 449495638 | 460403139 | 462402416 | 470140422 | 482556454 |
| 393887637 | 449495736 | 460403141 | 462404228 | 470140426 | 482557289 |
| 393887646 | 449499880 | 460403143 | 462406358 | 470140908 | 482558462 |
| 393887649 | 449502786 | 460403145 | 462408262 | 470141232 | 482558508 |
| 393990627 | 449503471 | 460405998 | 462409325 | 470142008 | 482558547 |
| 397746860 | 449503473 | 460407578 | 462409359 | 470142010 | 482561055 |
| 397789318 | 449515857 | 460407590 | 462409777 | 470142012 | 482561555 |
| 413924864 | 449518643 | 460409128 | 462411467 | 470143607 | 482562795 |
| 414590349 | 449519559 | 460409134 | 462414311 | 470143939 | 482562850 |
| 414590661 | 449522783 | 460409136 | 462414416 | 470145404 | 482565094 |
| 414591157 | 449524530 | 460409459 | 462414476 | 473923244 | 482566269 |
| 414879558 | 449524591 | 460409461 | 462415526 | 474114354 | 482566296 |
| 414879559 | 449528823 | 460409463 | 462415603 | 474143634 | 482566307 |
| 414879560 | 449528825 | 460409465 | 462415731 | 474202268 | 482568689 |
| 414888074 | 449534021 | 460409467 | 462416307 | 474299266 | 482570049 |
| 431812559 | 460365546 | 460410124 | 462416920 | 474363119 | 482570572 |
| 449432064 | 460366882 | 460410126 | 462416922 | 474366157 | 482575121 |
| 449432066 | 460369823 | 460410128 | 462416923 | 474429346 | |
| 449433069 | 460369829 | 460410130 | 462416924 | 475432777 | |
| 449436944 | 460369831 | 460410132 | 462417401 | 475473002 | |
| 449438665 | 460369833 | 460410134 | 462419769 | 475489790 | |
| 449438667 | 460370755 | 460410213 | 462420317 | 475511330 | |
| 449440431 | 460374714 | 460411200 | 462423366 | 475516200 | |

TABLE 1

| GI number | Accession | Origin |
|---|---|---|
| 190692175 | ACE87855.1 | *Stevia rebaudiana* |
| 41469452 | AAS07253.1 | *Oryza sativa* |
| 62857204 | BAD95881.1 | *Ipomoea nil* |
| 62857206 | BAD95882.1 | *Ipomoea purperea* |
| 56550539 | BAD77944.1 | *Bellis perennis* |
| 115454819 | NP_001051010.1 | *Oryza sativa Japonica* Group |
| 115459312 | NP_001053256.1 | *Oryza sativa Japonica* Group |
| 115471069 | NP_001059133.1 | *Oryza sativa Japonica* Group |
| 115471071 | NP_001059134.1 | *Oryza sativa Japonica* Group |
| 116310985 | CAH67920.1 | *Oryza sativa Indica* Group |
| 116788066 | ABK24743.1 | *Picea sitchensis* |
| 122209731 | Q2V6J9.1 | *Fragaria × ananassa* |
| 125534461 | EAY81009.1 | *Oryza sativa Indica* Group |
| 125559566 | EAZ05102.1 | *Oryza sativa Indica* Group |
| 125588307 | EAZ28971.1 | *Oryza sativa Japonica* Group |
| 148907340 | ABR16806.1 | *Picea sitchensis* |
| 148910082 | ABR18123.1 | *Picea sitchensis* |
| 148910612 | ABR18376.1 | *Picea sitchensis* |
| 15234195 | NP_194486.1 | *Arabidopsis thaliana* |
| 15239523 | NP_200210.1 | *Arabidopsis thaliana* |
| 15239937 | NP_196793.1 | *Arabidopsis thaliana* |
| 1685005 | AAB36653.1 | *Nicotiana tabacum* |
| 183013903 | ACC38471.1 | *Medicago truncatula* |
| 186478321 | NP_172511.3 | *Arabidopsis thaliana* |
| 187373030 | ACD03249.1 | *Avena strigosa* |
| 194701936 | ACF85052.1 | *Zea mays* |
| 19743740 | AAL92461.1 | *Solanum lycopersicum* |
| 212275846 | NP_001131009.1 | *Zea mays* |
| 222619587 | EEE55719.1 | *Oryza sativa Japonica* Group |
| 224055535 | XP_002298527.1 | *Populus trichocarpa* |
| 224101569 | XP_002334266.1 | *Populus trichocarpa* |
| 224120552 | XP_002318358.1 | *Populus trichocarpa* |
| 224121288 | XP_002330790.1 | *Populus trichocarpa* |

TABLE 1-continued

| GI number | Accession | Origin |
|---|---|---|
| 225444853 | XP_002281094 | *Vitis vinifera* |
| 225454342 | XP_002275850.1 | *Vitis vinifera* |
| 225454475 | XP_002280923.1 | *Vitis vinifera* |
| 225461556 | XP_002285222 | *Vitis vinifera* |
| 225469540 | XP_002270294.1 | *Vitis vinifera* |
| 226495389 | NP_001148083.1 | *Zea mays* |
| 226502400 | NP_001147674.1 | *Zea mays* |
| 238477377 | ACR43489.1 | *Triticum aestivum* |
| 240254512 | NP_565540.4 | *Arabidopsis thaliana* |
| 2501497 | Q43716.1 | *Petunia × hybrida* |
| 255555369 | XP_002518721.1 | *Ricinus communis* |
| 26452040 | BAC43110.1 | *Arabidopsis thaliana* |
| 296088529 | CBI37520.3 | *Vitis vinifera* |
| 297611791 | NP_001067852.2 | *Oryza sativa Japonica* Group |
| 297795735 | XP_002865752.1 | *Arabidopsis lyrata* subsp. *lyrata* |
| 297798502 | XP_002867135.1 | *Arabidopsis lyrata* subsp. *lyrata* |
| 297820040 | XP_002877903.1 | *Arabidopsis lyrata* subsp. *lyrata* |
| 297832276 | XP_002884020.1 | *Arabidopsis lyrata* subsp. *lyrata* |
| 302821107 | XP_002992218.1 | *Selaginella moellendorffii* |
| 30680413 | NP_179446.2 | *Arabidopsis thaliana* |
| 319759266 | ADV71369.1 | *Pueraria montana* var. *lobata* |
| 326507826 | BAJ86656.1 | *Hordeum vulgare* subsp. *Vulgare* |
| 343457675 | AEM37036.1 | *Brassica rapa* subsp. *oleifera* |
| 350534960 | NP_001234680.1 | *Solanum lycopersicum* |
| 356501328 | XP_003519477.1 | *Glycine max* |
| 356522586 | XP_003529927.1 | *Glycine max* |
| 356535480 | XP_003536273.1 | *Glycine max* |
| 357445733 | XP_003593144.1 | *Medicago truncatula* |
| 357452783 | XP_003596668.1 | *Medicago truncatula* |
| 357474493 | XP_003607531.1 | *Medicago truncatula* |
| 357500579 | XP_003620578.1 | *Medicago truncatula* |
| 357504691 | XP_003622634.1 | *Medicago truncatula* |
| 359477998 | XP_003632051.1 | *Vitis vinifera* |

TABLE 1-continued

| GI number | Accession | Origin |
|---|---|---|
| 359487055 | XP_002271587 | *Vitis vinifera* |
| 359495869 | XP_003635104.1 | *Vitis vinifera* |
| 387135134 | AFJ52948.1 | *Linum usitatissimum* |
| 387135176 | AFJ52969.1 | *Linum usitatissimum* |
| 387135192 | AFJ52977.1 | *Linum usitatissimum* |
| 387135282 | AFJ53022.1 | *Linum usitatissimum* |
| 387135302 | AFJ53032.1 | *Linum usitatissimum* |
| 387135312 | AFJ53037.1 | *Linum usitatissimum* |
| 388519407 | AFK47765.1 | *Medicago truncatula* |
| 393887646 | AFN26668.1 | *Barbarea vulgaris* subsp. *arcuata* |
| 414888074 | DAA64088.1 | *Zea mays* |
| 42572855 | NP_974524.1 | *Arabidopsis thaliana* |
| 449440433 | XP_004137989.1 | *Cucumis sativus* |
| 449446454 | XP_004140986.1 | *Cucumis sativus* |
| 449449004 | XP_004142255.1 | *Cucumis sativus* |
| 449451593 | XP_004143546.1 | *Cucumis sativus* |
| 449515857 | XP_004164964.1 | *Cucumis sativus* |
| 460382095 | XP_004236775.1 | *Solanum lycopersicum* |
| 460409128 | XP_004249992.1 | *Solanum lycopersicum* |
| 460409461 | XP_004250157.1 | *Solanum lycopersicum* |
| 460409465 | XP_004250159.1 | *Solanum lycopersicum* |
| 462396388 | EMJ02187.1 | *Prunus persica* |
| 462402118 | EMJ07675.1 | *Prunus persica* |
| 462409359 | EMJ14693.1 | *Prunus persica* |
| 462416923 | EMJ21660.1 | *Prunus persica* |
| 46806235 | BAD17459.1 | *Oryza sativa Japonica* Group |
| 470104266 | XP_004288529.1 | *Fragaria vesca* subsp. *vesca* |
| 470142008 | XP_004306714.1 | *Fragaria vesca* subsp. *vesca* |
| 475432777 | EMT01232.1 | *Aegilops tauschii* |
| 51090402 | BAD35324.1 | *Oryza sativa Japonica* Group |

TABLE 2

| GI number | Accession | Origin |
|---|---|---|
| 460409128 | XP.004249992.1 | *Solanum lycopersicum* |
| 460386018 | XP.004238697.1 | *Solanum lycopersicum* |
| 460409134 | XP.004249995.1 | *Solanum lycopersicum* |
| 460410132 | XP.004250485.1 | *Solanum lycopersicum* |
| 460410130 | XP.004250484.1 | *Solanum lycopersicum* |
| 460410128 | XP.004250483.1 | *Solanum lycopersicum* |
| 460378310 | XP.004234916.1 | *Solanum lycopersicum* |
| 209954733 | BAG80557.1 | *Lycium barbarum* |
| 209954725 | BAG80553.1 | *Lycium barbarum* |

In yet another embodiment, the UDP-glucosyltransferase is any UDP-glucosyltransferase capable of adding at least one glucose unit to rebaudioside D to form rebaudioside M and/or rebaudioside M2. The UDP-glucosyltransferase may be, for example, UGT76G1 or UGT76G1 variant, having greater than 75% amino-acid sequence identity with UGT76G1.

Figure 3:
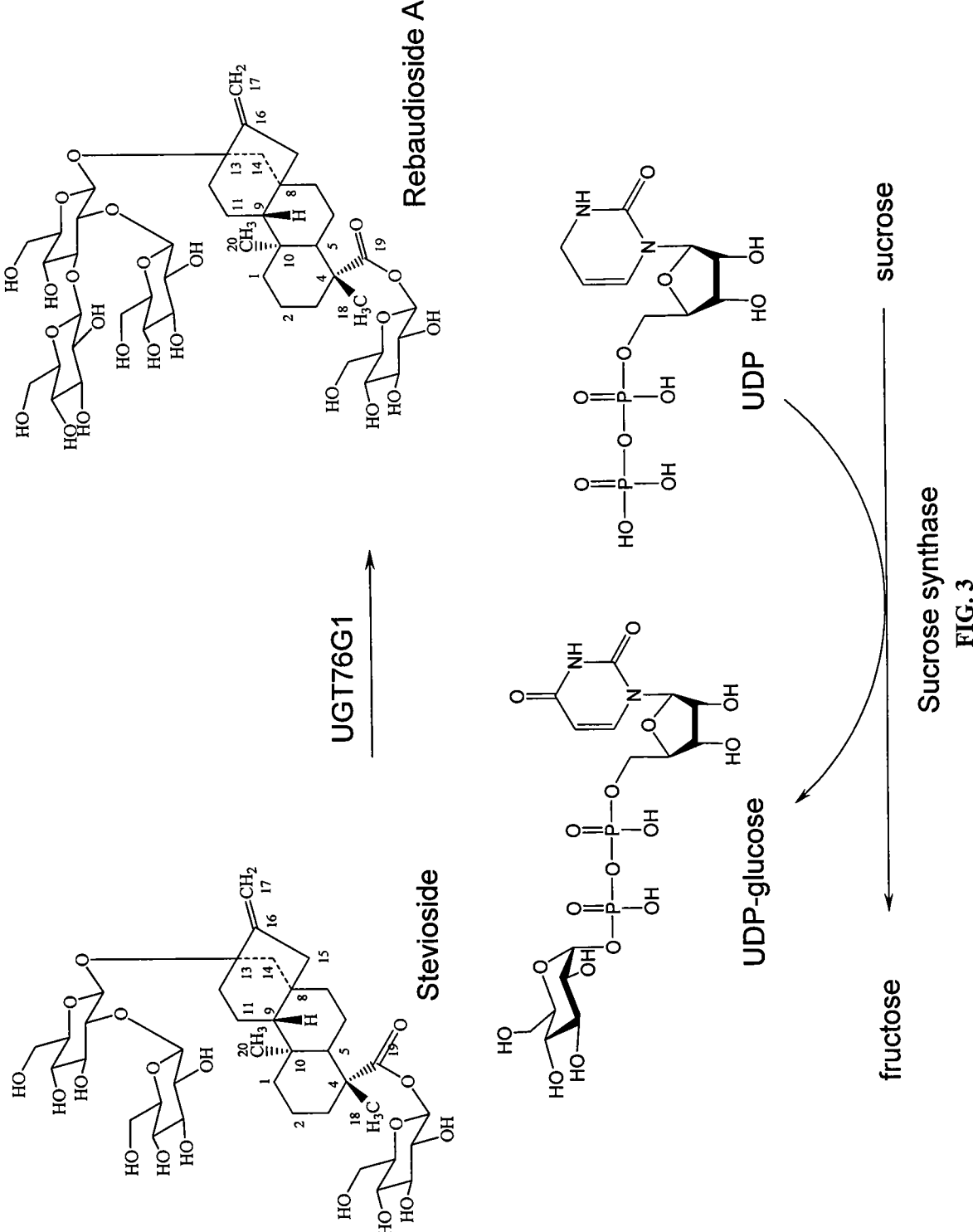
FIG. 3 shows the biocatalytic production of reb A from stevioside using the enzyme UGT76G1 and concomitant recycling of UDP to UDP glucose via sucrose synthase.

Optionally, the method of the present invention further comprises recycling UDP to provide UDP-glucose. In one embodiment, the method comprises recycling UDP by providing a recycling catalyst, i.e., a biocatalyst capable of UDP-glucose overproduction, and a recycling substrate, such that the conversion of the substrate steviol glycoside to the target steviol glycoside is carried out using catalytic amounts of UDP-glucosyltransferase and UDP-glucose (FIG. 3).

In one embodiment, the UDP-glucose recycling catalyst is sucrose synthase.

In one embodiment, the recycling substrate is sucrose.

Optionally, the method of the present invention further comprises hydrolysis of 1,6-β-glucosidic linkages in reb D2 and/or reb M2. In one embodiment, the method comprises hydrolysis of 1,6-β-glucosidic linkages in reb D2 and/or reb M2 by providing a β-glucosidase.

In one embodiment β-glucosidase is provided together with UDP-recycling biocatalyst and UGTs to minimize the content of reb D2 and/or reb M2 in final reaction mixture and maximize the yield of reb M In a particular embodiment to minimize the content of reb D2 and/or reb M2 in final reaction mixture and maximize the yield of reb M, β-glucosidase is provided together with UDP-recycling biocatalyst, UGT76G1 and UGTSL2, or their variants having greater than 75% amino-acid sequence identity with UGT76G1 or UGTSL2.

The target steviol glycoside is optionally purified from the resulting composition. Purification of the target steviol glycoside from the reaction medium can be achieved by any suitable method to provide a highly purified target steviol glycoside composition. Suitable methods include crystallization, separation by membranes, centrifugation, extraction (liquid or solid phase), chromatographic separation, HPLC (preparative or analytical) or a combination of such methods.

Compounds and Methods

The present invention also provides isolated and highly purified reb D2. Reb D2 is an isomer of reb D and has the following structure:

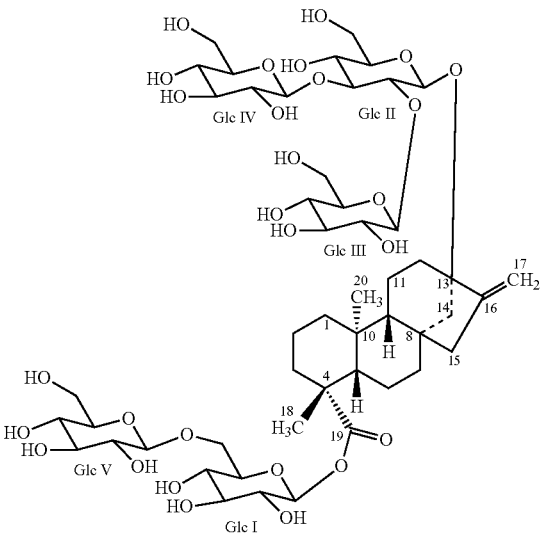

13-[(2-O-β-D-glucopyranosyl-3-O-β-D-glucopyranosyl-β-D-glucopyranosyl)oxy] ent-kaur-16-en-19-oic acid-[(6-O-β-D-glucopyranosyl-β-D-glucopyranosyl) ester]

In another embodiment, the present invention provides reb D2 having a purity greater than about 95% by weight on an anhydrous basis, such as, for example, greater than about 96% by weight, greater than about 97% by weight, greater than about 98% by weight or greater than about 99% by weight.

In still another embodiment, the present invention provides reb D2 having a purity greater than about 95% by weight in a steviol glycoside mixture, such as, for example, greater than about 96% by weight, greater than about 97% by weight, greater than about 98% by weight or greater than about 99% by weight.

The present invention also provides compositions comprising reb D2.

In one embodiment, the present invention provides a method for preparing reb D2 comprising:

a. contacting a starting composition comprising reb A with an enzyme capable of transforming reb A to reb D2, UDP-glucose, and optionally UDP-glucose recycling enzymes, to produce a composition comprising reb D2; and b. isolating the composition comprising reb D2.

In some embodiments, the enzyme capable of transforming reb A to reb D2 is a UDP-glucosyltransferase, such as, for example, UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11.

The enzyme capable of transforming reb A to reb D2 can be immobilized or provided in the form of a recombinant microorganism.

In one embodiment, the enzyme is immobilized. In another embodiment, the enzyme is provided in the form of a recombinant microorganism.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

Suitable microorganisms include, but are not limited to, *E. coli, Saccharomyces* sp., *Aspergillus* sp., *Pichia* sp., *Bacillus* sp., *Yarrowia* sp.

In one embodiment the microorganism is in an aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment the medium can also include an organic solvent.

In a particular embodiment, the enzyme is a UDP-glucosyltransferase capable of transforming reb A to reb D2 and is contained in *E. coli.*

In a more particular embodiment, the enzyme is selected from UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11 and is contained in *E. coli.*

In a still more particular embodiment, the enzyme is UGTSL2 and is contained in *E. coli.*

Isolation of reb D2 from the reaction medium can be achieved by any suitable method to provide a composition comprising reb D2. Suitable methods include, but are not limited to, lysis, crystallization, separation by membranes, centrifugation, extraction (liquid or solid phase), chromatographic separation, HPLC (preparative or analytical) or a combination of such methods. In a particular embodiment, isolation can be achieved by lysis and centrifugation.

In some embodiments, isolation may result in a reb D2 purity less than about 95% by weight on an anhydrous basis, and the composition may contain, e.g., steviol glycosides and/or residual reaction products. The composition comprising reb D2 can be further purified to provide highly purified reb D2, i.e. reb D2 having a purity greater than about 95% by weight on an anhydrous basis. In some embodiments, the compositions comprising reb D2 can be further purified to provide reb D2 having a purity greater than about 96%, greater than about 97%, greater than about 98% or greater than about 99% by weight on an anhydrous basis.

Purification can be affected by any means known to one of skill in the art including, but not limited to, crystallization, separation by membranes, centrifugation, extraction (liquid or solid phase), chromatographic separation, HPLC (preparative or analytical) or a combination of such methods. In a particular embodiment, HPLC is used to purify reb D2. In a more particular embodiment, semi-preparative HPLC is used to purify reb D2.

For example, a two-step semi-preparative HPLC purification can be used. The first step utilizes a C18 column with a mobile phase containing A (25% MeCN in water) and B (30% MeCN in water) with the following gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary step utilizes the same column and conditions, but with only an isocratic mobile phase: 20% MeCN in water.

Those of skill in the art will recognize that the particular column, mobile phases, injection volumes and other HPLC parameters can vary.

In one embodiment, the present invention provides isolated and highly purified reb M2. Reb M2 is an isomer of reb M and has the following structure:

(13-[(2-O-β-D-glucopyranosyl-3-O-β-D-glucopyra-
nosyl-β-D-glucopyranosyl)oxy] ent-kaur-16-en-19-
oic acid-[(2-O-β-D-glucopyranosyl-6-O-β-D-glu-
copyranosyl-β-D-glucopyranosyl) ester])

In another embodiment, the present invention provides reb M2 having a purity greater than about 95% by weight on an anhydrous basis, such as, for example, greater than about 96% by weight, greater than about 97% by weight, greater than about 98% by weight or greater than about 99% by weight.

In still another embodiment, the present invention provides reb M2 having a purity greater than about 95% by weight in a steviol glycoside mixture, such as, for example, greater than about 96% by weight, greater than about 97% by weight, greater than about 98% by weight or greater than about 99% by weight.

In yet another embodiment, the present invention provides reb M2 having a purity greater than about 95% by weight in a *Stevia* extract, such as, for example, greater than about 96% by weight, greater than about 97% by weight, greater than about 98% by weight or greater than about 99% by weight.

The present invention also provides compositions comprising reb M2.

It has been found that reb M2 is produced during biotransformation of reb A to reb D. As noted above, biotransformation of reb A to reb D also produces reb D2. Accordingly, in one embodiment, the present invention provides a method for preparing reb M2 comprising:

a. contacting a starting composition comprising reb A and/or reb D2 with an enzyme capable of transforming reb A and/or reb D2 to reb M2, UDP-glucose, and optionally UDP-glucose recycling enzymes to produce a composition comprising reb M2; and b. isolating a composition comprising reb M2.

Not wishing to be bound by theory, it is currently believed that the pathway begins with transformation of reb A to reb D2, followed by transformation of reb D2 to reb M2.

Accordingly, In one embodiment, the present invention provides a method for preparing reb M2 comprising:

a. contacting a starting composition comprising reb D2 with an enzyme capable of transforming reb D2 to reb M2, UDP-glucose, and optionally UDP-glucose recycling enzymes to produce a composition comprising reb M2; and b. isolating a composition comprising reb M2.

In yet another embodiment, a method for preparing reb M2 comprises:

a. contacting a starting composition comprising reb A with an enzyme capable of transforming reb A to reb D2, UDP-glucose, and optionally UDP-glucose recycling enzymes to produce a composition comprising reb D2;

b. optionally, isolating a composition comprising reb D2;

c. contacting the composition comprising reb D2 with an enzyme capable of transforming reb D2 to reb M2, UDP-glucose, and optionally UDP-glucose recycling enzymes to produce a composition comprising reb M2; and d. isolating a composition comprising reb M2.

The enzyme can be a UDP-glucosyltransferase, such as, for example, UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11.

The enzyme can be immobilized or in a recombinant microorganism.

In one embodiment, the enzyme is immobilized. In another embodiment, the enzyme is in a recombinant microorganism.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

Suitable microorganisms include, but are not limited to, *E. coli, Saccharomyces* sp., *Aspergillus* sp., *Pichia* sp., *Bacillus* sp., *Yarrowia* sp.

In one embodiment the microorganism is in aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment the medium can also include an organic solvent.

In a particular embodiment, the enzyme is a UDP-glucosyltransferase capable of transforming reb A and/or reb D2 to reb M2 and is contained in *E. coli*.

In a more particular embodiment, the enzyme is selected from UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11 and is contained in *E. coli*.

In a still more particular embodiment, the enzyme is UGTSL2 and is contained in *E. coli*.

Isolation of reb M2 from the reaction medium can be achieved by any suitable method to provide a composition comprising reb M2. Suitable methods include, but are not limited to, lysis, crystallization, separation by membranes, centrifugation, extraction (liquid or solid phase), chromatographic separation, HPLC (preparative or analytical) or a combination of such methods. In a particular embodiment, isolation can be achieved by lysis and centrifugation.

In some embodiments, isolation may result in a reb M2 purity less than about 95% by weight on an anhydrous basis, and the composition may contain, e.g., steviol glycosides and/or residual reaction products.

The composition comprising reb M2 can be further purified to provide highly purified reb M2, i.e. reb M2 having a purity greater than about 95% by weight on an anhydrous basis. In some embodiments, the compositions comprising reb M2 can be further purified to provide reb M2 having a purity greater than about 96%, greater than about 97%, greater than about 98% or greater than about 99% by weight on an anhydrous basis.

Purification can be affected by any means known to one of skill in the art including, but not limited to, crystallization, separation by membranes, centrifugation, extraction (liquid or solid phase), chromatographic separation, HPLC (preparative or analytical) or a combination of such methods. In a particular embodiment, HPLC is used to purify reb M2. In a more particular embodiment, semi-preparative HPLC is used to purify reb M2.

For example, a two-step semi-preparative HPLC purification can be used. The first step utilizes a C18 column with a mobile phase containing A (25% MeCN in water) and B (30% MeCN in water) with the following gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary step utilizes the same column and conditions, but with only an isocratic mobile phase: 20% MeCN in water.

Those of skill in the art will recognize that the particular column, mobile phases, injection volumes and other HPLC parameters can vary.

Purified steviol glycosides, prepared in accordance with the present invention, may be used in a variety of consumable products including, but not limited to, foods, beverages, pharmaceutical compositions, tobacco products, nutraceutical compositions, oral hygiene compositions, and cosmetic compositions.

Figure 4:
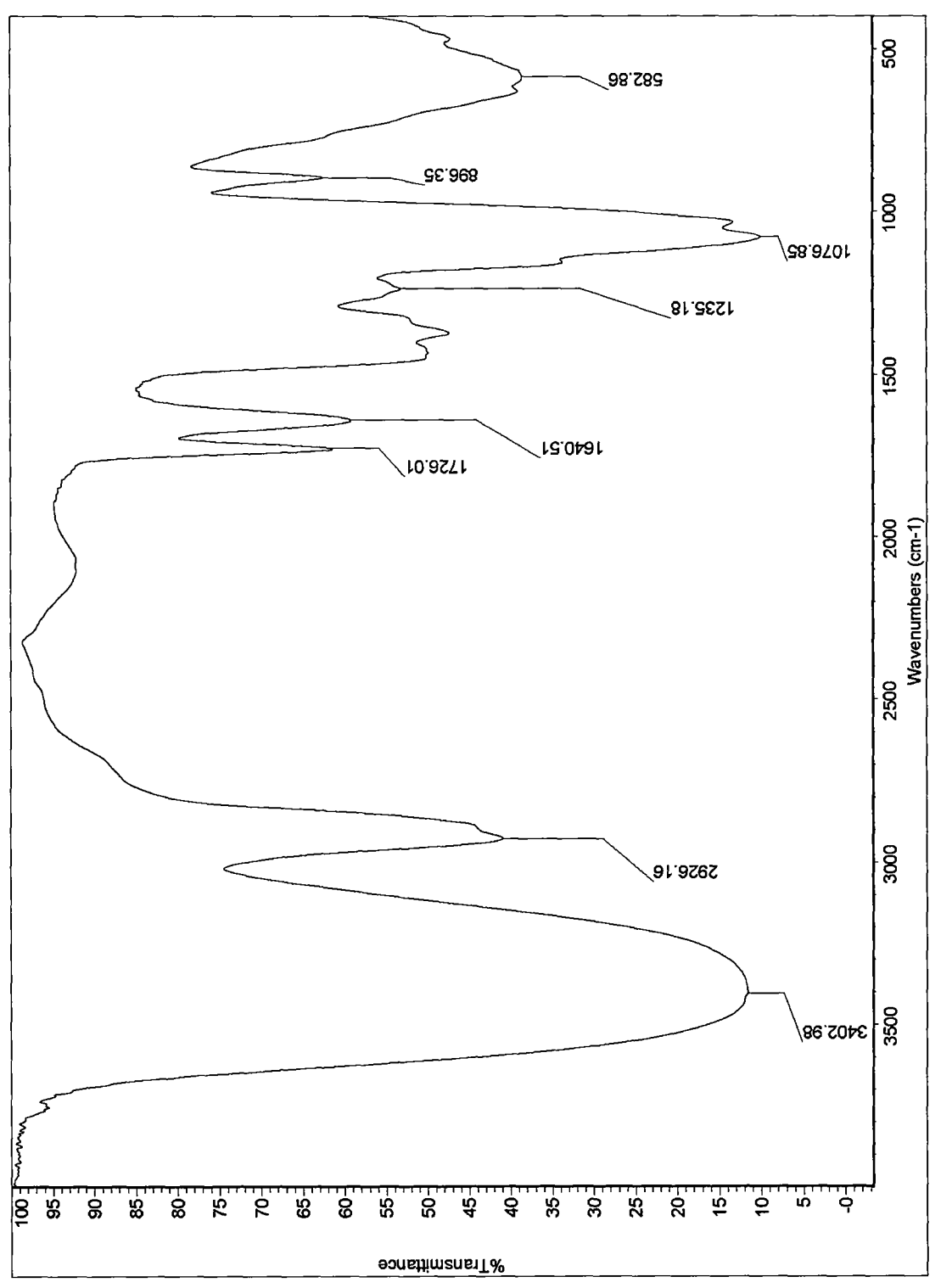
FIG. 4 shows the IR spectrum of reb M.

The high purity reb M obtained in this invention, having a molecular weight of 1291.29, a molecular formula of $C_{56}H_{90}O_{33}$, CAS registry number 1220616-44-3, and the structure presented in FIG. 1, is in the form of a white and odorless powder. The compound is about 200 times sweeter than sugar when compared to a 10% sucrose solution. The infrared absorption spectrum is shown in FIG. 4.

Other properties of the pure reb M compound include a melting point of 249-250° C., and a specific rotation of $[\alpha]_D^{25}$ −19.0° in 50% ethanol (C=1.0). The solubility of reb M in water is around 0.3%, and increases with an increase in temperature.

Reb M is soluble in diluted solutions of methanol, ethanol, n-propanol, and isopropanol. However, it is insoluble in acetone, benzene, chloroform, and ether.

Reb M obtained in accordance with the present invention is heat and pH-stable.

Highly purified target glycoside(s) particularly, reb D, reb D2, reb M and/or reb M2 obtained according to this invention can be used "as-is" or in combination with other sweeteners, flavors and food ingredients.

Non-limiting examples of flavors include lime, lemon, orange, fruit, banana, grape, pear, pineapple, mango, bitter almond, cola, cinnamon, sugar, cotton candy and vanilla flavors.

Non-limiting examples of other food ingredients include flavors, acidulants, organic and amino acids, coloring agents, bulking agents, modified starches, gums, texturizers, preservatives, antioxidants, emulsifiers, stabilizers, thickeners and gelling agents.

Highly purified target glycoside(s) particularly, reb D, reb D2, reb M and/or reb M2 obtained according to this invention can be prepared in various polymorphic forms, including but not limited to hydrates, solvates, anhydrous, amorphous forms and/or mixtures thereof.

Highly purified target steviol glycoside(s), particularly, reb D, reb D2, reb M and/or reb M2 obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc.

Highly purified target steviol glycoside(s), particularly, reb D, reb D2, reb M and/or reb M2 as a sweetening compound may be employed as the sole sweetener, or it may be used together with other naturally occurring high intensity sweeteners such as stevioside, reb A, reb B, reb C, reb D, reb E, reb F, steviolbioside, dulcoside A, rubusoside, mogrosides, brazzein, neohesperidin dihydrochalcone, glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, camosiflosides, cyclocarioside, pterocaryosides, polypodoside A, brazilin, hemandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, mogroside V, siamenoside and others.

In a particular embodiment, reb D2 and/or reb M2 can be used together in a sweetener composition comprising a compound selected from the group consisting of reb A, reb B, reb D, NSF-02, Mogroside V, erythritol and combinations thereof.

Highly purified target steviol glycoside(s), particularly, reb D, reb D2, reb M and/or reb M2 may also be used in combination with synthetic high intensity sweeteners such as sucralose, potassium acesulfame, aspartame, alitame, saccharin, neohesperidin dihydrochalcone, cyclamate, neotame, dulcin, suosan advantame, salts thereof, and the like.

Moreover, highly purified target steviol glycoside(s), particularly, reb D, reb D2, reb M and/or reb M2 can be used in combination with natural sweetener suppressors such as gymnemic acid, hodulcin, ziziphin, lactisole, and others. Reb D, reb D2, reb M and/or reb M2 may also be combined with various umami taste enhancers. Reb D, reb D2, reb M and/or reb M2 can be mixed with umami tasting and sweet amino acids such as glutamate, aspartic acid, glycine, alanine, threonine, proline, serine, glutamate, lysine and tryptophan.

Highly purified target steviol glycoside(s), particularly, reb D, reb D2, reb M can be used in combination with one or more additive selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

Highly purified target steviol glycoside(s), particularly, reb D, reb D2, reb M and/or reb M2 may be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition.

Highly purified target steviol glycoside(s), particularly, reb D, reb D2, reb M and/or reb M2 may be combined with reduced calorie sweeteners such as D-tagatose, L-sugars, L-sorbose, L-arabinose, and others.

Highly purified target steviol glycoside(s), particularly, reb D, reb D2, reb M and/or reb M2 may also be combined with various carbohydrates. The term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, Psicose, turanose, allose, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, gluconolactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

Highly purified target steviol glycoside(s), particularly, reb D, reb D2, reb M and/or reb M2 obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory. Exemplary functional ingredients are provided in WO2013/096420, the contents of which is hereby incorporated by reference.

Highly purified target steviol glycoside(s), particularly, reb D, reb D2, reb M and/or reb M2 obtained according to this invention may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, highly purified target steviol glycoside(s), particularly, reb D, reb D2, reb M and/or reb M2 can be used as a sweetener not only for drinks, foodstuffs, and other products dedicated for human consumption, but also in animal feed and fodder with improved characteristics.

Examples of consumable products in which highly purified target steviol glycoside(s), particularly, reb D, reb D2, reb M and/or reb M2 may be used as a sweetening compound include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Moreover, the highly purified target steviol glycoside(s), particularly, reb D, reb D2, reb M and/or reb M2 obtained in this invention may be used in dry or liquid forms. In one embodiment, a tabletop sweetener comprising reb D2 is provided. In another embodiment, a tabletop sweetener comprising reb M2 is provided.

The highly purified target steviol glycoside can be added before or after heat treatment of food products. The amount of the highly purified target steviol glycoside(s), particularly, reb D, reb D2, reb M and/or reb M2 depends on the purpose of usage. As discussed above, it can be added alone or in combination with other compounds.

The present invention is also directed to sweetness enhancement in beverages using reb D2. The present invention is also directed to sweetness enhancement in beverages containing reb M2. Accordingly, the present invention provides a beverage comprising a sweetener and reb D2 and/or reb M2 as a sweetness enhancer, wherein reb D2 and/or reb M2 is present in a concentration at or below their respective sweetness recognition thresholds.

As used herein, the term "sweetness enhancer" refers to a compound capable of enhancing or intensifying the perception of sweet taste in a composition, such as a beverage. The term "sweetness enhancer" is synonymous with the terms "sweet taste potentiator," "sweetness potentiator," "sweetness amplifier," and "sweetness intensifier."

The term "sweetness recognition threshold concentration," as generally used herein, is the lowest known concentration of a sweet compound that is perceivable by the human sense of taste, typically around 1.0% sucrose equivalence (1.0% SE). Generally, the sweetness enhancers may enhance or potentiate the sweet taste of sweeteners without providing any noticeable sweet taste by themselves when present at or below the sweetness recognition threshold concentration of a given sweetness enhancer; however, the sweetness enhancers may themselves provide sweet taste at concentrations above their sweetness recognition threshold concentration. The sweetness recognition threshold concentration is specific for a particular enhancer and can vary based on the beverage matrix. The sweetness recognition threshold concentration can be easily determined by taste testing increasing concentrations of a given enhancer until greater than 1.0% sucrose equivalence in a given beverage matrix is detected. The concentration that provides about 1.0% sucrose equivalence is considered the sweetness recognition threshold.

In some embodiments, sweetener is present in the beverage in an amount from about 0.5% to about 12% by weight, such as, for example, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, about 10.0% by weight, about 10.5% by weight, about 11.0% by weight, about 11.5% by weight or about 12.0% by weight.

In a particular embodiment, the sweetener is present in the beverage in an amount from about 0.5% of about 10%, such as for example, from about 2% to about 8%, from about 3% to about 7% or from about 4% to about 6% by weight. In a particular embodiment, the sweetener is present in the beverage in an amount from about 0.5% to about 8% by weight. In another particular embodiment, the sweetener is present in the beverage in an amount from about 2% to about 8% by weight.

In one embodiment, the sweetener is a traditional caloric sweetener. Suitable sweeteners include, but are not limited to, sucrose, fructose, glucose, high fructose corn syrup and high fructose starch syrup.

In another embodiment, the sweetener is erythritol.

In still another embodiment, the sweetener is a rare sugar. Suitable rare sugars include, but are not limited to, D-allose, D-psicose, L-ribose, D-tagatose, L-glucose, L-fucose, L-arabinose, D-turanose, D-leucrose and combinations thereof.

It is contemplated that a sweetener can be used alone, or in combination with other sweeteners.

In one embodiment, the rare sugar is D-allose. In a more particular embodiment, D-allose is present in the beverage in an amount of about 0.5% to about 10% by weight, such as, for example, from about 2% to about 8%.

In another embodiment, the rare sugar is D-psicose. In a more particular embodiment, D-psicose is present in the beverage in an amount of about 0.5% to about 10% by weight, such as, for example, from about 2% to about 8%.

In still another embodiment, the rare sugar is D-ribose. In a more particular embodiment, D-ribose is present in the beverage in an amount of about 0.5% to about 10% by weight, such as, for example, from about 2% to about 8%.

In yet another embodiment, the rare sugar is D-tagatose. In a more particular embodiment, D-tagatose is present in the beverage in an amount of about 0.5% to about 10% by weight, such as, for example, from about 2% to about 8%.

In a further embodiment, the rare sugar is L-glucose. In a more particular embodiment, L-glucose is present in the beverage in an amount of about 0.5% to about 10% by weight, such as, for example, from about 2% to about 8%.

In one embodiment, the rare sugar is L-fucose. In a more particular embodiment, L-fucose is present in the beverage in an amount of about 0.5% to about 10% by weight, such as, for example, from about 2% to about 8%.

In another embodiment, the rare sugar is L-arabinose. In a more particular embodiment, L-arabinose is present in the beverage in an amount of about 0.5% to about 10% by weight, such as, for example, from about 2% to about 8%.

In yet another embodiment, the rare sugar is D-turanose. In a more particular embodiment, D-turanose is present in the beverage in an amount of about 0.5% to about 10% by weight, such as, for example, from about 2% to about 8%.

In yet another embodiment, the rare sugar is D-leucrose. In a more particular embodiment, D-leucrose is present in the beverage in an amount of about 0.5% to about 10% by weight, such as, for example, from about 2% to about 8%.

The addition of the sweetness enhancer at a concentration at or below its sweetness recognition threshold increases the detected sucrose equivalent of the beverage comprising the sweetener and the sweetness enhancer compared to a corresponding beverage in the absence of the sweetness enhancer. Moreover, sweetness can be increased by an amount more than the detectable sweetness of a solution containing the same concentration of the at least one sweetness enhancer in the absence of any sweetener.

Accordingly, the present invention also provides a method for enhancing the sweetness of a beverage comprising a sweetener comprising providing a beverage comprising a sweetener and adding a sweetness enhancer selected from reb D2, reb M2 or a combination thereof, wherein reb D2 and reb M2 are present in a concentration at or below their sweetness recognition thresholds.

Addition of reb D2 and/or reb M2 in a concentration at or below the sweetness recognition threshold to a beverage containing a sweetener may increase the detected sucrose equivalent from about 1.0% to about 5.0%, such as, for example, about 1.0%, about 1.5%, about 2.0%, about 2.5%, about 3.0%, about 3.5%, about 4.0%, about 4.5% or about 5.0%.

The following examples illustrate preferred embodiments of the invention for the preparation of highly purified target steviol glycoside(s), particularly, reb D, reb D2, reb M and/or reb M2. It will be understood that the invention is not limited to the materials, proportions, conditions and procedures set forth in the examples, which are only illustrative.

Example 1

In-Vivo Production of UGT76G1

NcoI and NdeI restriction sites were added to the original nucleic sequence as described in Genbank accession no. AAR06912.1. After codon optimization the following nucleic sequence was obtained (SEQ ID NO: 1):

```
CCATGGCCCATATGGAAAACAAAACCGAAACCACCGTTCGTCGTCGTCGC

CGTATTATTCTGTTTCCGGTTCCGTTTCAGGGTCATATTAATCCGATTCT

GCAGCTGGCAAATGTGCTGTATAGCAAAGGTTTTAGCATTACCATTTTTC

ATACCAATTTTAACAAACCGAAACCAGCAATTATCCGCATTTTACCTTT

CGCTTTATTCTGGATAATGATCCGCAGGATGAACGCATTAGCAATCTGCC

GACACATGGTCCGCTGGCAGGTATGCGTATTCCGATTATTAACGAACATG

GTGCAGATGAACTGCGTCGTGAACTGGAACTGCTGATGCTGGCAAGCGAA

GAAGATGAAGAAGTTAGCTGTCTGATTACCGATGCACTGTGGTATTTTGC

ACAGAGCGTTGCAGATAGCCTGAATCTGCGTCGTCTGGTTCTGATGACCA
```

-continued
```
GCAGCCTGTTTAACTTTCATGCACATGTTAGCCTGCCGCAGTTTGATGAA

CTGGGTTATCTGGATCCGGATGATAAAACCCGTCTGGAAGAACAGGCAAG

CGGTTTTCCGATGCTGAAAGTGAAAGATATCAAAAGCGCCTATAGCAATT

GGCAGATTCTGAAAGAAATTCTGGGCAAAATGATTAAACAGACCAAAGCA

AGCAGCGGTGTTATTTGGAATAGCTTTAAAGAACTGGAAGAAAGCGAACT

GGAAACCGTGATTCGTGAAATTCCGGCACCGAGCTTTCTGATTCCGCTGC

CGAAACATCTGACCGCAAGCAGCAGCAGCCTGCTGGATCATGATCGTACC

GTTTTTCAGTGGCTGGATCAGCAGCCTCCGAGCAGCGTTCTGTATGTTAG

CTTTGGTAGCACCAGCGAAGTTGATGAAAAAGATTTTCTGGAAATTGCCC

GTGGTCTGGTTGATAGCAAACAGAGCTTTCTGTGGGTTGTTCGTCCGGGT

TTTGTTAAAGGTAGCACCTGGGTTGAACCGCTGCCGGATGGTTTTCTGGG

TGAACGTGGTCGTATTGTTAAATGGGTTCCGCAGCAAGAAGTTCTGGCAC

ACGGCGCAATTGGTGCATTTTGGACCCATAGCGGTTGGAATAGCACCCTG

GAAAGCGTTTGTGAAGGTGTTCCGATGATTTTTAGCGATTTTGGTCTGGA

TCAGCCGCTGAATGCACGTTATATGAGTGATGTTCTGAAAGTGGGTGTGT

ATCTGGAAAATGGTTGGGAACGTGGTGAAATTGCAAATGCAATTCGTCGT

GTTATGGTGGATGAAGAAGGTGAATATATTCGTCAGAATGCCCGTGTTCT

GAAACAGAAAGCAGATGTTAGCCTGATGAAAGGTGGTAGCAGCTATGAAA

GCCTGGAAAGTCTGGTTAGCTATATTAGCAGCCTGTAATAACTCGAG
```

After synthesis of the gene and subcloning into pET30A+ vector using NdeI and XhoI cloning sites, the UGT76G1_pET30a+ plasmid was introduced in E. coli Bl21(DE3) and E. coli EC100 by electroporation. The obtained cells were grown in petri-dishes in the presence of Kanamycin and suitable colonies were selected and allowed to grow in liquid LB medium (erlenmeyer flasks). Glycerol was added to the suspension as cryoprotectant and 400 μL aliquots were stored at −20° C. and at −80° C.

The storage aliquots of E. coli BL21(DE3) containing the pET30A+_UGT76G1 plasmid were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake at 135 rpm at 30° C. for 8 h.

The production medium contained 60 g/L of overnight express instant TB medium (Novagen), 10 g/L of glycerol and 50 mg/L of Kanamycin. The medium was allowed to stir at 20° C. while taking samples to measure the OD and pH. The cultures gave significant growth and a good OD was obtained. After 40 h, the cells were harvested by centrifugation and frozen to yield 12.7 g of cell wet weight.

Lysis was performed by addition of Bugbuster Master mix (Novagen) and the lysate was recovered by centrifugation and kept frozen. Activity tests were performed with thawed lysate.

Example 2

In-Vitro Production of UGT76G1

The S30 T7 High Yield Protein expression system kit from Promega was used. 4 μg of UGT76G1_pET30a+ plasmid from E. coli EC100 was mixed with 80 μL of S30 premix plus and 72 μL of S30 T7 extract was added. Nuclease-free water was added in order to obtain a total volume of 200 µL and the resulting solution was incubated for 2 h at 30° C. 180 µL was used in the catalytic test reaction.

Example 3

In-Vitro Production of UGT91D2

NcoI and NdeI restriction sites were added to the original nucleic sequence as described in Genbank accession no. ACE87855.1. After codon optimization the following nucleic sequence was obtained (SEQ ID NO:2):

CCATGGCACATATGGCAACCAGCGATAGCATTGTTGATGATCGTAAACAG

CTGCATGTTGCAACCTTTCCGTGGCTGGCATTTGGTCATATTCTGCCGTA

TCTGCAGCTGAGCAAACTGATTGCAGAAAAAGGTCATAAAGTGAGCTTTC

TGAGCACCACCCGTAATATTCAGCGTCTGAGCAGCCATATTAGTCCGCTG

ATTAATGTTGTTCAGCTGACCCTGCCTCGTGTTCAAGAACTGCCGGAAGA

TGCCGAAGCAACCACCGATGTTCATCCGGAAGATATTCCGTATCTGAAAA

AAGCAAGTGATGGTCTGCAGCCGGAAGTTACCCGTTTTCTGGAACAGCAT

AGTCCGGATTGGATCATCTATGATTATACCCATTATTGGCTGCCGAGCAT

TGCAGCAAGCCTGGGTATTAGCCGTGCACATTTTAGCGTTACCACCCCGT

GGGCAATTGCATATATGGGTCCGAGCGCAGATGCAATGATTAATGGTAGT

GATGGTCGTACCACCGTTGAAGATCTGACCACCCCTCCGAAATGGTTTCC

GTTTCCGACCAAAGTTTGTTGGCGTAAACATGATCTGGCACGTCTGGTTC

CGTATAAAGCACCGGGTATTAGTGATGGTTATCGTATGGGTCTGGTTCTG

AAAGGTAGCGATTGTCTGCTGAGCAAATGCTATCATGAATTTGGCACCCA

GTGGCTGCCGCTGCTGGAAACCCTGCATCAGGTTCCGGTTGTTCCGGTGG

GTCTGCTGCCTCCGGAAGTTCCGGGTGATGAAAAAGATGAAACCTGGGTT

AGCATCAAAAAATGGCTGGATGGTAAACAGAAAGGTAGCGTGGTTTATGT

TGCACTGGGTAGCGAAGTTCTGGTTAGCCAGACCGAAGTTGTTGAACTGG

CACTGGGTCTGGAACTGAGCGGTCTGCCGTTTGTTTGGGCATATCGTAAA

CCGAAAGGTCCGGCAAAAAGCGATAGCGTTGAACTGCCGGATGGTTTTGT

TGAACGTACCCGTGATCGTGGTCTGGTTTGGACCAGCTGGGCACCTCAGC

TGCGTATTCTGAGCCATGAAAGCGTTTGTGGTTTTCTGACCCATTGTGGT

AGCGGTAGCATTGTGGAAGGTCTGATGTTTGGTCATCCGCTGATTATGCT

GCCGATTTTTGGTGATCAGCCGCTGAATGCACGTCTGCTGGAAGATAAAC

AGGTTGGTATTGAAATTCCGCGTAATGAAGAAGATGGTTGCCTGACCAAA

GAAAGCGTTGCACGTAGCCTGCGTAGCGTTGTTGTTGAAAAAGAAGGCGA

AATCTATAAAGCCAATGCACGTGAACTGAGCAAAATCTATAATGATACCA

AAGTGGAAAAAGAATATGTGAGCCAGTTCGTGGATTATCTGGAAAAAAAC

ACCCGTGCAGTTGCCATTGATCACGAAAGCTAATGACTCGAG

After synthesis of the gene and subcloning into pET30A+ vector using NcoI and XhoI cloning sites, the UGT91D2_pET30a+ plasmid was introduced into E. coli EC100 by electroporation. The obtained cells were grown in the presence of Kanamycin and suitable colonies were selected and allowed to grow in liquid LB medium (erlenmeyer flasks). Glycerol was added to the suspension as cryoprotectant and 400 µL aliquots were stored at –20° C. and at –80° C.

The S30 T7 High Yield Protein expression system kit from Promega was used for the in-vitro synthesis of the protein.

4 µg of UGT91D2_pET30a+ plasmid was mixed with 80 µL of S30 premix plus and 72 µL of S30 T7 extract was added. Nuclease-free water was added in order to obtain a total volume of 200 µL and the resulting solution was incubated for 2 h at 30° C. 5 µL was used for SDS-page analysis while the remaining 45 µL was used in the catalytic test reaction.

Example 4

Catalytic Reaction with In-Vivo Produced UGT76G1

Figure 51:
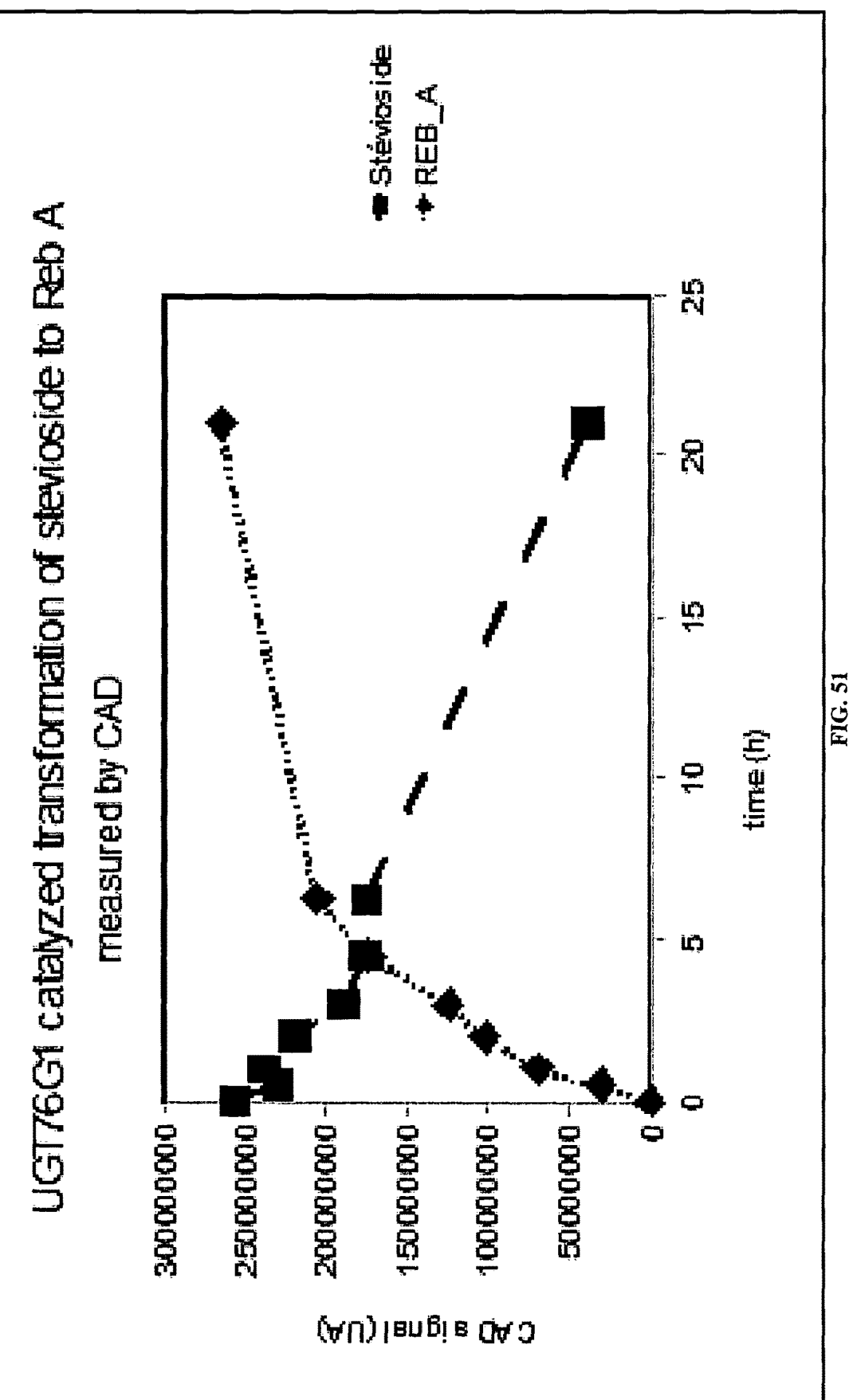
FIG. 51 shows an HPLC (CAD) graph showing conversion of stevioside to rebaudioside A.

The total volume of the reaction was 5.0 mL with the following composition: 50 mM sodium phosphate buffer pH 7.2, 3 mM $MgCl_2$, 2.5 mM UDP-glucose, 0.5 mM Stevioside and 500 µL of UGT76G1 thawed lysate. The reactions were run at 30° C. on an orbitary shaker at 135 rpm. For each sample, 460 µL of the reaction mixture was quenched with 40 µL of 2N $H_2SO_4$ and 420 µL of methanol/water (6/4). The samples were immediately centrifuged and kept at 10° C. before analysis by HPLC (CAD). HPLC indicated almost complete conversion of stevioside to rebaudioside A, as shown in FIG. 51.

Example 5

Catalytic Reaction with In-Vitro Produced UGT91D2

The total volume of the reaction was 0.5 mL with the following composition: 50 mM sodium phosphate buffer pH 7.2, 3 mM $MgCl_2$, 3.8 mM UDP-glucose, 0.1 mM Rebaudioside A and 180 µL of in-vitro produced UGT91D2. The reactions were run at 30° C. on an orbitary shaker at 135 rpm. For each sample, 450 µL of reaction mixture was quenched with 45 µL of 2N $H_2SO_4$ and 405 µL of 60% MeOH. After centrifugation, the supernatant was analyzed by HPLC (CAD). HPLC indicated a 4.7% conversion of rebaudioside A to rebaudioside D after 120 h.

Example 6

Catalytic Reaction with In-Vitro Produced UGT76G1

Figure 52:
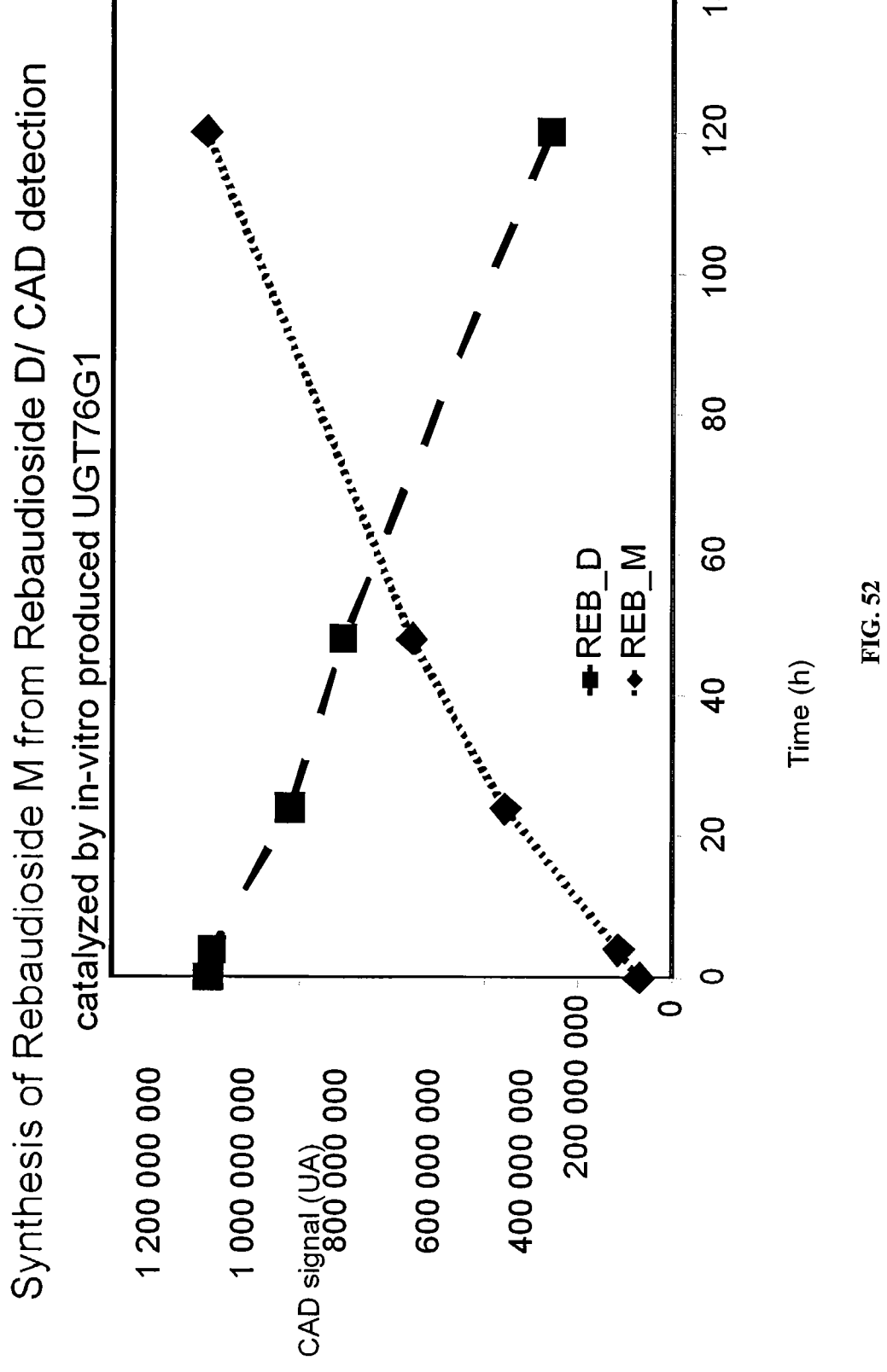
FIG. 52 shows an HPLC (CAD) graph showing conversion of rebaudioside D to rebaudioside M.
Figure 53A:
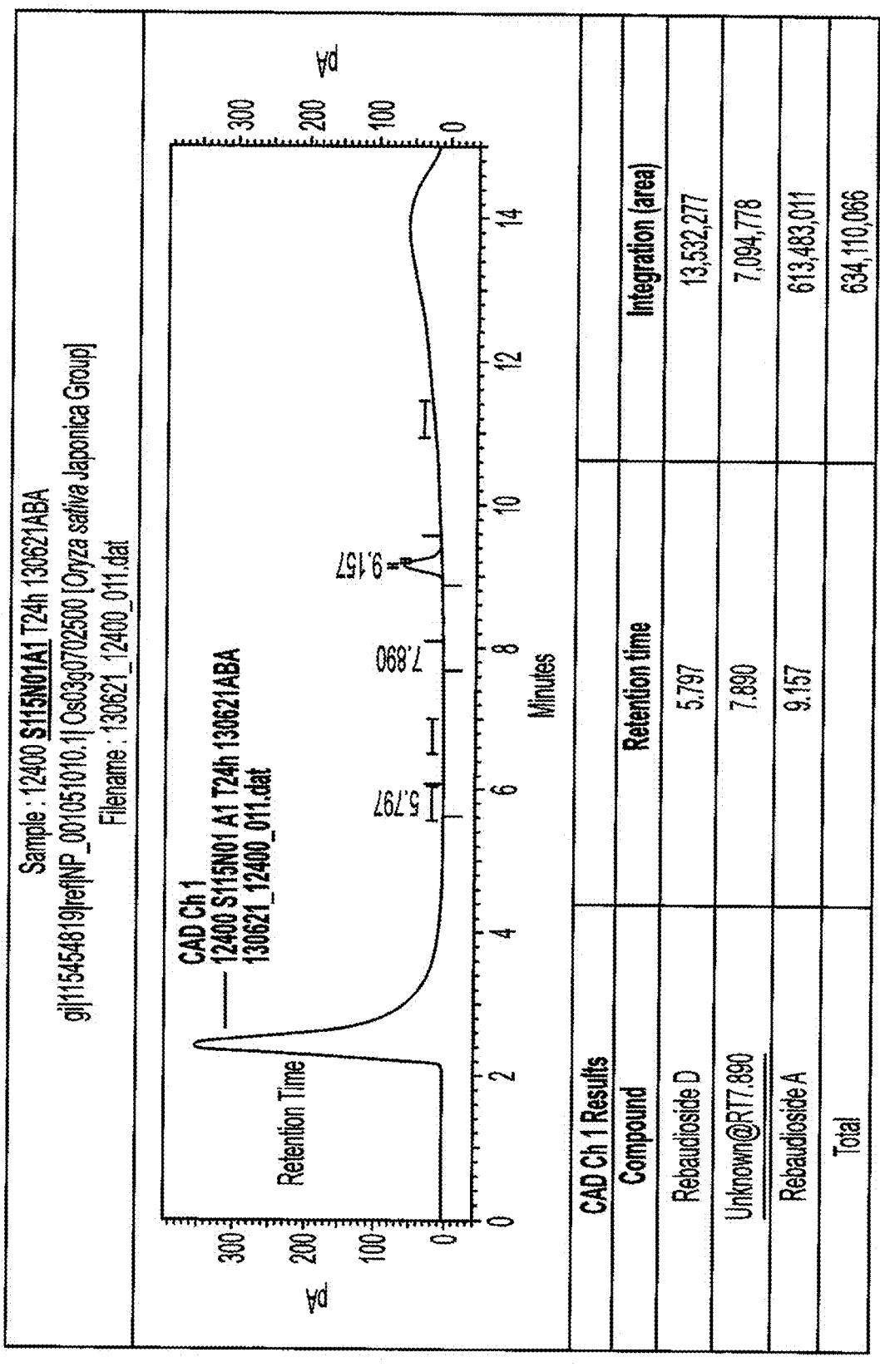
FIGS. 53A-53E show HPLC chromatograms showing HPLC assay results for Example 20.
Figure 53B:
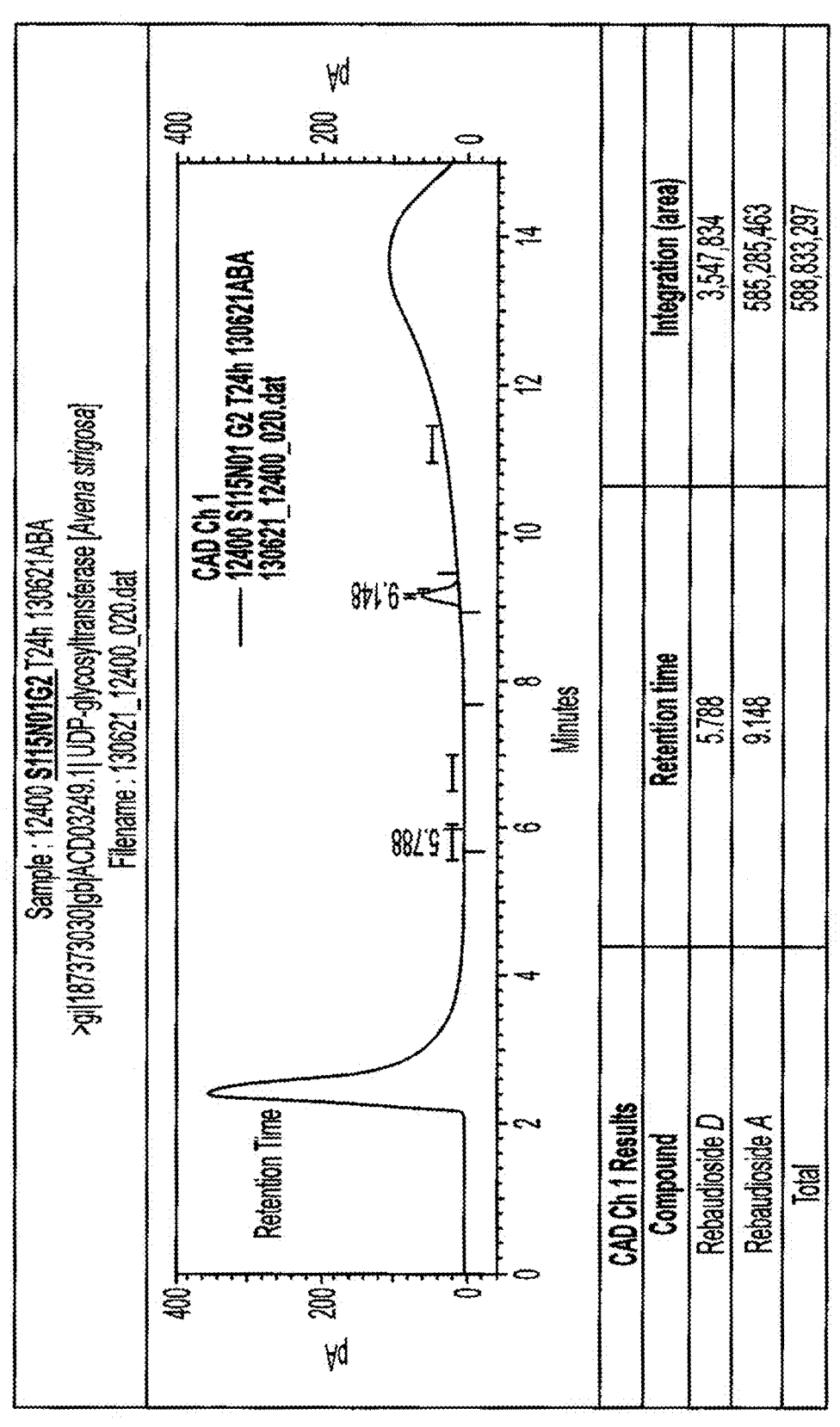
Figure 53C:
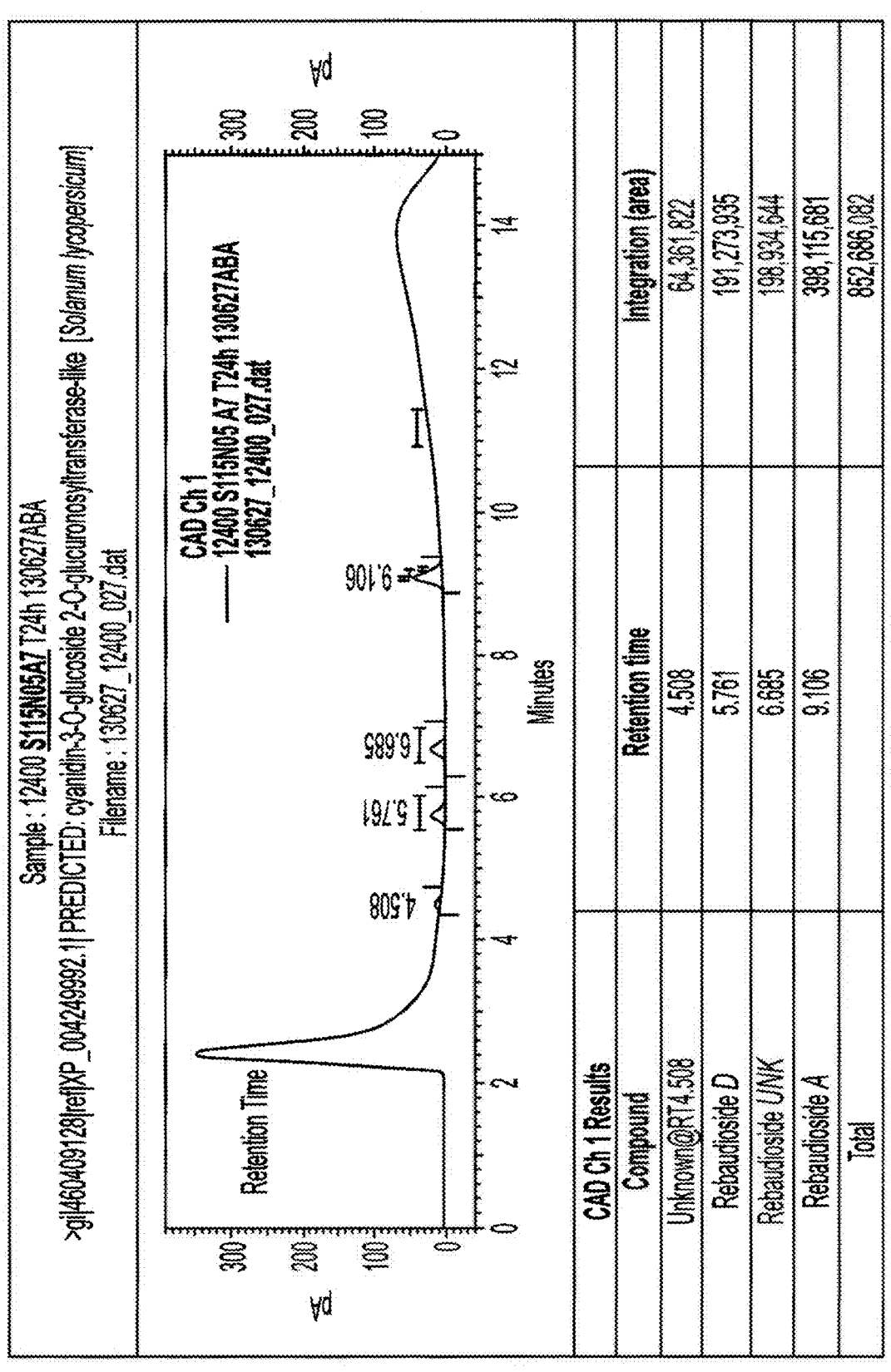
Figure 53D:
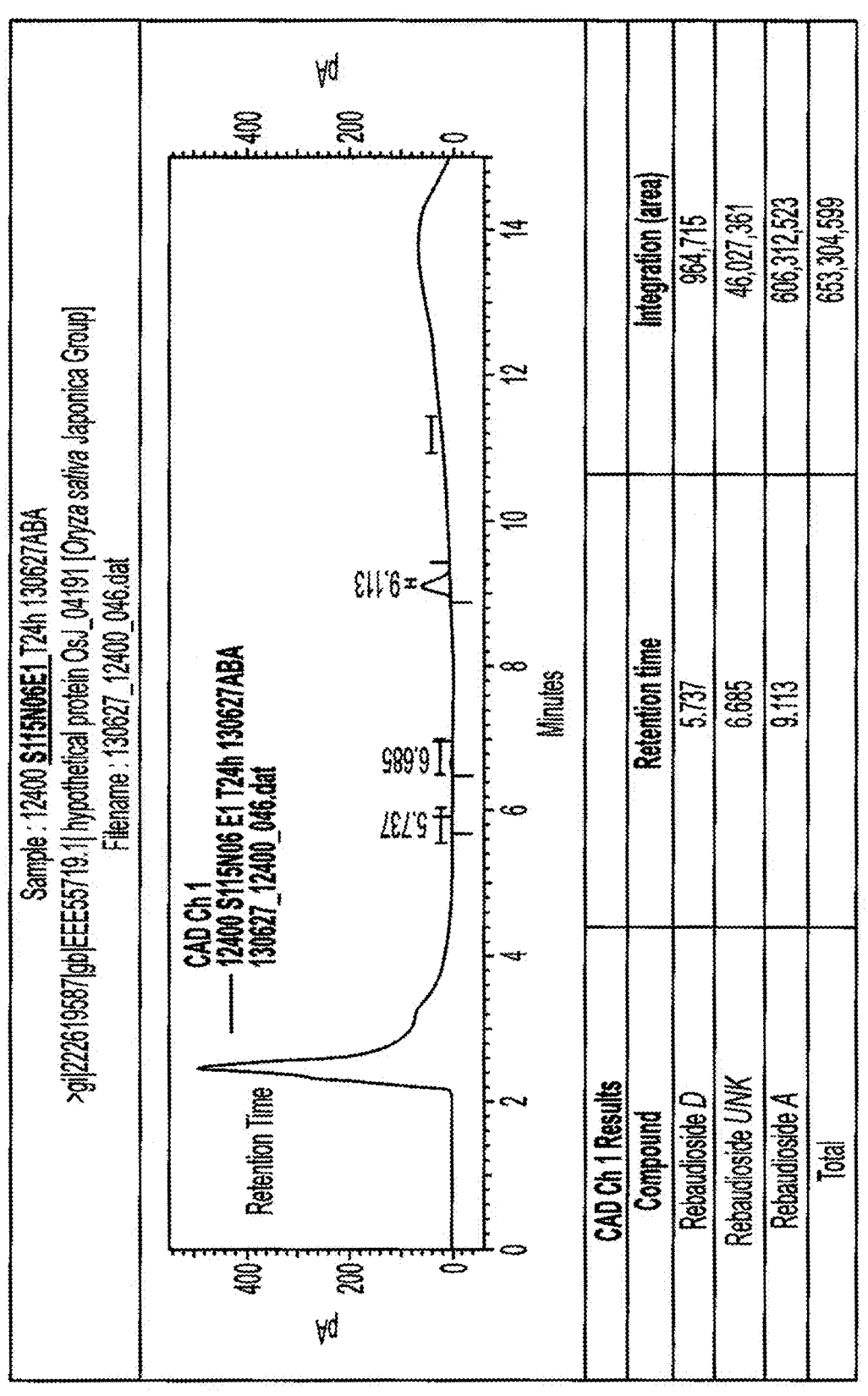
Figure 53E:
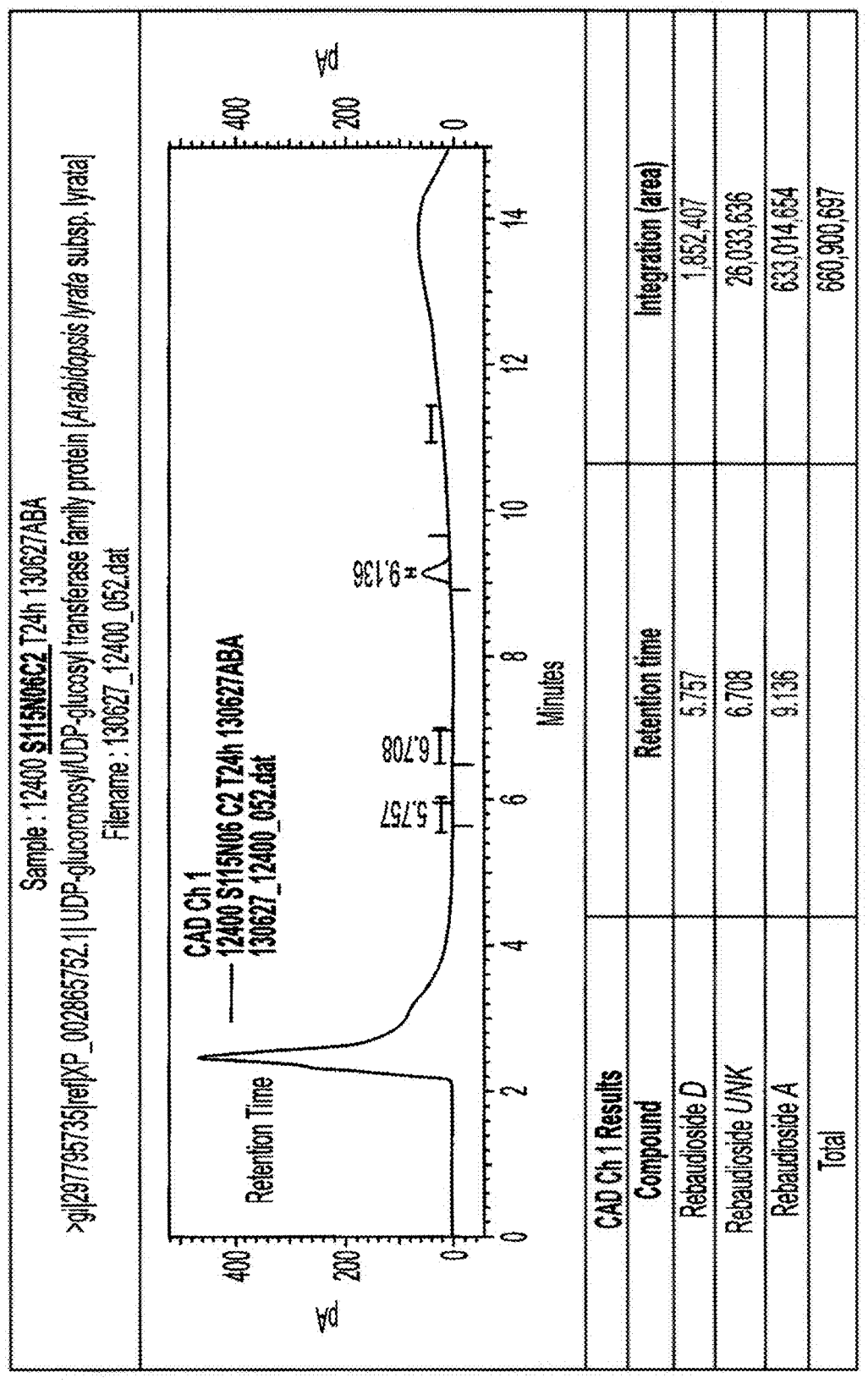

The total volume of the reaction was 2 mL with the following composition: 50 mM sodium phosphate buffer pH 7.2, 3 mM $MgCl_2$, 3.8 mM UDP-glucose, 0.5 mM Rebaudioside D and 180 µL of in-vitro produced UGT76G1. The reactions were run at 30° C. on an orbitary shaker at 135 rpm. For each sample, 400 µL of reaction mixture was quenched with 40 µL of 2N $H_2SO_4$ and 360 µL of 60% MeOH. After centrifugation, the supernatant was analyzed by HPLC (CAD). HPLC indicated 80% conversion of rebaudioside D to rebaudioside M after 120 h as shown in FIG. 52.

For examples 7 to 12, the following abbreviations were used:

LBGKP medium: 20 g/L Luria Broth Lennox; 50 mM PIPES buffer pH 7.00; 50 mM Phosphate buffer pH 7.00; 2.5 g/L glucose and 50 mg/L of Kanamycin or Ampicillin LB medium: (20 g/L Luria Broth Lennox)

Example 7

Preparation and Activity of UGT76G1 Prepared by pET30a+ Plasmid and BL21 (DE3) Expression Strain The pET30a+_UGT76G1 plasmid was transformed into BL21(DE3) expression strain (Lucigen E. Cloni® EXPRESS Electrocompetent Cells). The obtained cells were grown on LB Agar medium in petri-dishes in the presence of Kanamycin. Suitable colonies were selected and allowed to grow in liquid LBGKP medium containing Kanamycin. Glycerol was added and 400 μL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 20° C. while taking samples to measure the OD (600 nm) and pH. After 40 h, the cells were harvested by centrifugation and frozen. The obtained cell wet weight was 10.58 g.

3.24 g of obtained pellet was lysed by addition of 8.1 mL of "Bugbuster Master mix" (Novagen, reference 71456) and 3.5 mL of water. The lysate was recovered by centrifugation and kept frozen.

Example 8

Preparation and Activity of UGT76G1 Prepared by pET30a+ Plasmid and Tuner (DE3) Expression Strain The pET30a+_UGT76G1 plasmid was transformed into Tuner (DE3) expression strain (Novagen Tuner™ (DE3) Competent cells) by heat shock treatment. The obtained cells were grown on LB Agar medium in petri-dishes in the presence of Kanamycin. Suitable colonies were selected and allowed to grow in liquid LBGKP medium containing Kanamycin). Glycerol was added and 400 μL aliquots were stored at −20° C. and at −80° C.

A storage aliquot was thawed and added to 100 mL of LB medium containing 50 mg/L of Kanamycin. This culture allowed to shake at 30° C. for 15 h. 4.4 mL of this culture was used to inoculate 200 mL of production medium containing LB. This medium was allowed to stir at 37° C. until an OD (600 nm) of 0.9 was obtained, after which 400 μL of a 100 mM IPTG solution was added and the medium was allowed to stir at 30° C. for 4 h. The cells were harvested by centrifugation and frozen. The obtained cell wet weight was 1.38 g.

The obtained pellet was lysed by addition of 4.9 mL of "Bugbuster Master mix" (Novagen, reference 71456) and 2.1 mL of water. The lysate was recovered by centrifugation and kept frozen.

Example 9

Preparation and Activity of UGT76G1 Prepared by pMAL Plasmid and BL21 Expression Strain After subcloning the synthetic UGT76G1 gene into the pMAL plasmid using Nde1 and Sal1 cloning sites, the pMAL_UGT76G1 plasmid was transformed into BL21 expression strain (New England Biolabs BL21 Competent E. coli) by heat shock treatment. The obtained cells were grown on LB Agar medium in petri-dishes in the presence of Ampicillin. Suitable colonies were selected and allowed to grow in liquid LBGKP medium containing Ampicillin). Glycerol was added and 400 μL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. while taking samples to measure the OD and pH. After 40 h, the cells were harvested by centrifugation and frozen. The obtained cell wet weight was 5.86 g.

2.74 g of obtained pellet was lysed by addition of 9.6 mL of "Bugbuster Master Mix" (Novagen, reference 71456) and 4.1 mL of water. The lysate was recovered by centrifugation and kept frozen.

Example 10

Preparation and Activity of UGT76G1 Prepared by pMAL Plasmid and ArcticExpress Expression Strain The pMAL_UGT76G1 plasmid was transformed into ArticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing of Ampicillin and Geneticin. Glycerol was added and 400 μL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 12° C. while taking samples to measure the OD (600 nm) and pH. After 68 h, the cells were harvested by centrifugation and frozen. The obtained cell wet weight was 8.96 g.

2.47 g of the obtained pellet was lysed by addition of 8.73 mL of "Bugbuster Master Mix" (Novagen, reference 71456) and 3.79 mL of water. The lysate was recovered by centrifugation and kept frozen.

Example 11

Preparation and Activity of UGT76G1 Prepared by pCOL-DIII Plasmid and ArcticExpress Expression Strain After subcloning the synthetic UGT76G1 gene into the pCOLDIII plasmid using Nde1 and Xho1 cloning sites, the pCOLDIII_UGT76G1 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing Ampicillin and Geneticin. Glycerol was added and 400 μL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 12° C. while taking samples to measure the OD (600 nm) and pH. After 63 h, the cells were harvested by centrifugation and frozen. The obtained cell wet weight was 6.54 g.

2.81 g of the obtained pellet was lysed by addition of 9.8 mL of "Bugbuster Master Mix" (Novagen, reference 71456) and 4.2 mL of water. The lysate was recovered by centrifugation and kept frozen.

Example 12

Preparation and Activity of UGT76G1 Prepared by pCOL-DIII Plasmid and Origami2 (DE3) Expression Strain The pCOLDIII_UGT76G1 plasmid was transformed into Origami2 (DE3) expression strain (Novagen Origami™2 (DE3) Competent Cells) by heat shock treatment. The obtained cells were grown on LB Agar medium in petri-dishes in the presence of Ampicillin. Suitable colonies were selected and allowed to grow in liquid LBGKP medium containing Ampicillin. Glycerol was added and 400 µL aliquots were stored at –20° C. and at –80° C.

A storage aliquot was thawed and added to 30 mL of LBGKP medium (containing Ampicillin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 12° C. while taking samples to measure the OD (600 nm) and pH. After 68 h, the cells were harvested by centrifugation and frozen. The obtained cell wet weight was 2.53 g.

1.71 g of the obtained pellet was lysed by addition of 6.0 mL of "Bugbuster Master mix" (Novagen, reference 71456) and 1.9 mL of water. The lysate was recovered by centrifugation and kept frozen.

Example 13

Determination of Activity

Activity tests were performed on a 5 mL scale with 500 µL of thawed lysate for the transformation of Stevioside to Rebaudioside A and Rebaudioside D to Rebaudioside M using 0.5 mM of substrate, 2.5 mM of UDP-Glucose and 3 mM $MgCl_2$ in 50 mM Sodium Phosphate buffer at pH 7.2. Samples were taken and analyzed by HPLC. The results for the different preparations of UGT76G1 are summarized in the following table.

| | | | Transformation activity* | |
|---|---|---|---|---|
| Example | Plasmid | Expression strain | Stevioside to Rebaudioside A | Rebaudioside D to Rebaudioside M |
| 7 | pET30a+ | BL21 (DE3) | 29 U mL$^{-1}$ | 0.31 U mL$^{-1}$ |
| 8 | pET30a+ | Tuner (DE3) | 33 U mL$^{-1}$ | 0.40 U mL$^{-1}$ |
| 9 | pMAL | BL21 | 20 U mL$^{-1}$ | 0.15 U mL$^{-1}$ |
| 10 | pMAL | ArcticExpress | 15 U mL$^{-1}$ | 0.25 U mL$^{-1}$ |
| 11 | pCOLDIII | ArcticExpress | 15 U mL$^{-1}$ | 0.11 U mL$^{-1}$ |
| 12 | pCOLDIII | Origami2 (DE3) | 37 U mL$^{-1}$ | 0.20 U mL$^{-1}$ |

*Note
The activities for the transformation of Stevioside and Rebaudioside M are mentioned per mL of lysate. 1 U will transform 1 µmol of substance in 1 hour at 30° C. and pH 7.2

Example 14

50 mL Scale Reaction for the Transformation of Rebaudioside D to Rebaudioside M 5 mL of the lysate of Example 12 was used to transform Rebaudioside D to Rebaudioside M on a 50 mL scale. The reaction medium consisted of 50 mM Sodium Phosphate buffer pH 7.2, 3 mM of $MgCl_2$, 2.5 mM of UDP-Glucose and 0.5 mM of Rebaudioside D. After allowing the reaction to be shaken at 30° C. for 90 h. 50 mL of ethanol was added and the resulting mixture was allowed to stir at –20° C. for 1 h. After centrifugation at 5000 g for 10 min. the supernatant was purified via ultrafiltration (Vivaflow MWCO 30000). 78 mL of permeate was obtained and the 9 mL of retentate was diluted with 9 mL of ethanol and resubjected to Ultrafiltration (Vivaflow MWCO 30000). Another 14 mL of filtrate was obtained, which was combined with the first permeate. The combined permeates were concentrated under reduced pressure at 30° C. until 32 mL of a clear solution was obtained.

Figure 5:
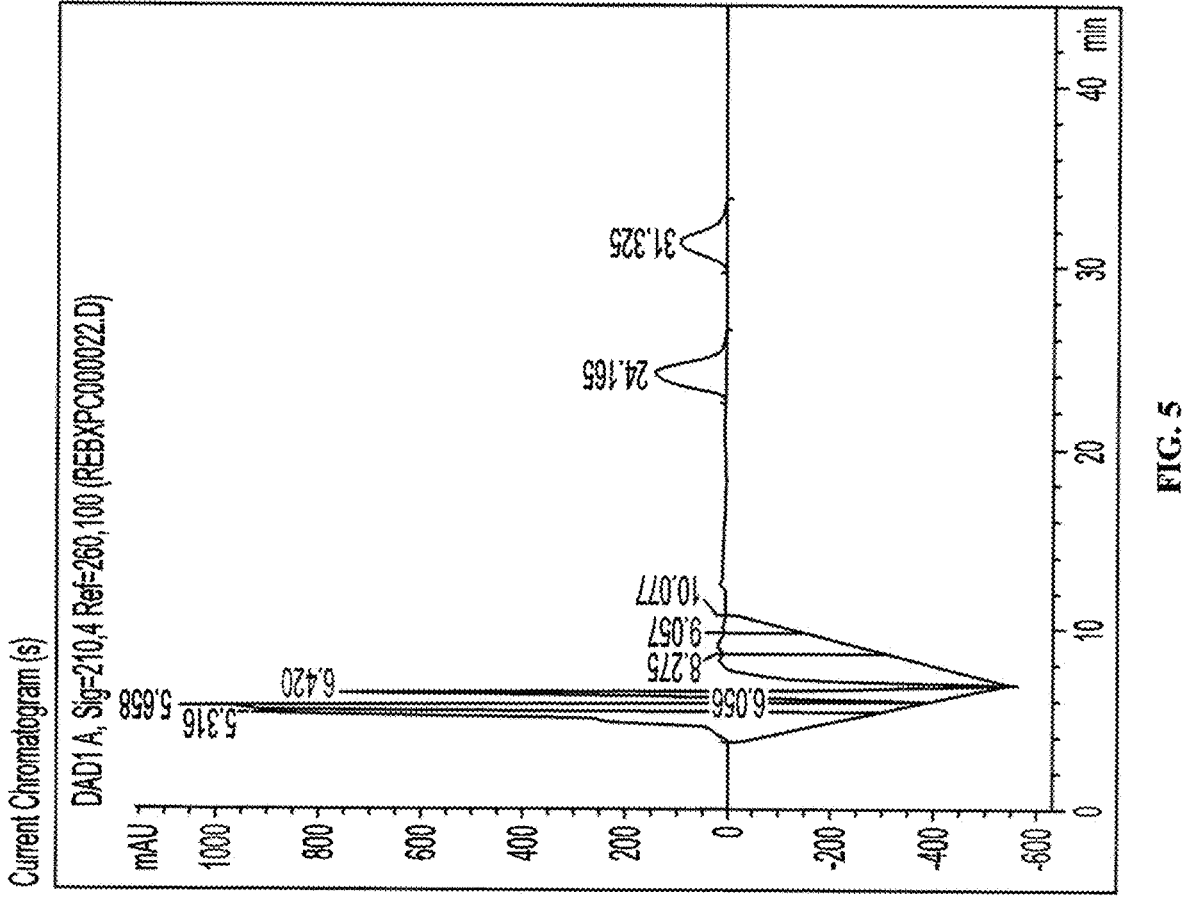
FIG. 5. shows the HPLC chromatogram of the product of the biocatalytic production of reb M from reb D, as detailed in Example 14. The peak with retention time of 24.165 minutes corresponds to unreacted reb D. The peak with retention time of 31.325 minutes corresponds to reb M.

The HPLC trace of the product mixture is shown in FIG. 5. HPLC was carried out on an Agilent 1200 series equipped with a binary pump, auto sampler, and thermostat column compartment. The method was isocratic, with a mobile phase composed of 70% water (0.1% formic acid): 30% acetonitrile. The flow rate was 0.1 µL/min. The column used was Phenomenex Prodigy 5 ODS (3) 100 A; 250×2 mm. The column temperature was maintained at 40° C. The injection volume was 20-40 µl.

Example 15

Preparation of UGT91D2 Using pMAL Plasmid and BL21 Expression Strain

After subcloning the synthetic UGT91D2 gene into the pMAL plasmid using Nde1 and Sal1 cloning sites, the pMAL_UGT91D2 plasmid was transformed into BL21 expression strain (New England Biolabs BL21 Competent E. coli) by heat shock treatment. The obtained cells were grown on LB Agar medium in petri-dishes in the presence of Ampicillin. Suitable colonies were selected and allowed to grow in liquid LBGKP medium containing Ampicillin). Glycerol was added and 400 µL aliquots were stored at –20° C. and at –80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. while taking samples to measure the OD and pH. After 40 h, the cells were harvested by centrifugation and frozen. The obtained cell wet weight is 12.32 g.

2.18 g of obtained pellet was lysed by addition of 7.7 mL of "Bugbuster Master Mix" (Novagen, reference 71456) and 3.2 mL of water. The lysate was recovered by centrifugation and used directly for activity testing.

Example 16

Preparation of UGT91D2 Using pMAL Plasmid and ArcticExpress Expression Strain

The pMAL_UGT91D2 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing Ampicillin and Geneticin. Glycerol was added and 400 µL aliquots were stored at –20° C. and at –80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. for 16 h. followed by another 50 h. at 12° C. while taking samples to measure the OD (600 nm) and pH. The cells were harvested by centrifugation and frozen. The obtained cell wet weight is 15.77 g.

2.57 g of the obtained pellet was lysed by addition of 9.0 mL of "Bugbuster Master Mix" (Novagen, reference 71456) and 3.8 mL of water. The lysate was recovered by centrifugation and used directly for activity testing.

Example 17

Preparation of UGT91D2 Using pET30a+ Plasmid and Tuner (DE3) Expression Strain

The pET30a+_UGT91D2 plasmid was transformed into Tuner (DE3) expression strain (Novagen Tuner™ (DE3) Competent cells) by heat shock treatment. The obtained cells were grown on LB Agar medium in petri-dishes in the presence of Kanamycin. Suitable colonies were selected and allowed to grow in liquid LBGKP medium (containing Kanamycin). Glycerol was added and 400 µL aliquots were stored at −20° C. and at −80° C.

A storage aliquot was thawed and added to 100 mL of LB medium containing 50 mg/L of Kanamycin. This culture allowed to shake at 30° C. for 15 h. 6.2 mL of this culture was used to inoculate 500 mL of production medium containing LB. This medium was allowed to stir at 37° C. until an OD (600 nm) of 0.9 was obtained after which 500 µL of a 100 mM IPTG solution was added (IPTG concentration in medium is 100 µM) and the medium was allowed to stir at 30° C. for 4 h, the cells were harvested by centrifugation and frozen. The obtained cell wet weight is 4.02 g.

1.92 g of the obtained pellet was lysed by addition of 6.8 mL of "Bugbuster Master mix" (Novagen, reference 71456) and 2.8 mL of water. The lysate was recovered by centrifugation and tested directly for activity.

Example 18

Preparation of UGT91D2 Using pET30a+ Plasmid and ArcticExpress Expression Strain The pET30a+_UGT91D2 plasmid was transformed into ArcticExpress (DE3) expression strain (Agilent ArcticExpress competent cells) by heat shock treatment. The obtained cells were grown on LB Agar medium in petri-dishes in the presence of Kanamycin and Geneticin. Suitable colonies were selected and allowed to grow in liquid LBGKP medium containing of Kanamycin and Geneticin. Glycerol was added and 400 µL aliquots were stored at −20° C. and at −80° C.

A storage aliquot was thawed and added to 30 mL of LBGKP medium (containing Kanamycin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. for 16 h. followed by another 50 h. at 12° C. while taking samples to measure the OD (600 nm) and pH. After 60 h, the cells were harvested by centrifugation and frozen. The obtained cell wet weight is 16.07 g.

3.24 g of the obtained pellet was lysed by addition of 11.4 mL of "Bugbuster Master Mix" (Novagen, reference 71456)

and 4.8 mL of water. The lysate was recovered by centrifugation and used directly for activity testing.

Example 19

Determination of Activity of In-Vivo Preparations of UGT91D2

Activity tests were performed at 5 mL scale with 1000 µL of lysate for the transformation of Rubusoside to Stevioside using 0.5 mM of substrate, 2.5 mM of UDP-Glucose and 3 mM $MgCl_2$ in 50 mM Sodium Phosphate buffer at pH 7.2. Samples were taken and analyzed by HPLC. The results for the different preparations of UGT91D2 are summarized in the following table.

| Example | Plasmid | Expression strain | Transformation activity* Rubusoside to Stevioside |
|---|---|---|---|
| 15 | pMAL | BL21 | 9 mU mL$^{-1}$ |
| 16 | pMAL | ArcticExpress | 60 mU mL$^{-1}$ |
| 17 | pET30a+ | Tuner (DE3) | 28 mU mL$^{-1}$ |
| 18 | pET30a+ | ArcticExpress (DE3) | 21 mU mL$^{-1}$ |

*Note:

The activities are mentioned per mL of lysate. 1 U will transform 1 µmol of substrate in 1 hour at 30° C. and pH 7.2

Example 20

Other Enzymes for Rebaudioside A to Rebaudioside D Conversion

The following genes of UDP-glucosyltransferases were identified from public databases, synthesized by DNA2.0 and subsequently subcloned in pET30a+ vector.

| Microplate | Position | Gene Name | Internal reference | Conversion RebA to RebD |
|---|---|---|---|---|
| C908201 | A1 | gi115454819_NP_ 001051010.1 | S115N01 A1 | Active |
| C908201 | G2 | gi187373030_ ACD03249.1 | S115N01 G2 | Active |
| C908201 | A7 | gi460409128_XP_ 004249992.1 | S115N05 A7 | Active |
| C912666 | E1 | gi222619587_ EEE55719.1 | S115N06 E1 | Active |
| C912666 | C2 | gi297795735_XP_ 002865752.1 | S115N06 C2 | Active |

The amino acid sequences are as follows:

SEQ ID NO: 3:
MDDAHSSQSPLHVVIFPWLAFGHLLPCLDLAERLAARGHRVSFVSTPRNL

ARLPPVRPELAELVDLVALPLPRVDGLPDGAEATSDVPFDKFELHRKAFD

GLAAPFSAFLDTACAGGKRPDWVLADLMHHWVALASQERGVPCAMILPCS

AAVVASSAPPTESSADQREAIVRSMGTAAPSFEAKRATEEFATEGASGVS

IMTRYSLTLQRSKLVAMRSCPELEPGAFTILTRFYGKPVVPFGLLPPRPD

GARGVSKNGKHDAIMQWLDAQPAKSVVYVALGSEAPMSADLLRELAHGLD

-continued

LAGTRFLWAMRKPAGVDADSVLPAGFLGRTGERGLVTTRWAPQVSILAHA

AVCAFLTHCGWGSVVEGLQFGHPLIMLPILGDQGPNARILEGRKLGVAVP

RNDEDGSFDRGGVAGAVRAVVVEEEGKTFFANARKLQEIVADREREERCI

DEFVQHLTSWNELKNNSDGQYP

SEQ ID NO: 4:
MAVKDEQQSPLHILLFPPFLAPGHLIPIADMAALFASRGVRCTILTTPVNA

AIIRSAVDRANDAFRGSDCPAIDISVVPFPDVGLPPGVENGNALTSPADR

LKFFQAVAELREPFDRFLADNHPDAVVSDSFFHWSTDAAAEHGVPRLGFL

GSSMFAGSCNESTLHNNPLETAADDPDALVSLPGLPHRVELRRSQMMDPK

KRPDHWALLESVNAADQKSFGEVFNSFHELEPDYVEHYQTTLGRRTWLVG

PVALASKDMAGRGSTSARSPDADSCLRWLDTKQPGSVVYVSFGTLIRFSP

AELHELARGLDLSGKNFVWVLGRAGPDSSEWMPQGFADLITPRGDRGFII

RGWAPQMLILNHRALGGFVTHCGWNSTLESVSAGVPMVTWPRFADQFQNE

KLIVEVLKVGVSIGAKDYGSGIENHDVIRGEVIAESIGKLMGSSEESDAI

QRKAKDLGAEARSAVENGGSSYNDVGRLMDELMARRSSVKVGEDIIPTND

GL

SEQ ID NO: 5:
MSPKLHKELFFHSLYKKTRSNHTMATLKVLMFPFLAYGHISPYLNVAKKL

ADRGFLIYFCSTPINLKSTIEKIPEKYADSIHLIELHLPELPQLPPHYHT

TNGLPPNLNQVLQKALKMSKPNFSKILQNLKPDLVIYDILQRWAKHVANE

QNIPAVKLLTSGAAVFSYFFNVLKKPGVEFPFPGIYLRKIEQVRLSEMMS

KSDKEKELEDDDDDDDLLVDGNMQIMLMSTSRTIEAKYIDFCTALTNWKV

VPVGPPVQDLITNDVDDMELIDWLGTKDENSTVFVSFGSEYFLSKEDMEE

VAFALELSNVNFIWVARFPKGEERNLEDALPKGFLERIGERGRVLDKFAP

QPRILNHPSTGGFISHCGWNSAMESIDFGVPIIAMPMHLDQPMNARLIVE

LGVAVEIVRDDDGKIHRGEIAETLKGVITGKTGEKLRAKVRDISKNLKTI

RDEEMDAAAEELIQLCRNGN

SEQ ID NO: 6:
MHVVMLPWLAFGHILPFAEFAKRVARQGHRVTLFSTPRNTRRLIDVPPSL

AGRIRVVDIPLPRVEHLPEHAEATIDLPSNDLRPYLRRAYDEAFSRELSR

LLQETGPSRPDWVLADYAAYWAPAAASRHGVPCAFLSLFGAAALCFFGPA

ETLQGRGPYAKTEPAHLTAVPEYVPFPTTVAFRGNEARELFKPSLIPDES

GVSESYRFSQSIEGCQLVAVRSNQEFEPEWLELLGELYQKPVIPIGMFPP

PPPQDVAGHEETLRWLDRQEPNSVVYAAFGSEVKLTAEQLQRIALGLEAS

ELPFIWAFRAPPDAGDGDGLPGGFKERVNGRGVVCRGWVPQVKFLAHASV

GGFLTHAGWNSIAEGLANGVRLVLLPLMFEQGLNARQLAEKKVAVEVARD

EDDGSFAANDIVDALRRVMVGEEGDEFGVKVKELAKVFGDDEVNDRYVRD

FLKCLSEYKMQRQG

SEQ ID NO: 7:
MDDKKEEVMHIAMFPWLAMGHLLPFLRLSKLLAQKGHKISFISTPRNILR

LPKLPSNLSSSITFVSFPLPSISGLPPSSESSMDVPYNKQQSLKAAFDLL

QPPLTEFLRLSSPDWIIYDYASHWLPSIAKELGISKAFFSLFNAATLCFM

GPSSSLIEESRSTPEDFTVVPPWVPFKSTIVFRYHEVSRYVEKTDEDVTG

VSDSVRFGYTIDGSDAVFVRSCPEFEPEWFSLLQDLYRKPVFPIGFLPPV

IEDDDDDTTWVRIKEWLDKQRVNSVVYVSLGTEASLRREELTELALGLEK

SETPFFWVLRNEPQIPDGFEERVKGRGMVHVGWVPQVKILSHESVGGFLT

HCGWNSVVEGIGFGKVPIFLPVLNEQGLNTRLLQGKGLGVEVLRDERDGS

FGSDSVADSVRLVMIDDAGEEIREKVKLMKGLFGNMDENIRYVDELVGFM

RNDESSQLKEEEEEDDCSDDQSSEVSSETDEKELNLDLKEEKRRISVYKS

LSSEFDDYVANEKMG

The tested plasmids were received in a microtiterplate containing a plasmid as freeze-dried solid in each separate well.

Suspension of plasmids. To each well was added 24 µL of ultra-pure sterile water and the microtiter plate was shaken for 30 minutes at Room Temperature. Subsequently, the plate was incubated at 4° C. for 1 hour. The content of each well were further mixed by pipetting up and down. The plasmid quantification was performed by Qubit2.0 analysis using 1 µL of suspension. Determined quantities of plasmids were:

| Microtiter plate | Position | Internal reference | [Plasmid] ng/µL |
|---|---|---|---|
| C908201 | A1 | S115N01 A1 | 32.8 |
| C908201 | G2 | S115N01 G2 | 41.0 |
| C908201 | A7 | S115N05 A7 | 56.6 |
| C912666 | E1 | S115N06 E1 | 64.0 |
| C912666 | C2 | S115N06 C2 | 31.4 |

Transformation of competent cells with plasmids. Aliquots of chemically competent EC100 cells were taken from freezer at −80° C. and stored on ice. The cells were allowed to thaw on ice for 10 minutes. 10 µL of a dilution of above described plasmid solution was added to a sterile microtube of 1.5 mL (in order to transform each cell with 50 pg of DNA) and stored on ice. 100 µL of chemically competent cells was added to each microtube. After incubation of the chemically competent cells plasmid mixtures on ice for 20 min a thermal shock of 30 seconds at 42° C. was performed.

Further incubation was performed on ice for 2 minutes. To each microtube 300 µL of SOC medium was added and the resulting mixture was transferred to a sterile 15 mL tube. After incubate for 1 hour at 37° C. while shaking at 135 rpm, the mixture is spread on solid Luria Broth medium containing Kanamycin 50 µg/mL. The petri-dishes are allowed to incubate for 16 hours at 37° C.

Preparation of stock solutions in glycerol and purification of plasmids. To a 50 mL sterile Falcon Tube 10 mL of Luria Broth medium containing 50 µg/mL of Kanamycin was added. The medium was seeded with an isolated colony from the above described Petri dish and the cultures were allowed to incubate for 16 hours at 37° C. while shaking at 135 rpm.

To sterile microtube of 1.5 mL containing 300 µL of a 60% sterile glycerol solution, 600 µL of the culture was added. The stock solution was stored at −80° C.

The remainder of the culture was centrifuged at 5,525 g for 10 minutes at 10° C. and after removal of the supernatant, the pellet was stored on ice. The produced plasmids were purified according to the Qiagen Qiaprep Spin Miniprep kit (ref: 27106) and the plasmid yield was measured at 260 nm. The plasmid solution was stored at 4° C. Plasmid quantities were determined as follows:

| Microtiter plate | Position | Internal reference of test | [Plasmid] ng/µL |
|---|---|---|---|
| C908201 | A1 | S115N01 A1 | 115.7 |
| C908201 | G2 | S115N01 G2 | 120.4 |
| C908201 | A7 | S115N05 A7 | 293.8 |
| C912666 | E1 | S115N06 E1 | 126.1 |
| C912666 | C2 | S115N06 C2 | 98.8 |

In-vitro Expression of enzymes. 18 µL of plasmid solution (containing approximately 1.5 µg of plasmid) was used for in-vitro expression according to the Promega S30 T7 High-Yield Protein Expression System (ref: L1110) kit. The expression medium was produced as follows:

|  | S30 Premix Plus | T7 S30 Extract | Total |
|---|---|---|---|
| Trials | 30 µL | 27 µL | 57 µL |
| reference | 20 µL | 18 µL | 38 µL |

The prepared expression medium mix was added to the plasmid solution and the solution was allowed to incubate at 30° C. for 3 hours while mixing the mixture every 45 minutes. 5 µL of the mixture was frozen whereas the remainder was used for the catalytic test for the conversion of Rebaudioside A to Rebaudioside D.

Catalytic test for transformation of Rebaudioside A to Rebaudioside D. 430 µL of a reaction mixture containing 0.5 mM Rebaudioside A, 3 mM MgCl$_2$, 50 mM phosphate buffer (pH7.2) and 2.5 mM UDP-glucose was added to a 1.5 mL sterile microtube. 52 µL of the enzyme expression medium was added and the resulting mixture was allowed to react at 30° C. for 24 hours. 125 µL samples were taken after 2 hours, 16 hours and 24 hours and added to a 115 µL of 60% methanol and 10 µL of 2 N H$_2$SO$_4$. The quenched sample was centrifuged at 18,000 g for 2 minutes at RT. 200 µL was transferred to an HPLC vial and analyzed.

HPLC Analysis The HPLC assay was performed as follows:

Apparatus

| Equipment | Supplier | Reference | Lot# |
|---|---|---|---|
| Elite | Hitachi | L-2130 | NA |
| Photodiode Array | Hitachi | L-2455 | NA |
| Corona CAD detector | ESA | 70-6186A | CO-2044 |
| Injector 100 µL | Hitachi |  | NA |
| Column Synergy 4 u Hydro-RP 80A (250 × 4.60 mm) | Phenomenex | 00G-4375-E0 | 588582-12 |

Instrument Conditions

| Column Temperature | 55° C. |
| Detection | UV 205 nm; bw 400 nm CAD detection |

-continued

| Analysis duration | 15 min |
| Injected volume | 10 µL |
| Flow rate | 1 mL/min |

Mobile Phase Gradient Program

| Time (min) | % Water containing 0.04% acetic acid | % methanol |
|---|---|---|
| 0 | 40 | 60 |
| 8 | 25 | 75 |
| 10 | 25 | 75 |
| 11 | 40 | 60 |
| 15 | 40 | 60 |

The HPLC assay results are provided below and shown in FIGS. 53a-e:

| Internal reference | Steviol glycoside conversion in reaction mixture (% area) | | |
|---|---|---|---|
|  | Reb D | Reb UNK | Reb A |
| S115N01 A1 | 2.1 | ND | 96.7 |
| S115N01 G2 | 0.6 | ND | 99.4 |
| S115N05 A7 | 22.4 | 23.3 | 46.7 |
| S115N06 E1 | 0.14 | 7.0 | 92.8 |
| S115N06 C2 | 0.28 | 3.9 | 95.8 |

The enzyme S115N05 A7 had the highest activity for Reb A to Reb D conversion (ca. 22.4%)

At least three enzymes produced a significant amount of an unknown glycoside (marked as Reb UNK; later identified as reb D2) along with reb D.

Example 21

Activity of In-Vitro Produced EUGT11

EUGT11 gene as was described in the Patent application WO/2013/022989A2 was synthesized by DNA2.0 and subsequently subcloned in pET30a+ vector.

| Micro-plate | Posi-tion | GI number | Version | Internal reference | Conversion RebA to RebD |
|---|---|---|---|---|---|
| C912666 | G4 | 41469452 | AAS07253.1 | S115N08 G4 | Active |

The amino-acid sequence is as follows:
>gi|41469452|gb|AAS07253.1| putative UDP-glucoronosyl and UDP-glucosyl transferase [*Oryza sativa japonica* Group] EUGT11 enzyme from patent application WO/2013/022989A2

SEQ ID NO: 8:
MHVVICPLLAFGHLLPCLDLAQRLACGHRVSFVSTPRNISRLPPVRPSLA

PLVSFVALPLPRVEGLPNGAESTHNVPHDRPDMVELHLRAFDGLAAPFSE

FLGTACADWVMPTSSAPRQTLSSNIHRNSSRPGTPAPSGRLLCPITPHSN

TLERAAEKLVRSSRQNARARSLLAFTSPPLPYRDVFRSLLGLQMGRKQLN

IAHETNGRRTGTLPLNLCRWMWKQRRCGKLRPSDVEFNTSRSNEAISPIG

ASLVNLQSIQSPNPRAVLPIASSGVRAVFIGRARTSTPTPPHAKPARSAA

-continued

```
PRAHRPPSSVMDSGYSSSYAAAAGMHVVICPWLAFGHLLPCLDLAQRLAS

RGHRVSFVSTPRNISRLPPVRPALAPLVAFVALPLPRVEGLPDGAESTND

VPHDRPDMVELHRRAFDGLAAPFSEFLGTACADWVIVDVFHHWAAAAALE

HKVPCAMMLLGSAHMIASIADRRLERAETESPAAAGQGRPAAAPTFEVAR

MKLIRTKGSSGMSLAERFSLTLSRSSLVVGRSCVEFEPETVPLLSTLRGK

PITFLGLMPPLHEGRREDGEDATVRWLDAQPAKSVVYVALGSEVPLGVEK

VHELALGLELAGTRFLWALRKPTGVSDADLLPAGFEERTRGRGVVATRWV

PQMSILAHAAVGAFLTHCGWNSTIEGLMFGHPLIMLPIFGDQGPNARLIE

AKNAGLQVARNDGDGSFDREGVAAAIRAVAVEEESSKVFQAKAKKLQEIV

ADMACHERYIDGFIQQLRSYKD
```

The tested plasmid was received in a microtiterplate containing a plasmid as freeze-dried solid in a separate well.

Suspension of plasmid To the well was added 24 μL of ultra-pure sterile water and the microtiter plate was shaken for 30 minutes at Room Temperature. Subsequently, the plate was incubated at 4° C. for 1 hour. The content of the well was further mixed by pipetting up and down. The plasmid quantification was performed by Qubit2.0 analysis using 1 μL of suspension. Plasmid quantity was determined as follows:

| Microtiter plate | Position | Internal reference of test | [Plasmid] ng/μL |
|---|---|---|---|
| C912666 | G4 | S115N08 G4 | 19.2 |

Transformation of competent cells with plasmid. An aliquot of chemically competent EC100 cells was taken from freezer at −80° C. and stored on ice. The cells were allowed to thaw on ice for 10 minutes. 10 μL of a dilution of above described plasmid solution was added to a sterile microtube of 1.5 mL (in order to transform each cell with 50 pg of DNA) and stored on ice. 100 μL of chemically competent cells was added to the microtube. After incubation of the chemically competent cells/plasmid mixture on ice for 20 min a thermal shock of 30 seconds at 42° C. was performed.

Further incubation was performed on ice for 2 minutes. To the microtube 300 μL of SOC medium was added and the resulting mixture was transferred to a sterile 15 mL tube. After incubate for 1 hour at 37° C. while shaking at 135 rpm, the mixture is spread on solid Luria Broth medium containing Kanamycin 50 μg/mL. The Petri dish is allowed to incubate for 16 hours at 37° C.

Preparation of stock solutions in glycerol and purification of plasmid. To a 50 mL sterile Falcon Tube 10 mL of Luria Broth medium containing 50 μg/mL of Kanamycin was added. The medium was seeded with an isolated colony from the above described Petri dish and the cultures were allowed to incubate for 16 hours at 37° C. while shaking at 135 rpm.

To sterile microtube of 1.5 mL containing 300 μL of a 60% sterile glycerol solution, 600 μL of the culture was added. The stock solution was stored at −80° C.

The remainder of the culture was centrifuged at 5,525 g for 10 minutes at 10° C. and after removal of the supernatant, the pellet was stored on ice. The produced plasmids were purified according to the Qiagen Qiaprep Spin Miniprep kit (ref: 27106) and the plasmid yield was measured at 260 nm. The plasmid solution was stored at 4° C. Plasmid quantity was determined as follows: PGP-51T1

| Microtiter plate | Position | Internal reference of test | [Plasmid] ng/μL |
|---|---|---|---|
| C912666 | G4 | S115N08 G4 | 38.4 |

In-vitro Expression of EUGT11. 18 μL of a diluted plasmid solution (containing approximately 1.5 μg of plasmid) was used for in-vitro expression according to the Promega S30 T7 High-Yield Protein Expression System (ref: L1110) kit. The expression medium was produced as follows:

| | S30 Premix Plus | T7 S30 Extract | DNA template | Total |
|---|---|---|---|---|
| Trials | 30 μL | 27 μL | 18 μL (~1.5 μg) | 75 μL |
| reference | 20 μL | 18 μL | 12 μL (~1.0 μg) | 50 μL |

The prepared expression medium mix was added to the plasmid solution and the solution was allowed to incubate at 30° C. for 3 hours while mixing the mixture every 45 minutes. 5 μL of the mixture was frozen whereas the remainder was used for the catalytic test for the conversion of Rebaudioside A to Rebaudioside D.

Catalytic test for transformation of Rebaudioside A to Rebaudioside D. 430 μL of a reaction mixture containing 0.5 mM Rebaudioside A, 3 mM MgCl$_2$, 50 mM phosphate buffer (pH7.2) and 2.5 mM UDP-glucose was added to a 1.5 mL sterile microtube. 52 μL of the enzyme expression medium was added and the resulting mixture was allowed to react at 30° C. for 24 hours. 125 μL samples were taken after 2 hours, 16 hours and 24 hours and added to a 115 μL of 60% methanol and 10 μL of 2 N H$_2$SO$_4$. The quenched sample was centrifuged at 18,000 g for 2 minutes at RT. 200 μL was transferred to HPLC vial and analyzed.

HPLC Analysis. The HPLC assay was performed as described in EXAMPLE 20.

Figure 54:
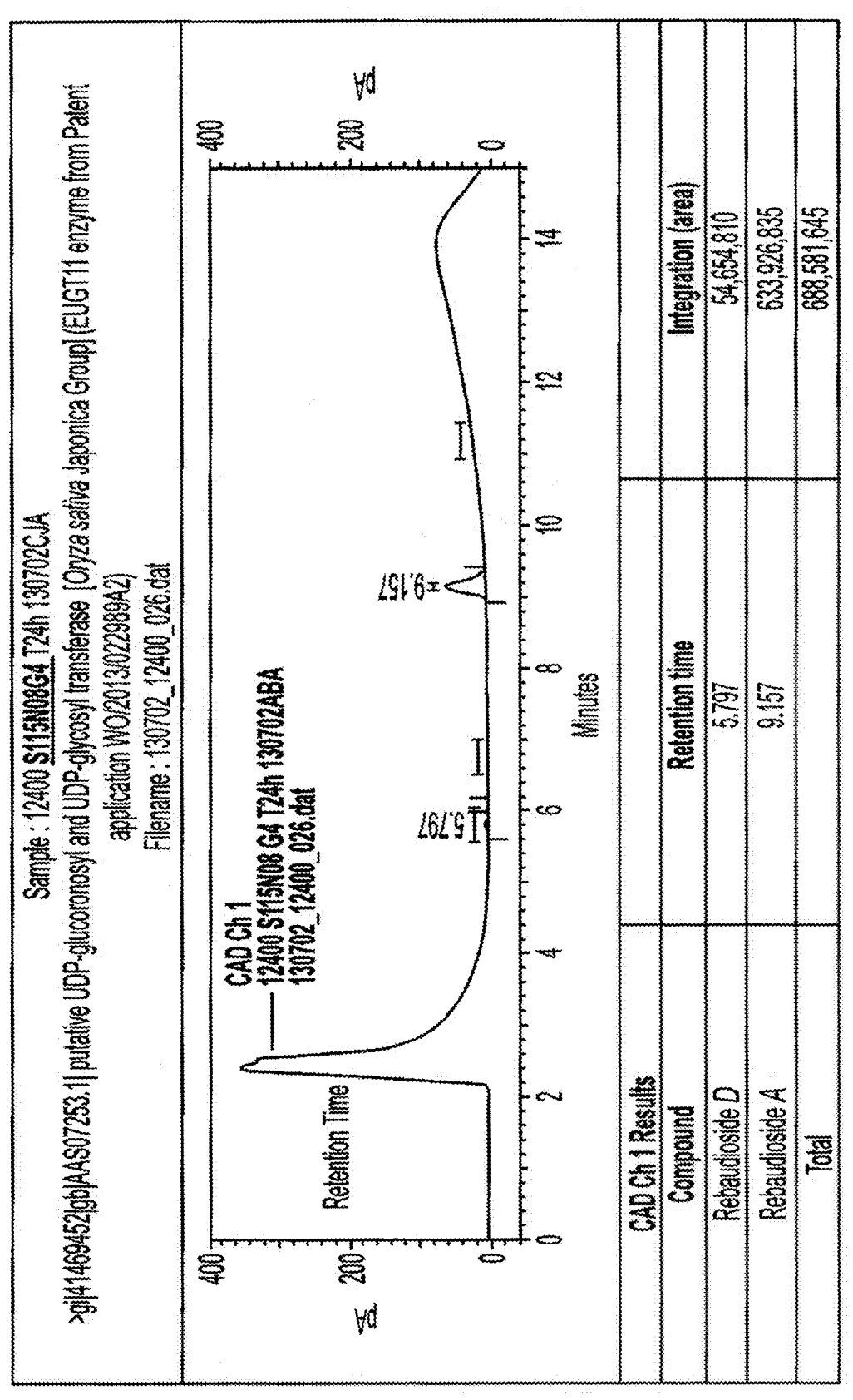
FIG. 54 shows an HPLC chromatogram showing the HPLC assay results for Example 21.
Figure 55A:
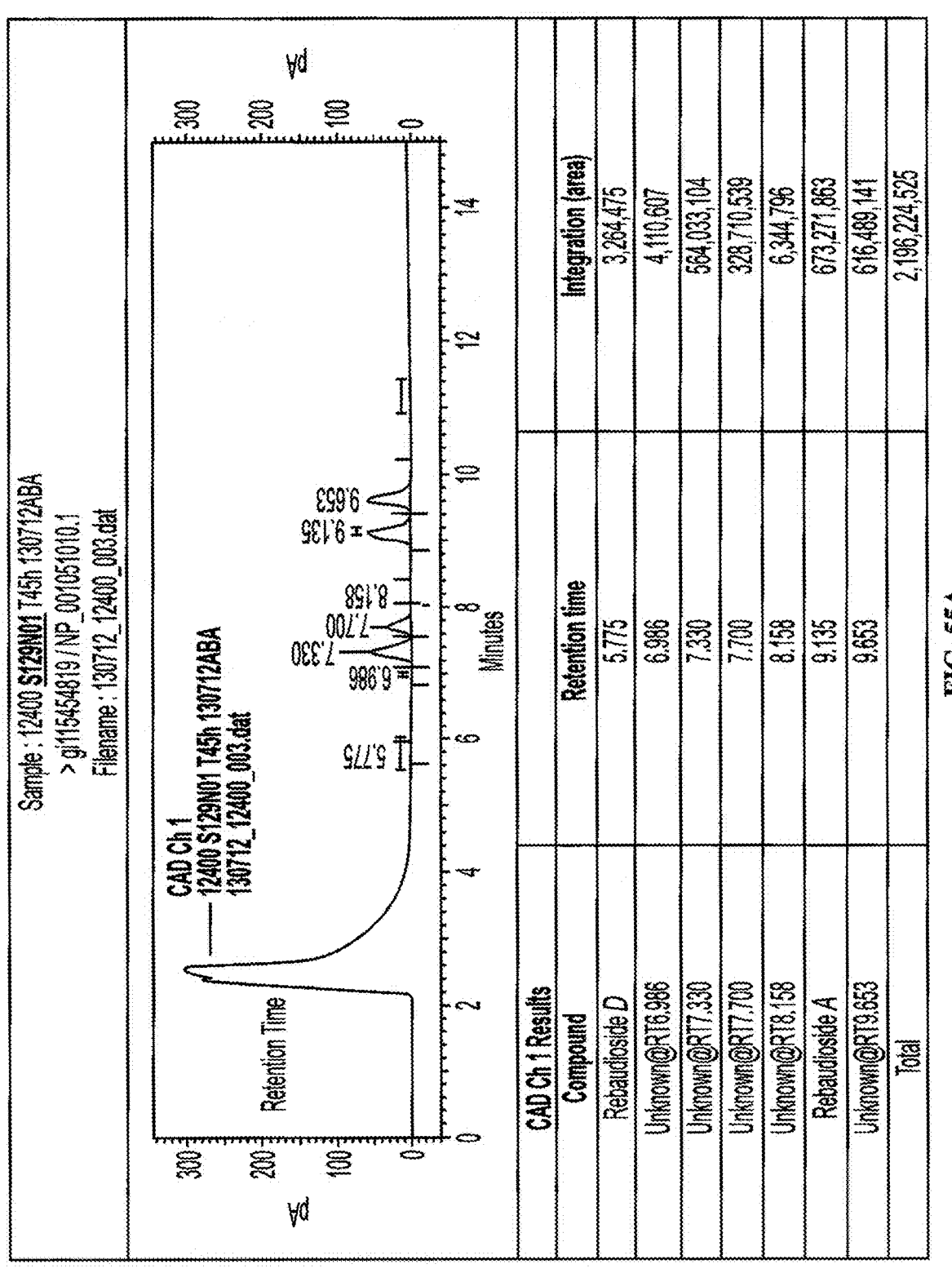
Figure 55B:
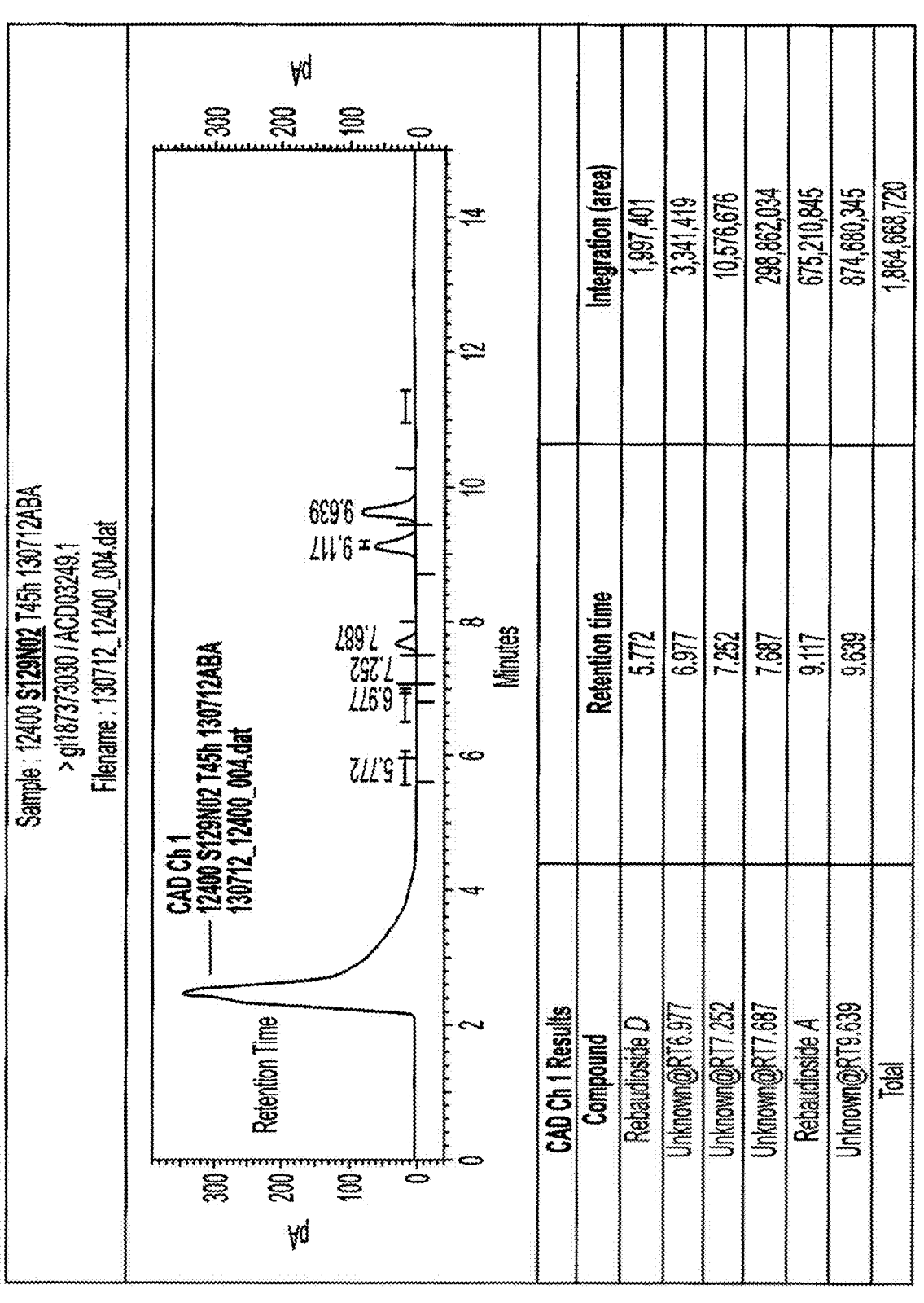
Figure 55D:
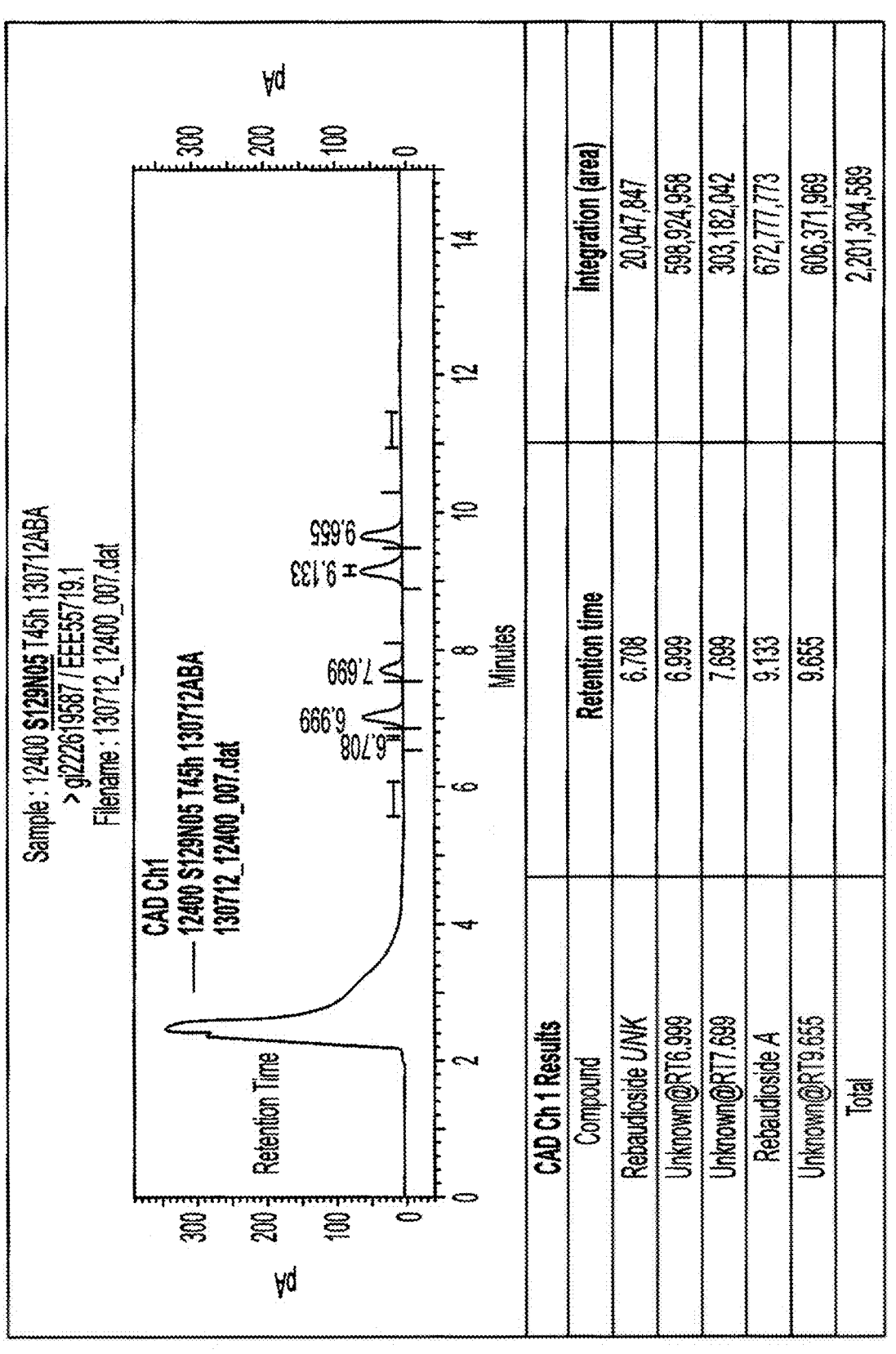
Figure 55E:
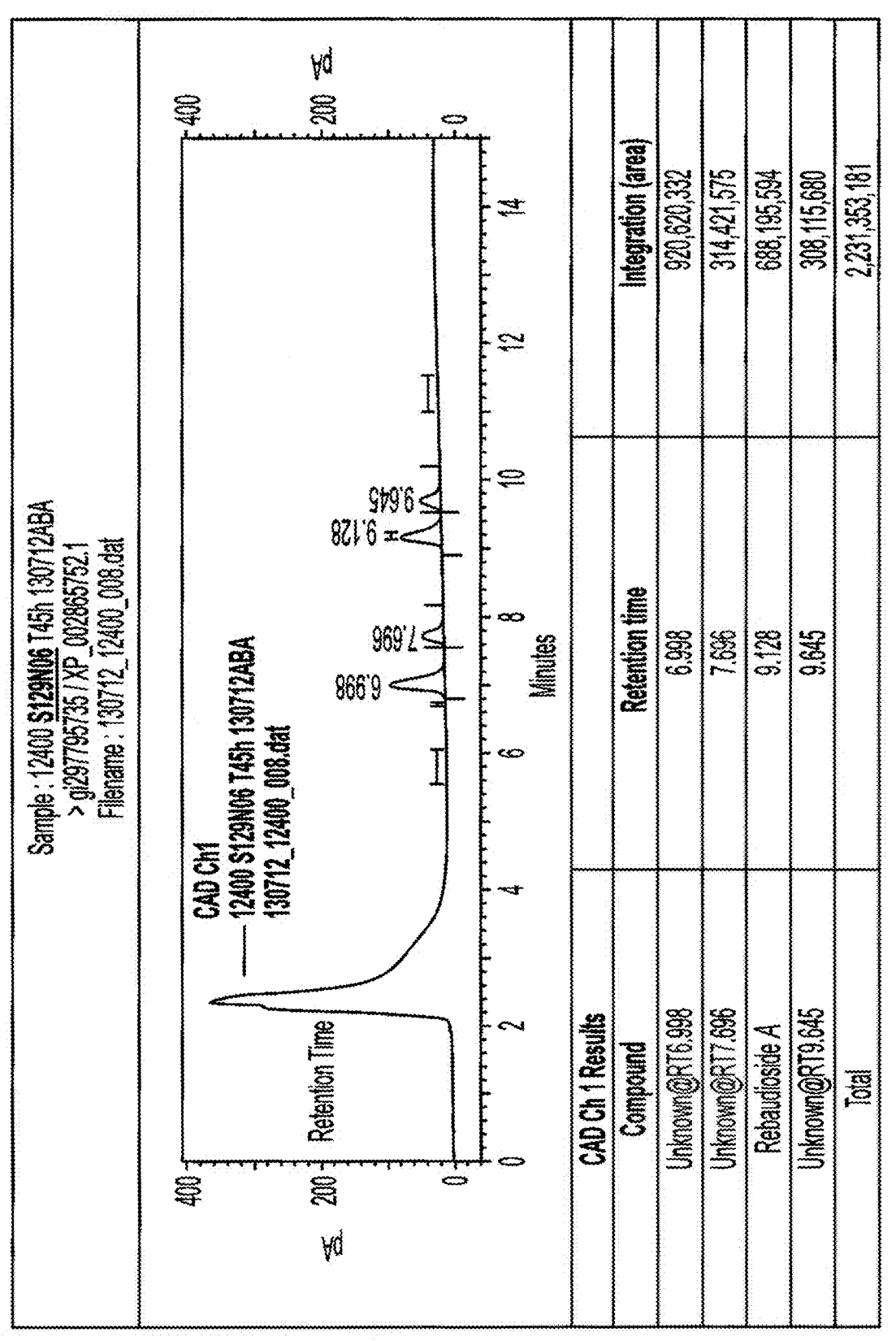
Figure 56A:
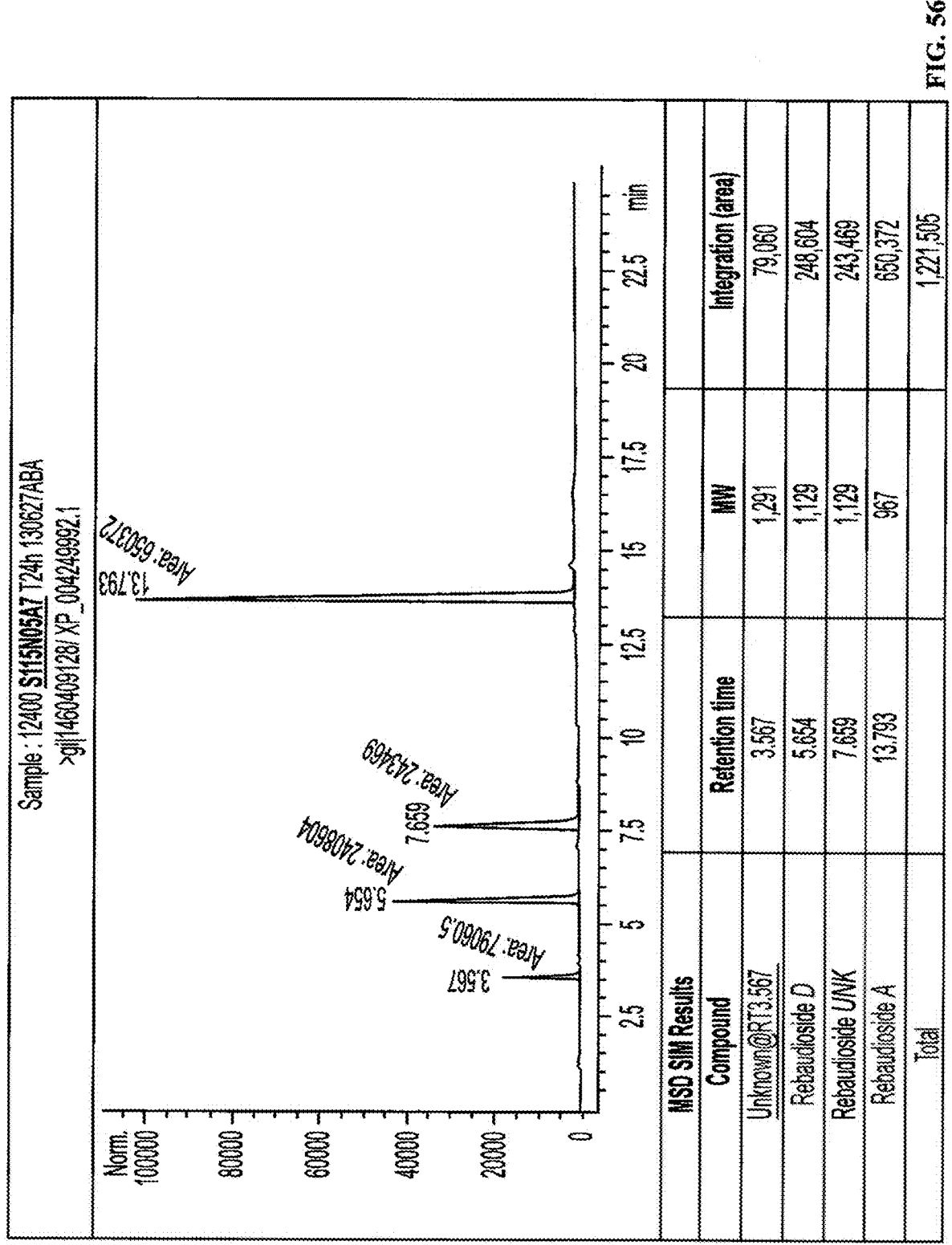
FIGS. 56A-56B show HPLC chromatograms showing the HPLC assay results for Example 23.
Figure 56B:
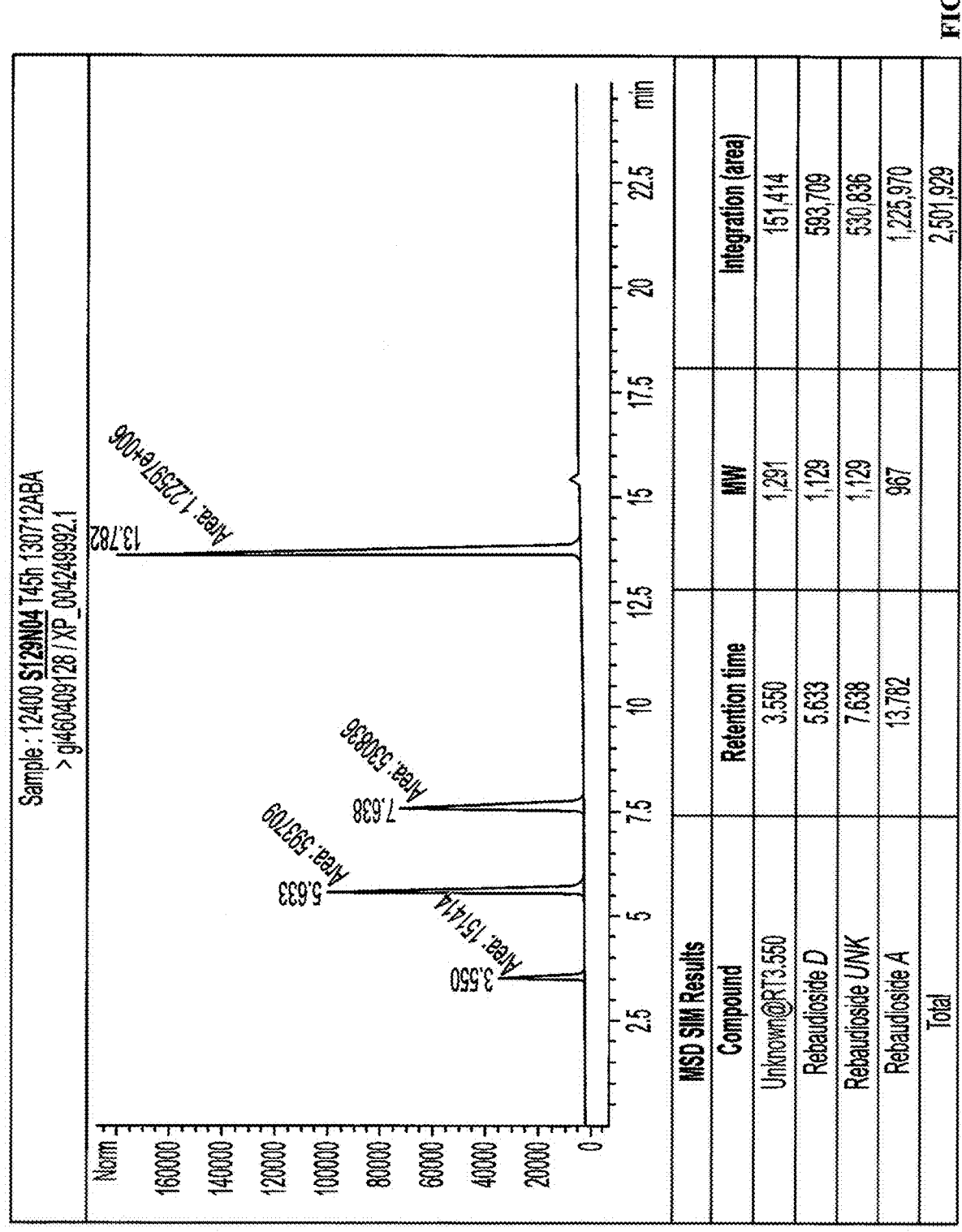

The HPLC assay results are shown in FIG. 54.

Example 22

In-Vivo Production of Enzymes

The enzymes described in EXAMPLE 20 were produced in vivo.

The pET30A+ vector containing the gene corresponding to the enzyme was introduced in E. coli BL21(DE3) by heat shock. The obtained cells were grown in Petri dishes in the presence of Kanamycin and suitable colonies were selected and allowed to grow in liquid LB medium (Erlenmeyer flasks). Glycerol was added to the suspension as cryoprotector and 400 μL aliquots were stored at −20° C. and at −80° C.

The storage aliquots of E. coli BL21(DE3) containing the pET30A+_UGT plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 hrs.

The production medium contained 60 g/L of overnight express instant TB medium (Novagen), 10 g/L of glycerol and 50 mg/L of Kanamycine. The preculture was added to 400 mL of this medium and the solution was allowed to stir at 20° C. while taking samples to measure the OD and pH.

The cultures gave significant growth and a good OD was obtained. After 40 hrs, the cells were harvested by centrifugation and frozen. The following yields of cell wet weights (CWW) are mentioned below.

| GI number | Version | CWW |
|---|---|---|
| 115454819 | NP_001051010.1 | 9.2 g |
| 187373030 | ACD03249.1 | 7.4 g |
| 460409128 | XP_004249992.1 | 6.8 g |
| 222619587 | EEE55719.1 | 7.5 g |
| 297795735 | XP_002865752.1 | 8.8 g |

Lysis was performed by addition of Bugbuster Master mix (Novagen) and the lysate was recovered by centrifugation and used fresh.

Determination of activity. Activity tests were performed at 5 mL scale with 1,000 µL of thawed lysate for the transformation of Rebaudioside A using 0.5 mM of substrate, 2.5 mM of UDP-Glucose and 3 mM $MgCl_2$ in 50 mM Sodium Phosphate buffer at pH 7.2. Samples were taken and analyzed by HPLC.

HPLC Analysis. The HPLC assay was performed as described in EXAMPLE 20.

The results for the different enzymes are provided below and shown in FIGS. 55a-e.

| GI Number | Version | Conversion after 45 hrs. | Reb D selectivity |
|---|---|---|---|
| 115454819 | NP_001051010.1 | 1.1% | 100% |
| 187373030 | ACD03249.1 | 0.8% | 100% |
| 460409128 | XP_004249992.1 | 62.1% | 43.6% |
| 222619587 | EEE55719.1 | 2.9% | Reb D Not detected |
| 297795735 | XP_002865752.1 | 0.0% | Reb D Not detected |

Example 23

Identification of Glycosides

The reaction mixtures representing GI No. 460409128, particularly the sample "12400 S115N05A7 T24h 130627ABA" of EXAMPLE 20 (hereinafter S115N05A7), and the sample "12400 S129N04 T45h 130712ABA" of EXAMPLE 22 (hereinafter S129N04) were additionally assayed by LC-MS to identify the unknown glycosides. An Agilent 1200 series HPLC system, equipped with binary pump (G1312B), autosampler (G1367D), thermostated column compartment (G1316B), DAD detector (G1315C), connected with Agilent 6110A MSD, and interfaced with "LC/MSD Chemstation" software, was used.

Instrument Conditions

| Column | Phenomenex Kinetex 2.6u C18 100 A, 4.6 mm × 150 mm, 2.6 µm |
|---|---|
| Column Temperature | 55° C. |
| Detection | DAD at 210 nm bw 360 nm |
| | MSD (Scan and SIM mode) |
| | Mode: ES-API, Negative Polarity |
| | Drying gas flow: 13.0 L/min |
| | Nebulizer pressure: 30 psig |
| | Drying gas temperature: 270° C. |
| Analysis duration | 25 min |
| Injected volume | 2 µL |
| Flow rate | 1 mL/min |

Mobile Phase Gradient Program

| Time (min) | A (%): Formic acid 0.1% | B (%): Acetonitrile |
|---|---|---|
| 0 | 75 | 25 |
| 8.5 | 75 | 25 |
| 10.0 | 71 | 29 |
| 16.5 | 70 | 30 |

The compound observed on LCMS system at 3.5 min, corresponds to compound "Unknown@4.508" in sample "S115N05A7" (EXAMPLE 20), and compound "Unknown@RT4.526" in sample "S129N04" (EXAMPLE 22). The LCMS data suggests that this compound has six glucosidic residues ($C_{56}H_{90}O_{33}$) in its structure, and was found to be an isomer form of reb M, namely reb M2 (see Example 40 for discussion).

Whereas the compound observed on LCMS system at 7.6 min, corresponds with compound "reb UNK" in sample "S115N05A7" (EXAMPLE 20), and compound "reb UNK" in sample "S129N04" (EXAMPLE 22), The LCMS data suggests that "reb UNK" has five glucosidic residues ($C_{50}H_{80}O_{28}$) in its structure, and was found to be an isomer form of reb D, namely reb D2 (see Example 39 for discussion). The ratio of these compounds and the LCMS chromatograms are provided below.

| | Steviol glycoside conversion in reaction mixture (% area) | | | |
|---|---|---|---|---|
| Sample | Unknown@RT3.5 | Reb D | Reb UNK | Reb A |
| S115N05A7 | 6.47 | 20.35 | 19.93 | 53.24 |
| S129N04 | 6.05 | 23.73 | 21.22 | 49.00 |

Example 24

Identification of Glycosides

The reaction mixture representing GI No. 460409128, particularly the sample "12400 S129N04 T45h 130712ABA" of EXAMPLE 22 (hereinafter S129N04) were additionally assayed by LC-MS along with Stevia rebaudiana Bertoni leaf extract "MLD1" produced by PureCircle Sdn Bhd (Malaysia) to determine the occurrence of S129N04 glycosides in nature.

Figure 57A:
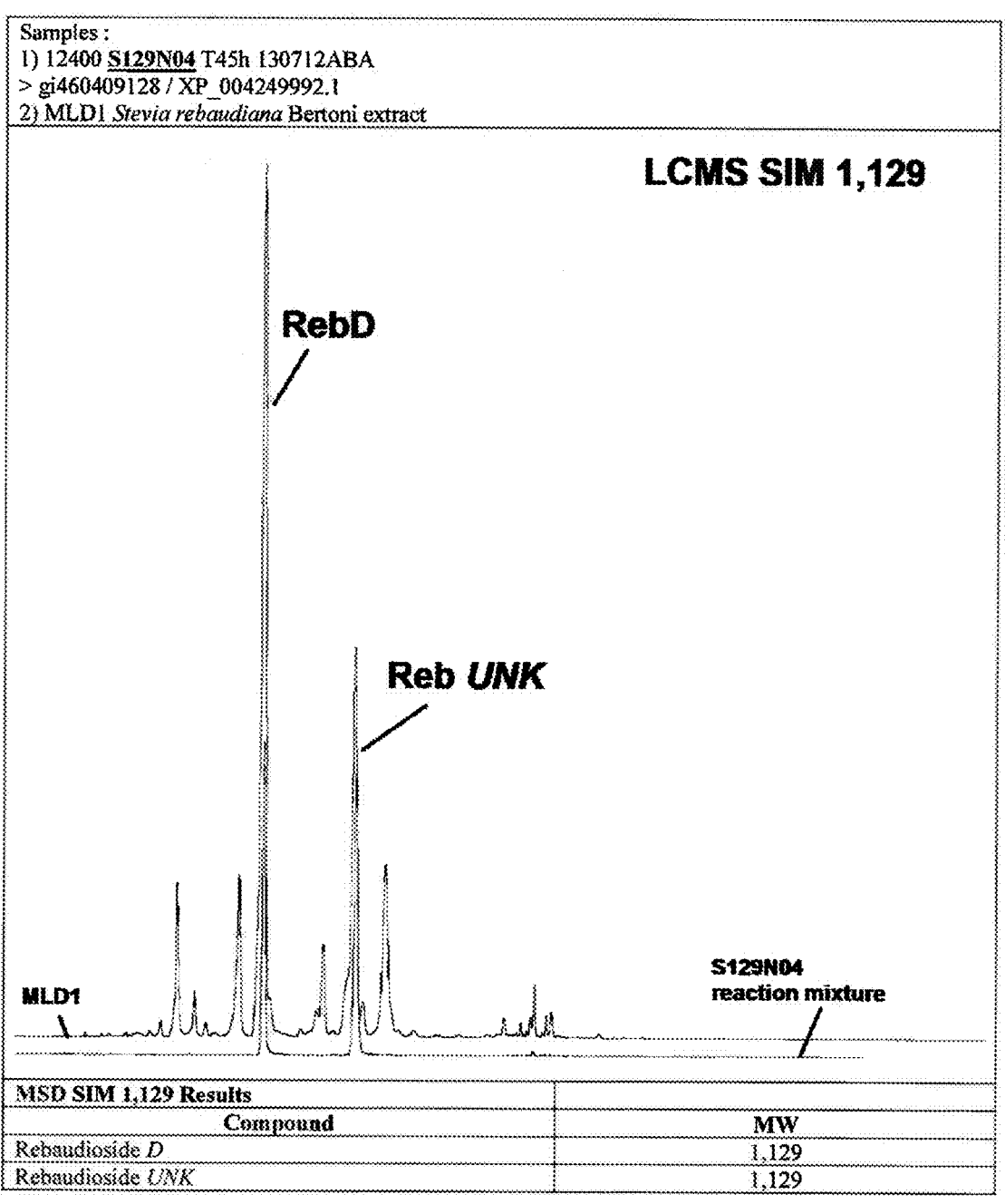
FIGS. 57A-57B show LC-MS spectrograms showing the LC-MS assay results for Example 24.
Figure 57B:
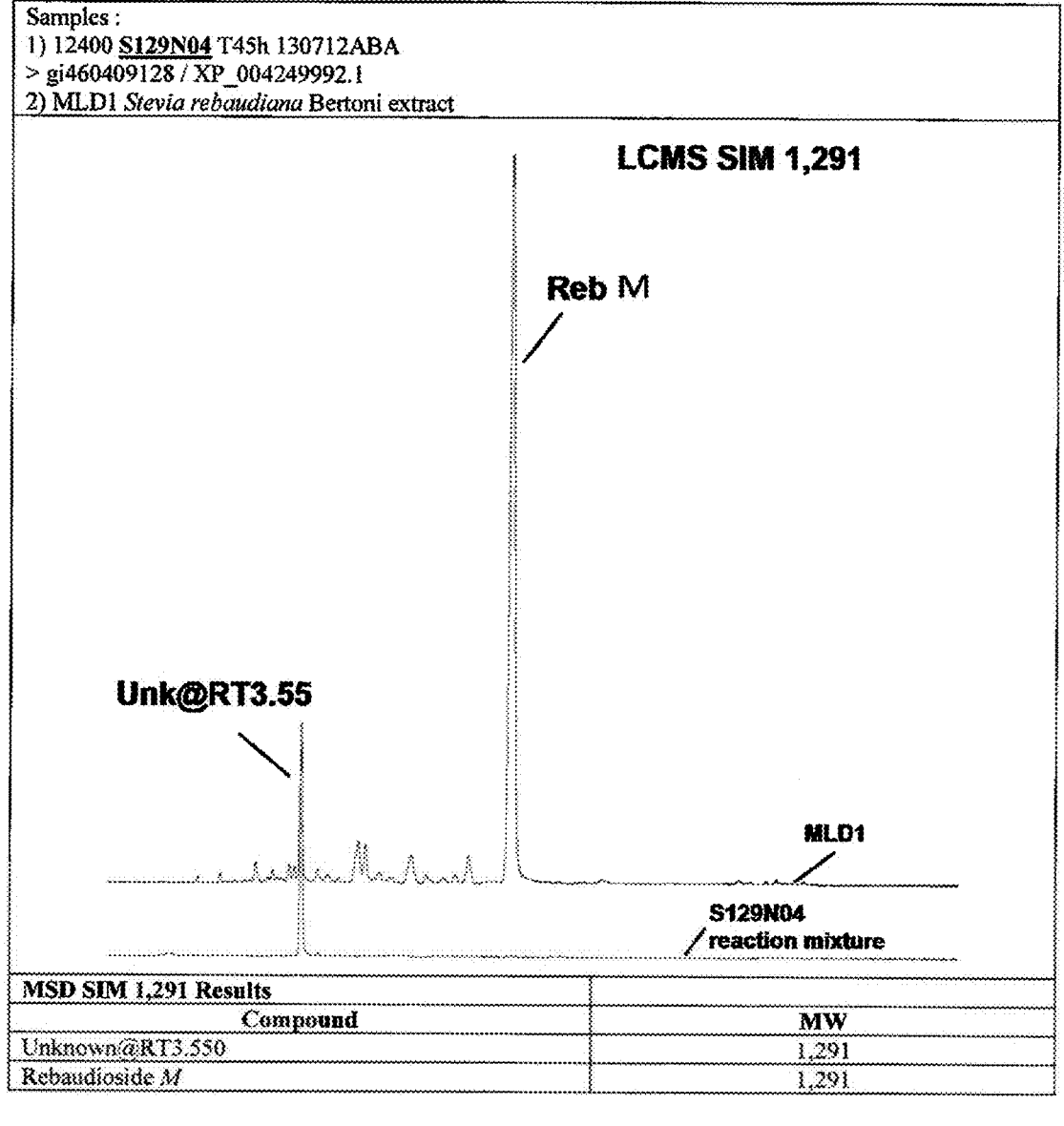

The assays in FIGS. 57a-b show that the compound observed on LCMS system at 3.5 min, in EXAMPLE 23 ($C_{56}H_{90}O_{33}$; later confirmed as reb M2), and the compound observed on LCMS system at 7.6 min, in EXAMPLE 23 ($C_{50}H_{80}O_{28}$; reb UNK; later confirmed as reb D2) occur in the extract of Stevia rebaudiana Bertoni plant.

Example 25

Conversion of Rebaudioside E to Rebaudioside D

Figure 58:
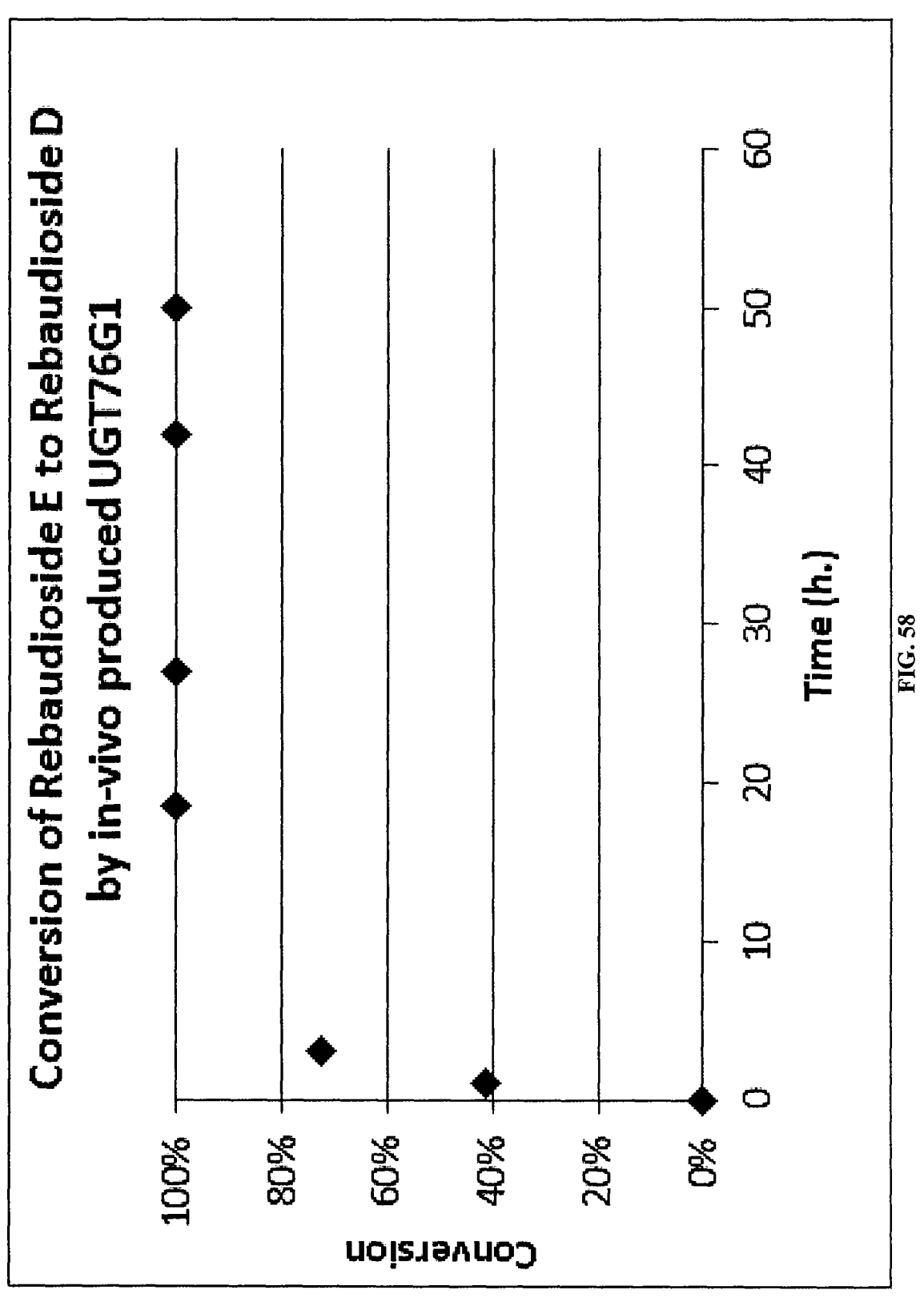
FIG. 58 shows a graph showing the reaction profile for Example 25.

The total volume of the reaction was 5.0 mL with the following composition: 100 mM potassium phosphate buffer pH 7.5, 3 mM $MgCl_2$, 2.5 mM UDP-glucose, 0.5 mM Rebaudioside E and 500 µL of UGT76G1 thawed lysate (UGT76G1 gene was cloned in pET30a+ vector and expressed in E. coli BL21 (DE3)). The reactions were run at 30° C. on an orbitary shaker at 135 rpm. For sampling 300 µL of the reaction mixture was quenched with 30 µL of 2N $H_2SO_4$ and 270 µL of methanol/water (6/4). The samples were immediately centrifuged and kept at 10° C. before analysis by HPLC (CAD detection). The reaction profile shown in FIG. 58 was obtained corresponding to a complete conversion of Rebaudioside E to Rebaudioside D.

Example 26

Directed Evolution of UGT76G1 for the Conversion of Rebaudioside D to Rebaudioside M Starting from the amino acid sequence of UGT76G1, as is described in Genbank (AAR06912.1), different mutations at various amino acid positions were identified that could alter the activity of the enzyme for the transformation of Rebaudioside D (Reb D) to Rebaudioside M (Reb M). This list of mutations, designed by DNA2.0 ProteinGPS™ strategy, was subsequently used to synthesize 96 variant genes that contained 3, 4 or 5 of these mutations that were codon-optimized for expression in *E. coli*. The genes were subcloned in the pET30a+ plasmid and used for transformation of *E. coli* BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of *E. coli* BL21(DE3) containing the pET30a+_UGT76G1var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 135 rpm at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm; 1 cm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 µL of fresh lysate that was added to a solution of Rebaudioside D (final concentration 0.5 mM), MgCl$_2$ (final concentration 3 mM) and UDP-Glucose (final concentration 2.5 mM) in 50 mM phosphate buffer pH 7.2.

The reaction was allowed to run at 30° C. and samples were taken after 2, 4, 7 and 24 h. to determine conversion and initial rate by HPLC (CAD detection) using the analytical method that was described above for the transformation of Rebaudioside D to Rebaudioside M. The results are depicted in the following table.

| Clone | Mutations* | conversion Reb D to Reb M after 24 h (%) | initial rate (Reb M area/min) |
|---|---|---|---|
| UGT76G1var1 | E224A_F314S_R334K | 51.8 | 5.5E+07 |
| UGT76G1var2 | S274G_T284I_L379G | 49.3 | 4.7E+07 |
| UGT76G1var3 | I295T_S357C_V366I | 9.6 | 1.6E+06 |
| UGT76G1var4 | E224D_E231A_F265I | 14.7 | 8.6E+06 |
| UGT76G1var5 | F22Y_I373L_P382M | 3.5 | 2.3E+06 |
| UGT76G1var6 | Q266S_S357N_I373L | 0.5 | 1.8E+06 |
| UGT76G1var7 | F22L_I43V_A239V | 0.2 | −6.0E+04 |
| UGT76G1var8 | E224A_Q266S_Q342E | 0.5 | 2.3E+04 |
| UGT76G1var9 | E231A_D301N_G348P | 52.0 | 4.9E+07 |
| UGT76G1var10 | A33G_L246F_Q342E | 0.3 | −7.7E+02 |
| UGT76G1var11 | F22L_A33G_V310I | 0.4 | 3.8E+04 |
| UGT76G1var12 | L243P_K303G_A352G | 0.5 | 8.7E+04 |
| UGT76G1var13 | L243A_S357C_A385T | 0.2 | −3.3E+04 |
| UGT76G1var14 | A239I_F265I_V396F | 5.3 | 1.5E+06 |
| UGT76G1var15 | F41L_L246F_Q425E | 5.6 | 1.5E+06 |
| UGT76G1var16 | F265I_P272A_I335V | 18.6 | 5.8E+06 |
| UGT76G1var17 | F265L_Q266E_Q342K | 0.7 | 7.2E+05 |
| UGT76G1var18 | L243P_S274G_N409R | 1.9 | 5.0E+05 |
| UGT76G1var19 | E224D_E229A_Q432E | 10.5 | 5.5E+06 |
| UGT76G1var20 | S375M_K393G_Y397E | 1.8 | 1.9E+06 |
| UGT76G1var21 | A239V_V300A_K303G | 41.9 | 3.3E+07 |
| UGT76G1var22 | E231A_V310I_R334K | 34.4 | 2.4E+07 |
| UGT76G1var23 | T263S_G348P_A352G | 47.8 | 4.1E+07 |
| UGT76G1var24 | A239I_P272A_Q425E | 31.0 | 2.1E+07 |
| UGT76G1var25 | T284L_Q342K_Y397Q | 0.9 | 6.3E+04 |
| UGT76G1var26 | S241I_F265L_F377C | 1.8 | 7.5E+05 |
| UGT76G1var27 | A239I_L379A_V394I | 29.0 | 1.5E+07 |
| UGT76G1var28 | L243A_S274G_P382M | 6.1 | 2.4E+06 |
| UGT76G1var29 | F22Y_V279I_N409R | 41.0 | 2.9E+07 |
| UGT76G1var30 | I43V_E224A_S241I | 13.6 | 5.6E+06 |
| UGT76G1var31 | E224D_L243P_V300A | 0.4 | 2.4E+05 |
| UGT76G1var32 | A239V_L243A_S375M | 0.0 | −4.4E+04 |
| UGT76G1var33 | A33G_R334H_Y397Q | 1.0 | 7.5E+06 |
| UGT76G1var34 | I43V_T284I_I295T | 3.4 | 1.5E+06 |
| UGT76G1var35 | T284L_F314S_S357N | 0.5 | 1.8E+05 |
| UGT76G1var36 | F265L_L379A_V396F | 20.0 | 8.8E+06 |
| UGT76G1var37 | E229A_L379G_I407V | 39.1 | 2.8E+07 |
| UGT76G1var38 | F41L_I295M_F377C | 8.2 | 3.7E+06 |
| UGT76G1var39 | F22Y_F41L_V366I | 7.2 | 3.3E+06 |
| UGT76G1var40 | T263S_Q266E_S375R | 47.6 | 3.3E+07 |
| UGT76G1var41 | L246F_A385T_K393G | 0.8 | 1.4E+06 |
| UGT76G1var42 | T263S_Q266S_R334H | 34.6 | 2.2E+07 |
| UGT76G1var43 | S241I_P272A_V279I | 19.9 | 9.4E+06 |
| UGT76G1var44 | I335V_S375R_I407V | 35.3 | 2.3E+07 |

-continued

| Clone | Mutations* | conversion Reb D to Reb M after 24 h (%) | initial rate (Reb M area/min) |
|---|---|---|---|
| UGT76G1var45 | V279I_D301N_S389E | 38.6 | 2.3E+07 |
| UGT76G1var46 | F22L_Q266E_I295M | 0.6 | 9.8E+05 |
| UGT76G1var47 | E229A_T284I_S389E | 4.8 | 2.7E+06 |
| UGT76G1var48 | V394I_Y397E_Q432E | 47.6 | 3.8E+07 |
| UGT76G1var49 | F41L_Q266E_T284I_Y397Q | 2.6 | 1.1E+06 |
| UGT76G1var50 | F22Y_V310I_S375M_F377C | 1.9 | 7.9E+05 |
| UGT76G1var51 | K303G_S357C_S389E_V396F | 18.7 | 9.5E+06 |
| UGT76G1var52 | D301N_I373L_F377C_I407V | 12.9 | 4.6E+06 |
| UGT76G1var53 | R334K_A352G_P382M_S389E | 9.3 | 4.1E+06 |
| UGT76G1var54 | E229A_T284L_R334K_Q342E | 0.7 | 4.3E+05 |
| UGT76G1var55 | I295M_Q342E_V366I_N409R | 1.0 | 2.2E+05 |
| UGT76G1var56 | L246F_A352G_S357N_Q432E | 0.4 | 4.1E+04 |
| UGT76G1var57 | S241I_T263S_L379G_A385T | 0.8 | 1.5E+05 |
| UGT76G1var58 | S357C_S375M_N409R_Q425E | 7.5 | 2.2E+06 |
| UGT76G1var59 | I335V_K393G_V394I_Y397Q | 33.0 | 2.7E+07 |
| UGT76G1var60 | E231A_L243A_V279I_S357N | 0.5 | 9.5E+04 |
| UGT76G1var61 | I43V_F265I_Q266S_L379A | 6.4 | 2.0E+06 |
| UGT76G1var62 | L243P_P272A_V394I_V396F | 0.1 | 3.4E+04 |
| UGT76G1var63 | F314S_R334H_Q342K_L379G | 3.4 | 1.2E+06 |
| UGT76G1var64 | F22L_A239I_R334H_I407V | 0.3 | 3.1E+04 |
| UGT76G1var65 | A33G_A239V_P382M_Q425E | 1.2 | 3.3E+05 |
| UGT76G1var66 | F265L_V310I_V366I_A385T | 0.8 | 3.7E+05 |
| UGT76G1var67 | E224D_F314S_S375R_Y397E | −2.1 | −5.6E+05 |
| UGT76G1var68 | Q342K_G348P_I373L_Y397E | −1.4 | −1.1E+05 |
| UGT76G1var69 | S274G_I295T_I335V_L379A | 24.7 | 8.3E+06 |
| UGT76G1var70 | E224A_I295T_V300A_G348P | 24.0 | 8.4E+06 |
| UGT76G1var71 | I295M_V300A_K393G_Q432E | 42.9 | 2.1E+07 |
| UGT76G1var72 | T284L_D301N_K303G_S375R | 19.2 | 9.1E+06 |
| UGT76G1var73 | F22Y_D301N_R334H_Q342E_V396F | 0.8 | 8.7E+05 |
| UGT76G1var74 | I295T_I373L_S375R_Y397Q_Q432E | 0.6 | 9.6E+04 |
| UGT76G1var75 | F41L_A239I_Q266S_S375M_P382M | 0.8 | −1.3E+05 |
| UGT76G1var76 | F22Y_A239I_L246F_I295M_R334K | 2.6 | 7.2E+05 |
| UGT76G1var77 | A239V_F265I_I295T_D301N_K393G | 1.9 | 4.4E+05 |
| UGT76G1var78 | V279I_V300A_V310I_I335V_S357C | 3.2 | 8.2E+05 |
| UGT76G1var79 | E224D_T284I_V366I_I373L_K393G | 8.5 | 3.8E+06 |
| UGT76G1var80 | L243P_L379A_S389E_Q425E_Q432E | 1.0 | 2.1E+05 |
| UGT76G1var81 | A33G_T263S_S274G_V279I_Y397E | 15.0 | 6.5E+06 |
| UGT76G1var82 | E224D_L243A_F265L_R334H_A352G | 1.1 | 2.5E+05 |
| UGT76G1var83 | I43V_Q342E_S357N_S375R_L379G | 0.5 | 4.3E+04 |
| UGT76G1var84 | F22L_Q266S_F314S_A352G_S357C | 1.2 | 2.3E+05 |
| UGT76G1var85 | T284L_G348P_F377C_P382M_N409R | 1.8 | 4.0E+05 |
| UGT76G1var86 | E224A_T284L_V396F_Y397E_I407V | 1.6 | 3.8E+05 |
| UGT76G1var87 | S241I_L243A_V300A_F314S_N409R | 35.7 | 2.1E+07 |
| UGT76G1var88 | A239V_T284I_V310I_Q342K_L379A | 1.6 | 3.8E+05 |
| UGT76G1var89 | F41L_E229A_E231A_F265L_P272A | 1.2 | 2.1E+05 |
| UGT76G1var90 | E231A_S241I_S274G_Y397Q_Q425E | 34.5 | 1.9E+07 |
| UGT76G1var91 | E224A_L246F_T263S_F265I_Q342K | 1.2 | 2.3E+05 |
| UGT76G1var92 | K303G_S357N_V366I_V394I_I407V | 1.6 | 3.6E+05 |
| UGT76G1var93 | I43V_Q266E_S375M_S389E_V394I | 1.8 | 4.5E+05 |
| UGT76G1var94 | Q266E_P272A_R334K_G348P_L379G | 72.0 | 7.9E+07 |
| UGT76G1var95 | A33G_I295M_K303G_I335V_A385T | −1.3 | −1.7E+05 |
| UGT76G1var96 | F22L_E229A_L243P_F377C_A385T | 1.2 | 2.7E+05 |

*Mutations are noted as follows: original amino acid-position-new amino acid: For example the mutation of an alanine at position 33 to a glycine is noted as A33G.

Example 27

In-Vivo Production of UGTSL2

UGTSL2 (GI_460410132/XP_004250485.1) amino acid sequence (SEQ ID NO: 9):
MATNLRVLMFPWLAYGHISPFLNIAKQLADRGFLIYLCSTRINLESIIKK

IPEKYADSIHLIELQLPELPELPPHYHTTNGLPPHLNPTLHKALKMSKPN

FSRILQNLKPDLLIYDVLQPWAEHVANEQNIPAGKLLTSCAAVFSYFFSF

RKNPGVEFPFPAIHLPEVEKVKIREILAKEPEEGGRLDEGNKQMMLMCTS

RTIEAKYIDYCTELCNWKVVPVGPPFQDLITNDADNKELIDWLGTKHENS

TVFVSFGSEYFLSKEDMEEVAFALELSNVNFIWVARFPKGEERNLEDALP

-continued

KGFLERIGERGRVLDKFAPQPRILNHPSTGGFISHCGWNSAMESIDFGVP

IIAMPIHNDQPINAKLMVELGVAVEIVRDDDGKIHRGEIAETLKSVVTGE

TGEILRAKVREISKNLKSIRDEEMDAVAEELIQLCRNSNKSK

The pET30A+ vector containing the UGTSL2 gene was introduced in *E. coli* B121(DE3) by heat shock. The obtained cells were grown in petri-dishes in the presence of Kanamycin and suitable colonies were selected and allowed to grow in liquid LB medium (erlenmeyer flasks). Glycerol was added to the suspension as cryoprotection and 400 μL aliquots were stored at −20° C. and at −80° C.

The storage aliquots of *E. coli* BL21(DE3) containing the pET30A+_UGTSL2 plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake at 135 rpm at 30° C. for 8 h.

The production medium contained 60 g/L of overnight express instant TB medium (Novagen), 10 g/L of glycerol and 50 mg/L of Kanamycin. The preculture was added to 200 mL of this medium and the solution was allowed to stir at 20° C. while taking samples to measure the OD and pH. The culture gave significant growth and a good OD was obtained. After 40 h, the cells were harvested by centrifugation and frozen to obtain 6.22 g of cell wet weight.

Lysis was performed on 1.4 g of cells by addition of Bugbuster Master mix (Novagen) and the lysate was recovered by centrifugation and used fresh.

Example 28

Determination of Activity for Stevioside to Rebaudioside E Conversion with UGTSL and UGTSL2

UGTSL was prepared according to EXAMPLE 22, and UGTSL2 was prepared according to EXAMPLE 27.

Activity tests were performed at 3 mL scale with 600 μL of lysate for the transformation of Stevioside using 0.5 mM of substrate, 2.5 mM of UDP-Glucose and 3 mM $MgCl_2$ in 50 mM Sodium Phosphate buffer at pH 7.2. Samples were taken and analyzed by HPLC. HPLC Analysis. The HPLC assay was performed as described in EXAMPLE 20.

Figures 1, 59A:
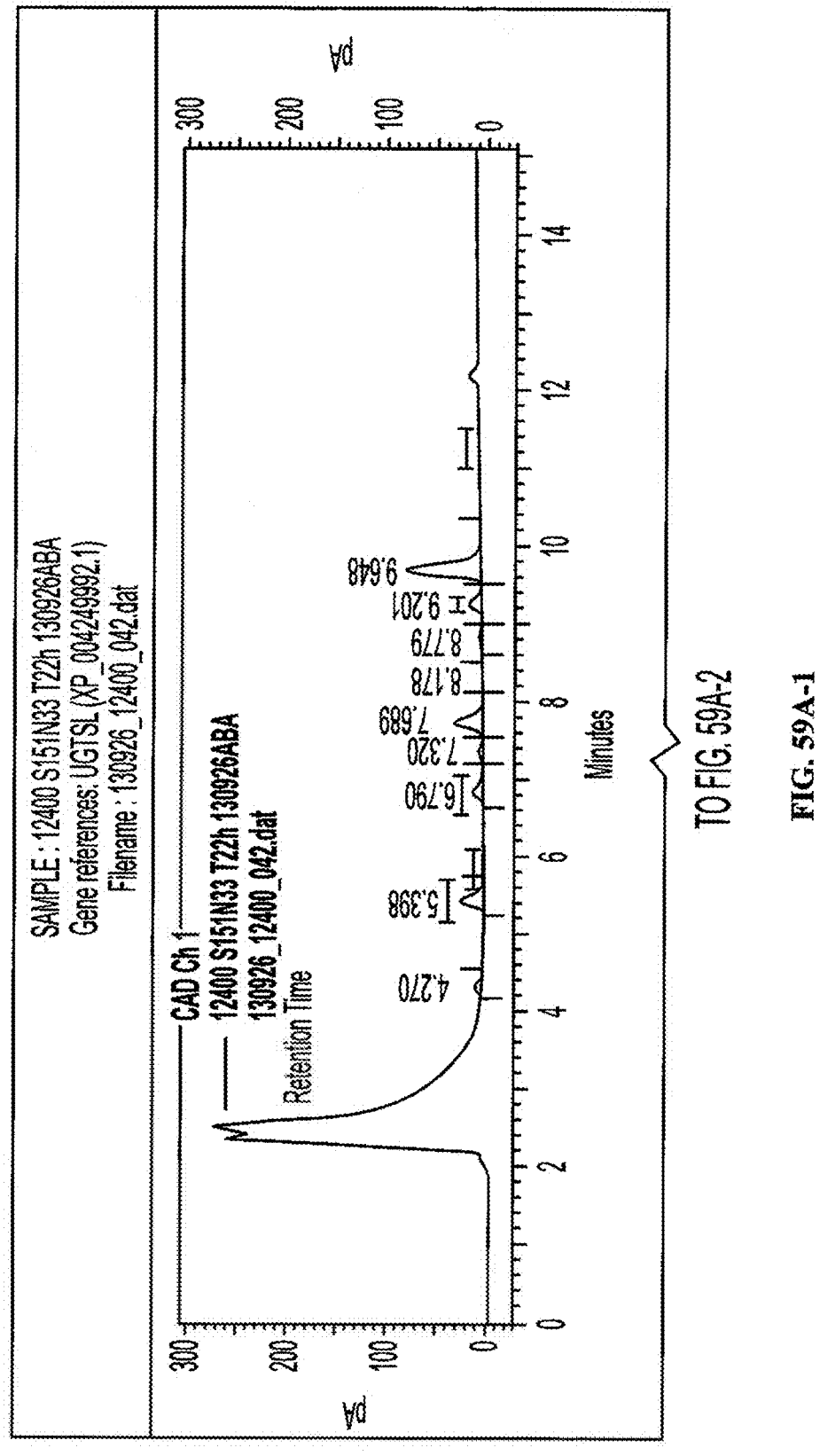
Figures 1, 59B:
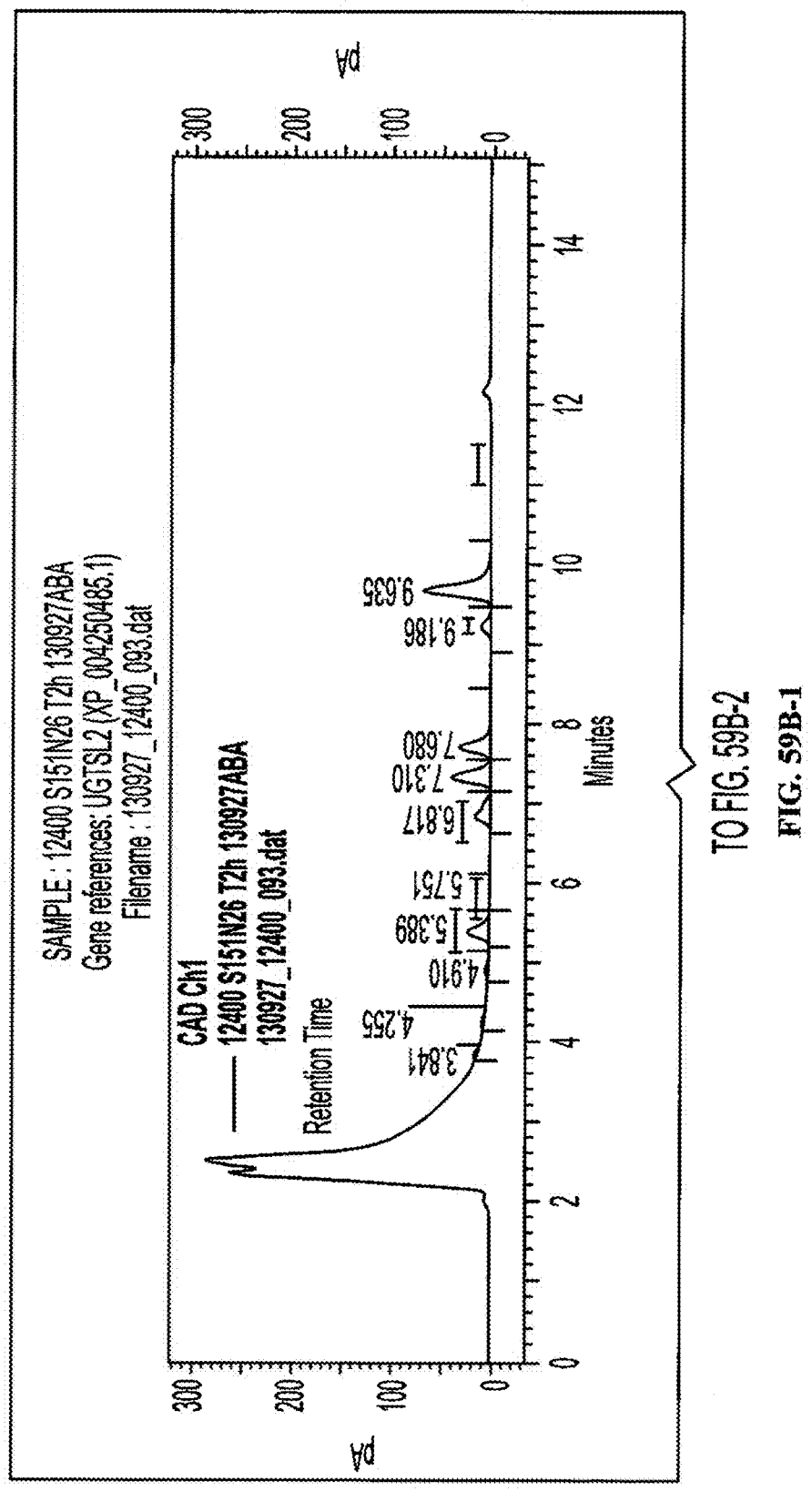

The results for the different enzymes and the corresponding chromatograms are provided below and shown in FIGS. 59a-b

| Enzyme internal reference | GI Number | Version | Stevioside conv.[1] (reaction time) | Rebaudioside E formation[1] |
|---|---|---|---|---|
| UGTSL | 460409128 | XP_004249992.1 | 74% (22 h.) | 46% |
| UGTSL2 | 460410132 | XP_004250485.1 | 77% (2 h.) | 50% |

Note:
[1]Based on initial concentration of Stevioside

Example 29

Determination of Activity for Rubusoside to Rebaudioside E Conversion with UGTSL and UGTSL2

UGTSL was prepared according to EXAMPLE 22, and UGTSL2 was prepared according to EXAMPLE 27.

Activity tests were performed at 3 mL scale with 600 μL of lysate for the transformation of Rubusoside using 0.5 mM of substrate, 2.5 mM of UDP-Glucose and 3 mM $MgCl_2$ in 50 mM Sodium Phosphate buffer at pH 7.2. Samples were taken and analyzed by HPLC. The HPLC assay was performed as described in EXAMPLE 20.

Figures 1, 60A:
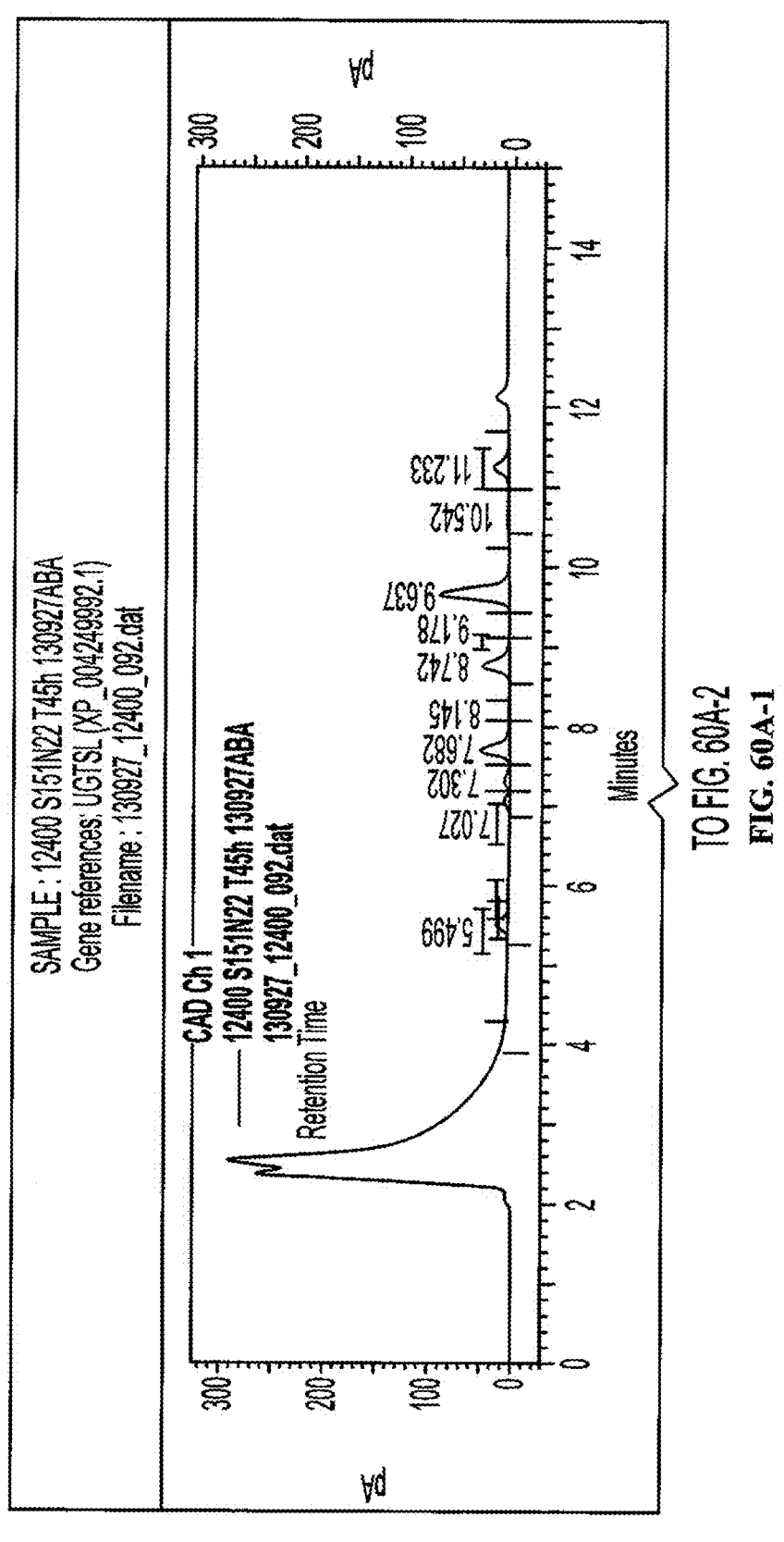
Figures 1, 60B:
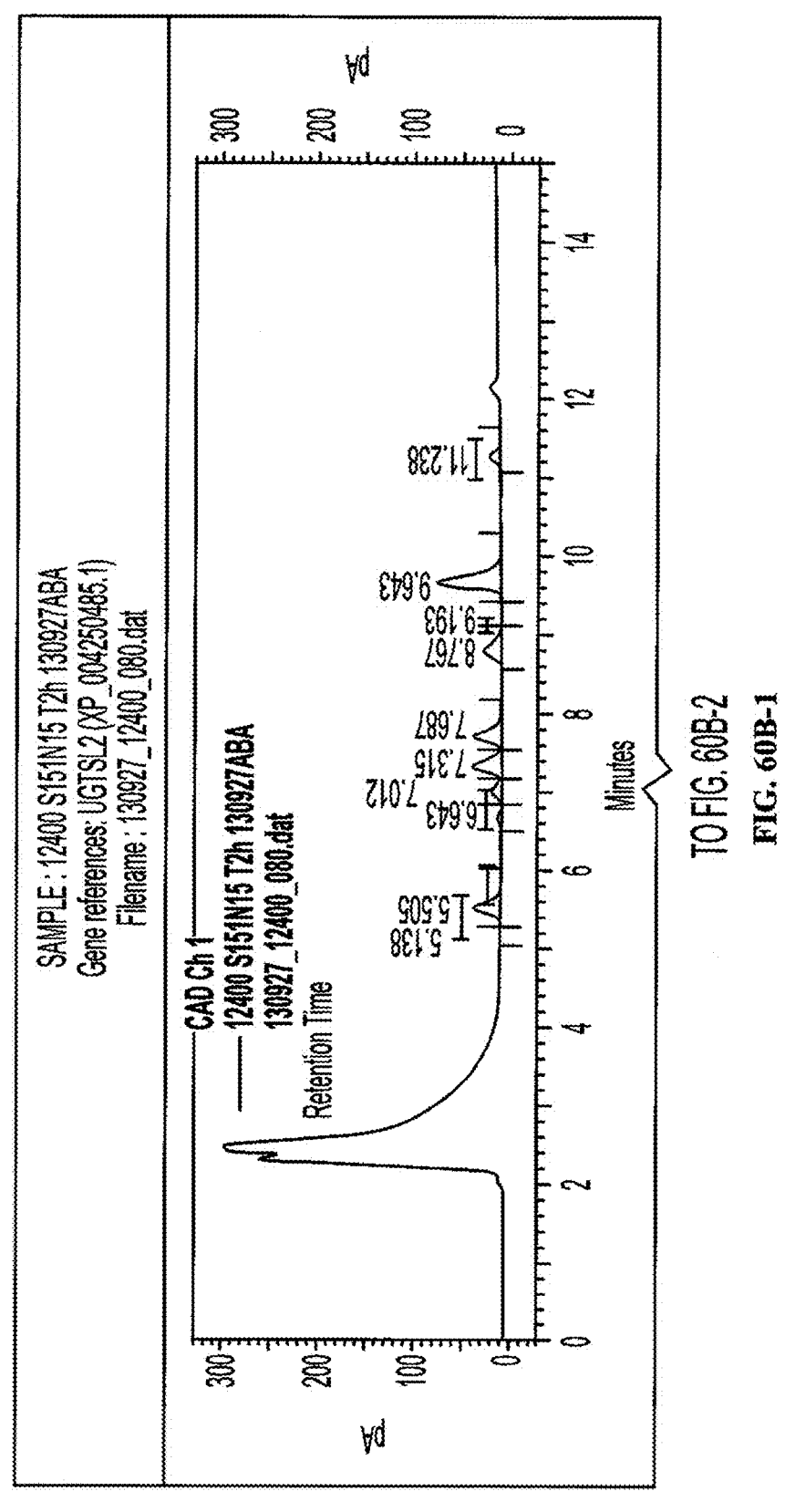

The results for the different enzymes and the corresponding chromatograms are provided below and shown in FIGS. 60a-b.

| Enzyme internal reference | GI Number | Version | Rubusoside conv.[1] (reactiontime) | Rebaudioside E formation[1] |
|---|---|---|---|---|
| UGTSL | 460409128 | XP_004249992.1 | 70% (45 h.) | 27% |
| UGTSL2 | 460410132 | XP_004250485.1 | 80% (2 h.) | 55% |

Note:
[1]Based on initial concentration of Rubusoside

Example 30

Determination of Activity for Rebaudioside A to Rebaudioside D Conversion with UGTSL2 UGTSL2 was prepared according to EXAMPLE 27.

Activity tests were performed at 3 mL scale with 60 µL of lysate for the transformation of Rebaudioside A using 0.5 mM of substrate, 2.5 mM of UDP-Glucose and 3 mM MgCl$_2$ in 50 mM Sodium Phosphate buffer at pH 7.2. Samples were taken and analyzed by HPLC. The HPLC assay was performed as described in EXAMPLE 20.

Figure 61A:
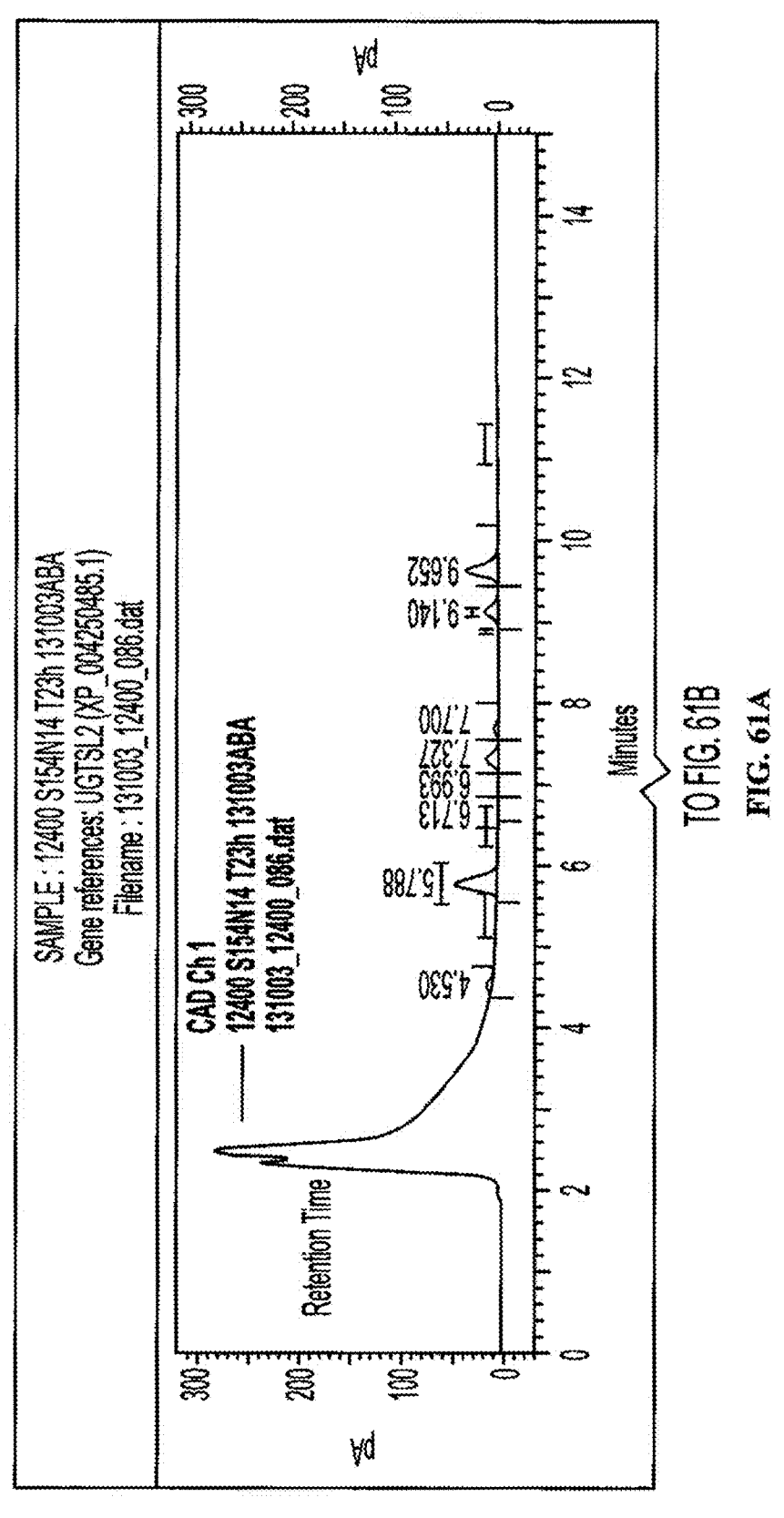

The result after 23 h. of reaction and the corresponding chromatogram is provided below and shown in FIG. 61.

| Enzyme internal reference | GI Number | Version | Rebaudioside A conv.[1] (reaction time) | Rebaudioside D formation[1] |
|---|---|---|---|---|
| UGTSL2 | 460410132 | XP_004250485.1 | 78% (23 h.) | 75% |

Note:
[1]Based on initial concentration of Rebaudioside A

Example 31

Identification of Glycosides

The reaction mixtures prepared according to EXAMPLE 30 and incubated for 45 hrs was analyzed by LC-MS, along with Stevia rebaudiana Bertoni leaf extract "MLD1" produced by PureCircle Sdn Bhd (Malaysia), to determine the occurrence of formed glycosides in nature.

An Agilent 1200 series HPLC system, equipped with binary pump (G1312B), autosampler (G1367D), thermostated column compartment (G1316B), DAD detector (G1315C), connected with Agilent 6110A MSD, and interfaced with "LC/MSD Chemstation" software, was used.

Instrument Conditions

| | |
|---|---|
| Column | Phenomenex Prodigy 3u C18 100 A, 4.6 mm × 250 mm, 3 µm |
| Column Temperature | 55° C. |
| Detection | DAD at 210 nm bw 360 nm |
| | MSD (Scan and SIM mode) |
| | Mode: ES-API, Negative Polarity |
| | Drying gas flow: 13.0 L/min |
| | Nebulizer pressure: 30 psig |
| | Drying gas temperature: 270° C. |
| Analysis duration | 75 min |
| Injected volume | 10 µL |
| Flow rate | 0.5 mL/min |

Mobile Phase Gradient Program

| Time (min) | A (%): Formic acid 0.1% | B (%): Acetonitrile |
|---|---|---|
| 0 | 75 | 25 |
| 30 | 75 | 25 |
| 33 | 68 | 32 |
| 75 | 68 | 32 |

Figure 62:
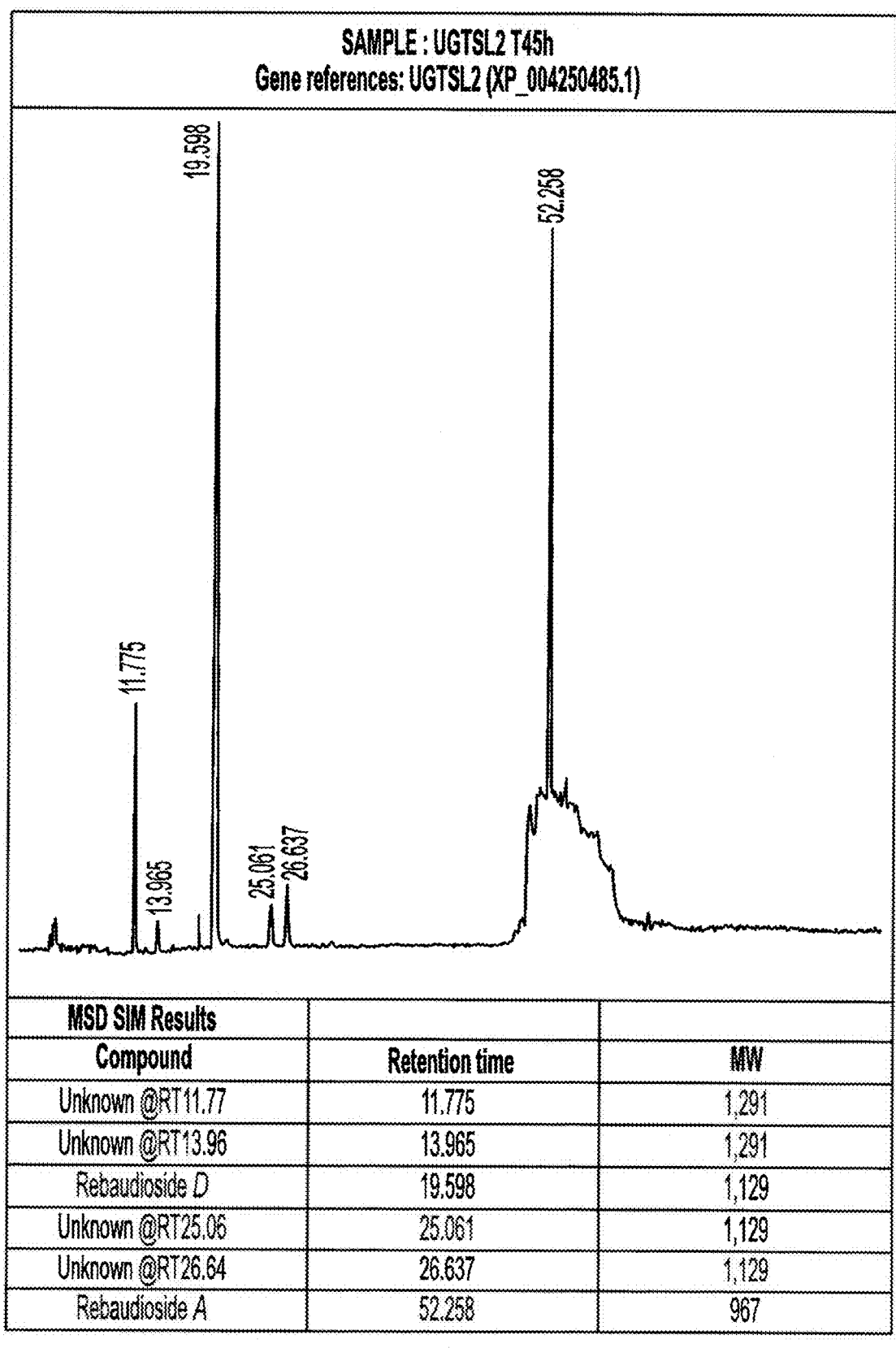
FIG. 62 shows an LS-MS spectrogram showing the LS-MS assay results for Example 31.

The assay shown in FIG. 62 shows that the compound observed on LC-MS system at 11.77 min is the same as the compound at 3.5 min, in EXAMPLE 23 (C$_{56}$H$_{90}$O$_{33}$; later confirmed as reb M2), and the compound observed at 26.64 min is the same as the compound at 7.6 min, in EXAMPLE 23 (C$_{50}$H$_{80}$O$_{28}$; reb UNK; later confirmed as reb D2). Other isomers of reb X were observed at 13.96 min and also another isomer form of reb D was observed at 25.06 min. All observed compounds occurred in the extract of Stevia rebaudiana Bertoni plant.

Example 32

In Vivo Preparation and Activity Determination of UGTLB

```
UGTLB (GI_209954733/BAG80557.1) amino acid
sequence (SEQ ID NO: 10):
MGTEVTVHKNTLRVLMFPWLAYGHISPFLNVAKKLVDRGFLIYLCSTAI -continued
NLKSTIKKIPEKYSDSIQLIELHLPELPELPPHYHTTNGLPPHLNHTLQ

KALKMSKPNFSKILQNLKPDLVIYDLLQQWAEGVANEQNIPAVKLLTSG

AAVLSYFFNLVKKPGVEFPFPAIYLRKNELEKMSELLAQSAKDKEPDGV

DPFADGNMQVMLMSTSRIIEAKYIDYFSGLSNWKVVPVGPPVQDPIADD

ADEMELIDWLGKKDENSTVFVSFGSEYFLSKEDREEIAFGLELSNVNFI

WVARFPKGEEQNLEDALPKGFLERIGDRGRVLDKFAPQPRILNHPSTGG

FISHCGWNSVMESVDFGVPIIAMPIHLDQPMNARLIVELGVAVEIVRDD

YGKIHREEIAEILKDVIAGKSGENLKAKMRDISKNLKSIRDEEMDTAAE

ELIQLCKNSPKLK
```

The pET30A+ vector containing the UGTLB gene was introduced in E. coli Bl21(DE3) by heat shock. The obtained cells were grown in petri-dishes in the presence of Kanamycin and suitable colonies were selected and allowed to grow in liquid LB medium (erlenmeyer flasks). Glycerol was added to the suspension as cryoprotecteur and 400 µL aliquots were stored at −20° C. and at −80° C.

The storage aliquots of E. coli BL21(DE3) containing the pET30A+_UGTLB plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 h.

The production medium contained 60 g/L of overnight express instant TB medium (Novagen), 10 g/L of glycerol and 50 mg/L of Kanamycine. The preculture was added to 200 mL of this medium and the solution was allowed to stir at 20° C. while taking samples to measure the OD and pH. The culture gave significant growth and a good OD was obtained. After 40 h, the cells were harvested by centrifugation and frozen to obtain 5.7 g of cell wet weight.

Lysis was performed on 1.2 g of cells by addition of 6 mL Bugbuster Master mix (Novagen) and the lysate was recovered by centrifugation and used fresh.

Figures 1, 63A:
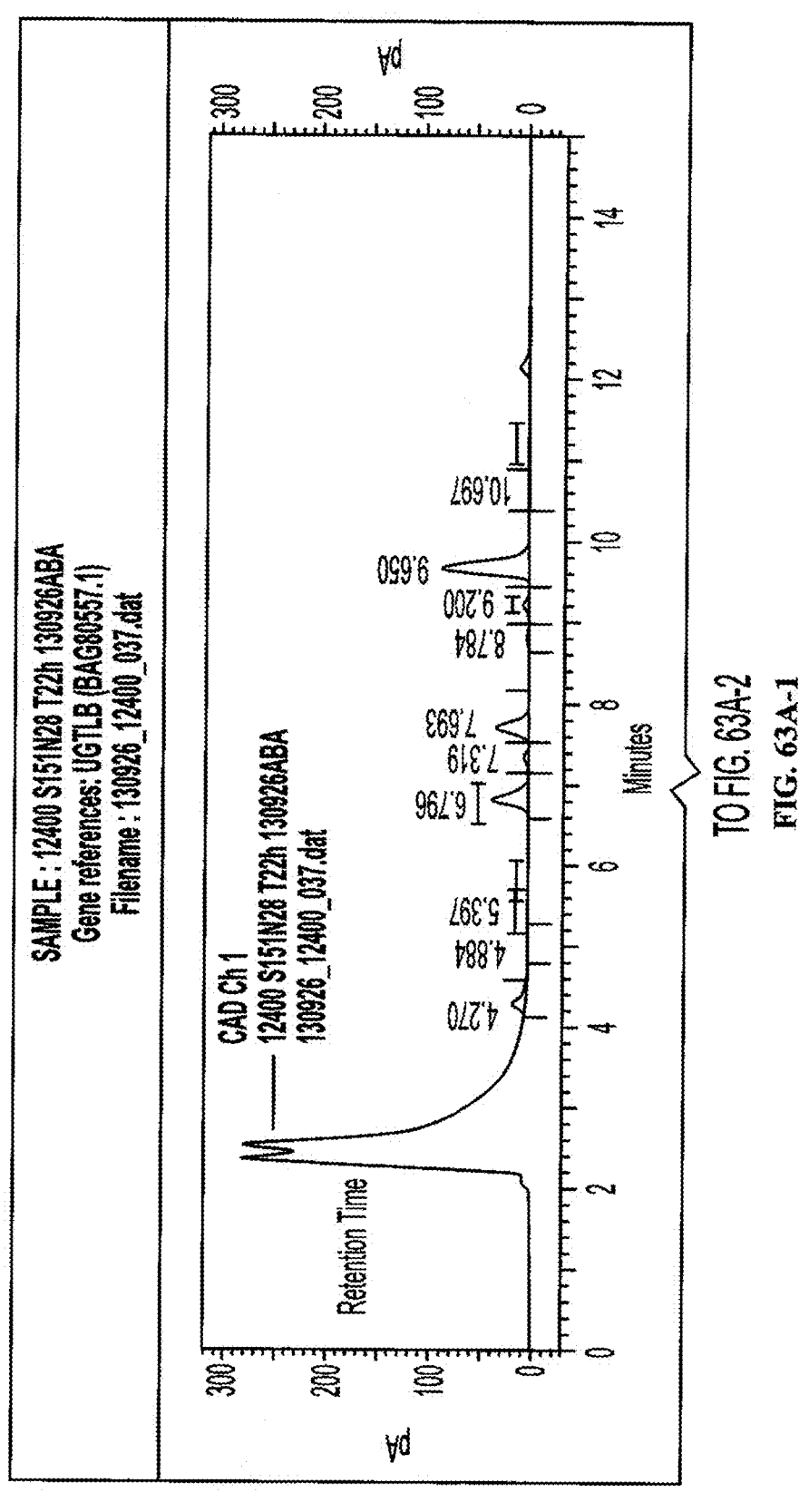

Determination of Activity for Stevioside to Rebaudioside E Conversion with UGTLB Activity tests were performed at 3 mL scale with 600 µL of lysate for the transformation of Stevioside using 0.5 mM of substrate, 2.5 mM of UDP-Glucose and 3 mM MgCl$_2$ in 50 mM Sodium Phosphate buffer at pH 7.2. Samples were taken and analyzed by HPLC. The corresponding chromatograms are depicted in FIG. 63a.

| Enzyme internal reference | GI Number | Version | Stevioside conv.[1] (reaction time) | Rebaudioside E formation[1] |
|---|---|---|---|---|
| UGTLB | 209954733 | BAG80557.1 | 89% (22 h.) | 3% |

Note:
[1]Based on initial concentration of Stevioside

Figures 1, 63B:
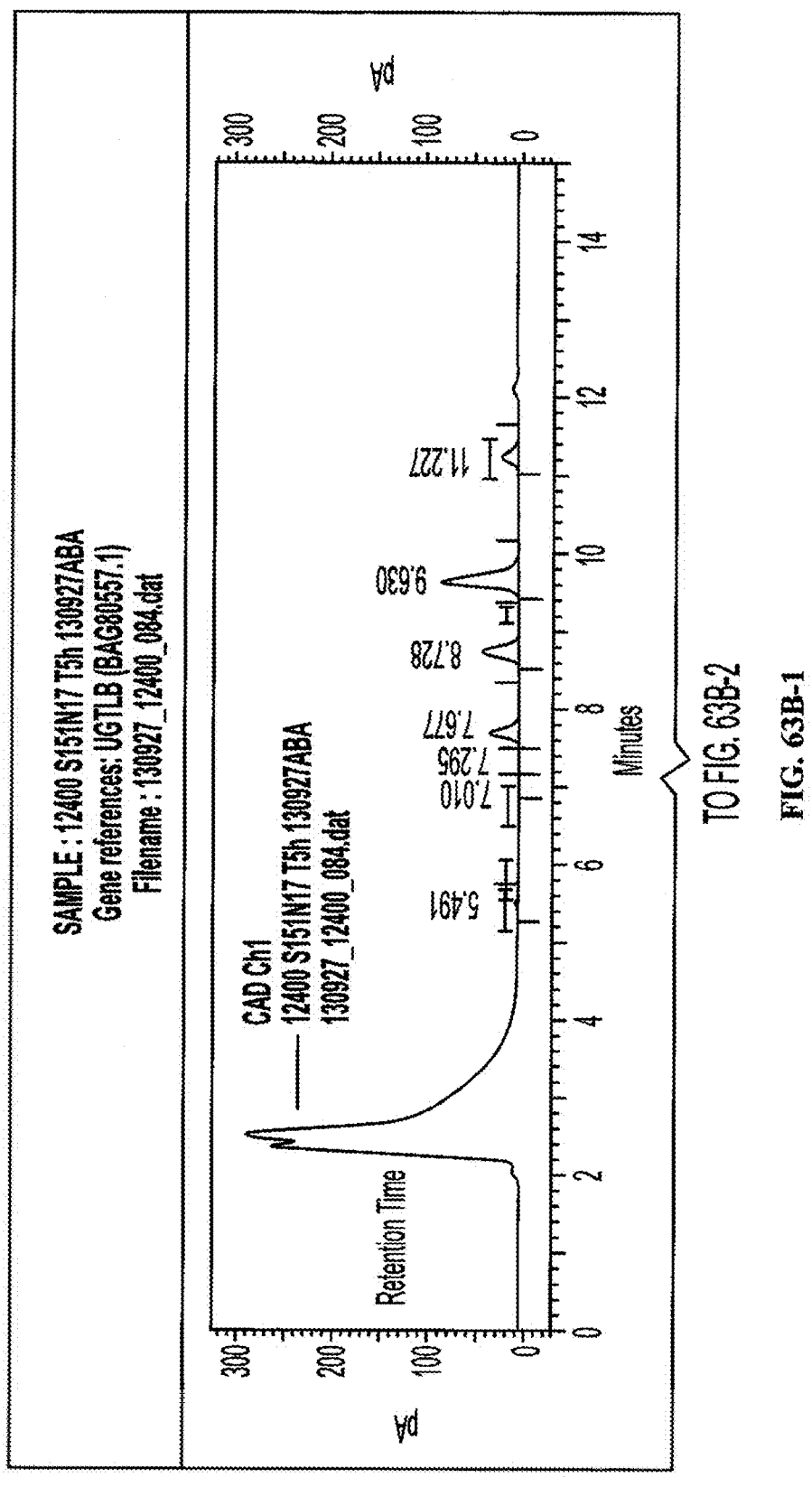

Determination of Activity for Rubusoside to Rebaudioside E Conversion with UGTLB Activity tests were performed at 3 mL scale with 600 μL of lysate for the transformation of Rubusoside using 0.5 mM of substrate, 2.5 mM of UDP-Glucose and 3 mM $MgCl_2$ in 50 mM Sodium Phosphate buffer at pH 7.2. Samples were taken and analyzed by HPLC. The corresponding chromatograms are depicted in FIG. 63b.

| Enzyme internal reference | GI Number | Version | Rubusoside conv.[1] (reaction time) | Rebaudioside E formation[1] |
|---|---|---|---|---|
| UGTLB | 209954733 | BAG80557.1 | 65% (5 h.) | 4% |

Note:
[1]Based on initial concentration of Rubusoside

Figures 1, 63C:
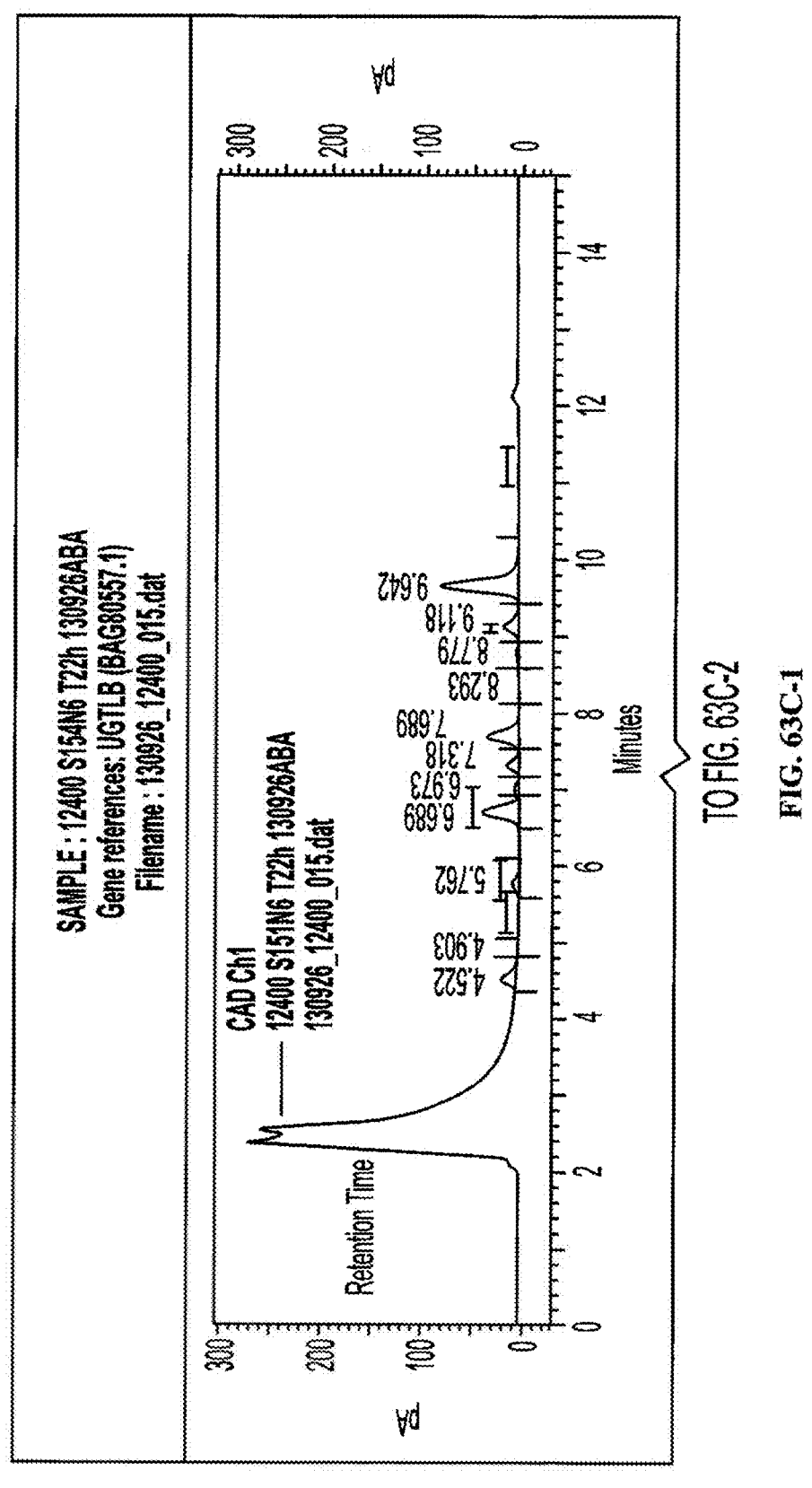

Determination of Activity for Rebaudioside A to Rebaudioside D Conversion with UGTLB Activity tests were performed at 3 mL scale with 600 μL of lysate for the transformation of Rebaudioside A using 0.5 mM of substrate, 2.5 mM of UDP-Glucose and 3 mM $MgCl_2$ in 50 mM Sodium Phosphate buffer at pH 7.2. Samples were taken and analyzed by HPLC. The corresponding chromatogram after 23 h. of reaction is depicted in FIG. 63c.

| Enzyme internal reference | GI Number | Version | Rebaudioside A conv.[1] (reaction time) | Rebaudioside D formation[1] |
|---|---|---|---|---|
| UGTLB | 209954733 | BAG80557.1 | 72% (22 h.) | 10% |

Note:
[1]Based on initial concentration of Rebaudioside A

Example 33

Determination of Reaction Products for Rubusoside and Stevioside Conversion with UGTSL, UGTSL2, and UGTLB Conversion of stevioside with UGTSL and UGTSL2 was conducted in similar manner to Example 28, and the conversion of rubusoside with UGTSL and UGTSL2 was conducted similarly to Example 29. Conversions of rubusoside and stevioside with UGTLB was conducted similarly to Example 32.

The reaction mixtures were analyzed by LCMS to determine all reaction products.

| | | | | | | LC-MS, peak area ratio (%) | | |
|---|---|---|---|---|---|---|---|---|
| Sample ID | UGT (reaction time) | Rub | Stev | REb E | Reb D | Unknown peak #1 (MW804) RT 30.70 min | Unknown peak #2 (MW804) RT 49.50 min | Unknown peak #3 (MW804) RT 50.40 min |
| S151N15 | UGTSL2 (2 hrs) | 3.54 | 2.12 | 52.88 | 6.73 | 12.02 | 9.94 | 12.77 |
| S151N17 | UGTLB (5 hrs) | 13.49 | ND | 9.21 | 1.29 | 4.07 | 66.67 | 5.27 |
| S151N22 | UGTSL (45 hrs) | 7.82 | 2.37 | 35.88 | 3.45 | 20.38 | 27.75 | 2.35 |

| | | | | | LC-MS, peak area ratio (%) | | |
|---|---|---|---|---|---|---|---|
| Sample ID | UGT (reaction time) | Stev | Reb E | Reb D | Unknown peak #1 (MW966) RT = 22.60 min | Unknown peak #2 (MW966) RT = 26.50 min | Unknown peak #3 (MW966) RT = 29.50 min |
| S151N26 | UGTSL2 (2 hrs) | 20.01 | 42.56 | 1.70 | 4.48 | 5.56 | 25.70 |
| S151N28 | UGTLB (2 hrs) | 43.11 | 3.12 | ND | ND | 53.78 | ND |
| S151N33 | UGTSL (22 hrs) | 25.24 | 49.68 | 0.54 | 3.97 | 20.56 | ND |

It can be seen that amongst Rubusoside conversion products, besides Stevioside, Reb E and Reb D, there are at least 3 additional compounds with Molecular Weight of 804. The retention time of these compounds do not match with Reb B which is known to have same Molecular Weight as Stevioside. Since these compounds have same molecular weight with Stevioside it can be assumed that these novel steviol glycosides are isomers of Stevioside. On the other hand amongst Stevioside conversion products, besides Reb E and Reb D, there are at least 3 additional compounds with Molecular Weight of 966. The retention time of these compounds do not match with Reb A which is known to have same Molecular Weight as Reb E. Since these compounds have same molecular weight with Reb A and Reb E it can be assumed that these novel steviol glycosides are isomers of Reb A (Reb E).

Example 34

In Vivo Production of UGT76G1 in *S. cerevisiae*

SEQ ID NO: 11:
MENKTETTVRRRRRIILFPVPFQGHINPILQLANVLYSKGFSITIFHTNF

NKPKTSNYPHFTFRFILDNDPQDERISNLPTHGPLAGMRIPIINEHGADE

LRRELELLMLASEEDEEVSCLITDALWYFAQSVADSLNLRRLVLMTSSLF

NFHAHVSLPQFDELGYLDPDDKTRLEEQASGFPMLKVKDIKSAYSNWQIL

KEILGKMIKQTKASSGVIWNSFKELEESELETVIREIPAPSFLIPLPKHL

TASSSSLLDHDRTVFQWLDQQPPSSVLYVSFGSTSEVDEKDFLEIARGLV

DSKQSFLWVVRPGFVKGSTWVEPLPDGFLGERGRIVKWVPQQEVLAHGAI

GAFWTHSGWNSTLESVCEGVPMIFSDFGLDQPLNARYMSDVLKVGVYLEN

GWERGEIANAIRRVMVDEEGEYIRQNARVLKQKADVSLMKGGSSYESLES

LVSYISSL

The above mentioned amino acid sequence was codon optimized for expression in *S. cerevisiae*. Furthermore the yeast consensus sequence AACACA was added before the ATG start codon. The synthetic gene was subcloned in the pYES2 vector using Hind III and Xba I restriction sites. The pYES2_UGT76G1_Sc vector was used to transform chemically competent *S. cerevisiae* INVSc1 cells (Invitrogen).

The cells were grown on a solid synthetic minimal medium containing 2% glucose lacking Uracil and a single colony was picked and allowed to grow in liquid synthetic minimal medium lacking Uracil (SC-U containing 2% glucose). After centrifugation, the cells were suspended with SC-U (containing 2% glucose) and 60% glycerol/water. Aliquots were stored at −80° C. and one aliquot was used to start a culture in SC-U (containing 2% glucose) for 43 h at 30° C. Part of this culture was centrifuged and suspended in induction medium (SC-U containing 2% galactose) for 19 h30 at 30° C.

Cells were obtained by centrifugation and lysis with five volumes of CelLytic™ Y Cell Lysis Reagent (Sigma). The lysates were used directly for activity testing (UGT76G1_Sc).

Example 35

Figure 64A:
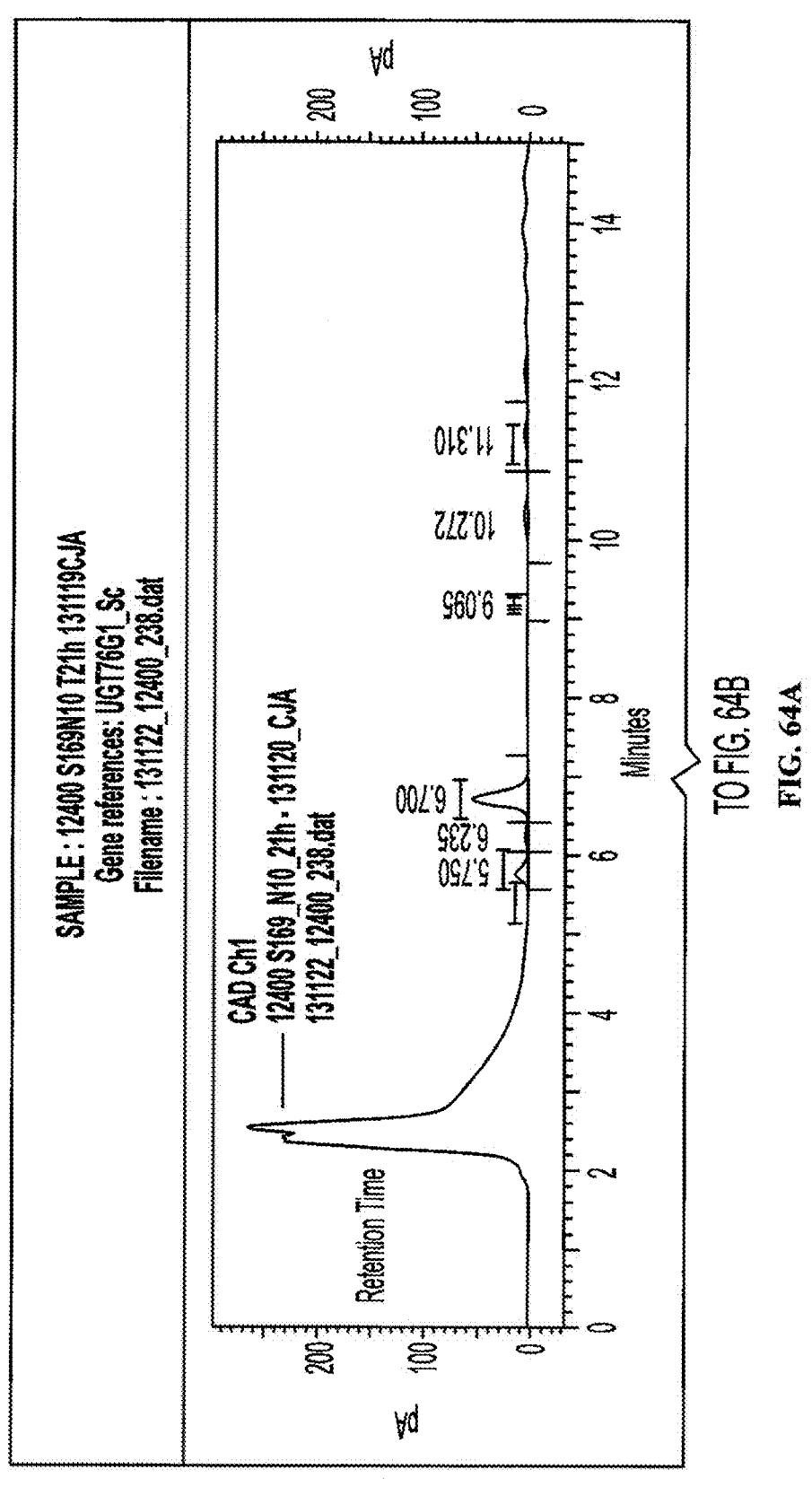

Determination of Activity of UGT76G1_Sc for the Conversion of Rebaudioside D to Rebaudioside M UGT76G1_Sc was prepared according to EXAMPLE 34. Activity tests were performed at 2 mL scale with 200 μL of lysate for the transformation of Rebaudioside D using 0.5 mM of substrate, 2.5 mM of UDP-Glucose and 3 mM $MgCl_2$ in 50 mM Sodium Phosphate buffer at pH 7.2. Samples were taken and analyzed by HPLC. The corresponding chromatogram is depicted in FIG. 64.

| Enzyme internal reference | Rebaudioside D conv.[1] (reaction time) | Rebaudioside M selectivity[1] |
|---|---|---|
| UGT76G1_Sc | 85% (21 h.) | 100% |

Note:
[1]Based on initial concentration of Rebaudioside D

Example 36

In Vivo Production of UGTSL in *S. cerevisiae*

SEQ ID NO: 12:
MSPKLHKELFFHSLYKKTRSNHTMATLKVLMFPFLAYGHISPYLNVAKKL

ADRGFLIYFCSTPINLKSTIEKIPEKYADSIHLIELHLPELPQLPPHYHT

TNGLPPNLNQVLQKALKMSKPNFSKILQNLKPDLVIYDILQRWAKHVANE

QNIPAVKLLTSGAAVFSYFFNVLKKPGVEFPFPGIYLRKIEQVRLSEMMS

KSDKEKELEDDDDDDDLLVDGNMQIMLMSTSRTIEAKYIDFCTALTNWKV

VPVGPPVQDLITNDVDDMELIDWLGTKDENSTVFVSFGSEYFLSKEDMEE

VAFALELSNVNFIWVARFPKGEERNLEDALPKGFLERIGERGRVLDKFAP

QPRILNHPSTGGFISHCGWNSAMESIDFGVPIIAMPMHLDQPMNARLIVE

LGVAVEIVRDDDGKIHRGEIAETLKGVITGKTGEKLRAKVRDISKNLKTI

RDEEMDAAAEELIQLCRNGN

The above mentioned amino acid sequence was codon optimized for expression in *S. cerevisiae*. Furthermore the yeast consensus sequence AACACA was added before the ATG start codon. The synthetic gene was subcloned in the pYES2 vector using Hind III and Xba I restriction sites. The pYES2_UGTSL_Sc vector was used to transform chemically competent *S. cerevisiae* INVSc1 cells (Invitrogen).

The cells were grown on a solid synthetic minimal medium containing 2% glucose, lacking Uracil and a single colony was picked and allowed to grow in liquid synthetic minimal medium lacking Uracil (SC-U containing 2% glucose). After centrifugation, the cells were suspended with SC-U (containing 2% glucose) and 60% glycerol/water. Aliquots were stored at −80° C. and one aliquot was used to start a culture in SC-U (containing 2% glucose) for 43 h at 30° C. Part of this culture was centrifuged and suspended in induction medium (SC-U containing 2% galactose) for 19 h30 at 30° C. Cells were obtained by centrifugation and lysis with five volumes of CelLytic™ Y Cell Lysis Reagent (Sigma). The lysates were used directly for activity testing (UGTSL_Sc).

Example 37

Figure 65A:
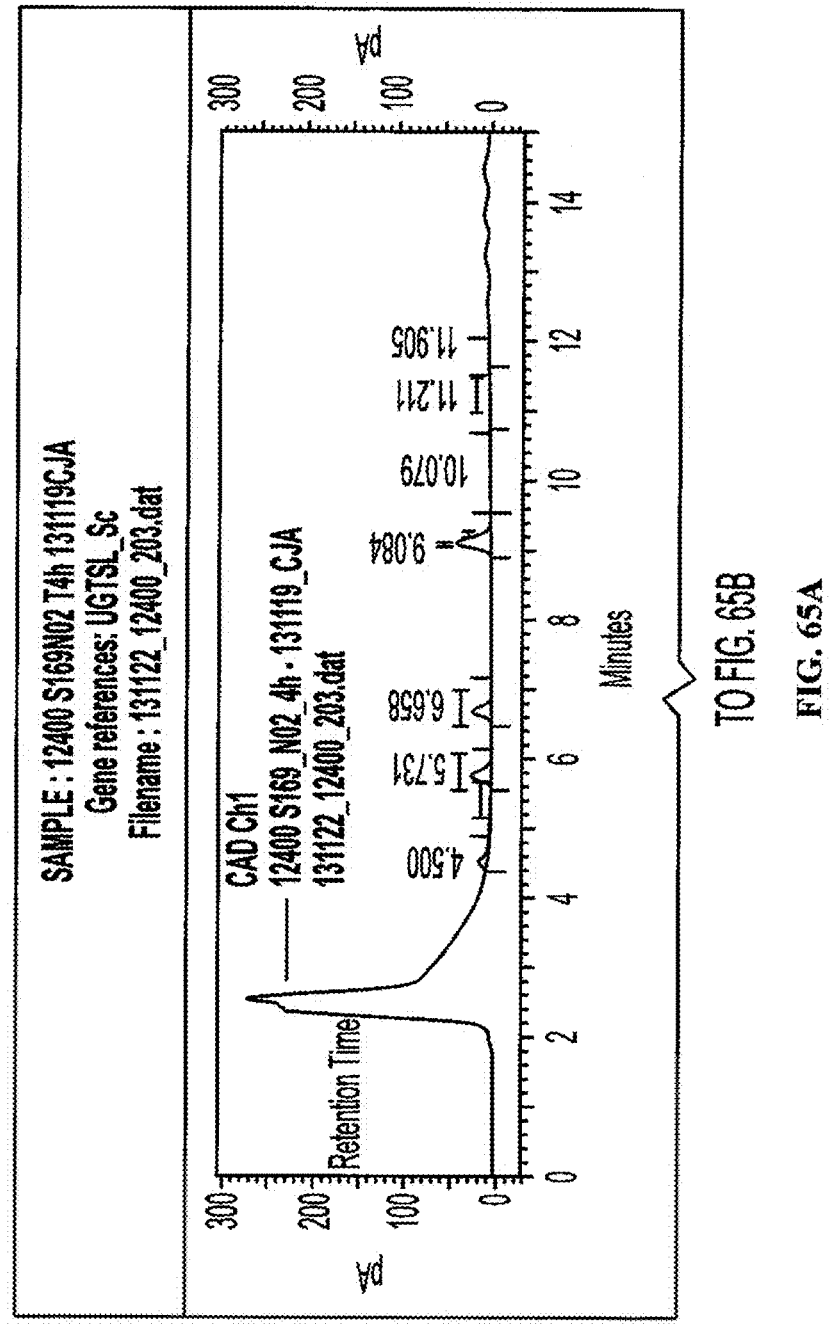

Determination of Activity of UGTSL_Sc for the Conversion of Rebaudioside A to Rebaudioside D UGTSL_Sc was prepared according to EXAMPLE 36. Activity tests were performed at 2 mL scale with 200 μL of lysate for the transformation of Rebaudioside A using 0.5 mM of substrate, 2.5 mM of UDP-Glucose and 3 mM MgCl$_2$ in 50 mM Sodium Phosphate buffer at pH 7.2. Samples were taken and analyzed by HPLC. The corresponding chromatogram is depicted in FIG. 65.

| Enzyme internal reference | Rebaudioside A conv.[1] (reaction time) | Rebaudioside D selectivity[1] |
|---|---|---|
| UGTSL_Sc | 46% (4 h) | 42% |

Note:
[1]Based on initial concentration of Rebaudioside A

Example 38

Isolation of Rebaudioside M

The amount of the product mixture of Example 14 was not large enough to separate via preparative HPLC methods. Accordingly, analytical HPLC with a series of injections was used to separate the components of the mixture. Separation was conducted according to the method described above in Example 14 to provide two fractions corresponding to the two main peaks in the HPLC trace of FIG. 5: Fraction A (retention time 24.165 minutes) and Fraction B (retention time 31.325 minutes).

The retention time of Fraction A was consistent with reb D, indicating unreacted starting material from the biotransformation reaction.

Figure 6:
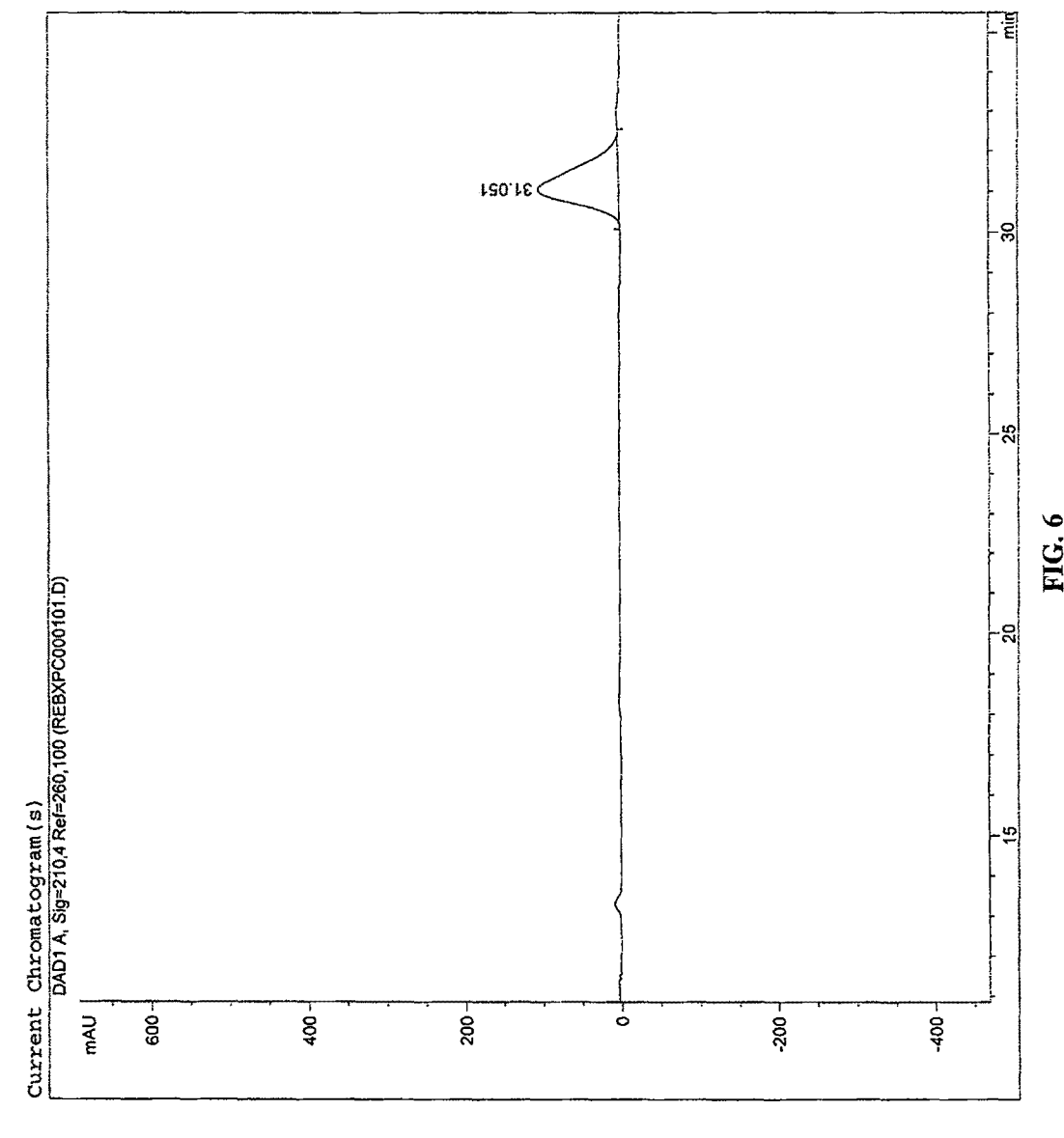
FIG. 6. shows the HPLC chromatogram of purified reb M produced by biocatalysis from reb D.
Figure 7:
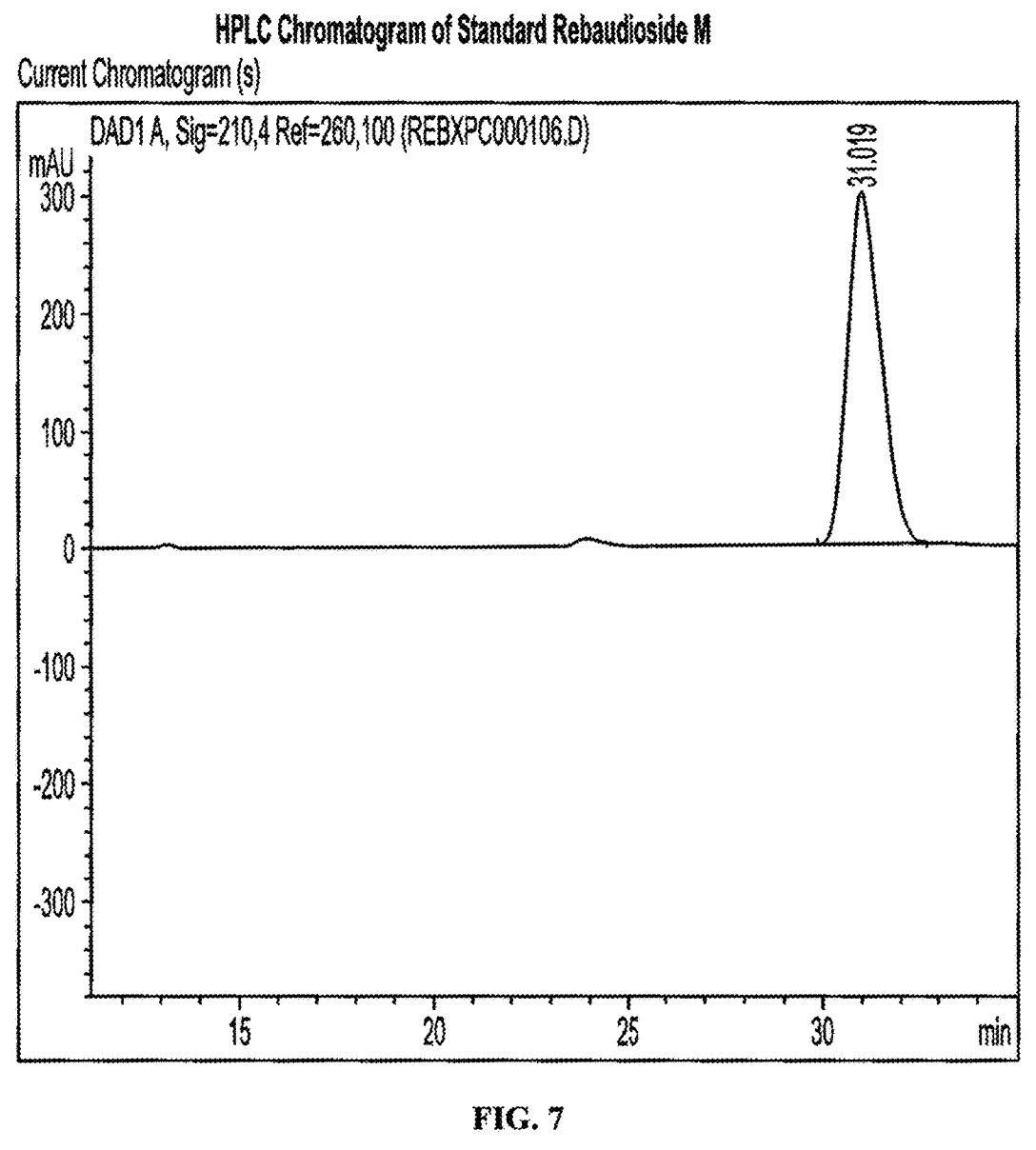
Figure 8:
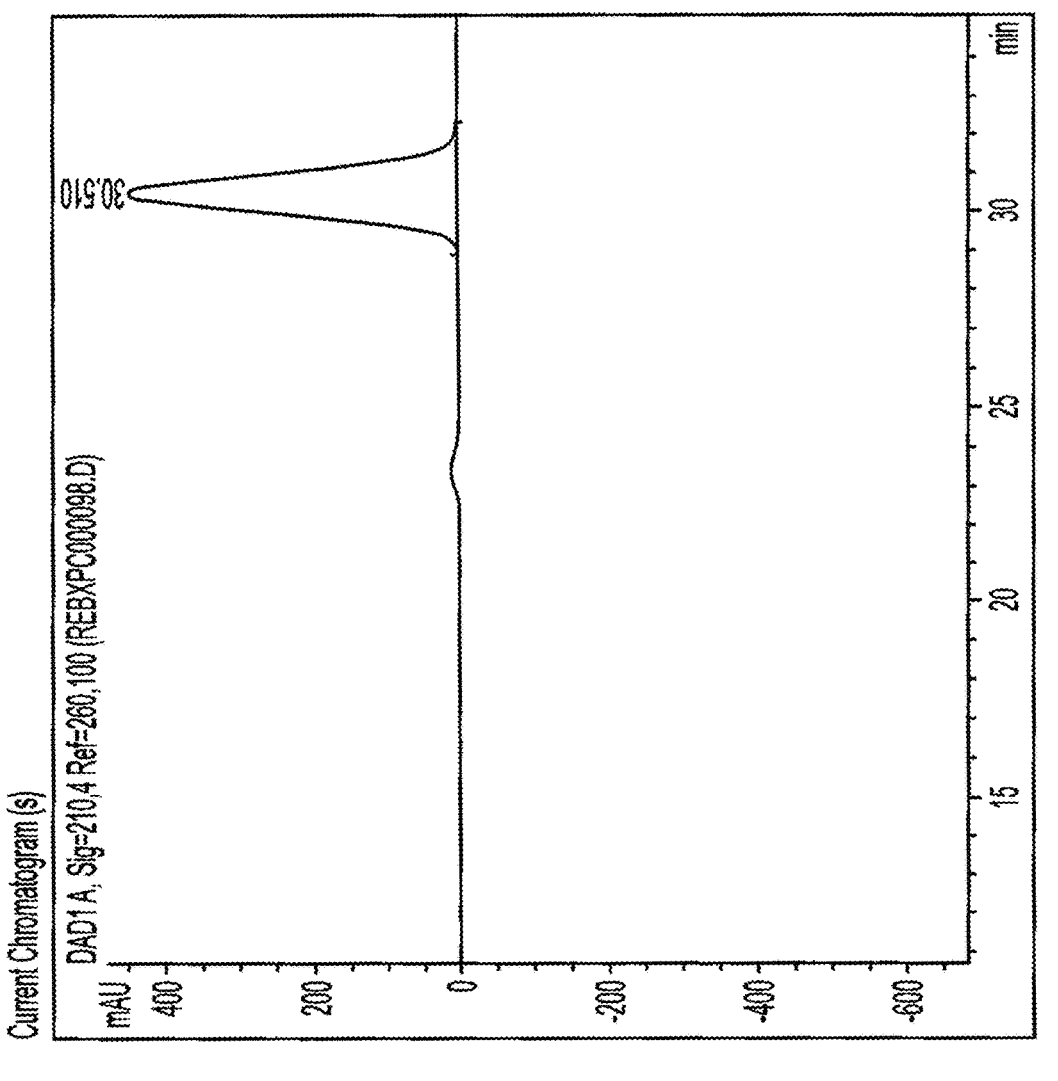
FIG. 8 shows the HPLC chromatogram of co-injection of a reb M standard and reb M purified from biotransformation from reb D.

The retention time of purified Fraction B (FIG. 6) was consistent with reb M, indicating successful biotransformation from reb D. The identity of the material collected in Fraction B as reb M was confirmed by co-injection of purified Fraction B with a reb M standard (available from PureCircle, HPLC trace of reb M standard shown in FIG. 7). Both Fraction B and the reb M standard were found to elute at the same retention time (FIG. 8), indicating Fraction B was reb M.

The identity of Fraction B as reb M was also separately confirmed by NMR and HRMS. For sampling, Fraction B was concentrated under rotary evaporator, freeze dried and dried for 40 h at 40° C.

The NMR sample was dissolved in deuterated pyridine (C5D5N) and spectra were acquired on a Varian Unity Plus 600 MHz instrument using standard pulse sequences. The NMR spectra of Fraction B was compared to the NMR spectra of reb M. An overlay of the two spectra (FIG. 9) showed consistency of peaks of Fraction B with reb M. A table of the NMR assignments for reb M is shown below:

| $^1$H and $^{13}$C NMR spectral data for Rebaudioside M in $C_5D_5N^{a\text{-}c}$. | | |
|---|---|---|
| Position | $^{13}$C NMR | $^1$H NMR |
| 1 | 40.3 | 0.75 t (13.2) |
| | | 1.76 m |
| 2 | 19.6 | 1.35 m |
| | | 2.24 m |
| 3 | 38.4 | 1.01 m |
| | | 2.30 d (13.3) |
| 4 | 44.3 | — |
| 5 | 57.4 | 1.06 d (12.8) |
| 6 | 23.5 | 2.23 m |
| | | 2.41 q (13.2) |
| 7 | 42.6 | 1.41 m |
| | | 1.80 m |

-continued

| $^1$H and $^{13}$C NMR spectral data for Rebaudioside M in $C_5D_5N^{a\text{-}c}$. | | |
|---|---|---|
| Position | $^{13}$C NMR | $^1$H NMR |
| 8 | 41.2 | — |
| 9 | 54.3 | 0.91 d (7.7) |
| 10 | 39.7 | — |
| 11 | 20.2 | 1.65 m |
| | | 1.75 m |
| 12 | 38.5 | 1.86 m |
| | | 2.73 m |
| 13 | 87.6 | — |
| 14 | 43.3 | 2.02 m |
| | | 2.74 m |
| 15 | 46.5 | 1.88 d (16.4) |
| | | 2.03 m |
| 16 | 153.3 | — |
| 17 | 104.9 | 4.90 s |
| | | 5.69 s |
| 18 | 28.2 | 1.32 s |
| 19 | 176.9 | — |
| 20 | 16.8 | 1.38 s |
| 1' | 94.9 | 6.39 d (8.2) |
| 2' | 76.9 | 4.51 t (8.5) |
| 3' | 88.6 | 5.09 t (8.5) |
| 4' | 70.1 | 4.18 m |
| 5' | 78.4 | 4.13 m |
| 6' | 61.8 | 4.20 m |
| | | 4.31 m |
| 1" | 96.2 | 5.46 d (7.1) |
| 2" | 81.4 | 4.13 m |
| 3" | 87.9 | 4.98 t (8.5) |
| 4" | 70.4 | 4.07 t (9.6) |
| 5" | 77.7 | 3.94 m |
| 6" | 62.6 | 4.19 m |
| | | 4.32 m |
| 1''' | 104.8 | 5.48 d (7.7) |
| 2''' | 75.8 | 4.15 m |
| 3''' | 78.6 | 4.13 m |
| 4''' | 73.2 | 3.98 m |
| 5''' | 77.6 | 3.74 ddd (2.8, 6.4, 9.9) |
| 6''' | 64.0 | 4.27 m |
| | | 4.51 m |
| 1'''' | 103.9 | 5.45 d (7.5) |
| 2'''' | 75.6 | 3.98 m |
| 3'''' | 77.8 | 4.50 t (7.8) |
| 4'''' | 71.3 | 4.14 m |
| 5'''' | 78.0 | 3.99 m |
| 6'''' | 62.1 | 4.20 m |
| | | 4.32 m |
| 1''''' | 104.2 | 5.81 d (7.2) |
| 2''''' | 75.5 | 4.20 m |
| 3''''' | 78.4 | 4.20 m |
| 4''''' | 73.6 | 4.10 m |
| 5''''' | 77.8 | 3.90 ddd (2.8, 6.4, 9.9) |
| 6''''' | 64.0 | 4.32 m |
| | | 4.64 d (10.3) |
| 1'''''' | 104.1 | 5.31 d (8.0) |
| 2'''''' | 75.5 | 3.95 m |
| 3'''''' | 78.0 | 4.37 t (9.1) |
| 4'''''' | 71.1 | 4.10 m |
| 5'''''' | 78.1 | 3.85 ddd (1.7, 6.1, 9.9) |
| 6'''''' | 62.1 | 4.10 m |
| | | 4.32 m |

$^a$assignments made on the basis of COSY, HMQC and HMBC correlations;
$^b$Chemical shift values are in δ (ppm);
$^c$Coupling constants are in Hz.

Figure 10:
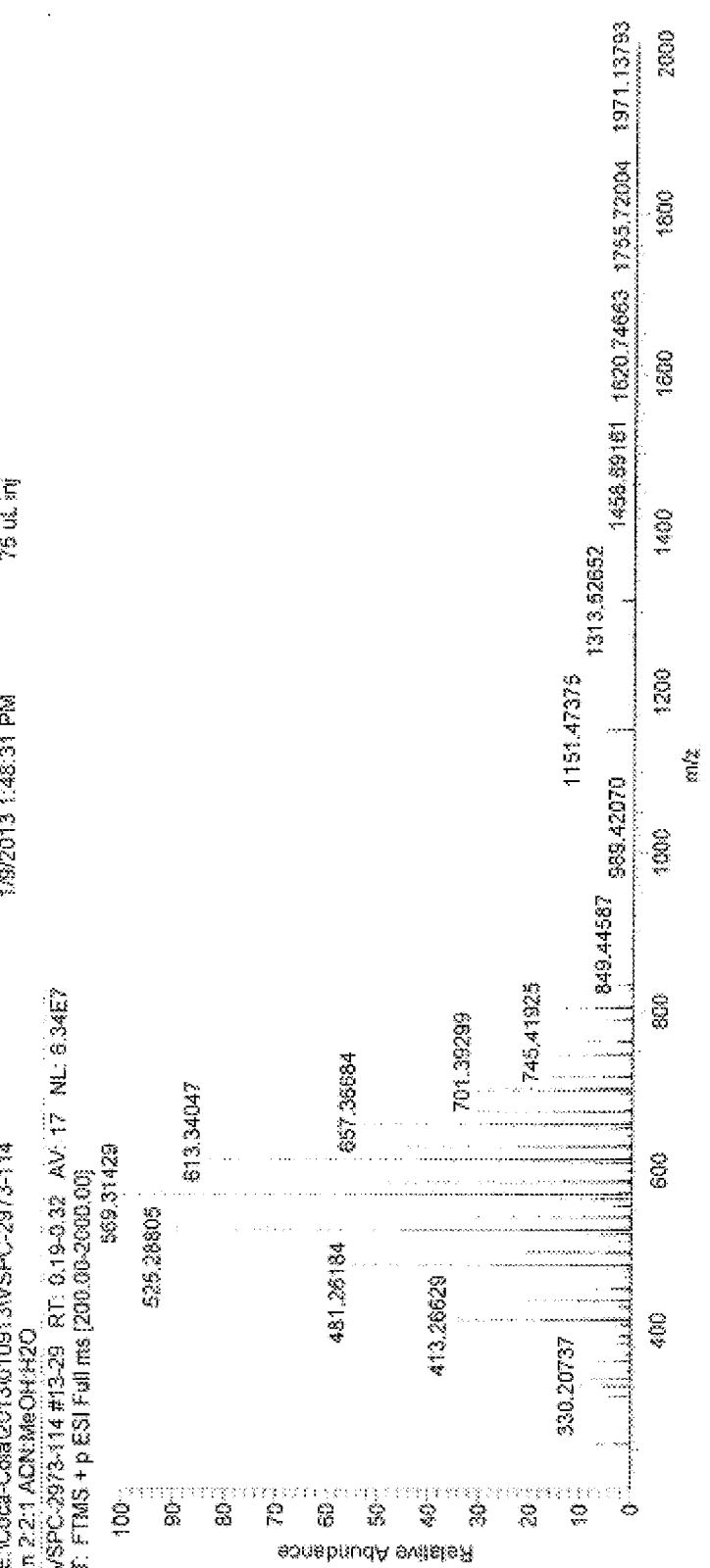
FIG. 10 shows the HRMS spectrum of reb M purified following biocatalytic production from reb D.

HRMS (FIG. 10) was generated with a Waters Premier Quadropole Time-of-Flight (Q-TOF) mass spectrometer equipped with an electrospray ionization source operated in the positive-ion mode. The sample was dissolved in methanol and eluted in 2:2:1 methanol:acetonitrile:water and introduced via infusion using the onboard syringe pump. The presence of reb M was confirmed by a [M+Na]$^+$ adduct at m/z 1313.5265, which corresponds to a molecular formula of $C_{56}H_{90}O_{33}$ Rebaudioside D
Chemical Formula: $C_{50}H_{80}O_{28}$
Molecular Weight: 1128

Rebaudioside M
Chemical Formula: $C_{56}H_{90}O_{33}$
Molecular Weight: 1290

Example 39

Isolation and Characterization of Reb D2

Crude Reaction Sample. The sample, Lot CB-2977-106, used for isolation, was prepared according to Example 22 with UGTSL (GI #460409128).

HPLC Analysis. Preliminary HPLC analyses of samples were performed using a Waters 2695 Alliance System with the following method: Phenomenex Synergi Hydro-RP, 4.6× 250 mm, 4 µm (p/n 00G-4375-E0); Column Temp: 55° C.; Mobile Phase A: 0.0284% ammonium acetate ($NH_4OAc$) and 0.0116% acetic acid (HOAc) in water; Mobile Phase B: Acetonitrile (MeCN); Flow Rate: 1.0 mL/min; Injection volume: 10 µL. Detection was by UV (210 nm) and CAD.

Gradient:

| Time (min) | % A | % B |
| --- | --- | --- |
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31-37 | 30 | 70 |
| 38 | 75 | 25 |

Analyses of semi-preparative purification fractions were performed with the following method: Waters Atlantis dC18, 4.6×100 mm, 5 µm (p/n 186001340); Mobile Phase A: 25% MeCN in water; Mobile Phase B: 30% MeCN in water; Flow Rate: 1.0 mL/min; Injection volume: 10 µL. Detection was by CAD.
Gradient:

| Time (min) | % A | % B |
| --- | --- | --- |
| 0.0-5.0 | 100 | 0 |
| 20 | 20 | 80 |
| 25 | 20 | 80 |
| 30 | 100 | 0 |

LC-MS. Preliminary analysis of the semi-synthetic steviol glycoside mixture was carried out on a Waters AutoPurification HPLC/MS System with a Waters 3100 Mass Detector operating in negative ion mode. Analysis of the sample was performed using the following method: Phenomenex Synergi Hydro-RP, 4.6×250 mm, 4 µm (p/n 00G-4375-E0); Column Temp: 55° C.; Mobile Phase A: 0.0284% $NH_4OAc$ and 0.0116% HOAc in water; Mobile Phase B: Acetonitrile; Flow Rate: 1.0 mL/min; Injection volume: 10 µL. Detection was by UV (210 nm), and MSD (–ESI m/z 500-2000). Gradient conditions were as listed above.

Isolation by HPLC. The purification was performed in two steps. The first method used for the semi-preparative purification is summarized below. Column: Waters Atlantis dC18, 30×100 mm, 5 µm (p/n 186001375); Mobile Phase A: 25% MeCN in water; Mobile Phase B: 30% MeCN in water; Flow Rate: 45 mL/min; Injection load: 160 mg dissolved in 20 mL of water. Detection was by UV (205 nm).
Gradient:

| Time (min) | % A | % B |
| --- | --- | --- |
| 0.0-5.0 | 100 | 0 |
| 20 | 20 | 80 |
| 25 | 20 | 80 |
| 30 | 100 | 0 |

The secondary purification used the same column and conditions, but isocratic mobile phase: 20% MeCN in water.

Purification from Natural Extracts. The purification was performed in three steps. The first method used for the preparative purification is summarized below. Primary Process: Waters Symmetry C18, 50×250 mm, 7 µm (p/n WAT248000); Isocratic mobile phase: 50% methanol (MeOH) in water with 0.05% HOAc; Flow Rate: 85 mL/min; Injection load: 6 g crude extract dissolved in 50 mL of mobile phase. Detection was by UV (210 nm). Following the elution of target analytes, the column was flushed with 85% MeOH in water.

Secondary Process: Waters Symmetry Shield RP18, 50×250 mm, 7 µm (p/n WAT248000); Isocratic mobile phase: 20% MeCN in water; Flow Rate: 100 mL/min; Injection load: 0.5 g primary fraction dissolved in 30 mL of water. Detection was by UV (210 nm).

Tertiary Process: Waters Symmetry Shield RP18, 50×250 mm, 7 μm (p/n WAT248000); Isocratic mobile phase: 20% MeCN in water; Flow Rate: 100 mL/min; Injection load: 0.5 g secondary fraction dissolved in 30 mL of water. Detection was by UV (210 nm).

MS and MS/MS. MS and MS/MS data were generated with a Waters QT of Premier mass spectrometer equipped with an electrospray ionization source. Samples were analyzed by negative ESI. Samples were diluted with $H_2O$: acetonitrile (1:1) by 50 fold and introduced via infusion using the onboard syringe pump. The samples were diluted to yield good s/n which occurred at an approximate concentration of 0.01 mg/mL.

NMR. The sample was prepared by dissolving 1-2 mg in 150 μL of pyridine-$d_5$ and NMR data were acquired on a Bruker Avance 500 MHz instrument with a 2.5 mm inverse detection probe. The $^1$H NMR spectrum was referenced to the residual solvent signal ($\delta_H$ 8.74 and $\delta_C$ 150.35 for pyridine-$d_5$).

Results and Discussion

Figure 11:
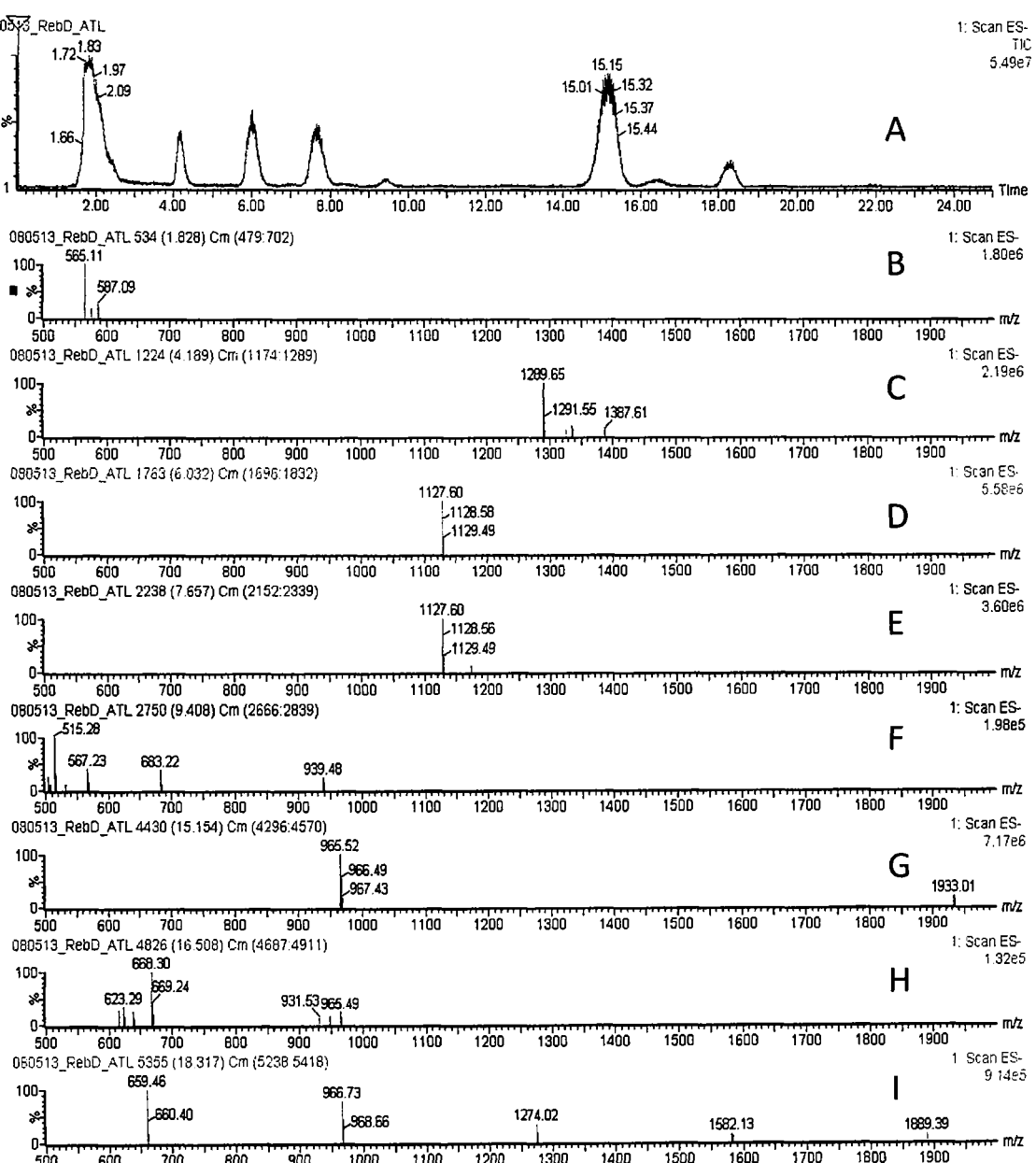
FIG. 11 shows LC-MS analysis of semi-synthetic steviol glycoside mixture, Lot number CB-2977-106, showing TIC (A), MS of peak at 1.8 min (B), MS of reb M2 peak at 4.1 min (C), MS of reb D peak at 6.0 min (D), MS of reb D2 peak at 7.7 min (E), MS of peak at 9.4 min (F), MS of rebaudioside A peak at 15.2 min (G), MS of peak at 16.5 min (H), and MS of peak at 18.3 min (I).

Isolation and Purification. Isolation was performed on steviol glycoside mixture, Lot number CB-2977-106, prepared according to Example 22 with UGTSL (GI #460409128) The material was analyzed by LC-MS using the method described above and results are provided in FIG. 11. The targeted peak of interest was that at 7.7 min in the TIC chromatogram. The mass spectrum of this peak provided a [M-H]$^-$ ion at m z 1127.6. The provided sample was preliminarily processed in a single injection (160 mg) using the first method condition provided above. This method fractionated the material into 'polar' and 'non-polar' mixtures of glycosides. The 'polar' mixture was then reprocessed using the second-step conditions above. The semi-preparative HPLC trace is provided in FIG. 12. From this semi-preparative collection, the compound was isolated with a purity >99% (CAD, AUC). The fraction analysis is provided in FIG. 13. Following the purification, the combined fractions were concentrated by rotary evaporation at 35° C. and lyophilized. Approximately 1-2 mg was obtained for characterization.

Mass Spectrometry. The ESI– TOF mass spectrum acquired by infusing a sample showed a [M-H]$^-$ ion at m z 1127.4709. The mass of the [M-H]$^-$ ion was in good agreement with the molecular formula $C_{50}H_{80}O_{28}$ (calcd for $C_{50}H_{79}O_{28}$ 1127.4758, error: –4.3 ppm). The MS data confirmed a nominal mass of 1128 Daltons with the molecular formula, $C_{50}H_{80}O_{28}$.

The MS/MS spectrum (selecting the [M-H]$^-$ ion at m z 1127.5 for fragmentation) indicated the loss of two glucose units and sequential loss of three glucose moieties at m z 641.3187, 479.2655 and 317.2065.

Figure 14A:
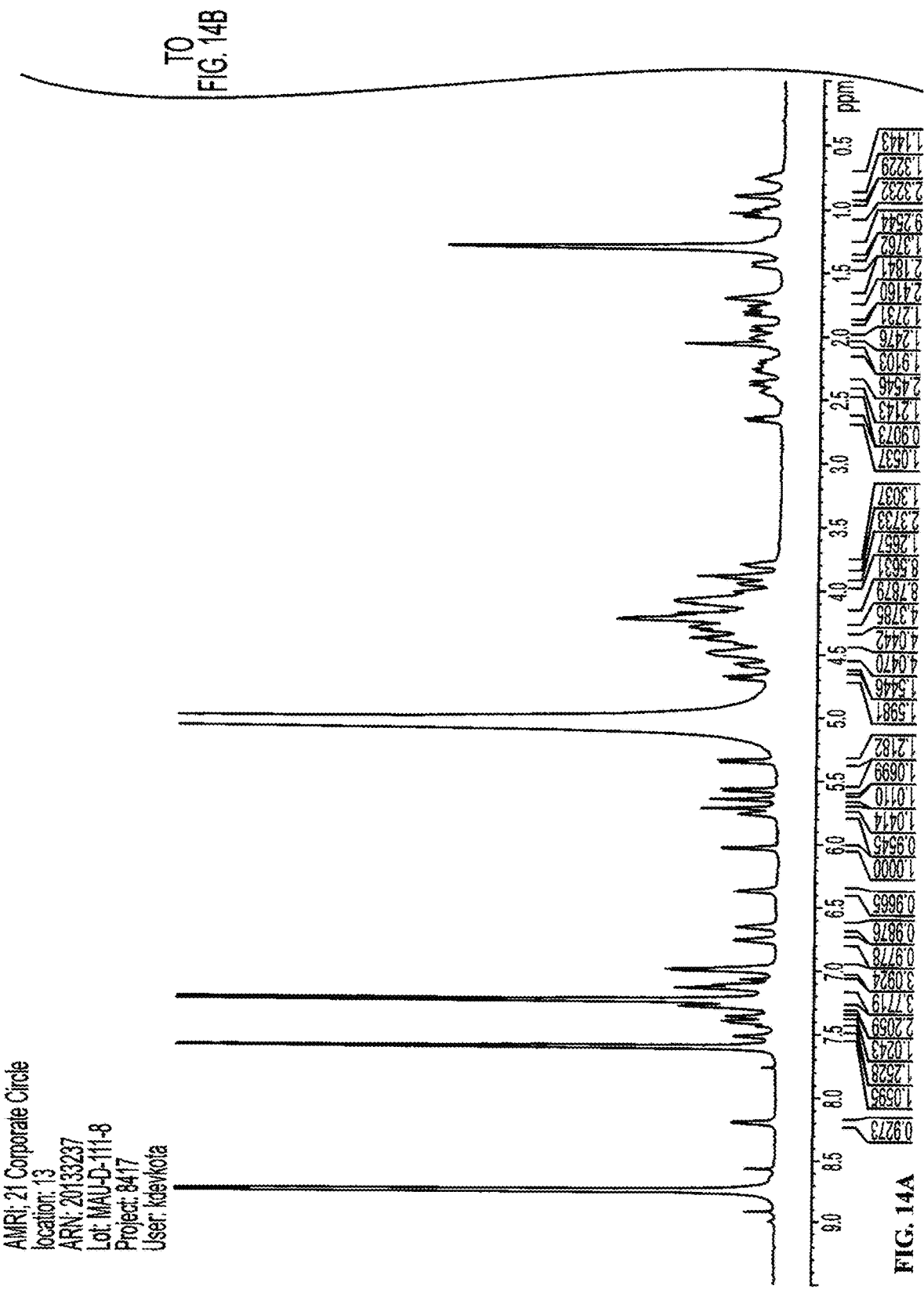
Figure 15A:
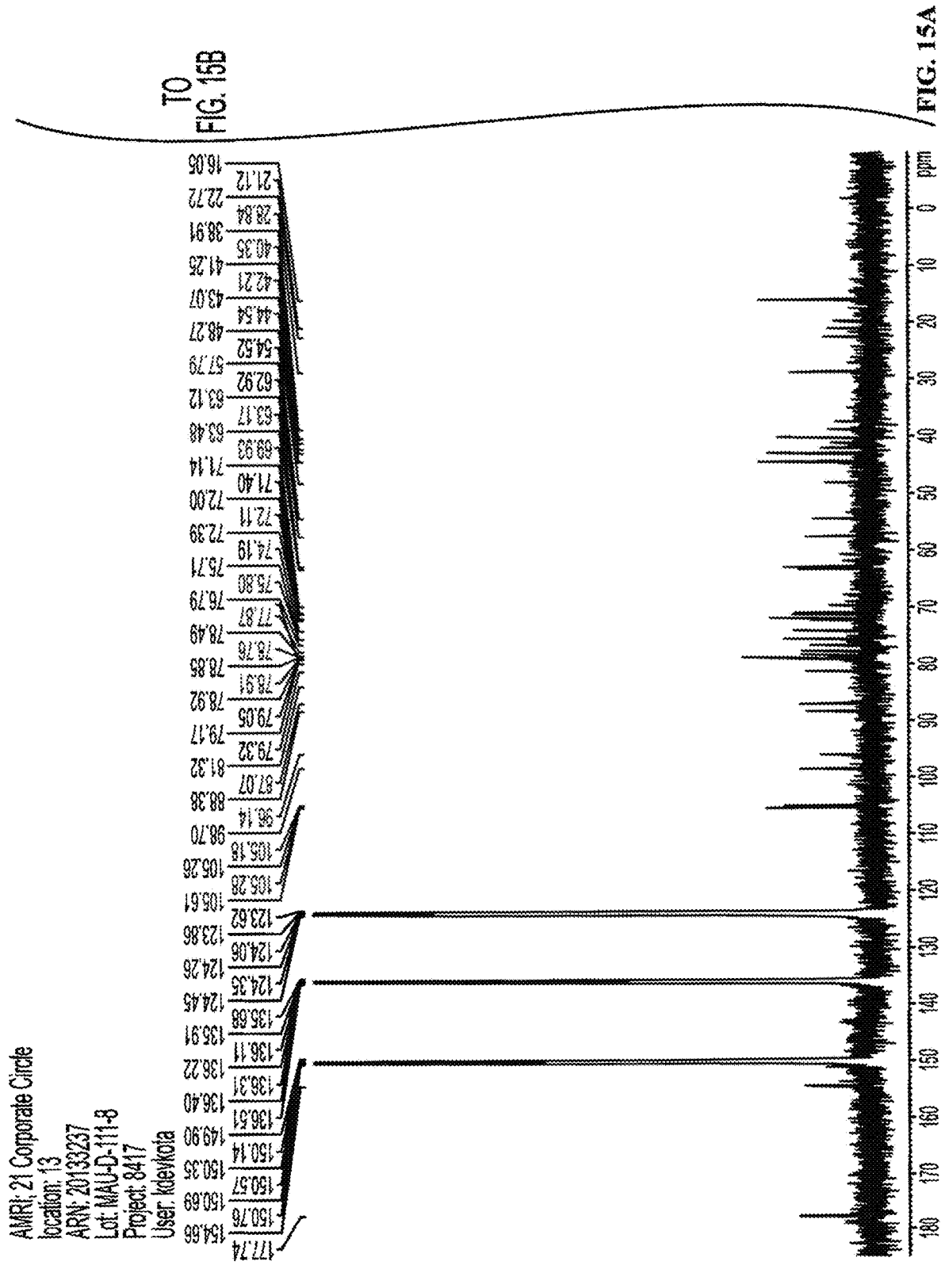
FIGS. 15A-15C show the $^{13}$C NMR spectrum of reb D2 (125 MHz, pyridine-d$_5$).
Figures 15A, 15B, 15C:
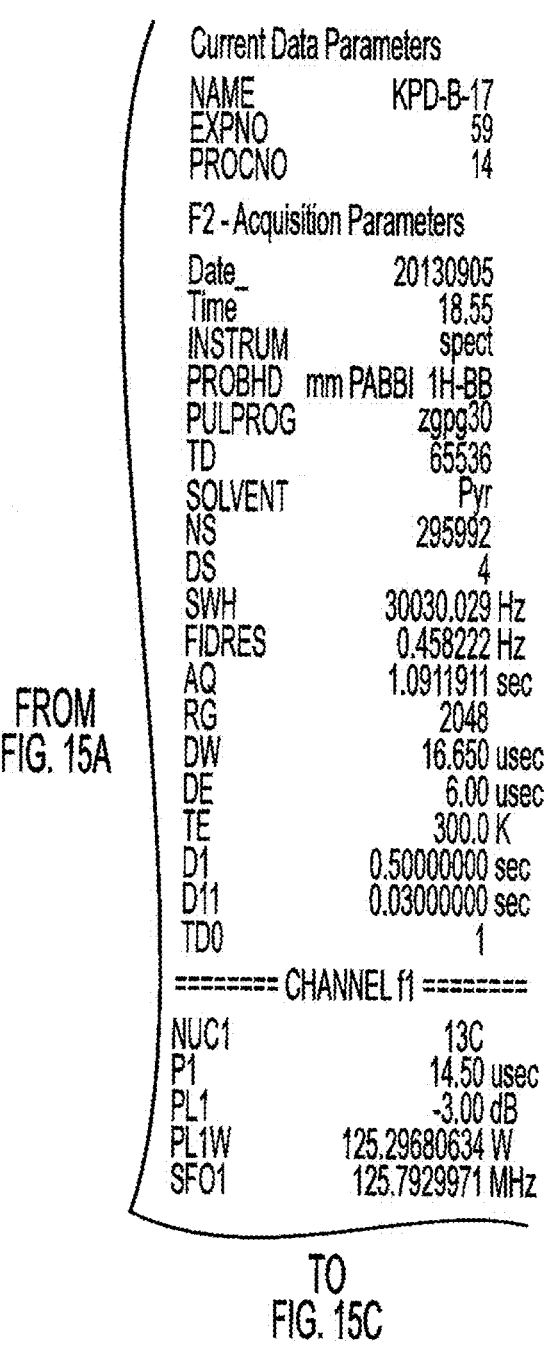
Figure 15C:
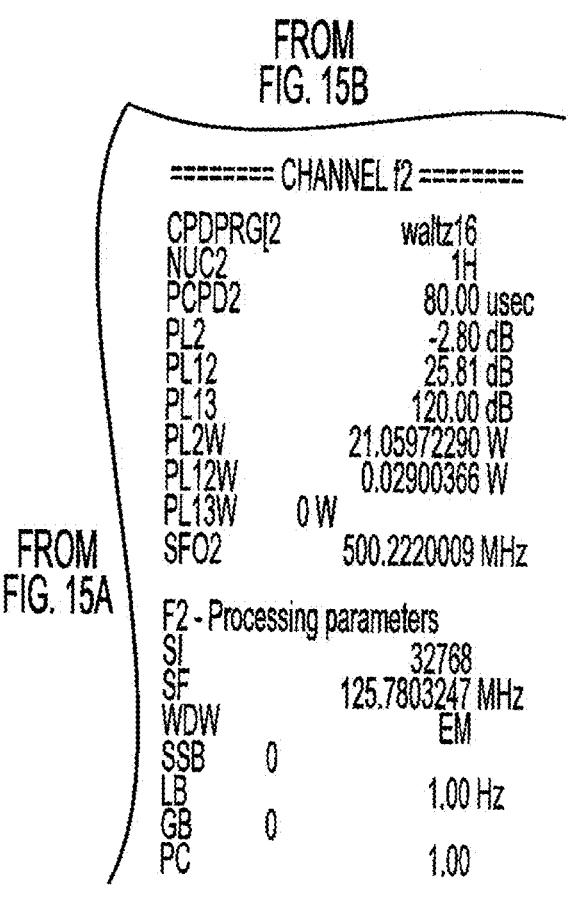
Figure 16A:
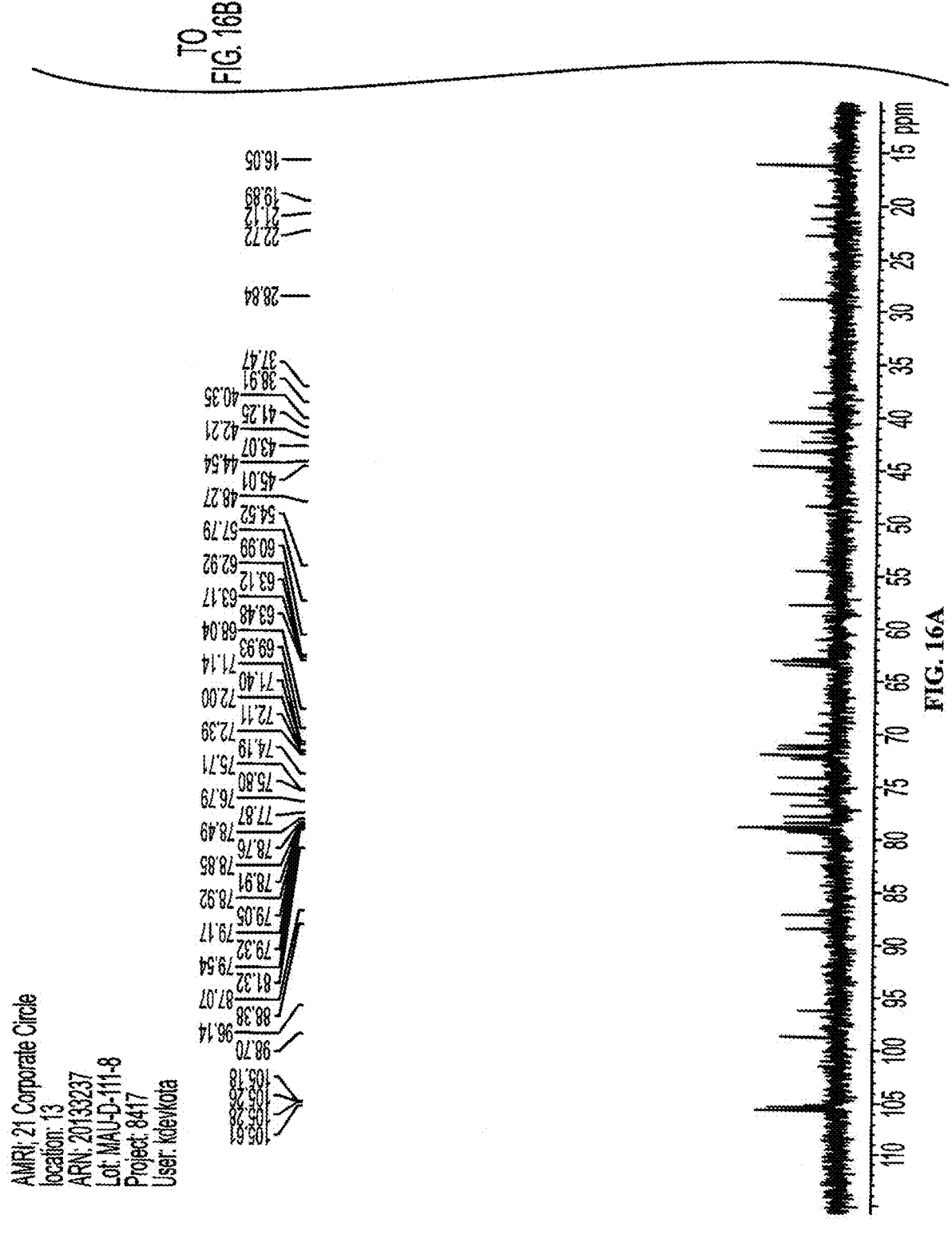
FIGS. 16A-16C show an expansion of the $^{13}$C NMR spectrum of reb D2 (125 MHz, pyridine-d$_5$).
Figures 16A, 16B, 16C:
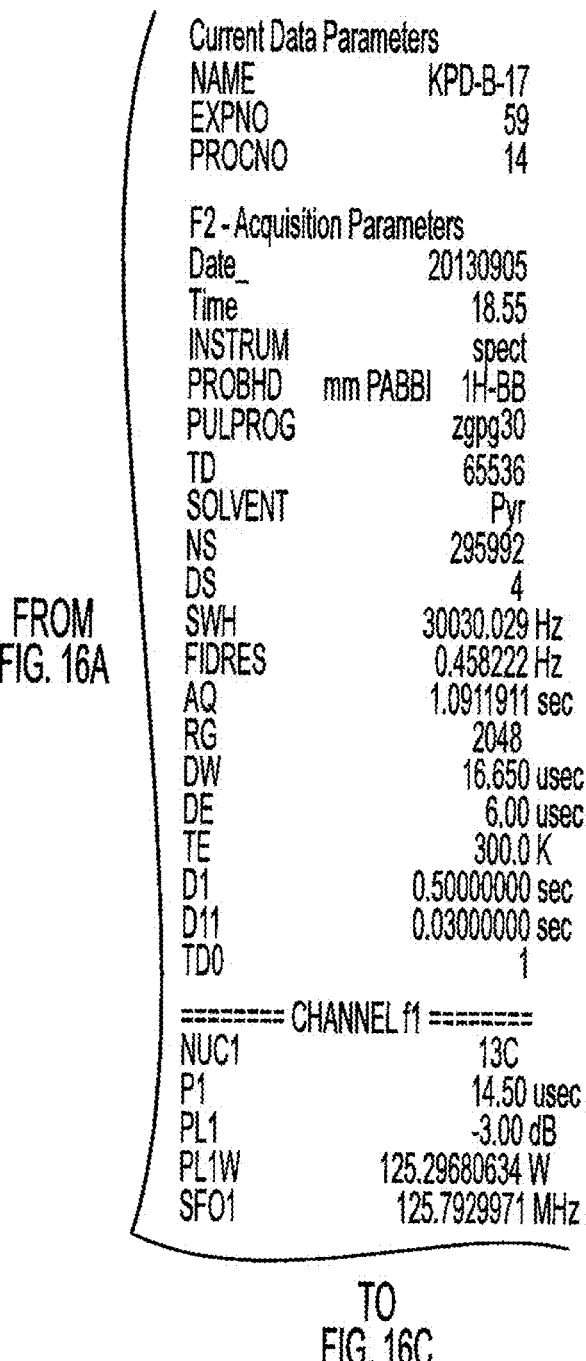
Figures 16A, 16B, 16C:
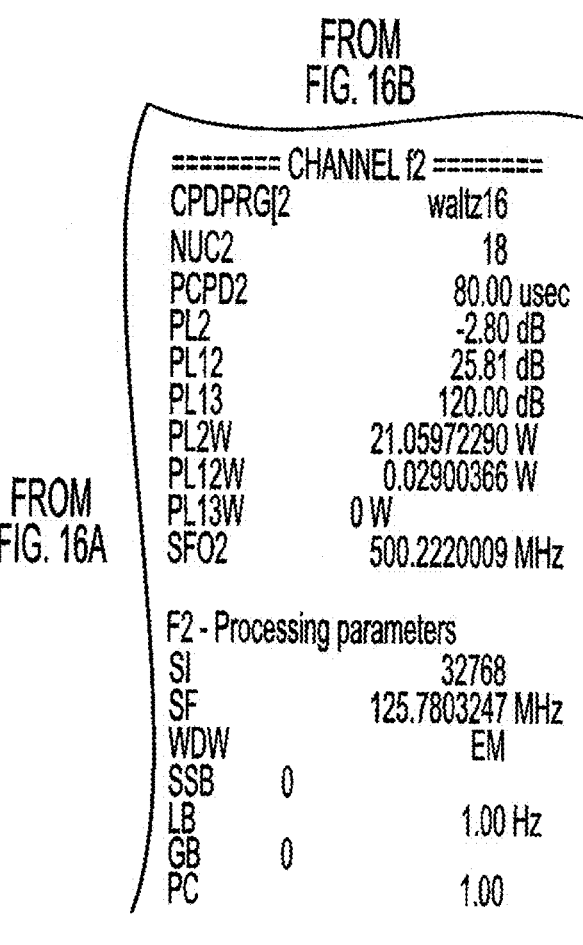
Figures 17A, 17B:
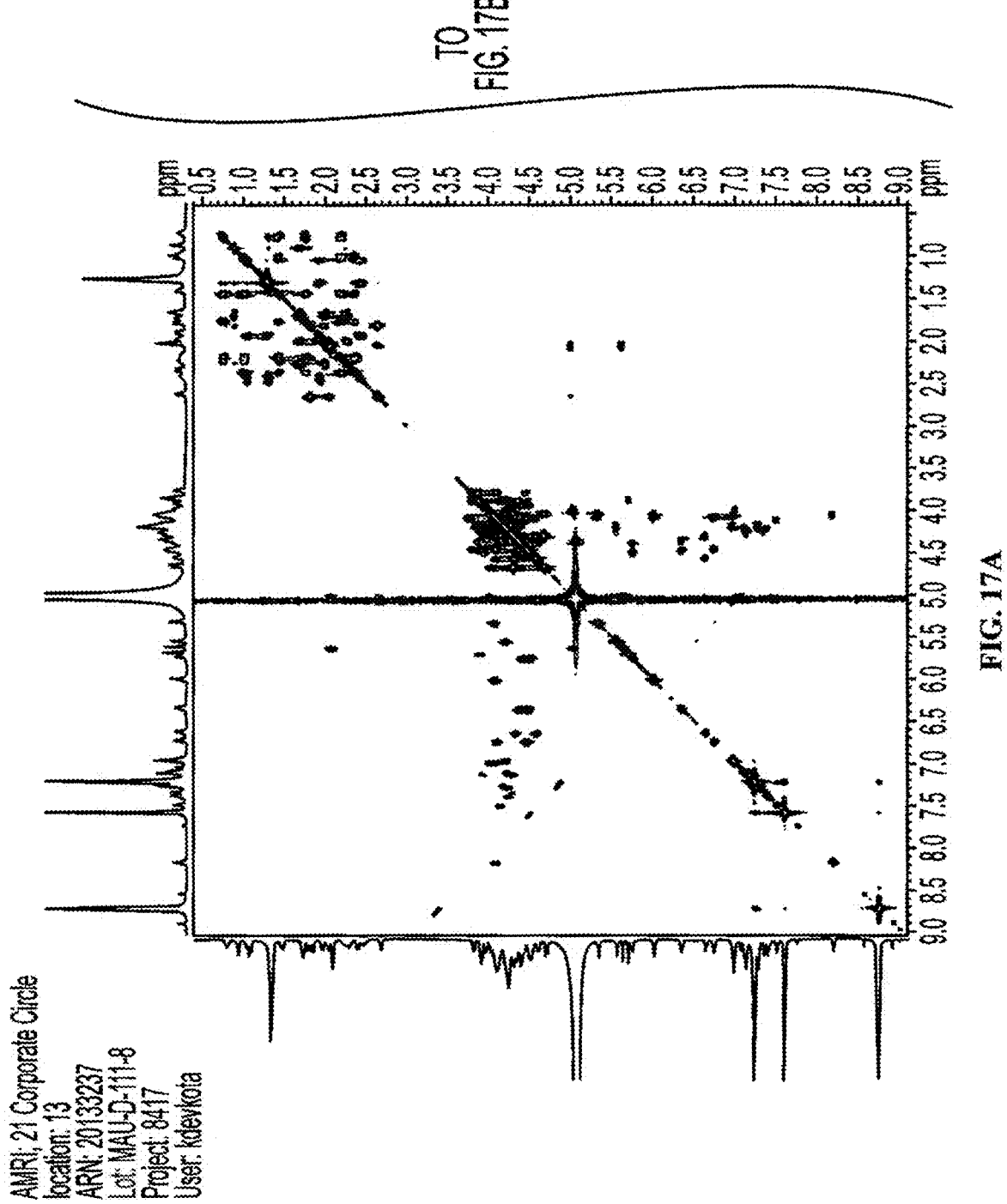
FIGS. 17A-17C show the $^1$H-$^1$H COSY Spectrum of reb D2 (500 MHz, pyridine-d$_5$).
Figures 17A, 17B, 17C:
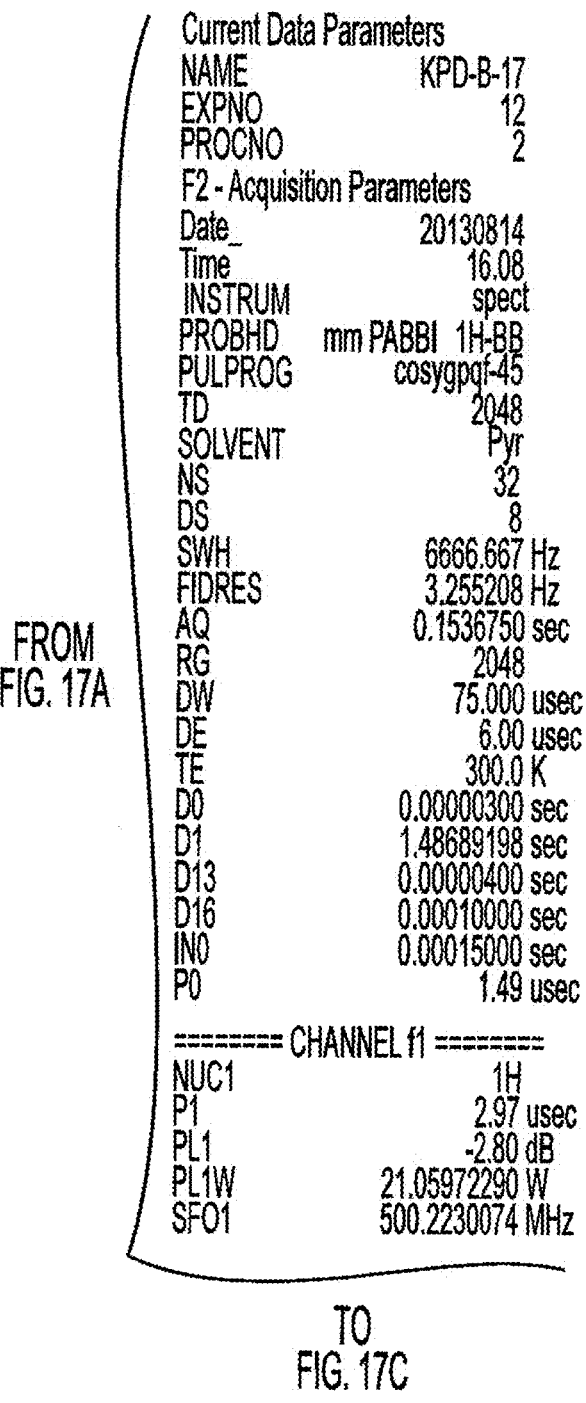
Figure 17C:
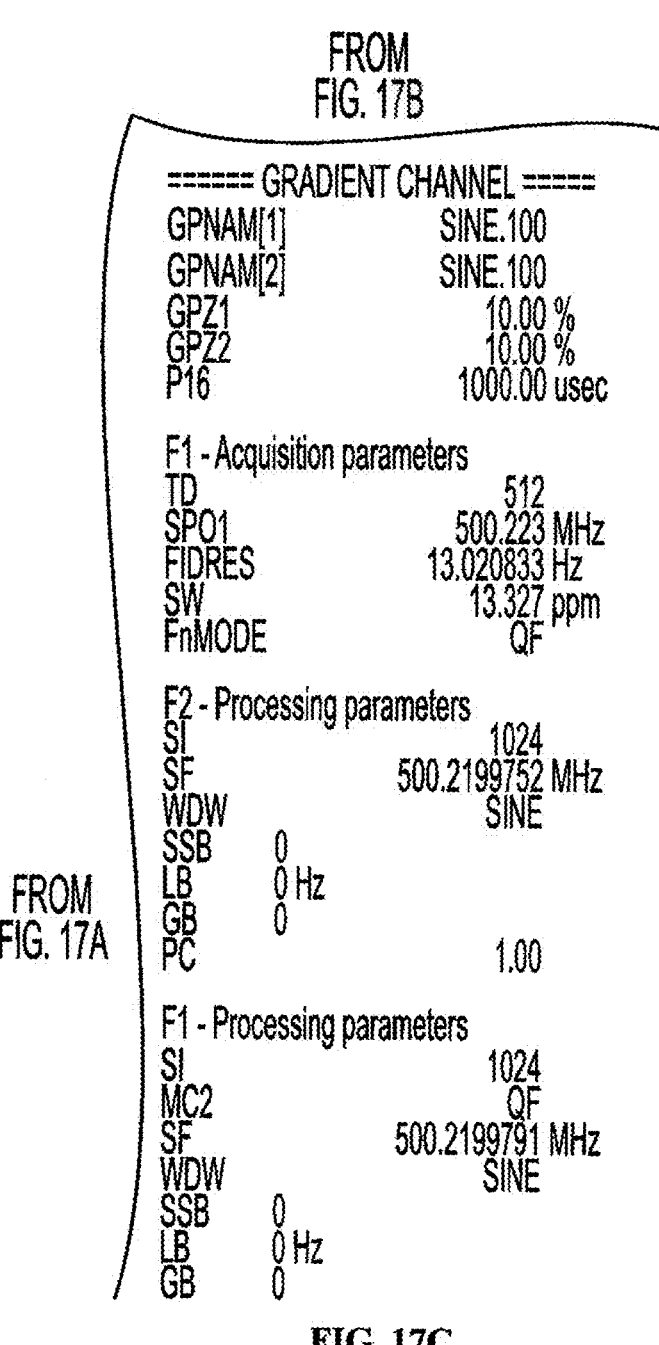
Figures 18A, 18B:
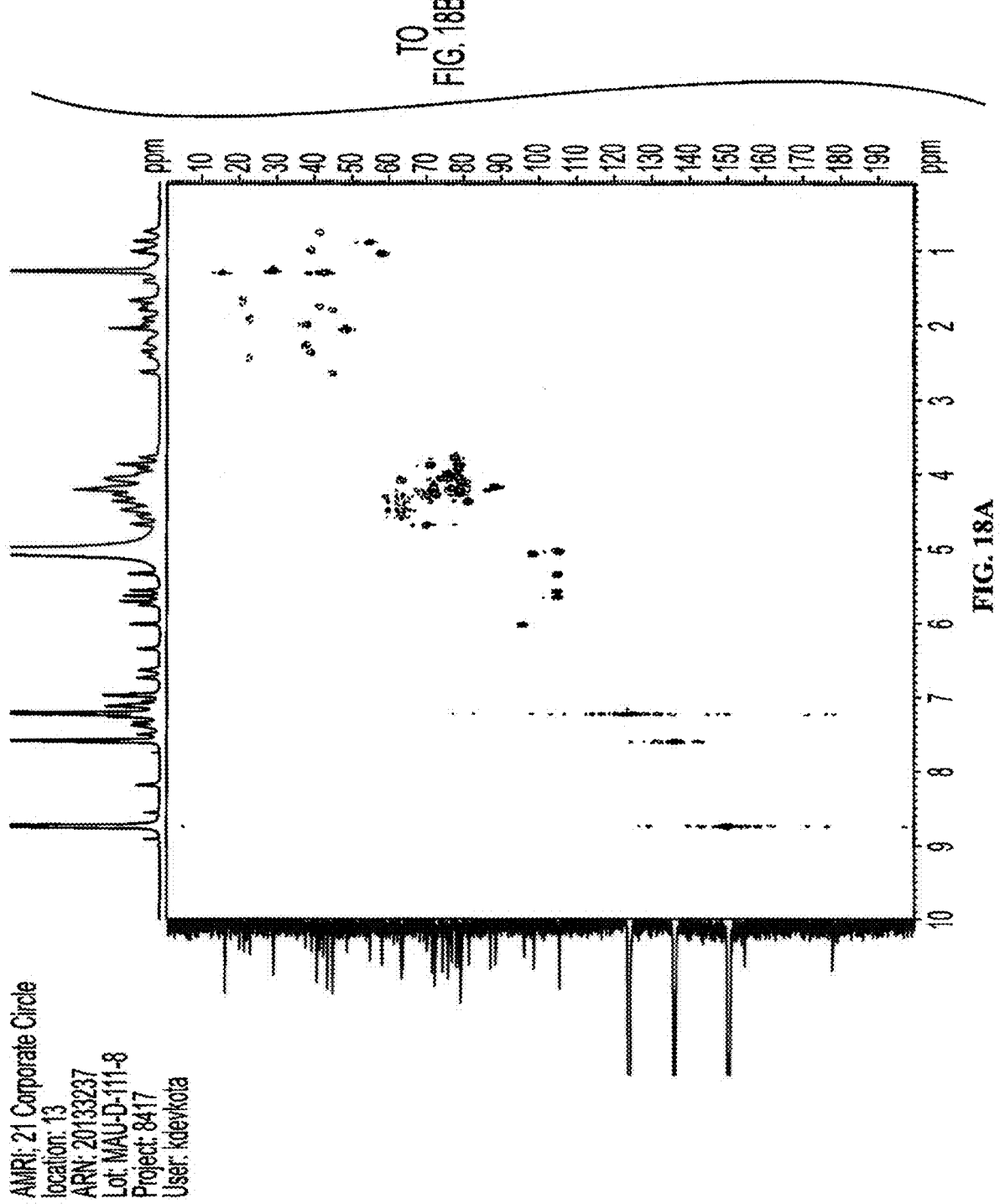
FIGS. 18A-18C show the HSQC-DEPT spectrum of reb D2 (500 MHz, pyridine-d$_5$).
Figures 18A, 18B, 18C:
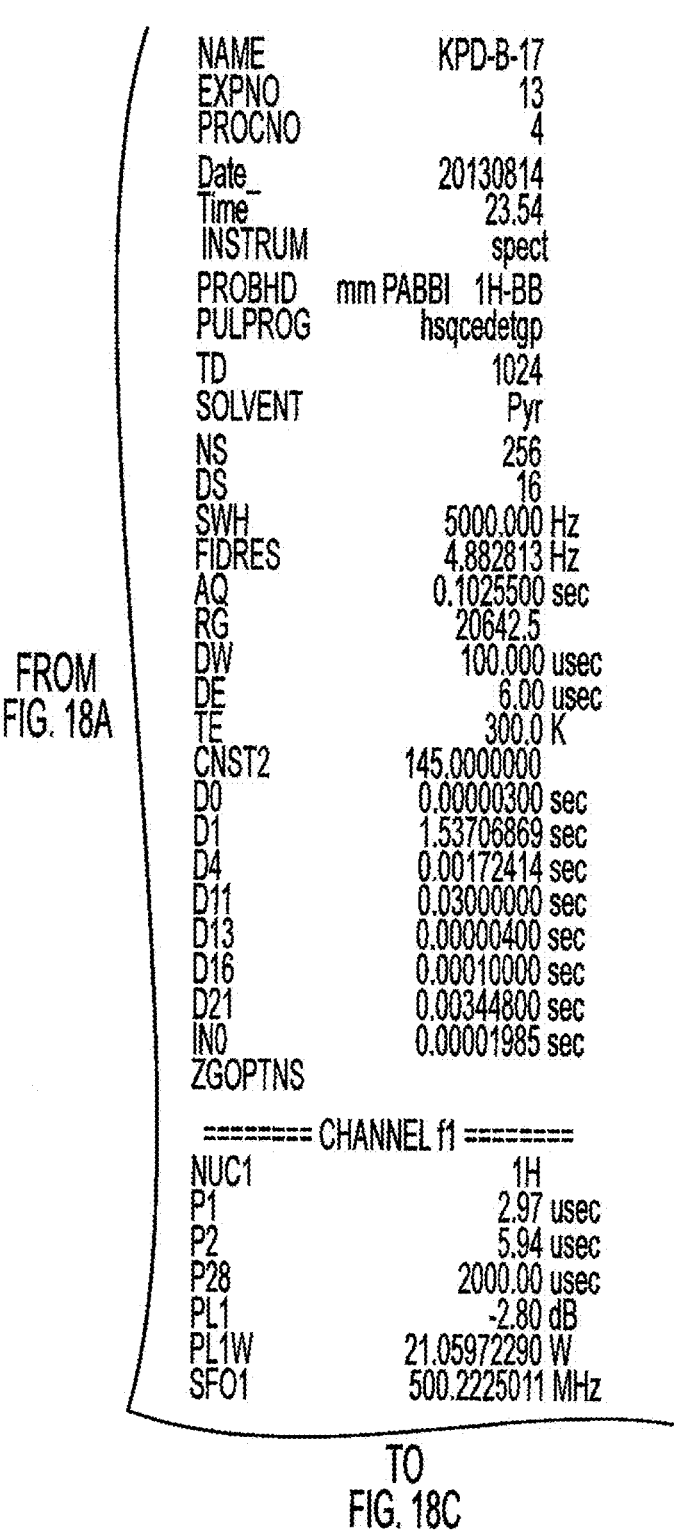
Figures 18A, 18B, 18C:
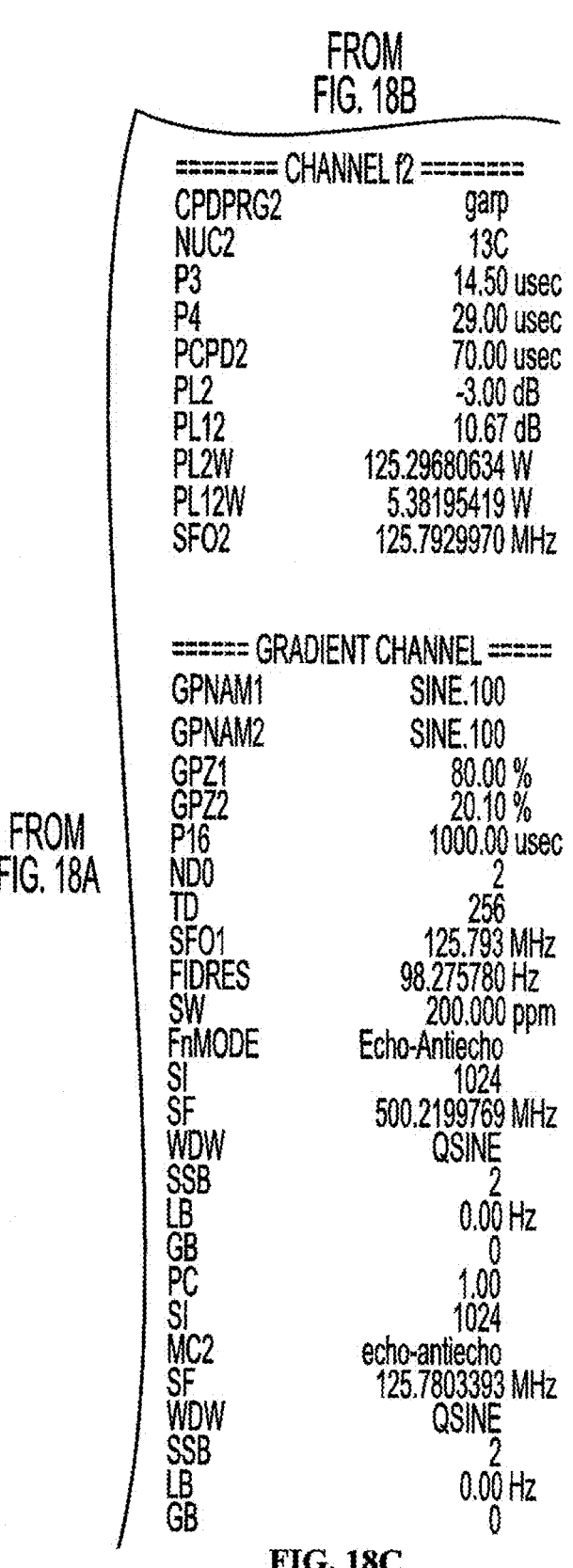
Figure 19A:
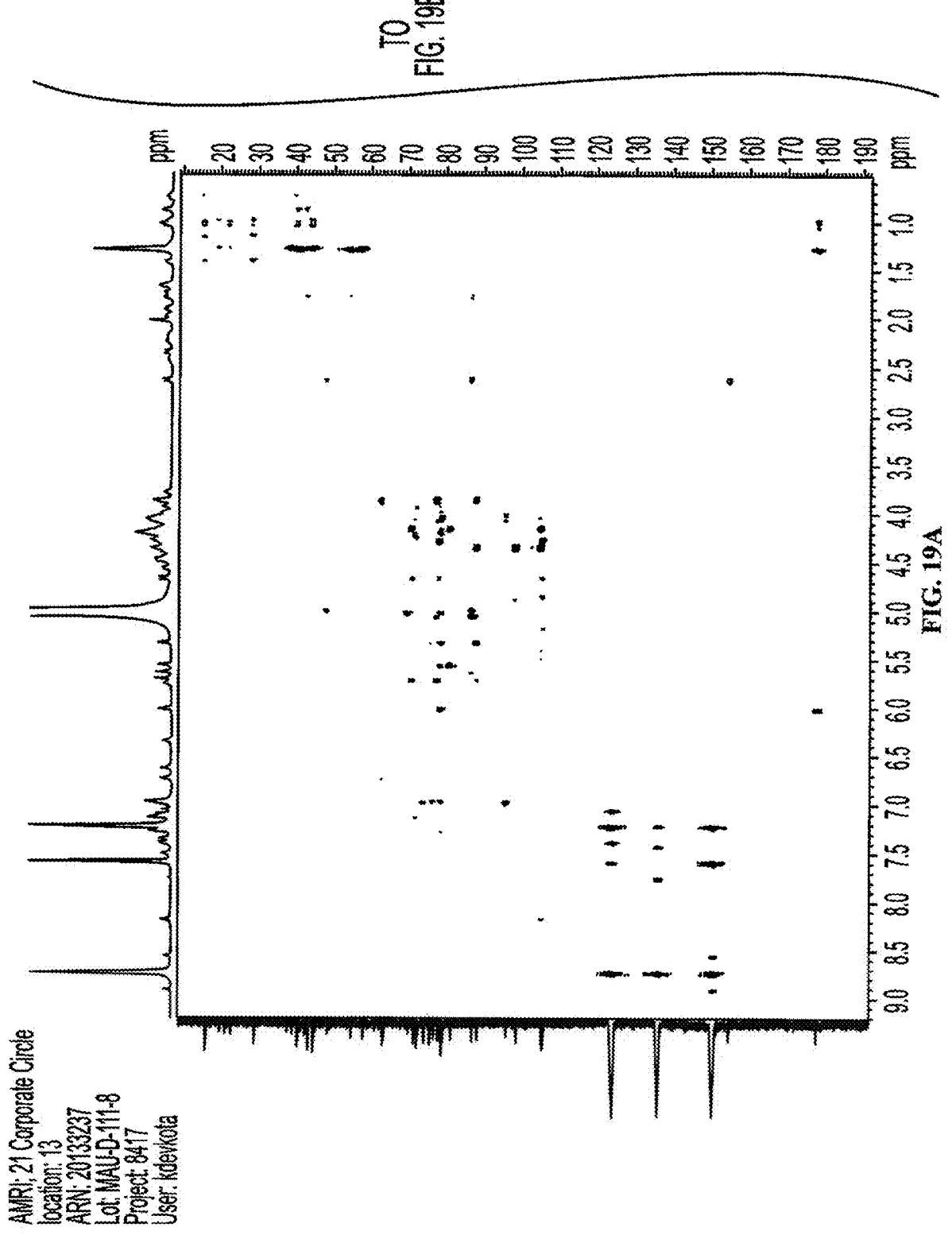
FIGS. 19A-19C show the HMBC spectrum of reb D2.
Figures 19A, 19B, 19C:
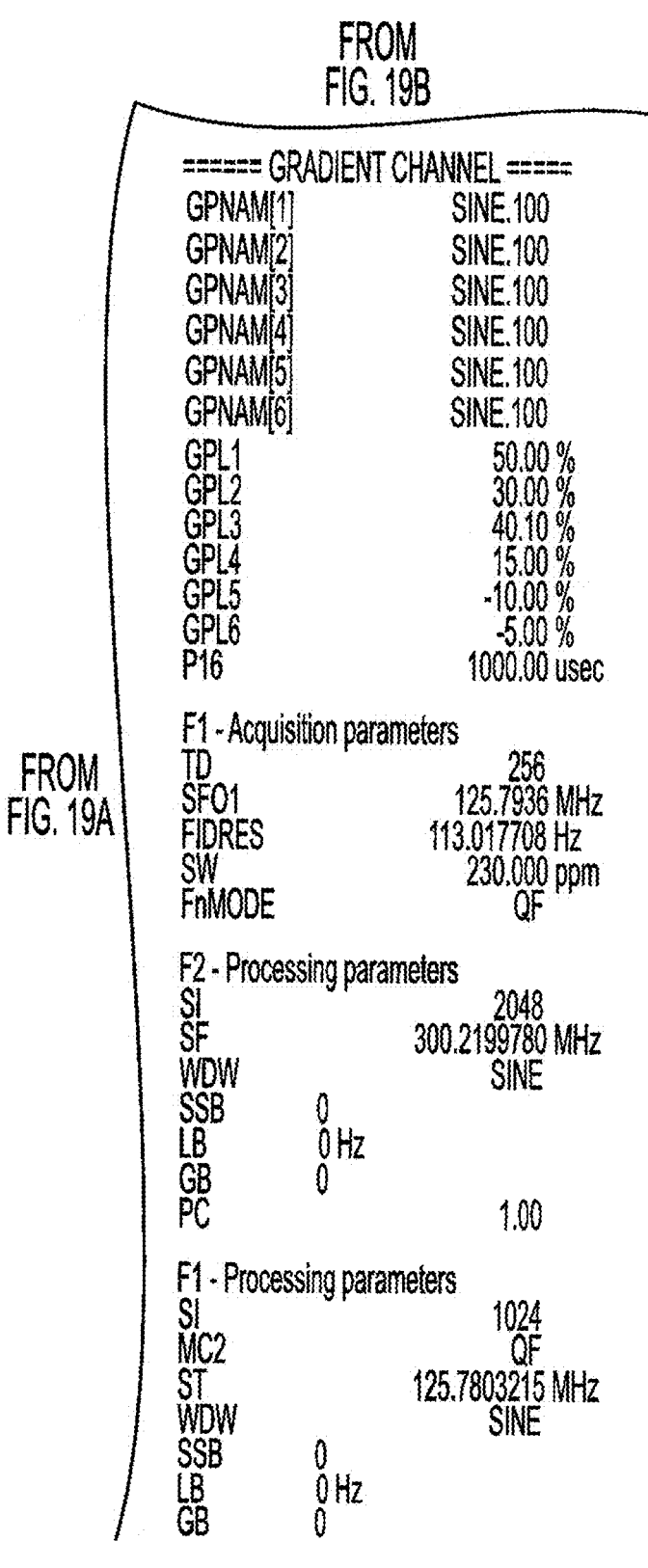
Figures 20A, 20B:
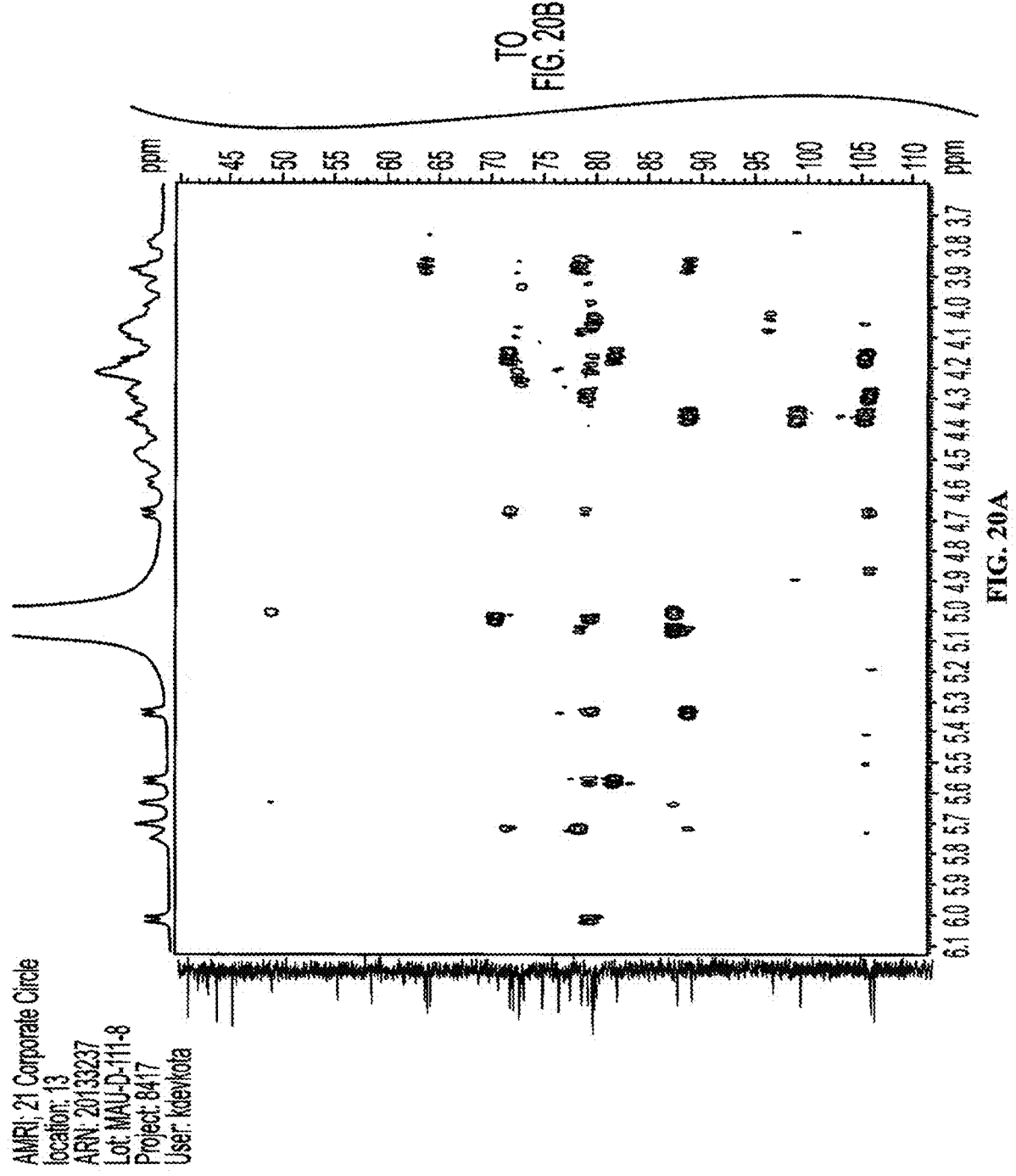
FIGS. 20A-20C show an expansion of HMBC spectrum of reb D2 (500 MHz, pyridine-d$_5$).
Figures 20A, 20B, 20C:
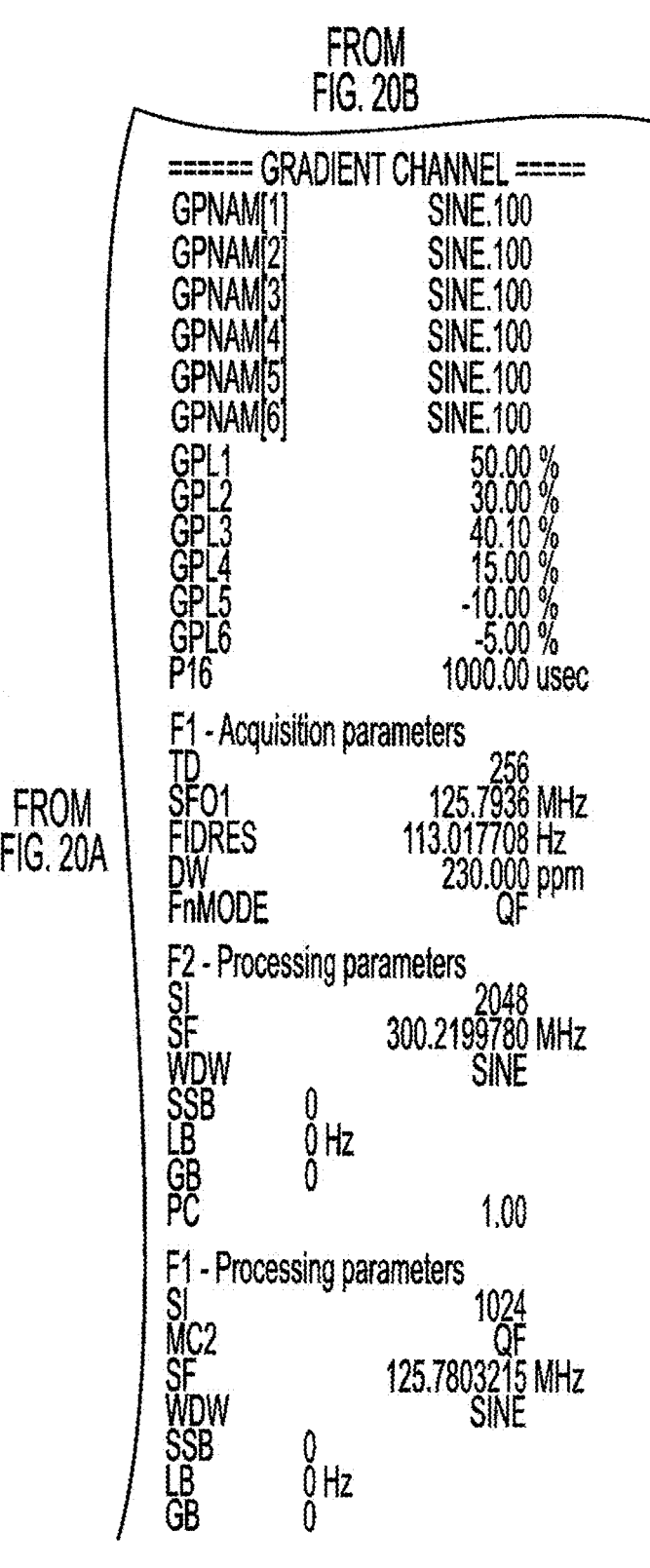

NMR Spectroscopy. A series of NMR experiments including $^1$H NMR (FIG. 14), $^{13}$C NMR (FIGS. 15 and 16), $^1$H-$^1$H COSY (FIG. 17), HSQC-DEPT (FIG. 18), HMBC (FIGS. 19 and 20), and 1D-TOCSY were performed to allow assignment of the compound.

The $^1$H, $^1$H-$^1$H COSY, $^1$H-$^{13}$C HSQC-DEPT and $^1$H-$^{13}$C HMBC NMR data indicated that the central core of the glycoside is a diterpene. The presence of five anomeric protons observed in the $^1$H and $^1$H-$^{13}$C HSQC-DEPT spectra confirm five sugar units in the structure. The methylene $^{13}$C resonance at $\delta_C$ 69.9 in the $^1$H-$^{13}$C HSQC-DEPT spectrum indicated the presence of a 1→6 sugar linkage in the structure. The linkages of sugar units were assigned using $^1$H-$^{13}$C HMBC and 1D-TOCSY correlations.

A HMBC correlation from the methyl protons at $\delta_H$ 1.29 to the carbonyl at $\delta_C$ 177.7 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.9, 45.0, and 57.8 allowed assignment of C-3, C-4, and C-5. Analysis of the $^1$H-$^{13}$C HSQC-DEPT data indicated that the carbon at $\delta_C$ 38.9 was a methylene group and the carbon at $\delta_C$ 57.8 was a methine which were assigned as C-3 and C-5, respectively. This left the carbon at $\delta_C$ 45.0, which did not show a correlation in the HSQC-DEPT spectrum, to be assigned as the quaternary carbon, C-4. The $^1$H chemical shifts for C-3 ($\delta_H$ 0.98 and 2j.36) and C-5 ($\delta_H$ 1.04) were assigned using the HSQC-DEPT data. A COSY correlation between one of the H-3 protons ($\delta_H$ 0.98) and a proton at $\delta_H$ 1.43 allowed assignment of one of the H-2 protons which in turn showed a correlation with a proton at $\delta_H$ 0.75 which was assigned to C-1. The remaining $^1$H and $^{13}$C chemical shifts for C-1 and C-2 were then assigned on the basis of additional COSY and HSQC-DEPT correlations and are summarized in the following table.

$^1$H and $^{13}$C NMR (500 and 125 MHz, pyridine-$d_5$), Assignments of Reb D2.

| Position | Reb D2 | |
| --- | --- | --- |
| | $^{13}$C | $^1$H |
| 1 | 41.3 | 0.75 t (11.0) |
| | | 1.76 m |
| 2 | 19.9 | 1.43 m |
| | | 2.20 m |
| 3 | 38.9 | 0.98 m |
| | | 2.36 d (12.1) |
| 4 | 45.0 | — |
| 5 | 57.8 | 1.04 d (12.5) |
| 6 | 22.7 | 1.92 m |
| | | 2.43 m |
| 7 | 42.2 | 1.22 m |
| | | 1.30 m |
| 8 | 43.1 | — |
| 9 | 54.5 | 0.88 brs |
| 10 | 40.3 | — |
| 11 | 21.1 | 1.65 m |
| | | 1.69 m |
| 12 | 37.5 | 1.99 m |
| | | 2.25 m |
| 13 | 87.1 | — |
| 14 | 44.5 | 1.80 d (11.7) |
| | | 2.65 d (11.7) |
| 15 | 48.3 | 1.31 m |
| | | 2.04 brs |
| 16 | 154.7 | — |
| 17 | 105.2 | 5.01 s |
| | | 5.64 s |
| 18 | 28.8 | 1.29 s |
| 19 | 177.7 | — |
| 20 | 16.0 | 1.30 s |

The other tertiary methyl singlet, observed at $\delta_H$ 1.30 showed HMBC correlations to C-1 and C-5 and was assigned as C-20. The methyl protons showed additional HMBC correlations to a quaternary carbon ($\delta_C$ 40.3) and a methine carbon ($\delta_C$ 54.5) which were assigned as C-10 and C-9, respectively. COSY correlations between H-5 ($\delta_H$ 1.04) and protons at $\delta_H$ 1.92 and 2.43 then allowed assignment of the H-6 protons which in turn showed correlations to protons at $\delta_H$ 1.22 and 1.30 which were assigned to C-7. The $^{13}$C chemical shifts for C-6 ($\delta_C$ 22.7) and C-7 ($\delta_C$ 42.2) were then determined from the HSQC-DEPT data. COSY correlations between H-9 ($\delta_H$ 0.88) and protons at $\delta_H$ 1.65 and 1.69 allowed assignment of the H-11 protons which in turn showed COSY correlations to protons at $\delta_H$ 1.99 and 2.25 which were assigned as the H-12 protons. The HSQC-DEPT data was then used to assign C-11 ($\delta_C$ 21.1) and C-12 ($\delta_C$ 37.5). HMBC correlations from the H-12 proton ($\delta_H$ 2.25) to carbons at $\delta_C$ 87.1 and 154.7 allowed assignment of C-13 and C-16, respectively. The olefinic protons observed at $\delta_H$ 5.01 and 5.64 showed HMBC correlations to C-13 and were assigned to C-17 ($\delta_C$ 105.2 via HSQC-DEPT). The olefinic protons H-17 and the methine proton H-9 showed HMBC correlations to a carbon at $\delta_C$ 48.3 which was assigned as C-15. An additional HMBC correlation from H-9 to a methylene carbon at $\delta_C$ 44.5 then allowed assignment of C-14. The $^1$H chemical shifts at C-14 ($\delta_H$ 1.80 and 2.65) and C-15 ($\delta_H$ 1.31 and 2.04) were assigned using the HSQC-DEPT data.

The key HMBC and COSY correlations used to assign the aglycone region are provided below:

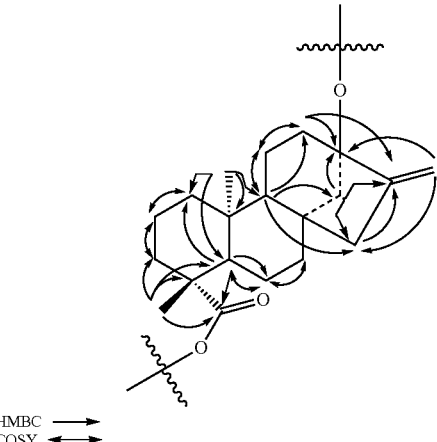

HMBC →
COSY ←→

Analysis of the $^1$H-$^{13}$C HSQC-DEPT data confirmed the presence of five anomeric protons. Three of the anomeric protons were well resolved at $\delta_H$ 6.02 ($\delta_C$ 96.1), 5.57 ($\delta_C$ 105.3), and 5.34 ($\delta_C$ 105.3) in the $^1$H NMR spectrum. The remaining two anomeric protons observed at $\delta_H$ 5.04 ($\delta_C$ 105.6) and 5.07 ($\delta_C$ 98.7) which were obscured by solvent (HOD) resonance in the $^1$H spectrum were identified by $^1$H-$^{13}$C HSQC-DEPT data. The anomeric proton observed at $\delta_H$ 6.02 showed HMBC correlation to C-19 which indicated that it corresponds to the anomeric proton of $Glc_I$. Similarly, the anomeric proton observed at $\delta_H$ 5.07 showed an HMBC correlation to C-13 allowing it to be assigned as the anomeric proton of $Glc_{II}$.

The $Glc_I$ anomeric proton ($\delta_H$ 6.02) showed a COSY correlation to a proton at $\delta_H$ 4.07 was assigned as $Glc_I$ H-2 which in turn showed a COSY correlation to a proton at $\delta_H$ 4.22 ($Glc_I$ H-3) which showed a COSY correlation with a proton at $\delta_H$ 4.12 ($Glc_I$ H-4). Due to data overlap, the COSY spectrum did not allow assignment of H-5 or the H-6 protons. Therefore, a series of 1D-TOCSY experiments were performed using selective irradiation of the $Glc_I$ anomeric proton with several different mixing times. In addition to confirming the assignments for $Glc_I$ H-2 through H-4, the 1D-TOCSY data showed a proton at $\delta_H$ 4.04 assigned as $Glc_I$ H-5 and a proton at $\delta_H$ 4.68 assigned as one of the $Glc_I$ H-6 protons. The latter proton was also used for 1D-TOCSY experiments. The selective irradiation of H-6 with several different mixing times also confirmed the assignment of $Glc_I$ H-1 to H-5 as well as the remaining methylene proton of H-6 ($\delta_H$ 4.30). Assignment of the $^{13}$C chemical shifts for $Glc_I$ C-2 ($\delta_C$ 74.2), C-3 ($\delta_C$ 79.1), C-4 ($\delta_C$ 72.1), C-5 ($\delta_C$ 78.5), and C-6 ($\delta_C$ 69.9) was determined using the $^1$H-$^{13}$C HSQC-DEPT data to complete the assignment of $Glc_I$. Furthermore, the presence of a methylene $^{13}$C resonance at $\delta_C$ 69.9 in the $^1$H-$^{13}$C HSQC-DEPT spectrum indicated a 1→6 sugar linkage of $Glc_I$ in the structure.

Out of four remaining unassigned glucose moieties, one was assigned as a substituent at C-6 of $Glc_I$ on the basis of $^1$H-$^{13}$C HSQC-DEPT, HMBC, and 1D-TOCSY correlations. The relatively downfield shift of a methylene $^{13}$C resonance of $Glc_I$ at $\delta_C$ 69.9 in the HSQC-DEPT spectrum indicated a 1→6 sugar linkage of $Glc_I$. The anomeric proton observed at $\delta_H$ 5.04 showed HMBC correlation to $Glc_I$ C-6 and was assigned as the anomeric proton of $Glc_V$. Similarly, methylene protons of $Glc_I$ showed HMBC correlations to anomeric carbon of $Glc_V$ confirming the presence of a 1→6 sugar linkage between $Glc_I$ and $Glc_V$. The $Glc_V$ anomeric proton showed a COSY correlation to a proton at $\delta_H$ 4.00 which was assigned as $Glc_V$ H-2 which in turn showed a COSY correlation to a proton at $\delta_H$ 4.22 ($Glc_V$ H-3). Due to data overlap, the COSY spectrum did not allow assignment of $Glc_V$ H-4 based on the COSY correlation of $Glc_V$ H-3. However, in the HMBC spectrum, $Glc_V$ H-3 showed a correlation to $Glc_V$ C-5 ($\delta_C$ 78.9). In HSQC-DEPT spectrum, $Glc_V$ C-5 showed a correlation to $\delta_H$ 3.89 ($Glc_V$ H-5). The $Glc_V$ H-5 showed COSY correlations to $\delta_H$ 4.21, 4.37, and 4.48. In the HSQC-DEPT spectrum, $\delta_H$ 4.21 showed a correlation to $\delta_C$ 71.4 ($Glc_V$ H-4), while $\delta_H$ 4.37 and 4.48 showed a correlation to $\delta_C$ 63.1 and were assigned to $Glc_V$ H-6a and H-6b, respectively. Assignment of the $^{13}$C chemical shifts for $Glc_V$ C-2 ($\delta_C$ 75.7) and C-3 ($\delta_C$ 79.1) was determined using the $^1$H-$^{13}$C HSQC-DEPT data to complete the assignment of $Glc_V$.

A summary of the $^1$H and $^{13}$C chemical shifts for the glycoside at C-19 are shown in the following table:

| $^1$H and $^{13}$C NMR (500 and 125 MHz, pyridine-$d_5$), Assignments of the reb D2 C-19 glycoside. | | |
|---|---|---|
| | | Reb D2 |
| Position | $^{13}$C | $^1$H |
| $Glc_I$-1 | 96.1 | 6.02 d (8.1) |
| $Glc_I$-2 | 74.2 | 4.07 m |
| $Glc_I$-3 | 79.1[#] | 4.22 m[#] |
| $Glc_I$-4 | 72.1 | 4.12 m |
| $Glc_I$-5 | 78.5 | 4.04 m |
| $Glc_I$-6 | 69.9 | 4.30 m |
| | | 4.68 d (10.7) |
| $Glc_V$-1 | 105.6 | 5.04* |
| $Glc_V$-2 | 75.7 | 4.00 m |
| $Glc_V$-3 | 79.1[#] | 4.22 m[#] |
| $Glc_V$-4 | 71.4 | 4.21 m |
| $Glc_V$-5 | 78.9 | 3.89 m |
| $Glc_V$-6 | 63.1 | 4.37 m |
| | | 4.48 m |

*Anomeric proton was obscured by solvent (HDO) resonance. Therefore, the coupling constant value could not be determined.
[#]$^1$H and $^{13}$C values can be exchangeable between positions $Glc_I$-3, $Glc_V$-3 and $Glc_{II}$-3.

A summary of the key HMBC, COSY, and 1D-TOCSY correlations used to assign the C-19 glycoside region are provided below.

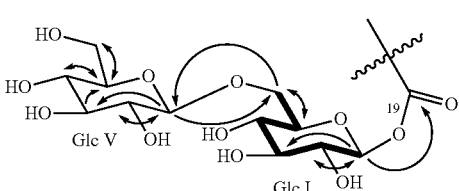

= $^1$H-$^{13}$C HMBC

= $^1$H-$^1$H COSY

= $^1$H-$^1$H spin system based on 1D-TOCSY

Assignment of Glc$_{II}$ was carried out in a similar manner. The Glc$_{II}$ anomeric proton ($\delta_H$ 5.07) showed a COSY correlation to a proton at $\delta_H$ 4.37, assigned as Glc$_{II}$ H-2, which in turn showed a COSY correlation to a proton at $\delta_H$ 4.18 (Glc$_{II}$ H-3). This latter proton showed an additional correlation with a proton at $\delta_H$ 3.88 (Glc$_{II}$ H-4) which also showed a COSY correlation to a proton at $\delta_H$ 3.79 (Glc$_{II}$ H-5). Glc$_{II}$ H-5 also showed a COSY correlation to Glc$_{II}$ H-6 protons ($\delta_H$ 4.08 and 4.46). Assignment of the $^{13}$C chemical shifts for Glc$_{II}$ C-2 ($\delta_C$ 81.3), C-3 ($\delta_C$ 88.4), C-4 ($\delta_C$ 71.1), C-5 ($\delta_C$ 77.9), and C-6 ($\delta_C$ 63.2) was determined using the HSQC-DEPT data. HMBC correlations from Glc$_{II}$ H-3 to C-2 and C-4 and also from Glc$_{II}$ H-4 to C-2 and C-5 confirmed the assignments made above. Additional HMBC correlations of Glc$_{II}$ H-4 to Glc$_{II}$ C-6 further support to complete the assignment of Glc$_{II}$.

Two of the remaining unassigned glucose moieties were assigned as substituents at C-2 and C-3 of Glc$_{II}$ on the basis of HMBC correlations. The anomeric proton observed at $\delta_H$ 5.57 showed a HMBC correlation to Glc$_{II}$ C-2 and was assigned as the anomeric proton of Glc$_{II}$. The anomeric proton observed at $\delta_H$ 5.34 showed a HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{II}$ and from Glc$_{II}$ H-3 to the anomeric carbon of Glc$_{IV}$ were also observed.

The anomeric proton of Glc$_{II}$ ($\delta_H$ 5.57) showed a COSY correlation with a proton at $\delta_H$ 4.19 which was assigned as Glc$_{II}$ H-2. Due to data overlap, the COSY spectrum did not allow assignment of H-3 to H-6 protons. Therefore, a series of 1D-TOCSY experiments were performed using selective irradiation of the Glc$_{II}$ anomeric proton with several different mixing times. In addition to confirming the assignments for Glc$_{III}$ H-2, the 1D-TOCSY data showed protons at $\delta_H$ 4.24 (Glc$_{III}$ H-3), $\delta_H$ 4.27 (Glc$_{III}$ H-4), and SH 3.94 (Glc$_{III}$ H-5). Once H-4 was assigned using 1D-TOCSY data, COSY correlations from H-4 to H-5 and in turn to H-6 were used to assign H-6. In the COSY spectrum, Glc$_{III}$ H-4 showed a correlation to Glc$_{III}$ H-5, which in turn showed COSY correlations to $\delta_H$ 4.41 and 4.50 of Glc$_{III}$ H-6a and H-6b, respectively. The $^{13}$C chemical shifts for Glc$_{II}$ C-2 ($\delta_C$ 76.8), C-3 ($\delta_C$ 78.9), C-4 ($\delta_C$ 72.4), C-5 ($\delta_C$ 78.8), and C-6 ($\delta_C$ 63.5) were then determined using the $^1$H-$^{13}$C HSQC-DEPT correlations to complete the assignment of Glc$_{III}$.

The anomeric proton of Glc$_{IV}$ ($\delta_H$ 5.34) showed a COSY correlation with a proton at $\delta_H$ 4.06 which was assigned as Glc$_{IV}$ H-2. Due to data overlap, the COSY spectrum did not allow assignment of H-3 to H-6 protons. Therefore, a series of 1D-TOCSY experiments were performed using selective irradiation of the Glc$_{IV}$ anomeric proton with several different mixing times. In addition to confirming the assignments for Glc$_{IV}$ H-2, the 1D-TOCSY data showed protons at $\delta_H$ 4.22 (Glc$_{IV}$ H-3), SH 4.18 (Glc$_{IV}$ H-4), and SH 4.10 (Glc$_{IV}$ H-5). Once H-4 was assigned using 1D-TOCSY data, COSY correlations from H-4 to H-5 and in turn to H-6 were used to assign H-6. In the COSY spectrum, Glc$_{IV}$ H-4 showed a correlation to Glc$_{IV}$ H-5, which in turn showed COSY correlations to $\delta_H$ 4.32 and 4.58, Glc$_{IV}$ H-6a and H-6b, respectively. The $^{13}$C chemical shifts for Glc$_{IV}$ C-2 ($\delta_C$ 75.8), C-3 ($\delta_C$ 78.9), C-4 ($\delta_C$ 72.0), C-5 ($\delta_C$ 79.3), and C-6 ($\delta_C$ 62.9) were then determined using the $^1$H-$^{13}$C HSQC-DEPT correlations to complete the assignment of Glc$_{IV}$.

A summary of the $^1$H and $^{13}$C chemical shifts for the glycoside at C-13 are shown in the table below:

| $^1$H and $^{13}$C NMR (500 and 125 MHz, pyridine-d$_5$), Assignments of the Reb D2 C-13 glycoside. | | |
|---|---|---|
| | Reb D2 | |
| Position | $^{13}$C | $^1$H |
| Glc$_{II}$-1 | 98.7 | 5.07* |
| Glc$_{II}$-2 | 81.3 | 4.37 m |
| Glc$_{II}$-3 | 88.4 | 4.18 t (9.0) |
| Glc$_{II}$-4 | 71.1 | 3.88 t (8.6) |
| Glc$_{II}$-5 | 77.9 | 3.79 m |
| Glc$_{II}$-6 | 63.2 | 4.08 m |
| | | 4.46 m |
| Glc$_{III}$-1 | 105.3 | 5.57 d (7.6) |
| Glc$_{III}$-2 | 76.8 | 4.19 m |
| Glc$_{III}$-3 | 78.9 | 4.24 m |
| Glc$_{III}$-4 | 72.4 | 4.27 m |
| Glc$_{III}$-5 | 78.8 | 3.94 m |
| Glc$_{III}$-6 | 63.5 | 4.41 m |
| | | 4.50 m |
| Glc$_{IV}$-1 | 105.3 | 5.34 d (7.9) |
| Glc$_{IV}$-2 | 75.8 | 4.06 m |
| Glc$_{IV}$-3 | 78.9$^#$ | 4.22 m$^#$ |
| Glc$_{IV}$-4 | 72.0 | 4.18 m |
| Glc$_{IV}$-5 | 79.3 | 4.10 m |
| Glc$_{IV}$-6 | 62.9 | 4.32 m |
| | | 4.58 m |

A summary of the key HMBC, COSY, and 1D-TOCSY correlations used to assign the C-13 glycoside region are provided below:

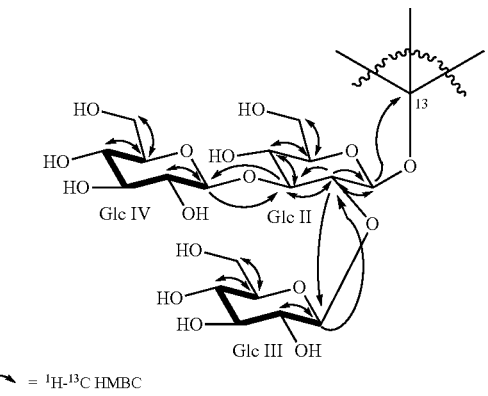

= $^1$H-$^{13}$C HMBC

= $^1$H-$^1$H COSY

= $^1$H-$^1$H spin system based on 1D-TOCSY

NMR and MS analyses allowed a full assignment of structure, shown below. The chemical name of the compound is 13-[(2-O-β-D-glucopyranosyl-3-O-β-D-glucopyranosyl-β-D-glucopyranosyl)oxy] ent-kaur-16-en-19-oic acid-[(6-O-β-D-glucopyranosyl-β-D-glucopyranosyl) ester] (rebaudioside D2 or reb D2). The compound is an isomer of rebaudioside D.

Example 40

Isolation and Characterization of Reb M2

Crude Reaction Sample. The sample, Lot CB-2977-106, used for isolation was prepared according to Example 22 with UGTSL (GI #460409128).

HPLC Analysis. Preliminary HPLC analyses was performed using a Waters 2695 Alliance System with the following method: Phenomenex Synergi Hydro-RP, 4.6×250 mm, 4 μm (p/n 00G-4375-E0); Column Temp: 55° C.; Mobile Phase A: 0.0284% NH₄OAc and 0.0116% HOAc in water; Mobile Phase B: Acetonitrile (MeCN); Flow Rate: 1.0 mL/min; Injection volume: 10 μL. Detection was by UV (210 nm) and CAD.
Gradient:

| Time (min) | % A | % B |
|---|---|---|
| 0.0-5.0 | 100 | 0 |
| 20 | 20 | 80 |
| 25 | 20 | 80 |
| 30 | 100 | 0 |

Analyses of semi-preparative purification fractions were performed with the following method: Waters Atlantis dC18, 4.6×100 mm, 5 μm (p/n 186001340); Mobile Phase A: 25% MeCN in water; Mobile Phase B: 30% MeCN in water; Flow Rate: 1.0 mL/min; Injection volume: 10 μL. Detection was by CAD.
Gradient:

| Time (min) | % A | % B |
|---|---|---|
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31-37 | 30 | 70 |
| 38 | 75 | 25 |

LC-MS. Preliminary analysis of the semi-synthetic steviol glycoside mixture was carried out on a Waters AutoPurification HPLC/MS System with a Waters 3100 Mass Detector operating in negative ion mode. Analysis of the sample was performed using the following method: Phenomenex Synergi Hydro-RP, 4.6×250 mm, 4 μm (p/n 00G-4375-E0); Column Temp: 55° C.; Mobile Phase A: 0.0284% NH₄OAc and 0.0116% HOAc in water; Mobile Phase B: MeCN; Flow Rate: 1.0 mL/min; Injection volume: 10 μL. Detection was by UV (210 nm), and MSD (−ESI m/z 500-2000). Gradient conditions were as listed above.

Isolation by HPLC. The purification was performed in two steps. The first method used for the semi-preparative purification is summarized below. Column: Waters Atlantis dC18, 30×100 mm, 5 μm (p/n 186001375); Mobile Phase A: 25% MeCN in water; Mobile Phase B: 30% MeCN in water; Flow Rate: 45 mL/min; Injection load: 160 mg dissolved in 20 mL of water. Detection was by UV (205 nm).
Gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary purification used the same column and conditions, but isocratic mobile phase: 20% MeCN in water.

MS and MS/MS. MS and MS/MS data were generated with a Waters QT of Premier mass spectrometer equipped with an electrospray ionization source. Samples were analyzed by negative ESI. Samples were diluted with H₂O: MeCN (1:1) by 50 fold and introduced via infusion using the onboard syringe pump. The samples were diluted to yield good s/n which occurred at an approximate concentration of 0.01 mg/mL.

NMR. The sample was prepared by dissolving ~1.0 mg in 150 μL of D20 and NMR data were acquired on a Bruker Avance 500 MHz instrument with a 2.5 mm inverse detection probe. The ¹H NMR and ¹³C NMR spectra were referenced to the residual solvent signal HDO ($\delta_H$ 4.79 ppm) and TSP ($\delta_C$ 0.00 ppm), respectively.

Results and Discussion

Figure 12:
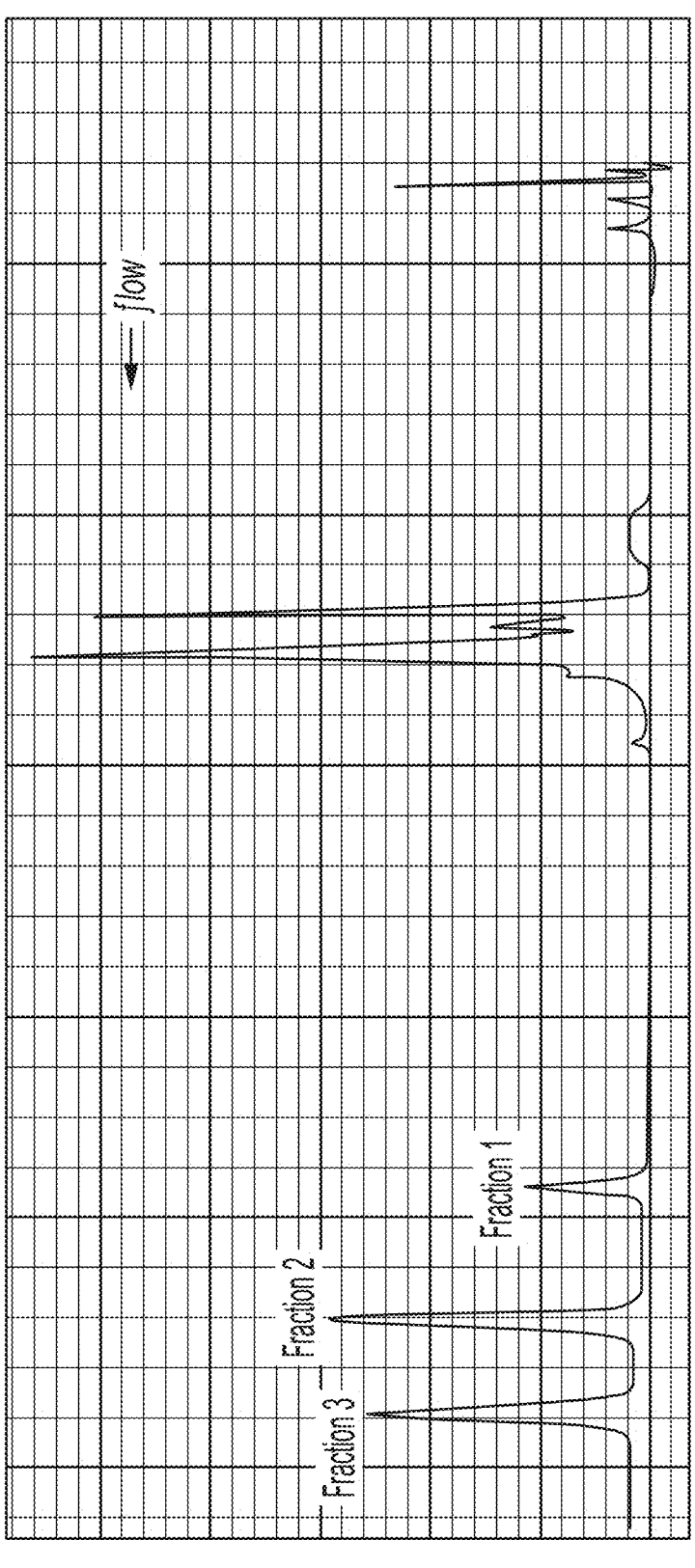
FIG. 12 shows the trace of semi-synthetic steviol glycoside mixture, Lot number CB-2977-106. Chromatogram gridlines are not homogeneous as the detector was re-calibrated 14 min following injection.
Figures 13A, 13B, 13C, 13D:
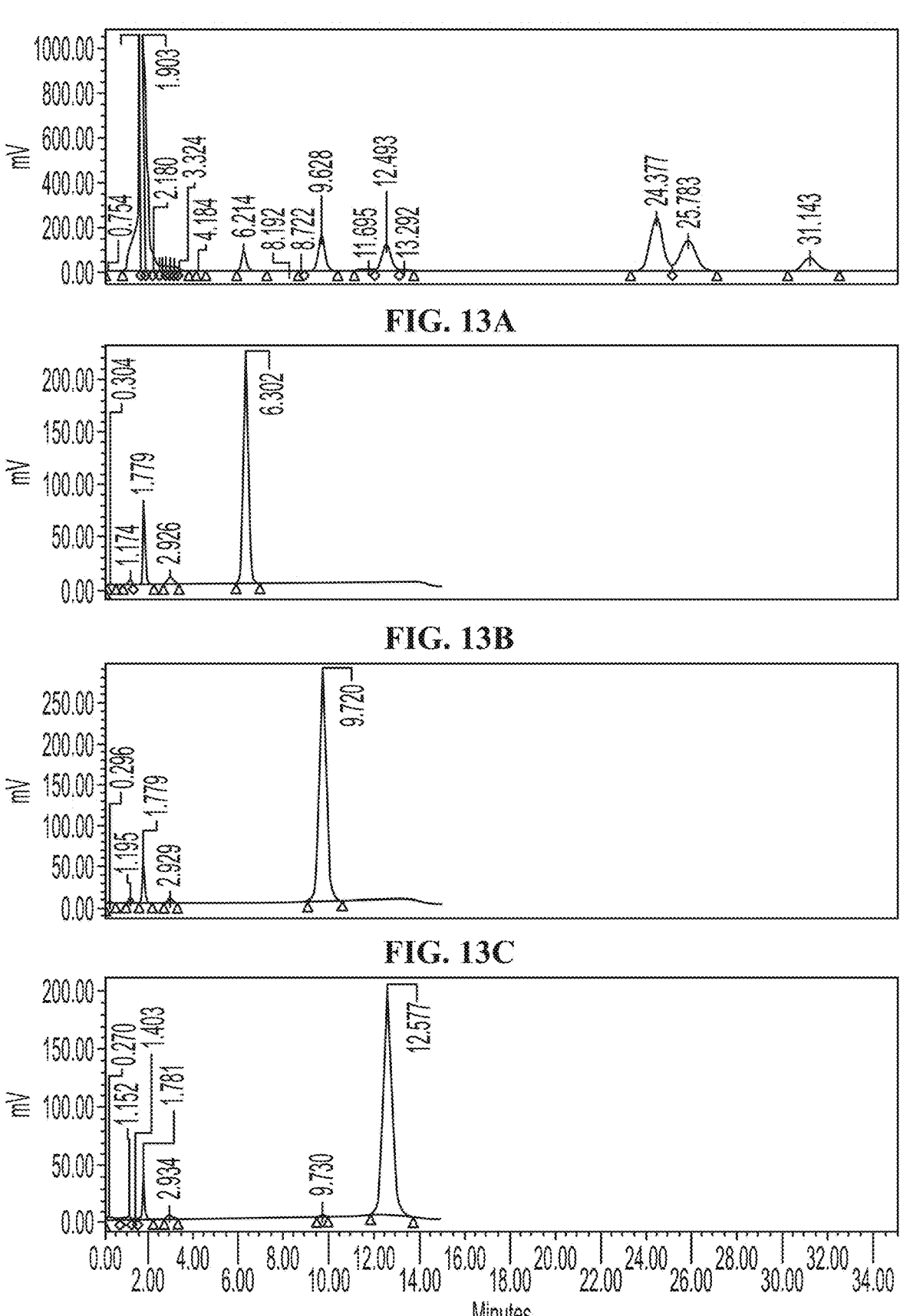
FIGS. 13A-13D show HPLC analysis of semi-synthetic steviol glycoside mixture, Lot number CB-2977-106 (A), Isolated reb M2 (B), isolated reb D (C) and isolated reb D2 (D).

Isolation and Purification. Isolation was performed using on a steviol glycoside mixture, Lot number CB-2977-106, prepared according to Example 22 with UGTSL (GI #460409128). The material was analyzed by LC-MS using the method described above (FIG. 11). The targeted peak of interest was that at 4.1 min in the TIC chromatogram. The mass spectrum of this peak provided a [M-H]⁻ ion at m z 1289.7. The provided sample was preliminarily processed in a single injection (160 mg) using the first method condition provided above. This method fractionated the material into 'polar' and 'non-polar' mixtures of glycosides. The 'polar' mixture was then reprocessed using the second-step conditions provided above. The semi-preparative HPLC trace is shown in FIG. 12. From this semi-preparative collection, the peak was isolated with a purity >99% (CAD, AUC). The fraction analysis is provided in FIG. 13. Following the purification, the fractions were concentrated by rotary evaporation at 35° C. and lyophilized. Approximately 1 mg was obtained.

Mass Spectrometry. The ESI− TOF mass spectrum acquired by infusing a sample of CC-00300 showed a [M-H]⁻ ion at m z 1289.5266. The mass of the [M-H]⁻ ion was in good agreement with the molecular formula $C_{56}H_{90}O_{33}$ (calcd for $C_{56}H_{89}O_{33}$: 1289.5286, error: −1.6 ppm) expected for reb M2. The MS data confirmed that CC-00300 has a nominal mass of 1290 Daltons with the molecular formula, $C_{56}H_{90}O_{33}$.

The MS/MS spectrum (selecting the $[M-H]^-$ ion at m z 1289.5 for fragmentation) indicated the loss of three glucose units at m/z 803.3688 and sequential loss of three glucose moieties at m z 641.3165, 479.2633 and 317.2082.

Figure 21A:
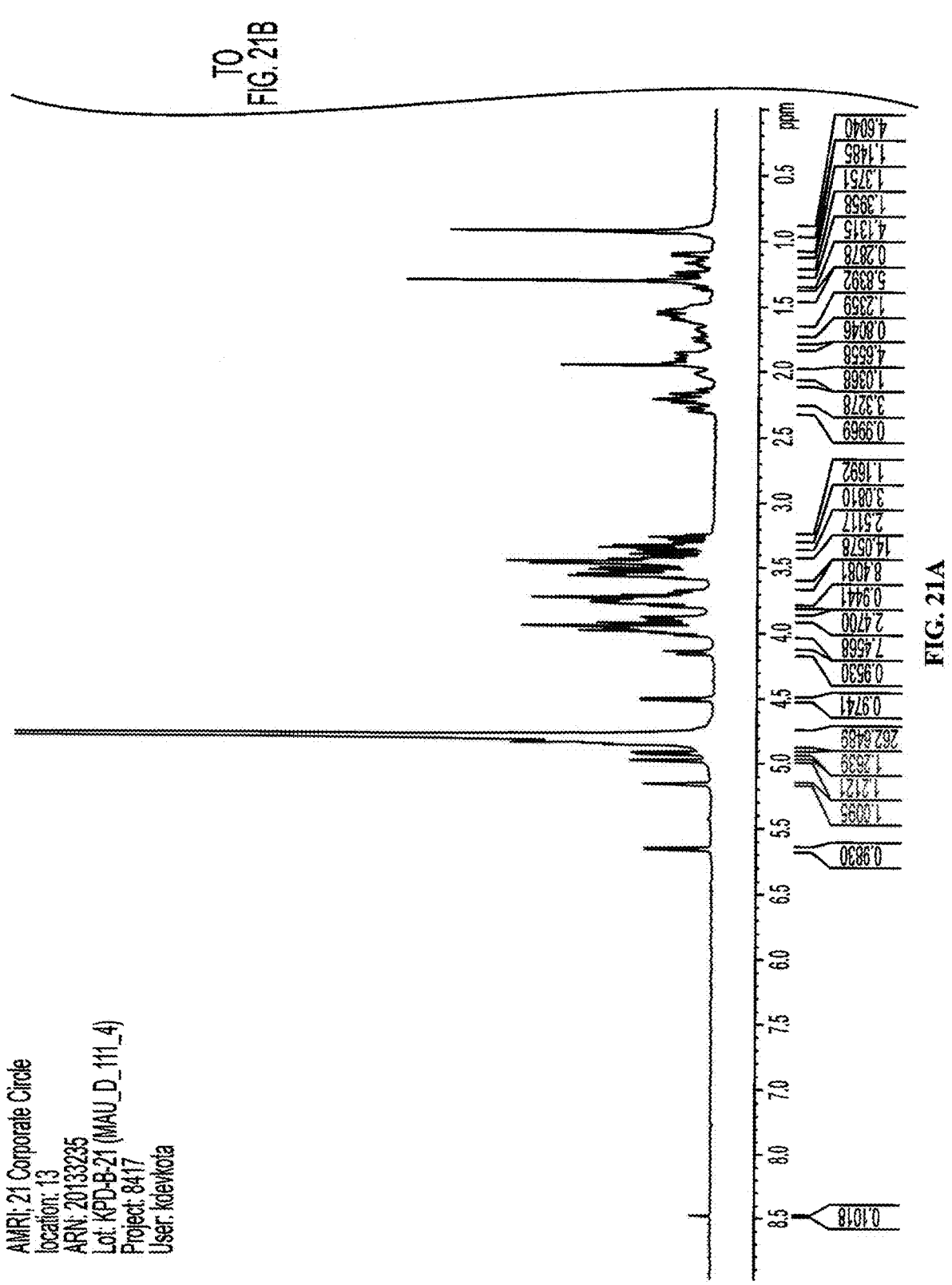
FIGS. 21A-21B show the $^1$H NMR spectrum of reb M2 (500 MHz, D20).
Figures 21A, 21B:
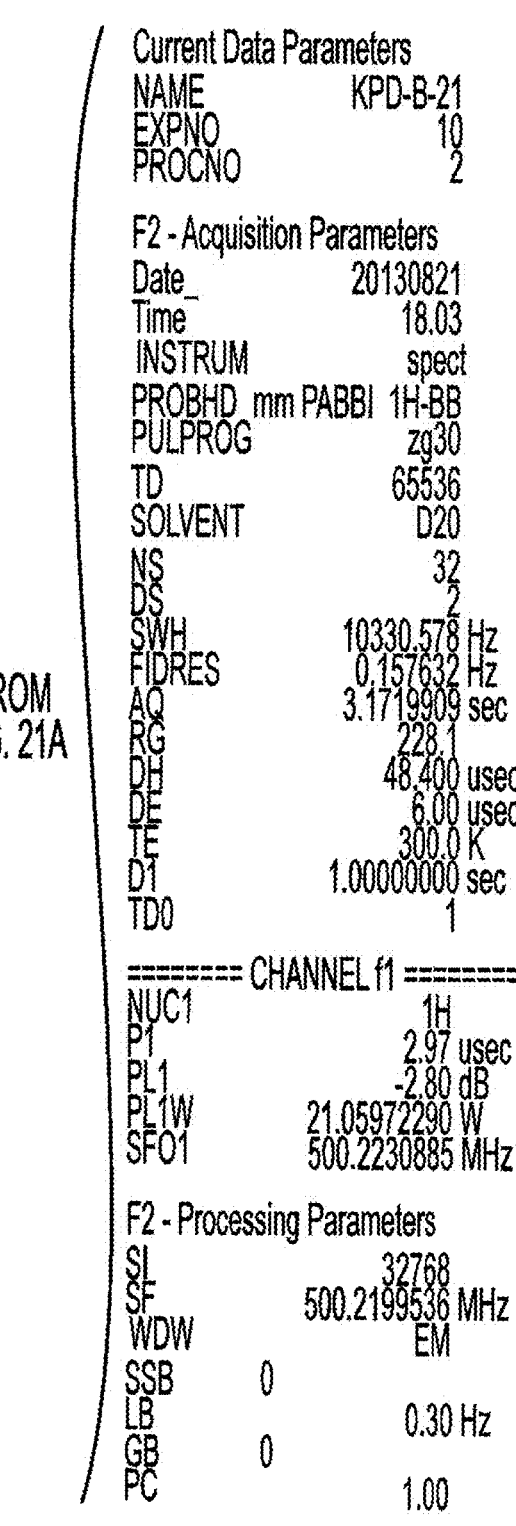
Figure 22:
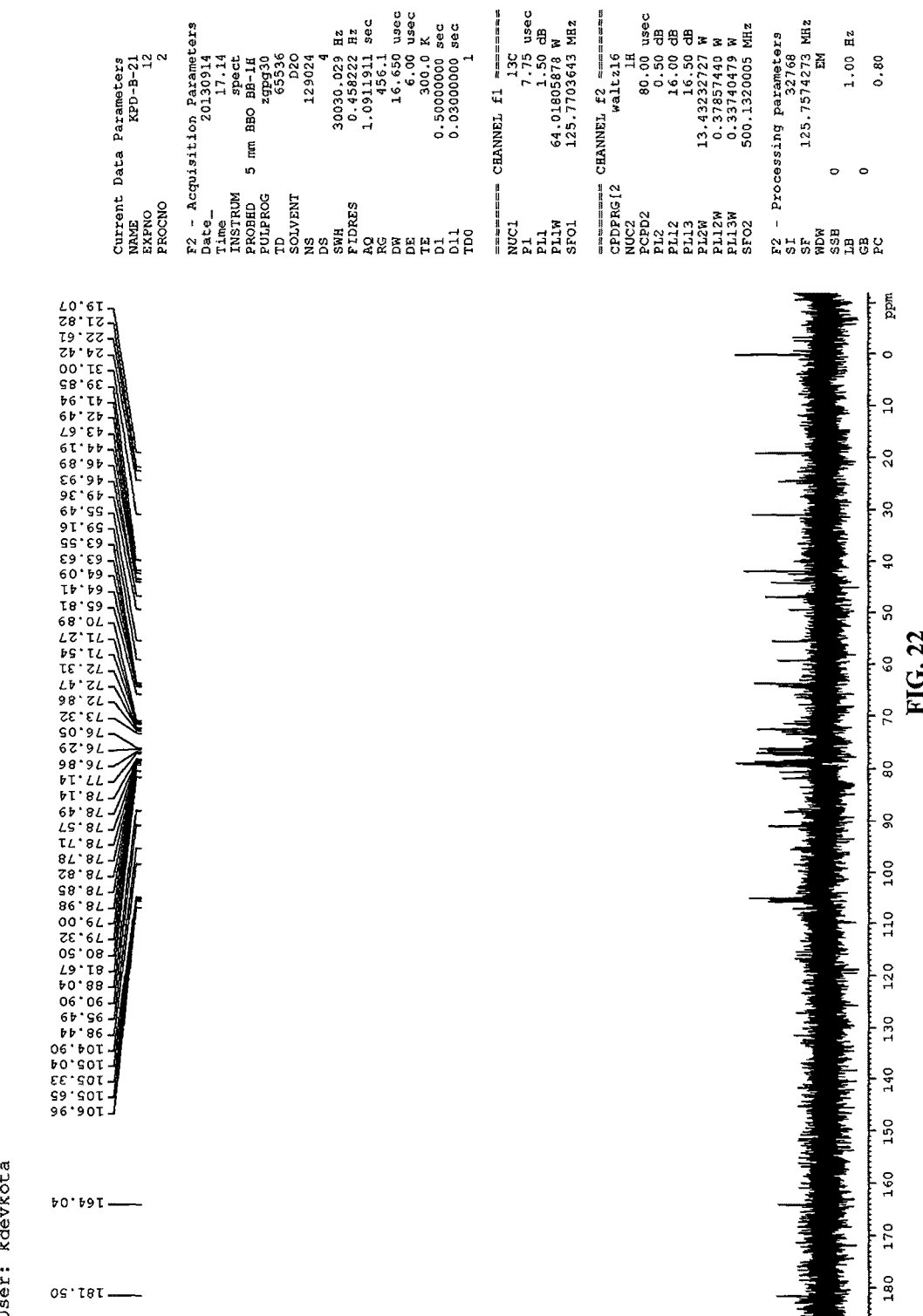
FIG. 22 shows the $^{13}$C NMR spectrum of reb M2 (125 MHz, D20/TSP).
Figure 23:
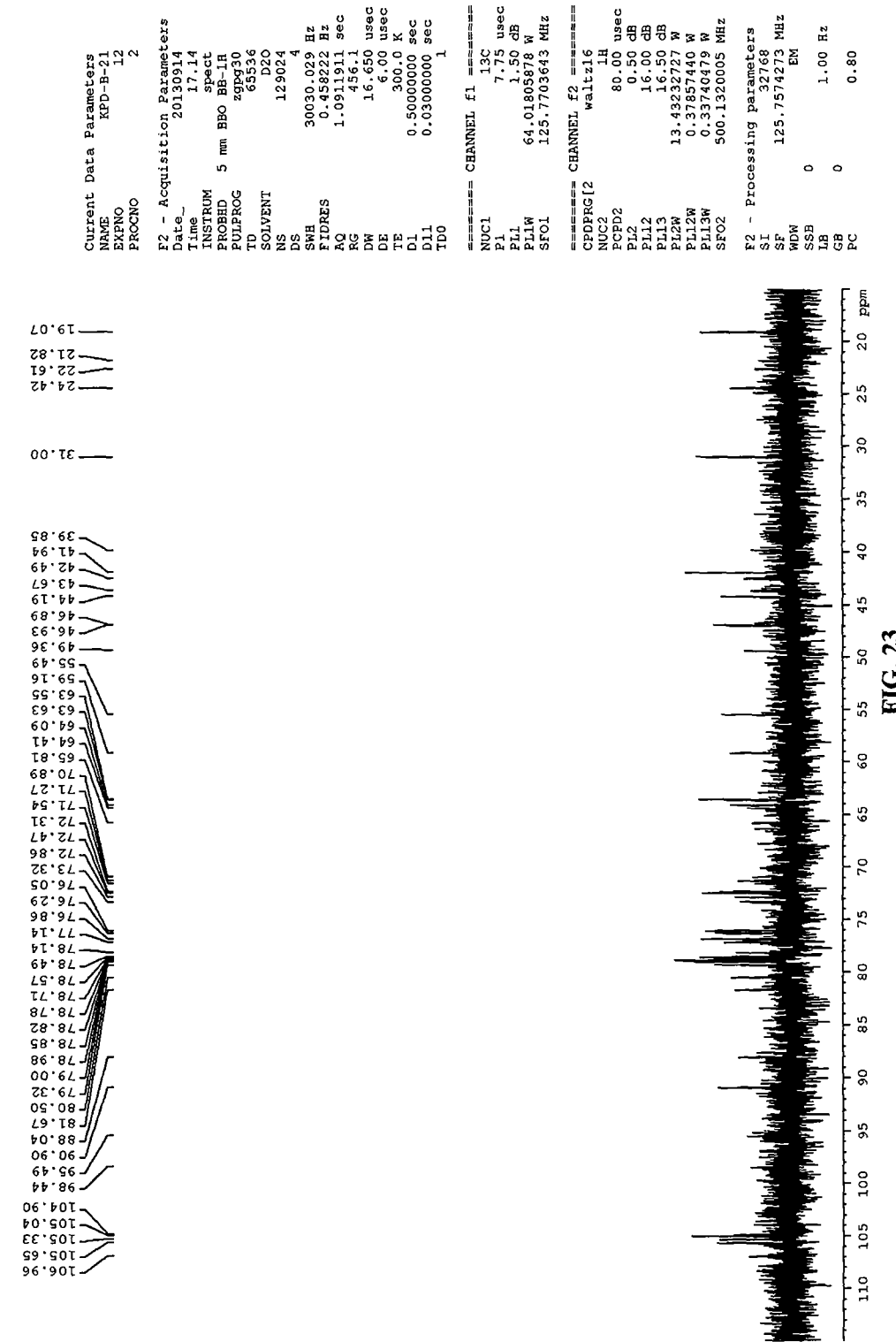
FIG. 23 shows an expansion of the $^{13}$C NMR spectrum of reb M2 (125 MHz, D20/TSP).
Figures 24A, 24B:
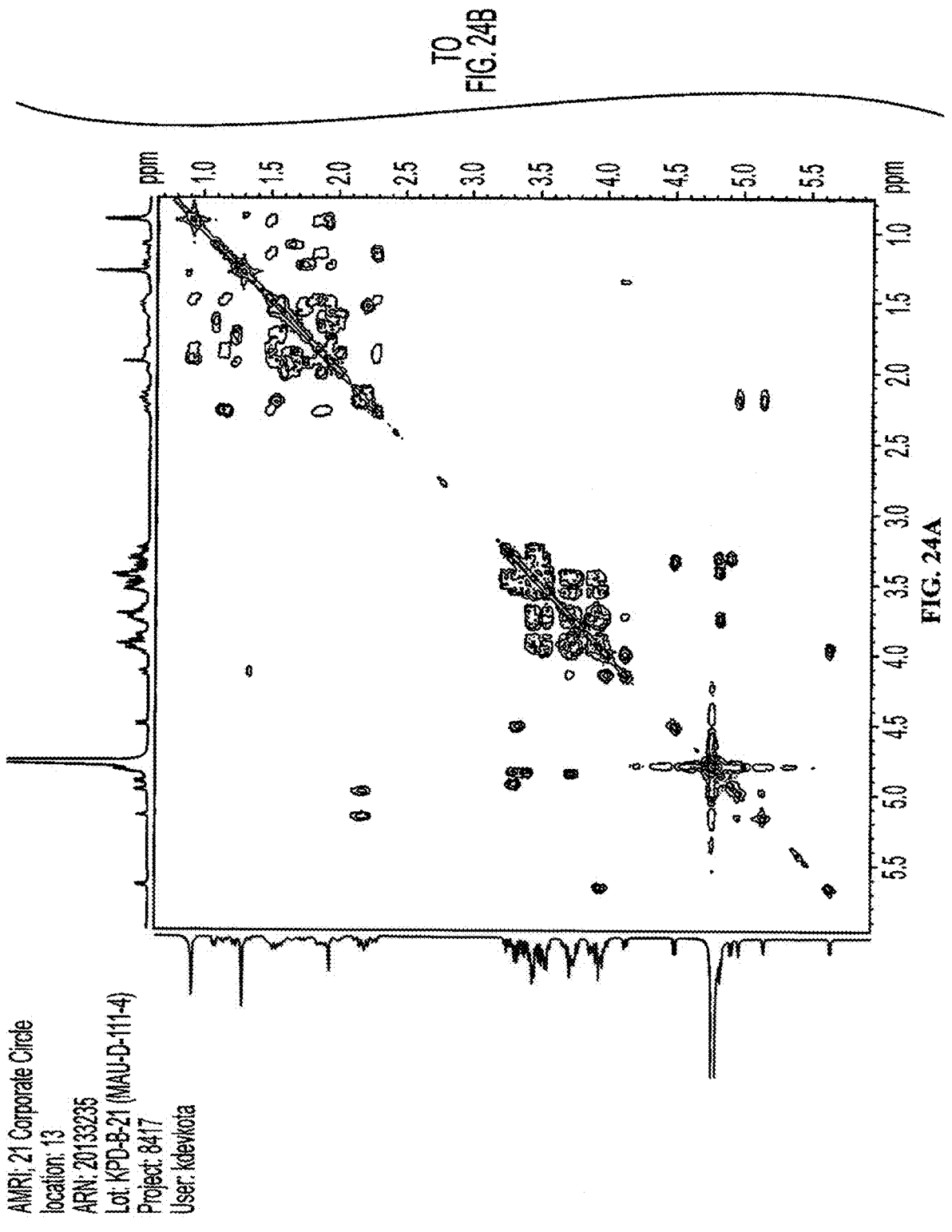
Figures 25A, 25B:
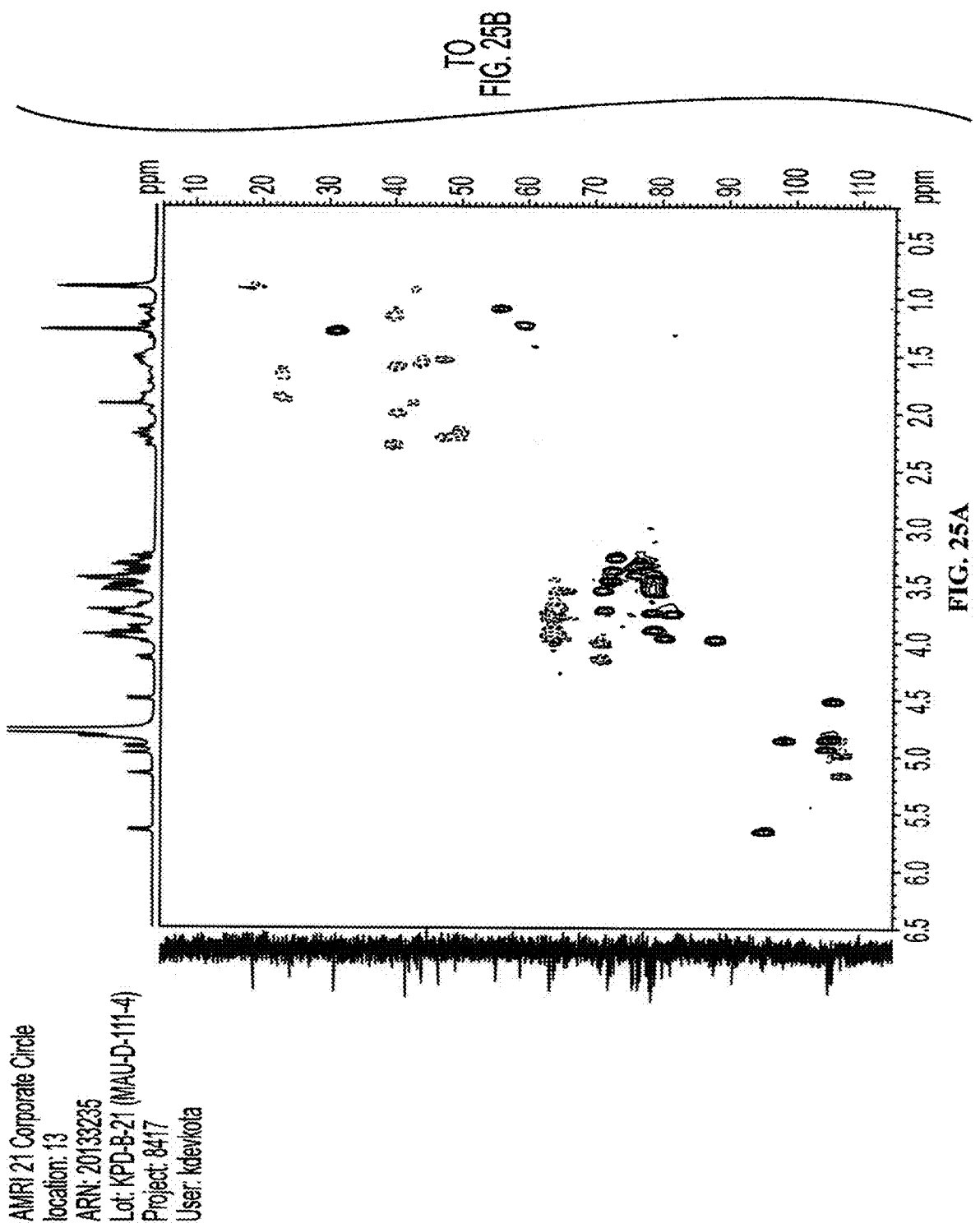
Figures 26A, 26B:
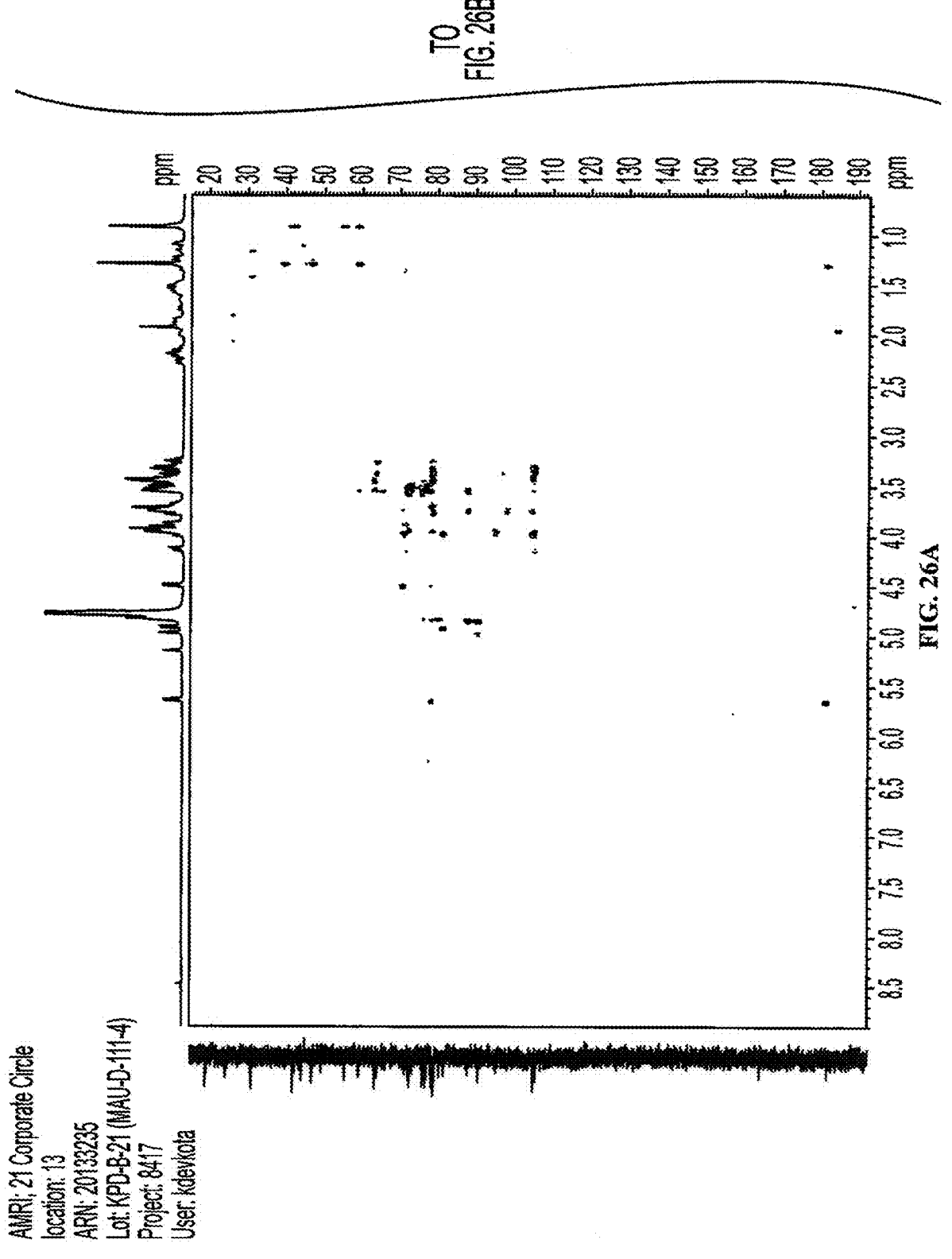
FIGS. 26A-26D show the HMBC spectrum of reb M2 (500 MHz, D20).
Figures 26A, 26B, 26C, 26D:
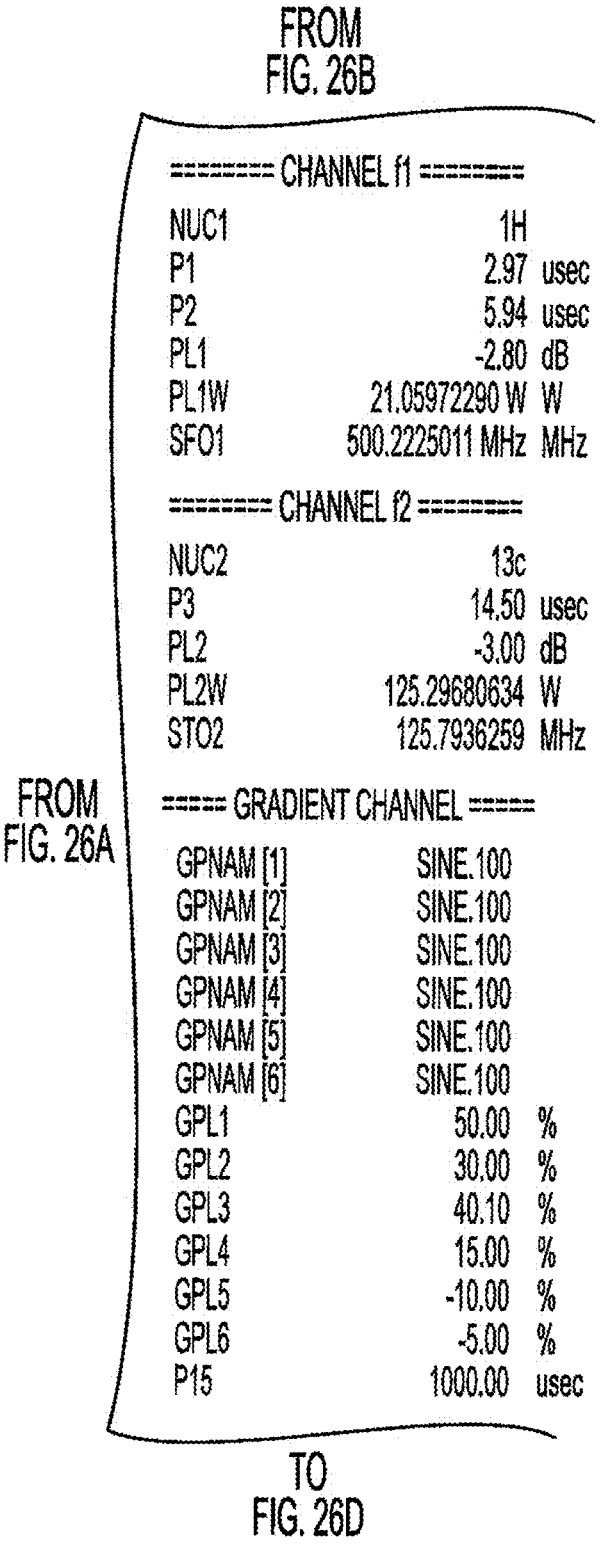
Figures 27A, 27B:
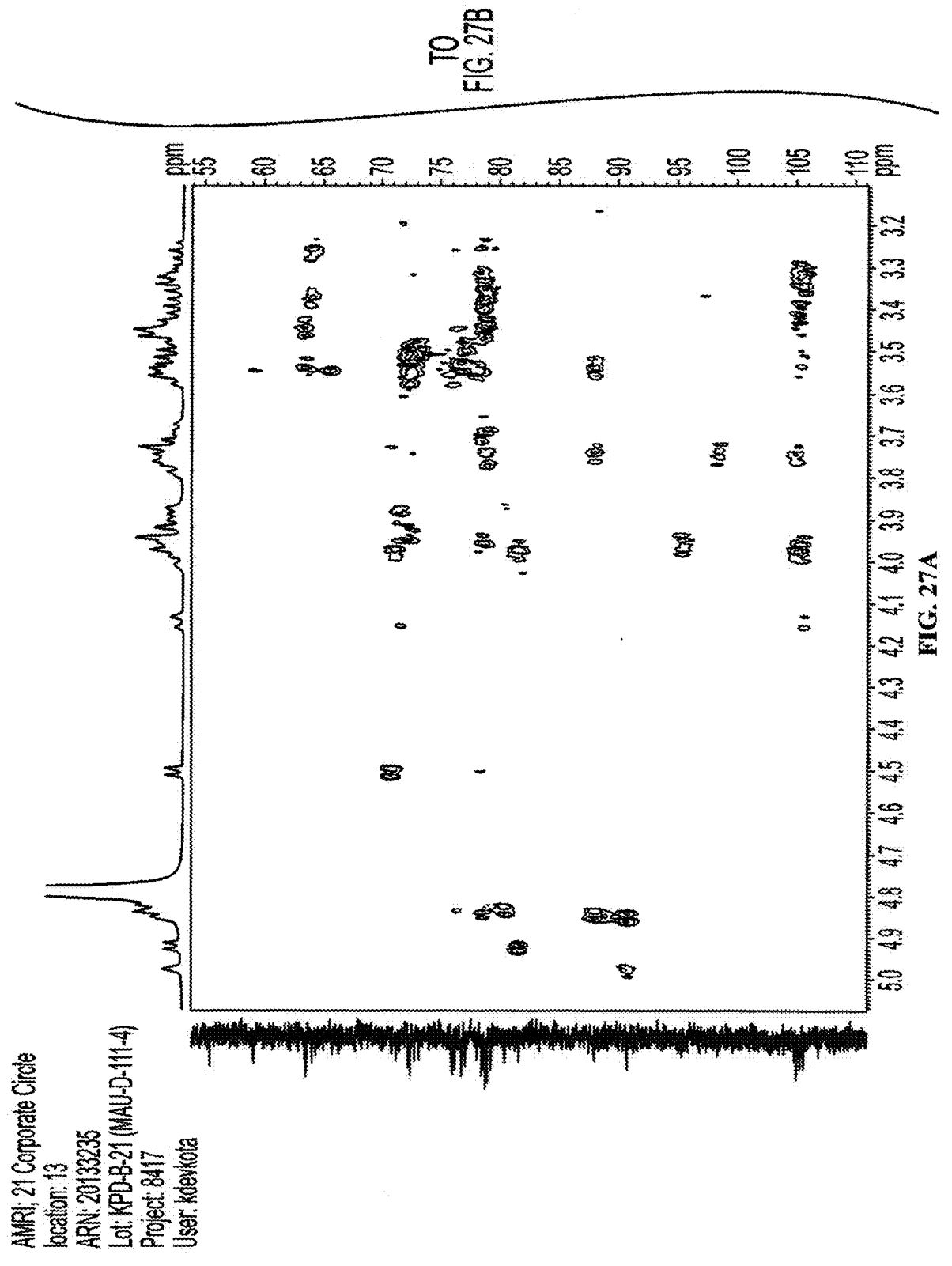
FIGS. 27A-27D show an expansion of HMBC spectrum of reb M2 (500 MHz, D20).
Figures 27A, 27B, 27C, 27D:
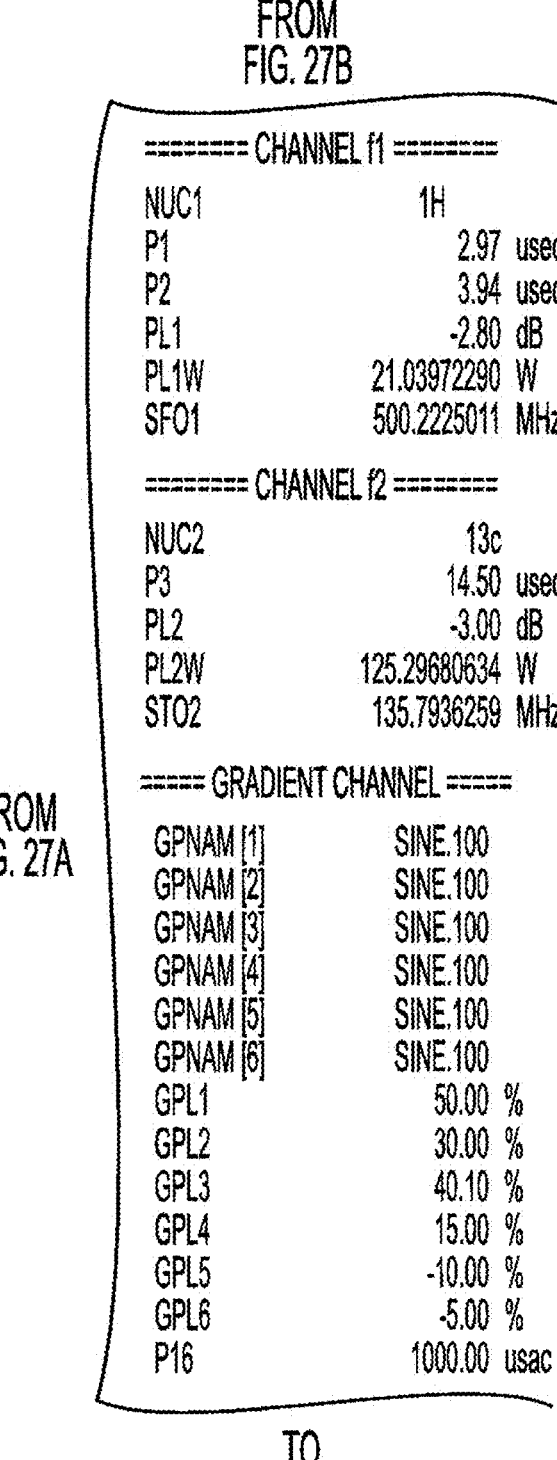

NMR Spectroscopy. A series of NMR experiments including $^1$H NMR (FIG. 21), $^{13}$C NMR (FIGS. 22 and 23), $^1$H-$^1$H COSY (FIG. 24), HSQC-DEPT (FIG. 25), HMBC (FIGS. 26 and 27), and 1D-TOCSY were performed to allow assignment of reb M2.

The $^1$H, $^1$H-$^1$H COSY, $^1$H-$^{13}$C HSQC-DEPT and $^1$H-$^{13}$C HMBC NMR data indicated that the central core of the glycoside is a diterpene. The presence of six anomeric protons observed in the $^1$H and $^1$H-$^{13}$C HSQC-DEPT spectra confirm six sugar units in the structure. The methylene $^{13}$C resonance at $\delta_C$ 70.9 in the $^1$H-$^{13}$C HSQC-DEPT spectrum indicated the presence of a 1→6 sugar linkage in the structure. The linkages of sugar units were assigned using $^1$H-$^{13}$C HMBC and 1D-TOCSY correlations.

A HMBC correlation from the methyl protons at $\delta_H$ 1.29 to the carbonyl at $\delta_C$ 181.5 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.8, 43.7, and 59.2 allowed assignment of C3, C4, and C5. Analysis of the $^1$H-$^{13}$C HSQC-DEPT data indicated that the carbon at $\delta_C$ 39.8 was a methylene group and the carbon at $\delta_C$ 59.2 was a methine which were assigned as C-3 and C-5, respectively. This left the carbon at $\delta_C$ 43.7, which did not show a correlation in the HSQC-DEPT spectrum, to be assigned as the quaternary carbon, C-4. The $^1$H chemical shifts for C-3 ($\delta_H$ 1.16 and 2.28) and C-5 ($\delta_H$ 1.24) were assigned using the HSQC-DEPT data. A COSY correlation between one of the H-3 protons ($\delta_H$ 1.16) and a proton at $\delta_H$ 1.49 allowed assignment of one of the H-2 protons which in turn showed a correlation with a proton at $\delta_H$ 0.92 which was assigned to C-1. The remaining $^1$H and $^{13}$C chemical shifts for C-1 and C-2 were then assigned on the basis of additional COSY and HSQC-DEPT correlations and are summarized in the table below.

| $^1$H NMR (500 MHz, $D_2O$) and $^{13}$C NMR (125 MHz, $D_2O$/TSP) Assignments of the Reb M2 aglycone. | | |
|---|---|---|
| Position | $^{13}$C | $^1$H |
| 1 | 41.9 | 0.92 m |
| | | 1.93 m |
| 2 | 21.8 | 1.49 m |
| | | 1.86 m |
| 3 | 39.8 | 1.16 m |
| | | 2.28 d (13.4) |
| 4 | 43.7 | — |
| 5 | 59.2 | 1.24 d (12.1) |
| 6 | 24.4 | 1.73 m |
| | | 1.94 m |
| 7 | 44.2 | 1.49 m |
| | | 1.56 m |
| 8 | 46.9 | — |
| 9 | 55.5 | 1.09 d (7.7) |
| 10 | 42.4 | — |
| 11 | 22.6 | 1.66 m |
| | | 1.70 m |
| 12 | 39.9 | 1.60 m |
| | | 2.00 m |
| 13 | 90.9 | — |

-continued

| $^1$H NMR (500 MHz, $D_2O$) and $^{13}$C NMR (125 MHz, $D_2O$/TSP) Assignments of the Reb M2 aglycone. | | |
|---|---|---|
| Position | $^{13}$C | $^1$H |
| 14 | 46.9 | 1.53 d (12.6) |
| | | 2.21 d (13.6) |
| 15 | 49.4 | 2.15 d (17.2) |
| | | 2.18 d (18.1) |
| 16 | 164.0 | — |
| 17 | 107.0 | 4.98 s |
| | | 5.16 s |
| 18 | 31.0 | 1.29 s |
| 19 | 181.5 | — |
| 20 | 19.1 | 0.92 s |

The other tertiary methyl singlet, observed at $\delta_H$ 0.92 showed HMBC correlations to C-1 and C-5 and was assigned as C-20. The methyl protons showed additional HMBC correlations to a quaternary carbon ($\delta_C$ 42.4) and a methine ($\delta_C$ 55.5) which were assigned as C-10 and C-9, respectively. COSY correlations between H-5 ($\delta_H$ 1.24) and protons at $\delta_H$ 1.73 and 1.94 then allowed assignment of the H-6 protons which in turn showed correlations to protons at $\delta_H$ 1.49 and 1.56 which were assigned to C-7. The $^{13}$C chemical shifts for C-6 ($\delta_C$ 24.4) and C-7 ($\delta_C$ 44.2) were then determined from the HSQC-DEPT data. COSY correlations between H-9 ($\delta_H$ 1.09) and protons at $\delta_H$ 1.66 and 1.70 allowed assignment of the H-11 protons which in turn showed COSY correlations to protons at $\delta_H$ 1.60 and 2.00 which were assigned as the H-12 protons. The HSQC-DEPT data was then used to assign C-11 ($\delta_C$ 22.6) and C-12 ($\delta_C$ 39.9). The olefinic protons observed at $\delta_H$ 4.98 and 5.16 showed HMBC correlations to C-13 ($\delta_C$ 90.9) and were assigned to C-17 (Sc 107.0 via HSQC-DEPT). The olefinic protons H-17 showed HMBC correlations to a carbon at $\delta_C$ 49.4 which was assigned as C-15. An additional HMBC correlation from H-9 to a methylene carbon at $\delta_C$ 46.9 then allowed assignment of C-14. The $^1$H chemical shifts at C-14 ($\delta_H$ 1.53 and 2.21) and C-15 ($\delta_H$ 2.15 and 2.18) were assigned using the HSQC-DEPT data.

A summary of the key HMBC and COSY correlations used to assign the aglycone region are provided below:

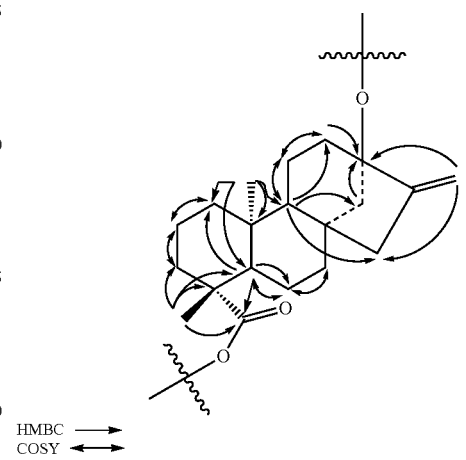

HMBC ———▶
COSY ◀——▶

Analysis of the $^1$H-$^{13}$C HSQC-DEPT data confirmed the presence of six anomeric protons. Three of the anomeric protons were well resolved at $\delta_H$ 5.65 ($\delta_C$ 95.5), 4.92 ($\delta_C$ 104.9), and 4.50 ($\delta_C$ 105.7) in the $^1$H NMR spectrum. The remaining three anomeric protons observed at $\delta_H$ 4.85 ($\delta_C$ 98.4), 4.84 ($\delta_C$ 105.0), and 4.83 ($\delta_C$ 105.3) were overlapped by the residual solvent resonance in the $^1$H spectrum. The anomeric proton observed at $\delta_H$ 5.65 showed a HMBC correlation to C-19 which indicated that it corresponds to the anomeric proton of Glc$_I$. Similarly, the anomeric proton observed at $\delta_H$ 4.85 showed a HMBC correlation to C-13 allowing it to be assigned as the anomeric proton of Glc$_{II}$.

The Glc$_I$ anomeric proton ($\delta_H$ 5.65) showed a COSY correlation to a proton at $\delta_H$ 3.96 which was assigned as Glc$_I$ H-2 which in turn showed a COSY correlation to a proton at $\delta_H$ 3.89 (Glc$_I$ H-3) which showed a COSY correlation with a proton at $\delta_H$ 3.71 (Glc$_I$ H-4). Due to data overlap, the COSY spectrum did not allow assignment of the H-5 or H-6 protons. Therefore, a series of 1D-TOCSY experiments were performed using selective irradiation of the Glc$_I$ anomeric proton with several different mixing times. In addition to confirming the assignments for Glc$_I$ H-2 through H-4, the 1D-TOCSY data showed a proton at $\delta_H$ 3.73 assigned as Glc$_I$ H-5 and a proton at $\delta_H$ 4.15 assigned as one of the Glc$_I$ H-6 protons. The latter proton was also used for 1D-TOCSY experiments. The selective irradiation of H-6 with several different mixing times also confirmed the assignment of Glc$_I$ H-1 to H-5 as well as the remaining methylene proton of Glc$_I$ ($\delta_H$ 4.00). Assignment of the $^{13}$C chemical shifts for Glc$_I$ C-2 ($\delta_C$ 80.5), C-3 ($\delta_C$ 79.0), C-4 ($\delta_C$ 71.5), C-5 ($\delta_C$ 79.0), and C-6 ($\delta_C$ 70.9) was determined using the $^1$H-$^{13}$C HSQC-DEPT data to complete the assignment of Glc$_I$. Furthermore, the presence of a methylene $^{13}$C resonance at $\delta_C$ 70.9 in the $^1$H-$^{13}$C HSQC-DEPT spectrum indicated a 1→6 sugar linkage of Glc$_I$ in the structure.

Two of the unassigned glucose moieties were assigned as substituents at C-2 and C-6 of Glc$_I$ on the basis of HMBC correlations. The anomeric proton observed at $\delta_H$ 4.83 showed an HMBC correlation to Glc$_I$ C-2 and was assigned as the anomeric proton of Glc$_V$. The anomeric proton observed at $\delta_H$ 4.50 showed a HMBC correlation to Glc$_I$ C-6 and was assigned as the anomeric proton of Glc$_{VI}$. The reciprocal HMBC correlations from Glc$_I$ H-2 to the anomeric carbon of Glc$_V$ and from Glc$_I$ H-6 to the anomeric carbon of Glc$_{VI}$ were also observed.

The anomeric proton of Glc$_V$ ($\delta_H$ 4.83) showed a COSY correlation with a proton at $\delta_H$ 3.32 which was assigned as Glc$_V$ H-2. The Glc$_V$ H-2 in turn showed a COSY correlation to a proton at $\delta_H$ 3.51 (Glc$_V$ H-3). This latter proton showed an additional correlation with a proton at $\delta_H$ 3.38 (Glc$_V$ H-4). H-4 also showed a COSY correlation to a proton at $\delta_H$ 3.55 (Glc$_V$ H-5) and Glc$_V$ H-5 in turn showed a COSY correlation to Glc$_V$ H-6 protons ($\delta_H$ 3.76 and 3.97). Assignment of the $^{13}$C chemical shifts for Glc$_V$ C-2 ($\delta_C$ 78.5), C-3 ($\delta_C$ 78.7), C-4 ($\delta_C$ 72.9), C-5 ($\delta_C$ 78.8), and C-6 ($\delta_C$ 63.6) was determined using the HSQC-DEPT data. HMBC correlations from Glc$_V$ H-3 to C-2 and C-4 and also from Glc$_V$ H-4 to C-3 and C-6 confirmed the assignments made above to complete the assignment of Glc$_V$.

Another glucose moiety was assigned as a substituent at C-6 of Glc$_I$ on the basis of $^1$H-$^{13}$C HSQC-DEPT and HMBC correlations. The relatively downfield shift of a methylene $^{13}$C resonance of Glc$_I$ at $\delta_C$ 70.9 in the HSQC-DEPT spectrum indicated a 1→6 sugar linkage of Glc$_I$. The anomeric proton observed at $\delta_H$ 4.50 showed a HMBC correlation to Glc$_I$ C-6 and was assigned as the anomeric proton of Glc$_V$1. Similarly, methylene protons of Glc$_I$ showed HMBC correlations to the anomeric carbon of Glc$_{VI}$ and this confirmed the presence of a 1→6 sugar linkage between Glc$_I$ and Glc$_{VI}$. The Glc$_{VI}$ anomeric proton showed a COSY correlation to a proton at $\delta_H$ 3.33 which was assigned as Glc$_{VI}$ H-2 which in turn showed a COSY correlation to a proton at $\delta_H$ 3.49 (Glc$_{VI}$ H-3). Due to data overlap, the COSY spectrum did not allow assignment of Glc$_V$ H-4 to H-6 based on the COSY correlations. Therefore, a series of 1D-TOCSY experiments were performed using selective irradiation of the Glc$_{VI}$ anomeric proton with different mixing times. In addition to confirming the assignments for Glc$_{VI}$ H-2 through H-3, the 1D-TOCSY data showed protons at $\delta_H$ 3.45 (Glc$_{VI}$ H-4) and $\delta_H$ 3.48 (Glc$_{VI}$ H-5) and protons at $\delta_H$ 3.92 and 3.94 assigned for Glc$_{VI}$ H-6 protons. Assignment of the $^{13}$C chemical shifts for Glc$_{VI}$1 C-2 ($\delta_C$ 78.1), C-3 ($\delta_C$ 78.6), C-4 ($\delta_C$ 72.3), C-5 ($\delta_C$ 78.8), and C-6 ($\delta_C$ 64.1) was determined using the $^1$H-$^{13}$C HSQC-DEPT data to complete the assignment of Glc$_{VI}$.

A summary of the $^1$H and $^{13}$C chemical shifts for the glycoside at C-19 are found in the table below:

H NMR (500 MHz, D$_2$O) and $^{13}$C NMR (125 MHz, D$_2$O/TSP) Assignments of the Reb M2 glycoside.

| Position | $^{13}$C | $^1$H |
|---|---|---|
| Glc$_I$-1 | 95.5 | 5.65 d (7.6) |
| Glc$_I$-2 | 80.5 | 3.96 m |
| Glc$_I$-3 | 79.0 | 3.89 m |
| Glc$_I$-4 | 71.5 | 3.71 m |
| Glc$_I$-5 | 79.0 | 3.73 m |
| Glc$_I$-6 | 70.9 | 4.00 m |
| | | 4.15 d (11.7) |
| Glc$_V$-1 | 105.3* | 4.83* d (8.0) |
| Glc$_V$-2 | 78.5 | 3.32 m |
| Glc$_V$-3 | 78.7 | 3.51 m |
| Glc$_V$-4 | 72.9 | 3.38 m |
| Glc$_V$-5 | 78.8 | 3.55 m |
| Glc$_V$-6 | 63.6 | 3.76 m |
| | | 3.97 m |
| Glc$_{VI}$-1 | 105.7 | 4.50 d (7.9) |
| Glc$_{VI}$-2 | 78.1 | 3.33 m |
| Glc$_{VI}$-3 | 78.6 | 3.49 m |
| Glc$_{VI}$-4 | 72.3 | 3.45 m |
| Glc$_{VI}$-5 | 78.8 | 3.48 m |
| Glc$_{VI}$-6 | 64.1 | 3.92 m |
| | | 3.94 m |

\*$^1$H and $^{13}$C values can be exchangeable with Glc$_{II}$-1 of the following table.

A summary of the key HMBC, COSY, and 1D-TOCSY correlations used to assign the C-19 glycoside region are provided below:

$^1$H NMR (500 MHz, D$_2$O) and $^{13}$C NMR (125 MHz, D$_2$O/TSP) Assignments of the Reb M2 glycoside.

| Position | $^{13}$C# | $^1$H |
|---|---|---|
| Glc$_{II}$-1 | 98.4 | 4.85 d (7.8) |
| Glc$_{II}$-2 | 81.7 | 3.75 m |
| Glc$_{II}$-3 | 88.0 | 3.98 m |
| Glc$_{II}$-4 | 71.3 | 3.54 m |
| Glc$_{II}$-5 | 80.5 | 3.96 m |
| Glc$_{II}$-6 | 63.6 | 3.45 m |
| | | 3.77 m |
| Glc$_{III}$-1 | 104.9 | 4.92 d (7.9) |
| Glc$_{III}$-2 | 76.3 | 3.32 m |
| Glc$_{III}$-3 | 78.8 | 3.51 m |
| Glc$_{III}$-4 | 73.3 | 3.26 t (9.5) |
| Glc$_{III}$-5 | 78.8 | 3.44 m |
| Glc$_{III}$-6 | 64.4 | 3.75 m |
| | | 3.94 m |
| Glc$_{IV}$-1 | 105.0 | 4.84 d (7.8) |
| Glc$_{IV}$-2 | 76.1 | 3.41 m |
| Glc$_{IV}$-3 | 78.8 | 3.46 m |

-continued

| <sup>1</sup>H NMR (500 MHz, D₂O) and <sup>13</sup>C NMR (125 MHz, D₂O/TSP) Assignments of the Reb M2 glycoside. | | |
|---|---|---|
| Position | <sup>13</sup>C# | <sup>1</sup>H |
| Glc$_{IV}$-4 | 72.5 | 3.45 m |
| Glc$_{IV}$-5 | 81.7 | 3.75 m |
| Glc$_{IV}$-6 | 65.8 | 3.55 m |
| | | 3.78 m |

Assignment of Glc$_{II}$ was carried out in a similar manner. The Glc$_{II}$ anomeric proton ($\delta_H$ 4.85) showed a COSY correlation to a proton at $\delta_H$ 3.75 which was assigned as Glc$_{II}$ H-2 which in turn showed a COSY correlation to a proton at $\delta_H$ 3.98 (Glc$_{II}$ H-3). This latter proton showed an additional correlation with a proton at $\delta_H$ 3.54 (Glc$_{II}$ H-4). H-4 also showed a COSY correlation to a proton at $\delta_H$ 3.96 (Glc$_{II}$ H-5). Glc$_{II}$ H-5 also showed a COSY correlation to Glc$_{II}$ H-6 protons ($\delta_H$ 3.77 and 3.45). Assignment of the $^{13}$C chemical shifts for Glc$_{II}$ C-2 ($\delta_C$ 81.7), C-3 ($\delta_C$ 88.0), C-4 ($\delta_C$ 71.3), C-5 ($\delta_C$ 80.5), and C-6 ($\delta_C$ 63.6) was determined using the HSQC-DEPT data. HMBC correlations from Glc$_{II}$ H-3 to C-2 and C-4 and also from Glc$_{II}$ H-4 to C-3 and C-6 confirmed the assignments made above to complete the assignment of Glc$_{II}$.

Two of the remaining unassigned glucose moieties were assigned as substituents at C-2 and C-3 of Glc$_{II}$ on the basis of HMBC correlations. The anomeric proton observed at $\delta_H$ 4.92 showed a HMBC correlation to Glc$_{II}$ C-2 and was assigned as the anomeric proton of Glc$_{III}$. The anomeric proton observed at $\delta_H$ 4.84 showed a HMBC correlation to Glc$_{II}$ C-3 and was assigned as the anomeric proton of Glc$_{IV}$. The reciprocal HMBC correlations between Glc$_{II}$ H-2 and the anomeric carbon of Glc$_{III}$ and between Glc$_{II}$ H-3 and the anomeric carbon of Glc$_{IV}$ were also observed.

The anomeric proton of Glc$_{III}$ ($\delta_H$ 4.92) showed a COSY correlation with a proton at $\delta_H$ 3.32 which was assigned as Glc$_{III}$ H-2. Due to data overlap, the COSY spectrum did not allow assignment of H-3 to H-6 protons. Therefore, a series of 1D-TOCSY experiments were performed using selective irradiation of the Glc$_{III}$ anomeric proton with different mixing times. In addition to confirming the assignments for Glc$_{III}$ H-2, the 1D-TOCSY data showed protons at $\delta_H$ 3.51 (Glc$_{III}$ H-3), $\delta_H$ 3.26 (Glc$_{III}$ H-4), and $\delta_H$ 3.44 (Glc$_{III}$ H-5). Once H-4 was assigned using 1D-TOCSY data, COSY correlations from H-4 to H-5 and in turn to H-6 were used to assign H-6. In the COSY spectrum, Glc$_{III}$ H-4 showed a correlation to Glc$_{III}$ H-5, which in turn showed COSY correlations to $\delta_H$ 3.94 and 3.75 of Glc$_{III}$ H-6a and H-6b, respectively. The $^{13}$C chemical shifts for Glc$_{II}$ C-2 ($\delta_C$ 76.3), C-3 ($\delta_C$ 78.8), C-4 ($\delta_C$ 73.3), C-5 ($\delta_C$ 78.8), and C-6 ($\delta_C$ 64.4) were then determined using the $^{1}$H-$^{13}$C HSQC-DEPT correlations to complete the assignment of Glc$_{III}$.

The anomeric proton of Glc$_{IV}$ ($\delta_H$ 4.84) which showed a COSY correlation to a proton at $\delta_H$ 3.41 was assigned as Glc$_{IV}$ H-2 which in turn showed a COSY correlation to a proton at $\delta_H$ 3.46 (Glc$_{IV}$ H-3). This latter proton showed an additional correlation with a proton at $\delta_H$ 3.45 (Glc$_{IV}$ H-4) which also showed a COSY correlation to a proton at $\delta_H$ 3.75 (Glc$_{IV}$ H-5). Glc$_{IV}$ H-5 also showed a COSY correlation to Glc$_{IV}$ H-6 protons ($\delta_H$ 3.55 and 3.78). Assignment of the $^{13}$C chemical shifts for Glc$_{IV}$ C-2 ($\delta_C$ 76.1), C-3 ($\delta_C$ 78.8), C-4 ($\delta_C$ 72.5), C-5 ($\delta_C$ 81.7), and C-6 ($\delta_C$ 65.8) was determined using the HSQC-DEPT data. HMBC correlations from Glc$_{IV}$ H-3 to C-4 and C-5 and also from Glc$_{IV}$ H-4 to C-3 and C-6 confirmed the assignments made above to complete the assignment of Glc$_{IV}$.

A summary of the $^{1}$H and $^{13}$C chemical shifts for the glycoside at C-13 are found in the following table:

| <sup>1</sup>H NMR (500 MHz, D₂O) and <sup>13</sup>C NMR (125 MHz, D₂O/TSP) Assignments of the Reb M2 glycoside. | | |
|---|---|---|
| Position | <sup>13</sup>C# | <sup>1</sup>H |
| Glc$_{II}$1 | 98.4 | 4.85 d (7.8) |
| Glc$_{II}$2 | 81.7 | 3.75 m |
| Glc$_{II}$3 | 88.0 | 3.98 m |
| Glc$_{II}$4 | 71.3 | 3.54 m |
| Glc$_{II}$5 | 80.5 | 3.96 m |
| Glc$_{II}$6 | 63.6 | 3.45 m |
| | | 3.77 m |
| Glc$_{III}$1 | 104.9 | 4.92 d (7.9) |
| Glc$_{III}$2 | 76.3 | 3.32 m |
| Glc$_{III}$3 | 78.8 | 3.51 m |
| Glc$_{III}$4 | 73.3 | 3.26 t (9.5) |
| Glc$_{III}$5 | 78.8 | 3.44 m |
| Glc$_{III}$6 | 64.4 | 3.75 m |
| | | 3.94 m |
| Glc$_{IV}$1 | 105.0 | 4.84 d (7.8) |
| Glc$_{IV}$2 | 76.1 | 3.41 m |
| Glc$_{IV}$3 | 78.8 | 3.46 m |
| Glc$_{IV}$4 | 72.5 | 3.45 m |
| Glc$_{IV}$5 | 81.7 | 3.75 m |
| Glc$_{IV}$6 | 65.8 | 3.55 m |
| | | 3.78 m |

A summary of the key HMBC, COSY, and 1D-TOCSY correlations used to assign the C-13 glycoside region are provided below:

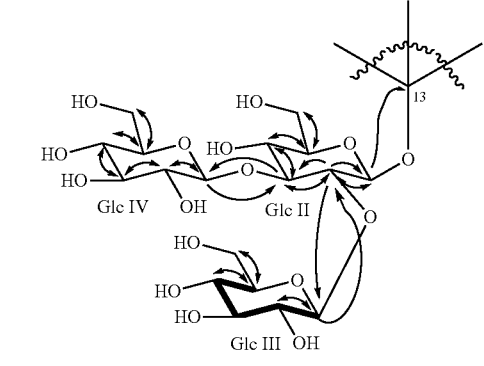

$\overset{\curvearrowright}{\phantom{x}}$ = $^{1}$H-$^{13}$C HMBC $\overset{\curvearrowright}{\phantom{x}}$ = $^{1}$H-$^{1}$H COSY ━━ = $^{1}$H-$^{1}$H spin system based on 1D-TOCSY NMR and MS analyses allowed a full assignment of its structure, shown below. The chemical name of the compound is 13-[(2-O-β-D-glucopyranosyl-3-O-β-D-glucopyranosyl-β-D-glucopyranosyl)oxy] ent-kaur-16-en-19-oic acid-[(2-O-β-D-glucopyranosyl-6-O-β-D-glucopyranosyl-β-D-glucopyranosyl) ester] (rebaudioside M2 or reb M2). The compound is an isomer of rebaudioside M.

Example 41

Directed Evolution of UGT76G1 for the Conversion of Rebaudioside D to Rebaudioside X (Round 2)

The most active clone from the first round of directed evolution of UGT76G1 (see EXAMPLE 26 UGT76G1var94 containing mutations: Q266E_P272A_R334K_G348P_L379G) was chosen as baseline clone for round 2. A list of 53 mutations was established containing different identified positive mutations from the first round and new mutations obtained by DNA2.0 ProteinGPS™ strategy. This list of mutations was subsequently used to design 92 variant genes that contained each 3 different mutations. After codon-optimized for expression in *E. coli* the genes were synthesized, subcloned in the pET30a+ plasmid and used for transformation of *E. coli* BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of *E. coli* BL21(DE3) containing the pET30a+_UGT76Glvar plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 µL of fresh lysate that was added to a solution of Rebaudioside D (final concentration 0.5 mM), MgCl$_2$ (final concentration 3 mM) and UDP-Glucose (final concentration 2.5 mM) in 50 mM phosphate buffer pH 7.2.

The reaction was allowed to run at 30° C. and samples were taken after 2, 4, 7 and 24 h. to determine conversion and initial rate by HPLC (CAD detection) using the analytical method that was described above for the transformation of Rebaudioside D to Rebaudioside X. In parallel the experiments were performed with baseline clone, Round1-Var94. The conversion after 22 h. and initial rate for this baseline clone was defined as 100% and the normalized conversions and initial rates for the round 2 clones are depicted in the following table:

| Clone | Mutations* | Normalized conversion Reb D to Reb X after 22 h. | Normalized initial rate (0-4 h) |
|---|---|---|---|
| Round1-Var94 | UGT76G1 (Q266E_P272A_R334K_G348P_L379G) baseline clone | 100% | 100% |
| Round2-Var1 | Round1-Var94 (A213N_P348G_I411V) | 70% | 86% |
| Round2-Var2 | Round1-Var94 (K303G_I423M_Q425E) | 120% | 134% |
| Round2-Var3 | Round1-Var94 (V20L_N138K_S147G) | 14% | 15% |
| Round2-Var4 | Round1-Var94 (I16V_V133A_L299I) | 37% | 43% |
| Round2-Var5 | Round1-Var94 (S241V_S274G_Q432E) | 75% | 72% |
| Round2-Var6 | Round1-Var94 (I16V_L139V_I218V) | 62% | 68% |
| Round2-Var7 | Round1-Var94 (K334R_N409K_Q432E) | 104% | 92% |
| Round2-Var8 | Round1-Var94 (I15L_R141T_I407V) | 17% | 26% |
| Round2-Var9 | Round1-Var94 (R141T_K303G_G379L) | 31% | 42% |
| Round2-Var10 | Round1-Var94 (I190L_K303G_P348G) | 131% | 149% |
| Round2-Var11 | Round1-Var94 (E266Q_F314S_N409R) | 106% | 132% |
| Round2-Var12 | Round1-Var94 (V133A_I295V_K303G) | 43% | 49% |
| Round2-Var13 | Round1-Var94 (I16V_S241V_N409R) | 80% | 79% |
| Round2-Var14 | Round1-Var94 (A239V_K334R_G379L) | 58% | 55% |
| Round2-Var15 | Round1-Var94 (I190L_K393R_V396L) | 118% | 126% |
| Round2-Var16 | Round1-Var94 (L101F_I295M_K393R) | 84% | 89% |
| Round2-Var17 | Round1-Var94 (A239V_E266Q_Q425E) | 96% | 101% |
| Round2-Var18 | Round1-Var94 (V20L_I190L_I423M) | 98% | 98% |
| Round2-Var19 | Round1-Var94 (V20L_G379L_S456L) | 84% | 81% |
| Round2-Var20 | Round1-Var94 (K334R_P348G_N409R) | 73% | 73% |
| Round2-Var21 | Round1-Var94 (E231A_S241V_E449D) | 53% | 50% |
| Round2-Var22 | Round1-Var94 (K188R_L299I_V394I) | 56% | 59% |
| Round2-Var23 | Round1-Var94 (E231A_S274G_V394I) | 110% | 124% |

-continued

| Clone | Mutations* | Normalized conversion Reb D to Reb X after 22 h. | Normalized initial rate (0-4 h) |
|---|---|---|---|
| Round2-Var24 | Round1-Var94 (S42A_I295V_Q432E) | 71% | 78% |
| Round2-Var25 | Round1-Var94 (A213N_A272P_K334R) | 95% | 80% |
| Round2-Var26 | Round1-Var94 (L158Y_S274K_N409K) | 80% | 50% |
| Round2-Var27 | Round1-Var94 (K188R_I295M_Q425E) | 132% | 116% |
| Round2-Var28 | Round1-Var94 (I15L_I295M_V394I) | 53% | 36% |
| Round2-Var29 | Round1-Var94 (V133A_A239V_V394I) | 47% | 30% |
| Round2-Var30 | Round1-Var94 (L158Y_F314S_K316R) | 107% | 72% |
| Round2-Var31 | Round1-Var94 (L158Y_A239V_A272P) | 54% | 30% |
| Round2-Var32 | Round1-Var94 (F46I_D301N_V396L) | 109% | 101% |
| Round2-Var33 | Round1-Var94 (L101F_I218V_Q432E) | 78% | 54% |
| Round2-Var34 | Round1-Var94 (I16V_F46I_I295M) | 110% | 95% |
| Round2-Var35 | Round1-Var94 (A213N_E266S_I407V) | 98% | 79% |
| Round2-Var36 | Round1-Var94 (A239V_S274K_I295M) | 102% | 89% |
| Round2-Var37 | Round1-Var94 (A239V_F314S_S450K) | 105% | 99% |
| Round2-Var38 | Round1-Var94 (L139V_K188R_D301N) | 66% | 51% |
| Round2-Var39 | Round1-Var94 (I45V_I218V_S274K) | 87% | 58% |
| Round2-Var40 | Round1-Var94 (S241V_K303G_V394I) | 78% | 57% |
| Round2-Var41 | Round1-Var94 (R141T_S274G_K334R) | 41% | 28% |
| Round2-Var42 | Round1-Var94 (V217L_S274G_L299I) | 47% | 34% |
| Round2-Var43 | Round1-Var94 (S274G_D301N_P348G) | 98% | 91% |
| Round2-Var44 | Round1-Var94 (E231A_N409R_S450K) | 87% | 65% |
| Round2-Var45 | Round1-Var94 (R64H_E231A_K316R) | 88% | 64% |
| Round2-Var46 | Round1-Var94 (V394I_N409K_I411V) | 110% | 100% |
| Round2-Var47 | Round1-Var94 (I45V_I295M_K303G) | 113% | 88% |
| Round2-Var48 | Round1-Var94 (L101F_V396L_L398V) | 46% | 43% |
| Round2-Var49 | Round1-Var94 (N27S_L101F_S447A) | 54% | 37% |
| Round2-Var50 | Round1-Var94 (S274G_F314S_L398V) | 129% | 156% |
| Round2-Var51 | Round1-Var94 (E266Q_L299I_K393R) | 70% | 51% |
| Round2-Var52 | Round1-Var94 (V217L_E266S_V394I) | 62% | 48% |
| Round2-Var53 | Round1-Var94 (N138K_A272P_N409R) | 118% | 102% |
| Round2-Var54 | Round1-Var94 (E266S_F314S_Q432E) | 124% | 146% |
| Round2-Var55 | Round1-Var94 (D301N_G379L_L398V) | 56% | 45% |
| Round2-Var56 | Round1-Var94 (F46I_E266S_K334R) | 123% | 142% |
| Round2-Var57 | Round1-Var94 (A272P_V394I_Q432E) | 133% | 142% |
| Round2-Var58 | Round1-Var94 (V394I_I407V_S456L) | 118% | 114% |
| Round2-Var59 | Round1-Var94 (I218V_E266Q_I423M) | 106% | 98% |
| Round2-Var60 | Round1-Var94 (A272P_G379L_I407V) | 80% | 63% |
| Round2-Var61 | Round1-Var94 (E231A_K303G_S456L) | 113% | 110% |
| Round2-Var62 | Round1-Var94 (I190L_E266Q_I407V) | 150% | 167% |
| Round2-Var63 | Round1-Var94 (N27S_L139V_I295V) | 43% | 25% |
| Round2-Var64 | Round1-Var94 (V217L_I423M_S447A) | 67% | 51% |
| Round2-Var65 | Round1-Var94 (L158Y_E266S_E449D) | 68% | 43% |
| Round2-Var66 | Round1-Var94 (S42A_F46I_I407V) | 160% | 203% |
| Round2-Var67 | Round1-Var94 (N138K_E231A_D301N) | 118% | 93% |
| Round2-Var68 | Round1-Var94 (K188R_G379L_N409R) | 52% | 35% |
| Round2-Var69 | Round1-Var94 (I15L_E231A_V396L) | 38% | 22% |
| Round2-Var70 | Round1-Var94 (E231A_Q425E_Q432E) | 115% | 119% |
| Round2-Var71 | Round1-Var94 (D301N_K316R_Q425E) | 126% | 121% |
| Round2-Var72 | Round1-Var94 (L139V_I295M_F314S) | 76% | 91% |
| Round2-Var73 | Round1-Var94 (S147G_E266S_D301N) | 30% | 18% |
| Round2-Var74 | Round1-Var94 (R64H_S147G_S447A) | 23% | 12% |
| Round2-Var75 | Round1-Var94 (S42A_K303G_L398V) | 95% | 110% |
| Round2-Var76 | Round1-Var94 (I45V_D301N_E449D) | 62% | 60% |
| Round2-Var77 | Round1-Var94 (V133A_E266S_I411V) | 37% | 28% |
| Round2-Var78 | Round1-Var94 (I45V_N409R_Q425E) | 63% | 59% |
| Round2-Var79 | Round1-Var94 (R141T_A272P_F314S) | 23% | 10% |
| Round2-Var80 | Round1-Var94 (E266S_S274G_N409R) | 81% | 91% |
| Round2-Var81 | Round1-Var94 (N409K_Q425E_S450K) | 81% | 84% |
| Round2-Var82 | Round1-Var94 (N27S_R64H_K393R) | 47% | 37% |
| Round2-Var83 | Round1-Var94 (S42A_A213N_V217L) | 62% | 46% |
| Round2-Var84 | Round1-Var94 (N27S_S274K_I407V) | 49% | 44% |
| Round2-Var85 | Round1-Var94 (I411V_Q425E_S456L) | 75% | 81% |
| Round2-Var86 | Round1-Var94 (A239V_K316R_E449D) | 83% | 72% |
| Round2-Var87 | Round1-Var94 (S147G_A239V_P348G) | 18% | 7% |
| Round2-Var88 | Round1-Var94 (V20L_S274G_S450K) | 71% | 68% |
| Round2-Var89 | Round1-Var94 (F314S_V394I_S447A) | 88% | 123% |
| Round2-Var90 | Round1-Var94 (R64H_E266Q_I295M) | 45% | 47% |
| Round2-Var91 | Round1-Var94 (N138K_I295V_I407V) | 50% | 51% |
| Round2-Var92 | Round1-Var94 (I15L_P348G_Q432E) | 18% | 13% |

*Mutations are noted as follows: reference gene-original amino acid-position-new amino acid: For example the mutation of an alanine at position 33 to a glycine for variant 94 from the first round of directed evolution of UGT76G1 is noted as Round1-Var94 (A33G)

Modeling of these results allowed to obtain a ranking of the effect of each mutation. The following mutations were determined as being beneficial for activity: S42A, F46I, I190L, S274G, I295M, K303G, F314S, K316R, K393R, V394I, I407V, N409K, N409R, Q425E, Q432E, S447A, S456L.

Example 42

In Vivo Production of AtSUS

SEQ ID NO: 13:
MANAERMITRVHSQRERLNETLVSERNEVLALLSRVEAKGKGILQQNQII

AEFEALPEQTRKKLEGGPFFDLLKSTQEAIVLPPWVALAVRPRPGVWEYL

RVNLHALVVEELQPAEFLHFKEELVDGVKNGNFTLELDFEPFNASIPRPT

LHKYIGNGVDFLNRHLSAKLFHDKESLLPLLKFLRLHSHQGKNLMLSEKI

QNLNTLQHTLRKAEEYLAELKSETLYEEFEAKFEEIGLERGWGDNAERVL

DMIRLLLDLLEAPDPCTLETFLGRVPMVFNVVILSPHGYFAQDNVLGYPD

TGGQVVYILDQVRALEIEMLQRIKQQGLNIKPRILILTRLLPDAVGTICG

ERLERVYDSEYCDILRVPFRTEKGIVRKWISRFEVWPYLETYTEDAAVEL

SKELNGKPDLIIGNYSDGNLVASLLAHKLGVTQCTIAHALEKTKYPDSDI

YWKKLDDKYHFSCQFTADIFAMNHTDFIITSTFQEIAGSKETVGQYESHT

AFTLPGLYRVVHGIDVFDPKFNIVSPGADMSIYFPYTEEKRRLTKFHSEI

EELLYSDVENKEHLCVLKDKKKPILFTMARLDRVKNLSGLVEWYGKNTRL

RELANLVVVGGDRRKESKDNEEKAEMKKMYDLIEEYKLNGQFRWISSQMD

RVRNGELYRYICDTKGAFVQPALYEAFGLTVVEAMTCGLPTFATCKGGPA

EIIVHGKSGFHIDPYHGDQAADTLADFFTKCKEDPSHWDEISKGGLQRIE

EKYTWQIYSQRLLTLTGVYGFWKHVSNLDRLEARRYLEMFYALKYRPLAQ

AVPLAQDD

The synthetic gene of AtSuS that was codon optimized for expression in E. coli and subcloned in the pET30a+ plasmid using the NdeI and XhoI restriction sites. The pET30A+ vector containing the AtSUS gene was used to transform electrocompetent E. coli Bl21(DE3) cells. The obtained cells were grown in petri-dishes in the presence of Kanamycin and suitable colonies were selected and allowed to grow in liquid LB medium (erlenmeyer flasks). Glycerol was added to the suspension as cryoprotectant and 400 µL aliquots were stored at −20° C. and at −80° C.

The storage aliquots of E. coli BL21(DE3) containing the pET30A+_AtSUS plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 h.

The production medium contained 60 g/L of overnight express instant TB medium (Novagen), 10 g/L of glycerol and 50 mg/L of Kanamycine. The preculture was added to 800 mL of this medium and the solution was allowed to stir at 20° C. while taking samples to measure the OD and pH. The culture gave significant growth and a good OD was obtained. After 40 h, the cells were harvested by centrifugation and frozen to obtain 30.1 g of cell wet weight.

Lysis was performed by Fastprep (MP Biomedicals, Lysing matrix B, speed 6.0, 3×40 sec) with a cell suspension of 200 mg of cells in 1.0 mL of 50 mM Tris buffer pH 7.5. The lysate was recovered by centrifugation and used fresh.

Example 43

Figure 66:
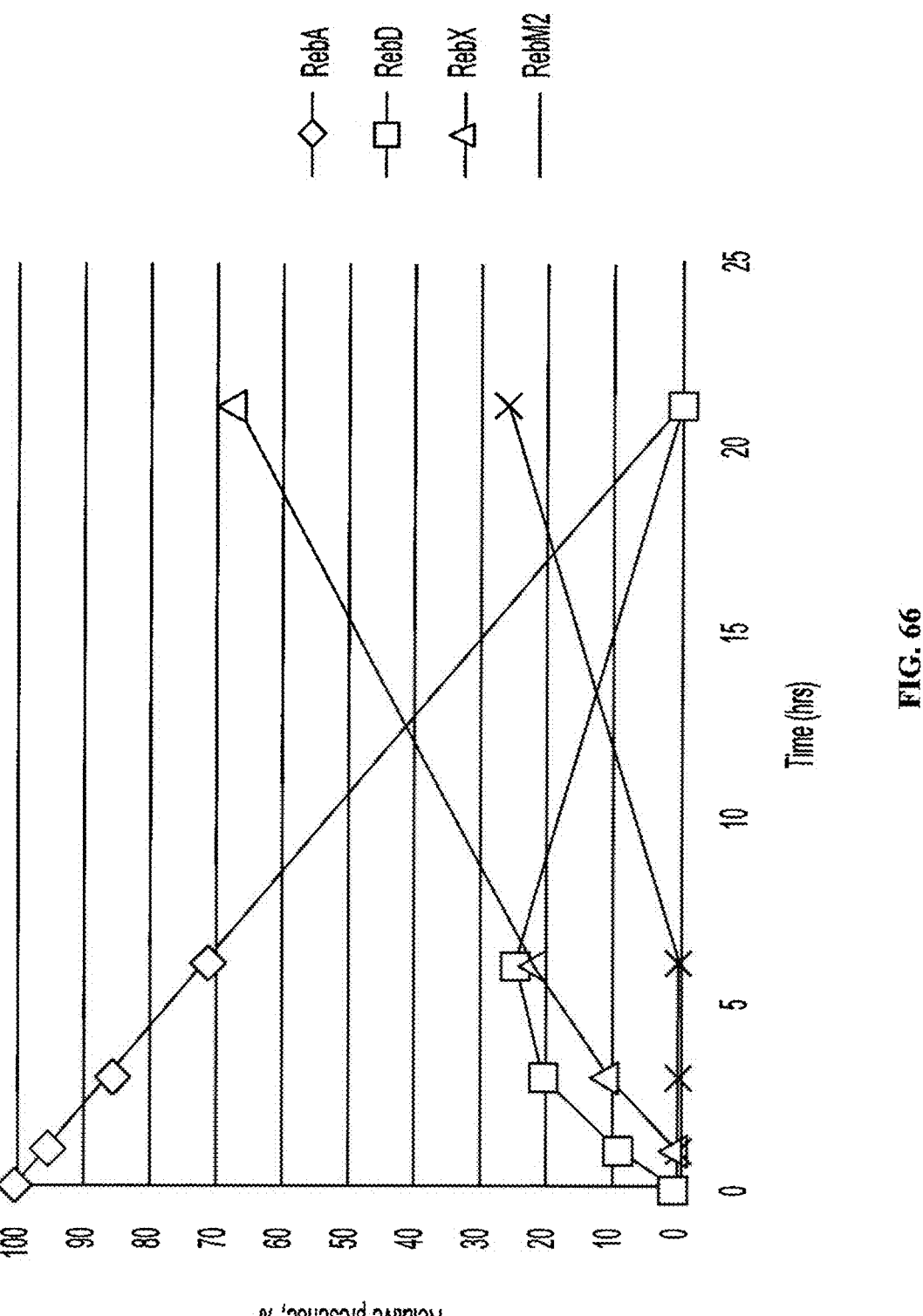
FIG. 66 shows a graph showing the HPLC results for Example 43.

Conversion of Rebaudioside A to Rebaudioside X with In Situ Prepared UDP-Glucose Using UGTSL2, UGT76G1-R1-F12 and AtSUS The reaction was performed at 1 mL scale using 100 mM of sucrose, 3 mM of $MgCl_2$, 0.25 mM of UDP and 0.5 mM of Rebaudioside A in potassium phosphate buffer (50 mM final concentration, pH 7.5). The reaction was started by adding 15 µL of UGTSL2 (see EXAMPLE 27) lysate (2 U/mL), 150 µL of UGT76G1var94 (see EXAMPLE 26) (2.5 U/mL) and 15 µL of AtSUS (see EXAMPLE 42) (400 U/mL). The reaction was followed by HPLC after quenching 125 µL samples with 10 µL of 2 N $H_2SO_4$ and 115 µL of 60% methanol. 68% of Rebaudioside X and 26% of Rebaudioside M2 was obtained after 21 h of reaction time, as shown in FIG. 66.

Example 44

Directed Evolution of UGT76G1 for the Conversion of Rebaudioside D to Rebaudioside X (Round 3)

The most active clone from the second round of directed evolution of UGT76G1 (see EXAMPLE 41 round2_UGT76G1var66 containing mutations: S42A_F46I_I407V) was chosen as baseline clone for round 3. A list of 56 mutations was established containing different identified positive mutations from the second round and 30 new mutations obtained by DNA2.0 ProteinGPS™ strategy. This list of mutations was subsequently used to design 92 variant genes that contained each 3 or 4 different mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of E. coli BL21(DE3) containing the pET30a+_UGT76Glvar plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 µL of fresh lysate that was added to a solution of Rebaudioside D (final concentration 0.5 mM), $MgCl_2$ (final concentration 3 mM) and UDP-Glucose (final concentration 2.5 mM) in 50 mM phosphate buffer pH 7.2.

The reaction was allowed to run at 30° C. and samples were taken after 1, 2, 4, 6 and 22 h. to determine conversion and initial rate by HPLC (CAD detection) using the analytical method that was described above for the transformation of Rebaudioside D to Rebaudioside X. In parallel the experiments were performed with baseline clone, Round2-

Var66. The conversion after 22 h. and initial rate for this baseline clone was defined as 10000 and the normalized conversions and initial rates for the round 3 clones are depicted in the following table:

| Clone | Mutations* | Normalized conversion Reb D to Reb X after 22 h. | Normalized initial rate (0-4 h) |
|---|---|---|---|
| Round2-Var66 | UGT76G1 (S42A_F46I_Q266E_P272A_R334K_G348P_L379G_I407V) Baseline clone | 100% | 100% |
| Round3-Var1 | Round2-Var66 (I46F_L121I_E229A_K393R) | 42% | 96% |
| Round3-Var2 | Round2-Var66 (F18V_A213N_E266S) | 7% | 36% |
| Round3-Var3 | Round2-Var66 (F41L_I190L_A239V_K316R) | 20% | 64% |
| Round3-Var4 | Round2-Var66 (N138K_S274G_Q425E_S456L) | 92% | 104% |
| Round3-Var5 | Round2-Var66 (F22Y_E229S_V407I_N409R) | 15% | 66% |
| Round3-Var6 | Round2-Var66 (F150A_G216A_T355S_S447A) | 15% | 50% |
| Round3-Var7 | Round2-Var66 (V394I_N409R_Q425E_S447A) | 72% | 97% |
| Round3-Var8 | Round2-Var66 (Y37H_F41L_N409R_Q425E) | 6% | 37% |
| Round3-Var9 | Round2-Var66 (L121V_F182L_K303G_E331G) | 75% | 95% |
| Round3-Var10 | Round2-Var66 (S274G_K303G_N409R_Q432E) | 99% | 106% |
| Round3-Var11 | Round2-Var66 (F41L_K303G_F314S) | 26% | 67% |
| Round3-Var12 | Round2-Var66 (F22Y_R141S_T284V) | 3% | 15% |
| Round3-Var13 | Round2-Var66 (I190L_E229A_T284V) | 31% | 70% |
| Round3-Var14 | Round2-Var66 (K303G_Q425E_S447A) | 109% | 114% |
| Round3-Var15 | Round2-Var66 (K316R_L383V_V394I) | 107% | 117% |
| Round3-Var16 | Round2-Var66 (I190L_K303G_S447A_S456L) | 112% | 110% |
| Round3-Var17 | Round2-Var66 (N138G_V264C_A352G_S447A) | 102% | 107% |
| Round3-Var18 | Round2-Var66 (S274K_V407I_Q425E) | 91% | 107% |
| Round3-Var19 | Round2-Var66 (I190L_S274G_K393R_V394I) | 120% | 108% |
| Round3-Var20 | Round2-Var66 (A213N_L277I_Q425E_E449D) | 79% | 101% |
| Round3-Var21 | Round2-Var66 (I46L_K303G_K393R) | 147% | 117% |
| Round3-Var22 | Round2-Var66 (S221T_S274G_S375Q) | 19% | 65% |
| Round3-Var23 | Round2-Var66 (Y37H_L383V_S456L) | 67% | 99% |
| Round3-Var24 | Round2-Var66 (N138G_I190L_I295T_N409R) | 45% | 84% |
| Round3-Var25 | Round2-Var66 (A42S_S119A_K303G_V407I) | 92% | 99% |
| Round3-Var26 | Round2-Var66 (F22Y_I46F_I190L_V394I) | 76% | 95% |
| Round3-Var27 | Round2-Var66 (N138K_A213N_F314S) | 83% | 92% |
| Round3-Var28 | Round2-Var66 (D301N_F314S_V394I_N409R) | 76% | 86% |
| Round3-Var29 | Round2-Var66 (G216A_E266S_Q432E) | 70% | 88% |
| Round3-Var30 | Round2-Var66 (N138K_A239V_P382R_K393R) | 42% | 76% |
| Round3-Var31 | Round2-Var66 (I46L_S274G_K316R_S456L) | 149% | 109% |
| Round3-Var32 | Round2-Var66 (F18V_I190L_S375Q_S456L) | 1% | 2% |
| Round3-Var33 | Round2-Var66 (N138K_R141S_S274G) | 18% | 57% |
| Round3-Var34 | Round2-Var66 (N138K_K393R_N409R_S447A) | 59% | 82% |
| Round3-Var35 | Round2-Var66 (I295T_K303G_P382R_V394I) | 31% | 70% |
| Round3-Var36 | Round2-Var66 (N138K_I218V_S456L) | 54% | 81% |
| Round3-Var37 | Round2-Var66 (M145R_S274K_L383V) | 1% | 1% |
| Round3-Var38 | Round2-Var66 (F182L_A352G_V394I) | 86% | 96% |
| Round3-Var39 | Round2-Var66 (A42S_N138G_E229A_S456L) | 21% | 77% |
| Round3-Var40 | Round2-Var66 (R141S_I190L_E331G_Q425E) | 6% | 35% |
| Round3-Var41 | Round2-Var66 (E229S_K316R_T355S) | 32% | 81% |
| Round3-Var42 | Round2-Var66 (I46F_N138K_F292L_N409R) | 30% | 83% |
| Round3-Var43 | Round2-Var66 (A42S_F182L_L277I_T355S) | 40% | 89% |
| Round3-Var44 | Round2-Var66 (S274G_T284V_Q425E) | 85% | 93% |
| Round3-Var45 | Round2-Var66 (A272P_E331G_V394I_S447A) | 88% | 96% |
| Round3-Var46 | Round2-Var66 (S274G_F314S_Q432E_S447A) | 112% | 104% |
| Round3-Var47 | Round2-Var66 (L121I_K316R_S375Q_N409R) | 24% | 76% |
| Round3-Var48 | Round2-Var66 (L121I_N138K_F150A_K303G) | 40% | 83% |
| Round3-Var49 | Round2-Var66 (I46F_V264C_Q432E) | 61% | 98% |
| Round3-Var50 | Round2-Var66 (F150A_A272P_D301N_K316R) | 44% | 88% |
| Round3-Var51 | Round2-Var66 (I46L_R64V_A239V) | 28% | 71% |
| Round3-Var52 | Round2-Var66 (L121I_I218V_F314S) | 87% | 94% |
| Round3-Var53 | Round2-Var66 (I190L_G216A_E449D) | 49% | 90% |
| Round3-Var54 | Round2-Var66 (S274G_I295M_F314S) | 128% | 106% |
| Round3-Var55 | Round2-Var66 (F22Y_S274G_P382R_Q432E) | 39% | 48% |
| Round3-Var56 | Round2-Var66 (N138K_I190L_K334R) | 93% | 97% |
| Round3-Var57 | Round2-Var66 (N138G_I295M_K303G) | 110% | 100% |
| Round3-Var58 | Round2-Var66 (L121V_G216A_Q425E_S456L) | 28% | 52% |
| Round3-Var59 | Round2-Var66 (F182L_F314S_K393R) | 92% | 97% |
| Round3-Var60 | Round2-Var66 (R64V_K316R_N409K) | 16% | 54% |
| Round3-Var61 | Round2-Var66 (V264C_S274G_K393R) | 102% | 98% |
| Round3-Var62 | Round2-Var66 (F41L_K393R_S456L) | 12% | 49% |
| Round3-Var63 | Round2-Var66 (A42S_S274G_F292L_V394I) | 75% | 87% |
| Round3-Var64 | Round2-Var66 (I190L_S221T_E266S_S447A) | 34% | 71% |
| Round3-Var65 | Round2-Var66 (R64V_E229S_S274K) | 12% | 49% |
| Round3-Var66 | Round2-Var66 (S221T_K334R_K393R_V394I) | 72% | 90% |
| Round3-Var67 | Round2-Var66 (I190L_K393R_Q425E_Q432E) | 101% | 102% |
| Round3-Var68 | Round2-Var66 (F18V_N138K_M145R) | 1% | 1% |
| Round3-Var69 | Round2-Var66 (I218V_F292L_K316R_S447A) | 40% | 79% |

-continued

| Clone | Mutations* | Normalized conversion Reb D to Reb X after 22 h. | Normalized initial rate (0-4 h) |
|---|---|---|---|
| Round3-Var70 | Round2-Var66 (L121V_E229A_K316R_Q432E) | 19% | 63% |
| Round3-Var71 | Round2-Var66 (Y37H_L121V_D301N) | 35% | 68% |
| Round3-Var72 | Round2-Var66 (N138K_V394I_Q432E_S456L) | 66% | 89% |
| Round3-Var73 | Round2-Var66 (T284V_I295M_A352G_L383V) | 69% | 89% |
| Round3-Var74 | Round2-Var66 (S119A_F150A_V394I_Q425E) | 66% | 88% |
| Round3-Var75 | Round2-Var66 (F18V_A239V_S447A) | 8% | 27% |
| Round3-Var76 | Round2-Var66 (K303G_N409R_Q432E) | 84% | 97% |
| Round3-Var77 | Round2-Var66 (Y37H_A272P_K334R_E449D) | 75% | 89% |
| Round3-Var78 | Round2-Var66 (K303G_F314S_V394I_Q425E) | 121% | 104% |
| Round3-Var79 | Round2-Var66 (R141S_I295T_F314S_Q432E) | 9% | 29% |
| Round3-Var80 | Round2-Var66 (N138K_I190L_F314S_N409R) | 90% | 97% |
| Round3-Var81 | Round2-Var66 (S119A_E331G_S456L) | 87% | 97% |
| Round3-Var82 | Round2-Var66 (K303G_F314S_K393R_S456L) | 100% | 100% |
| Round3-Var83 | Round2-Var66 (N138K_A352G_V407I_Q432E) | 72% | 95% |
| Round3-Var84 | Round2-Var66 (S274G_L277I_I295T) | 34% | 81% |
| Round3-Var85 | Round2-Var66 (R64V_L277I_F314S_S447A) | 34% | 61% |
| Round3-Var86 | Round2-Var66 (S221T_N409K_Q432E) | 39% | 75% |
| Round3-Var87 | Round2-Var66 (N409R_S447A_S456L) | 52% | 86% |
| Round3-Var88 | Round2-Var66 (K393R_Q425E_Q432E) | 102% | 99% |
| Round3-Var89 | Round2-Var66 (I46L_F292L_S375Q_N409K) | 8% | 35% |
| Round3-Var90 | Round2-Var66 (M145R_K393R_N409R) | 1% | 1% |
| Round3-Var91 | Round2-Var66 (S119A_M145R_T355S_P382R) | 0% | 1% |
| Round3-Var92 | Round2-Var66 (I190L_E229S_V264C_F314S) | 64% | 82% |

*Mutations are noted as follows: reference gene-original amino acid-position-new amino acid: For example the mutation of an isoleucine at position 190 to a leucine for variant 66 from the second round of directed evolution of UGT76G1 is noted as Round2-Var66 (I190L).

Modeling of these results allowed to obtain a ranking of the effect of each mutation. The following mutations were determined as being beneficial for activity: I46L, I295M, S119A, S274G, K334R, F314S, K303G, K316R, K393R, I190L, Q425E, Q432E, N138G, V394I, F182L, V407I, A272P, V264C, E449D, A352G.

Example 45

Directed Evolution of UGTSL2 for the Conversion of Rebaudioside A to Rebaudioside D (Round 1)

Starting from native enzyme UGTSL2 (GI_460410132) a list of 60 mutations was established containing different identified positive mutations from the first round and new mutations obtained by DNA2.0 ProteinGPS™ strategy. This list of mutations was subsequently used to design 92 variant genes that contained each 3 different mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 μL aliquots were stored at −20° C. and at −80° C.

These storage aliquots of E. coli BL21(DE3) containing the pET30a+_UGTSL2var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 μL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 μL of fresh lysate that was added to a solution of Rebaudioside D (final concentration 0.5 mM), MgCl$_2$ (final concentration 3 mM) and UDP-Glucose (final concentration 2.5 mM) in 50 mM phosphate buffer pH 7.2.

The reaction was allowed to run at 30° C. and samples were taken after 2, 4, 6 and 22 h. to determine the initial rate by HPLC (CAD detection) using the analytical method that was described above for the transformation of Rebaudioside A to Rebaudioside D. In parallel the experiments were performed with baseline clone, UGTSL2. The initial rate for this baseline clone was defined as 10000. As an indication of the specificity of the clones, Rebaudioside M2 content was determined at 100% UDP-Glucose conversion and Rebaudioside D2 content was determined at 50% UDP-Glucose conversion. Wherein UDP glucose conversion is defined as: ([Reb D]/[Reb A]$_0$)+([Reb D2]/[Reb A]$_0$)+2*([Reb M2]/[Reb A]$_0$).

The normalized initial rate, Rebaudioside M2 content at 100% UDP-glucose conversion and Rebaudioside D2 content at 50% UDP-glucose conversion are depicted in the following table

| Clone | Mutations* | Normalized initial rate (0-4 h) | Reb M2 content at 100% UDP-Glc conversion | Reb D2 content at 50% UDP-Glc conversion |
|---|---|---|---|---|
| UGTSL2 | baseline clone | 100% | 100% | 12.5% |
| Round1-Var1 | UGTSL2 (L276A_N278G_T329V) | 220% | 98% | 8.5% |

-continued

| Clone | Mutations* | Normalized initial rate (0-4 h) | Reb M2 content at 100% UDP-Glc conversion | Reb D2 content at 50% UDP-Glc conversion |
|---|---|---|---|---|
| Round1-Var2 | UGTSL2 (S19I_E259G_V270L) | 0% | 0% | |
| Round1-Var3 | UGTSL2 (I323V_S334T_V368E) | 0% | 0% | |
| Round1-Var4 | UGTSL2 (V125I_E259G_L393V) | 0% | 0% | |
| Round1-Var5 | UGTSL2 (Q27R_H247P_I333L) | 185% | 134% | 15.0% |
| Round1-Var6 | UGTSL2 (Q27R_N325S_G387E_T392A) | 148% | 116% | 17.0% |
| Round1-Var7 | UGTSL2 (F253Y_N325A_K365V_G371K) | 0% | 0% | |
| Round1-Var8 | UGTSL2 (T245R_N325A_G331A_S334T) | 8% | 17% | |
| Round1-Var9 | UGTSL2 (G331A_N339S_G371K) | 2% | 3% | |
| Round1-Var10 | UGTSL2 (R6H_F272L_I323V) | 3% | 6% | |
| Round1-Var11 | UGTSL2 (R6H_F21L_T329I) | 0% | 0% | |
| Round1-Var12 | UGTSL2 (F21L_N280P_I282L) | 0% | 0% | |
| Round1-Var13 | UGTSL2 (T245R_V254L_I333V) | 0% | 1% | |
| Round1-Var14 | UGTSL2 (L276A_I351L_M354L_I389L) | 2% | 2% | |
| Round1-Var15 | UGTSL2 (S19I_I240L_I351M) | 4% | 9% | |
| Round1-Var16 | UGTSL2 (I131V_I333V_S334T) | 3% | 8% | |
| Round1-Var17 | UGTSL2 (S200F_A285V_I351M_P361G) | 0% | 0% | |
| Round1-Var18 | UGTSL2 (R6H_L37F_A285L) | 8% | 21% | |
| Round1-Var19 | UGTSL2 (H247P_N249G_K289P) | 8% | 17% | |
| Round1-Var20 | UGTSL2 (R6H_S19I_N325A) | 50% | 59% | |
| Round1-Var21 | UGTSL2 (N280P_K289P_T329I_V368E) | 0% | 0% | |
| Round1-Var22 | UGTSL2 (I240L_N325S_V368E) | 26% | 43% | |
| Round1-Var23 | UGTSL2 (A205P_T245R_K365V) | 0% | 0% | |
| Round1-Var24 | UGTSL2 (L276A_A341V_T392A) | 255% | 115% | 7.5% |
| Round1-Var25 | UGTSL2 (L37F_I351L_K365V) | 7% | 17% | |
| Round1-Var26 | UGTSL2 (T199S_E259G_T329I) | 80% | 90% | 12.0% |
| Round1-Var27 | UGTSL2 (T245R_S258T_L405V) | 7% | 18% | |
| Round1-Var28 | UGTSL2 (K289S_I352V_P361G) | 9% | 15% | |
| Round1-Var29 | UGTSL2 (L37F_V254L_V270L_I323V) | 0% | 0% | |
| Round1-Var30 | UGTSL2 (I240L_S258T_G387E) | 127% | 107% | 11.0% |
| Round1-Var31 | UGTSL2 (V270I_I282L_T329V_N339S) | 0% | 0% | |
| Round1-Var32 | UGTSL2 (H247P_T329I_I351L) | 0% | 3% | |
| Round1-Var33 | UGTSL2 (N280P_A285L_I352V_G387E) | 37% | 62% | |
| Round1-Var34 | UGTSL2 (S19I_I323V_N325S_P361G) | 0% | 0% | |
| Round1-Var35 | UGTSL2 (L37F_Q65P_F272L) | 14% | 24% | |
| Round1-Var36 | UGTSL2 (H247P_N280R_A285V) | 32% | 54% | |
| Round1-Var37 | UGTSL2 (I240L_N339S_I352V_L405V) | 0% | 0% | |
| Round1-Var38 | UGTSL2 (V125I_N280P_G371K) | 2% | 5% | |
| Round1-Var39 | UGTSL2 (F253Y_I282L_A285V) | 25% | 45% | |
| Round1-Var40 | UGTSL2 (I282L_R312L_N325S) | 4% | 8% | |
| Round1-Var41 | UGTSL2 (T199S_S258T_N278G) | 0% | 9% | |
| Round1-Var42 | UGTSL2 (I114V_I351M_G387E) | 0% | 0% | |
| Round1-Var43 | UGTSL2 (S255C_S258T_V270L) | 29% | 59% | |
| Round1-Var44 | UGTSL2 (Q27R_R312L_T329V) | 86% | 92% | 12.0% |
| Round1-Var45 | UGTSL2 (V254L_N339S_I345L) | 0% | 0% | 11.0% |
| Round1-Var46 | UGTSL2 (I333V_A341V_M354L) | 84% | 86% | |
| Round1-Var47 | UGTSL2 (F253Y_F272L_T392A) | 125% | 116% | 12.0% |
| Round1-Var48 | UGTSL2 (F253Y_A285L_N339S) | 50% | 70% | |
| Round1-Var49 | UGTSL2 (K289S_I345L_G387E) | 0% | 2% | |
| Round1-Var50 | UGTSL2 (I131V_E259G_V270I) | 0% | 0% | |
| Round1-Var51 | UGTSL2 (F272L_N280R_T329V) | 0% | 4% | |
| Round1-Var52 | UGTSL2 (N278G_R312L_T329I_I333L) | 100% | 100% | 13.0% |
| Round1-Var53 | UGTSL2 (I114V_I131V_N325S) | 10% | 20% | |
| Round1-Var54 | UGTSL2 (A205P_K289P_I333V_G371K) | 0% | 0% | |
| Round1-Var55 | UGTSL2 (S19I_F21L_S200F) | 0% | 0% | |
| Round1-Var56 | UGTSL2 (I131V_H247P_N278G_A285L) | 109% | 120% | 13.0% |
| Round1-Var57 | UGTSL2 (R312L_A341V_M367V) | 14% | 25% | |
| Round1-Var58 | UGTSL2 (N280R_I333L_M354L) | 0% | 1% | |
| Round1-Var59 | UGTSL2 (S258T_E259G_A285V_I333V) | 0% | 0% | |
| Round1-Var60 | UGTSL2 (P361G_I389L_L405V) | 0% | 0% | |
| Round1-Var61 | UGTSL2 (S255C_N280R_I345L_V368E) | 0% | 0% | |
| Round1-Var62 | UGTSL2 (F21L_Q65P_N280R_K289S) | 0% | 0% | |
| Round1-Var63 | UGTSL2 (V270I_M367V_V368E) | 20% | 32% | |
| Round1-Var64 | UGTSL2 (T199S_V254L_A285L) | 0% | 0% | |
| Round1-Var65 | UGTSL2 (S255C_N280P_G331A) | 73% | 82% | 11.5% |
| Round1-Var66 | UGTSL2 (N249G_K365V_M367V_I389L) | 0% | 0% | |
| Round1-Var67 | UGTSL2 (S200F_I333L_I351L) | 0% | 0% | |
| Round1-Var68 | UGTSL2 (N249G_V270L_K289S) | 13% | 24% | |
| Round1-Var69 | UGTSL2 (I114V_V125I_N249G) | 6% | 9% | |
| Round1-Var70 | UGTSL2 (V125I_K289P_N325A) | 0% | 1% | |
| Round1-Var71 | UGTSL2 (N249G_N325A_I352V) | 43% | 76% | 11.5% |
| Round1-Var72 | UGTSL2 (V270I_A285V_M354L) | 196% | 158% | 11.5% |
| Round1-Var73 | UGTSL2 (Q65P_V254L_M367V) | 0% | 0% | |
| Round1-Var74 | UGTSL2 (V270I_K289P_S334T) | 0% | 0% | |
| Round1-Var75 | UGTSL2 (T199S_A205P_L393V) | 0% | 0% | |

-continued

| Clone | Mutations* | Normalized initial rate (0-4 h) | Reb M2 content at 100% UDP-Glc conversion | Reb D2 content at 50% UDP-Glc conversion |
|-------|-----------|-------------------------------|-------------------------------------------|------------------------------------------|
| Round1-Var76 | UGTSL2 (V125I_I345L_M367V_T392A) | 8% | 19% | |
| Round1-Var77 | UGTSL2 (A205P_I323V_T392A) | 0% | 0% | |
| Round1-Var78 | UGTSL2 (F21L_L37F_I131V) | 0% | 0% | |
| Round1-Var79 | UGTSL2 (F272L_I282L_A341V_I351L) | 0% | 2% | |
| Round1-Var80 | UGTSL2 (N278G_I352V_I389L) | 95% | 113% | 11.5% |
| Round1-Var81 | UGTSL2 (I114V_G331A_A341V_L405V) | 8% | 20% | |
| Round1-Var82 | UGTSL2 (Q27R_Q65P_I351M) | 0% | 0% | |
| Round1-Var83 | UGTSL2 (R6H_T329V_M354L_L393V) | 77% | 100% | 10.5% |
| Round1-Var84 | UGTSL2 (S200F_G331A_L393V) | 0% | 0% | |
| Round1-Var85 | UGTSL2 (T199S_K289S_R312L_I351M) | 0% | 0% | |
| Round1-Var86 | UGTSL2 (Q65P_A205P_L405V) | 0% | 0% | |
| Round1-Var87 | UGTSL2 (V270L_I345L_K365V) | 0% | 0% | |
| Round1-Var88 | UGTSL2 (S200F_F253Y_S255C) | 0% | 0% | |
| Round1-Var89 | UGTSL2 (I114V_G371K_I389L) | 0% | 3% | |
| Round1-Var90 | UGTSL2 (L276A_I333L_S334T_L393V) | 75% | 94% | 11.5% |
| Round1-Var91 | UGTSL2 (I240L_S255C_P361G) | 5% | 13% | |
| Round1-Var92 | UGTSL2 (Q27R_T245R_L276A) | 51% | 81% | 12.0% |

*Mutations are noted as follows: reference gene-original amino acid-position-new amino acid: For example the mutation of an isoleucine at position 240 to a Leucine for UGTSL2 is noted as UGTSL2 (I240L)

Modeling of these results allowed to obtain a ranking of the effect of each mutation. The following mutations were determined as being beneficial for activity:

L276A, T392A, Q27R, N278G, T329V, A341V, I333L, G387E, H247P, M354L, A285V, V270I, N325S, I240L, F253Y, A285L, I352V.

The following mutations were determined as being beneficial for lower Rebaudioside M2 formation:

Q27R, N325S, G387E, I333L, H247P, T329I, R312L, T199S, E259G, S334T, I131V, A285L, I389L, L393V, V254L, N339S, I345L, T245R.

Example 46

Conversion of Rebaudioside A to Rebaudioside I Using UGT76G1

The reaction was conducted using UGT76G1-R1-F12 (also known as UGT76G1var94 (see EXAMPLE 26))

The total volume of the reaction was 40 mL with the following composition: 50 mM potassium phosphate buffer pH 7.5, 3 mM $MgCl_2$, 2.5 mM UDP-glucose, 0.5 mM Rebaudioside A and 4 mL of UGT76G1-R1-F12 lysate (2.5 U/mL). The reaction was run at 30° C. on an orbitary shaker at 135 rpm. For sampling 125 μL of the reaction mixture was quenched with 10 μL of 2N $H_2SO_4$ and 115 μL of methanol/water (7/3). The samples were immediately centrifuged and kept at 10° C. before analysis by by LC-MS. An Agilent 1200 series HPLC system, equipped with binary pump (G1312B), autosampler (G1367D), thermostated column compartment (G1316B), DAD detector (G1315C), connected with Agilent 6110A MSD, and interfaced with "LC/MSD Chemstation" software, was used.

Instrument Conditions

| Column | Phenomenex Kinetex 2.6u C18 100A, 4.6 mm × 150 mm, 2.6 μm |
|--------|----------------------------------------------------------|
| Column Temperature | 55° C. |
| Detection | DAD at 210 nm bw 360 nm |
| | MSD (Scan and SIM mode) |
| | Mode: ES-API, Negative Polarity |
| | Drying gas flow: 13.0 L/min |
| | Nebulizer pressure: 30 psig |
| | Drying gas temperature: 270° C. |

-continued

| Analysis duration | 20 min |
|-------------------|--------|
| Injected volume | 2 μL |
| Flow rate | 0.8 mL/min |

Mobile Phase Gradient Program

| Time (min) | A (%): Formic acid 0.1% | B (%): Acetonitrile |
|------------|-------------------------|---------------------|
| 0 | 76 | 24 |
| 8.5 | 76 | 24 |
| 10.0 | 71 | 29 |
| 16.5 | 70 | 30 |

Figure 67A:
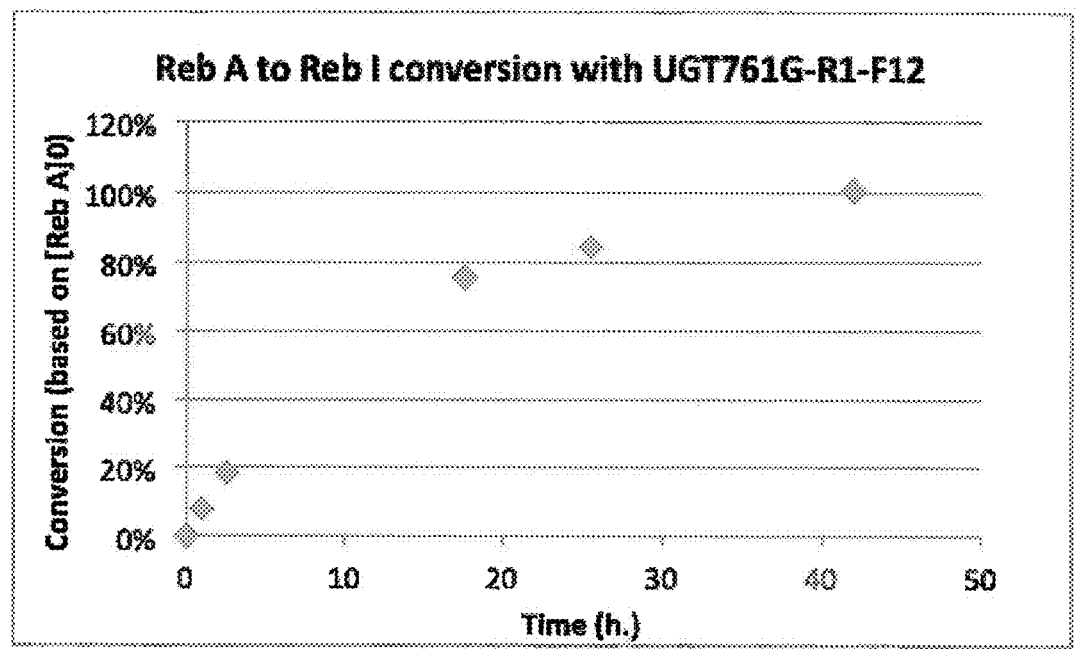
FIGS. 67A-67B show a graph showing the reaction profile for Example 46.

The reaction profile shown in FIG. 67a was obtained:

After 42 h. of reaction, 20 mL of the reaction mixture was quenched with 20 mL of ethanol and used for structure elucidation.

Figure 67B:
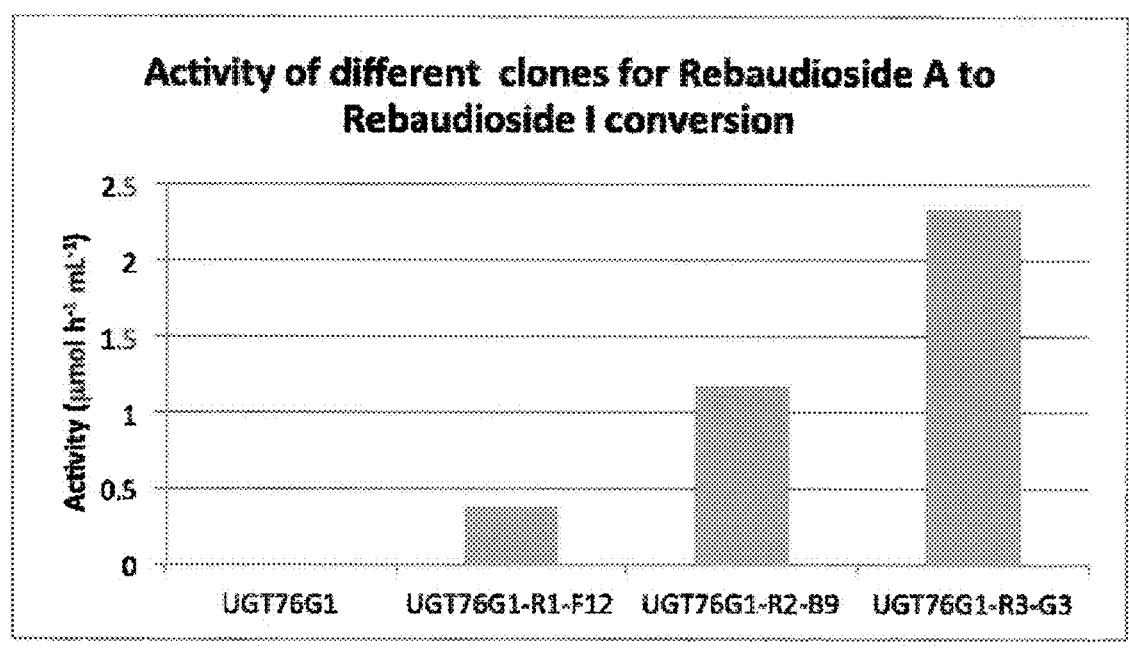
Figure 68A:
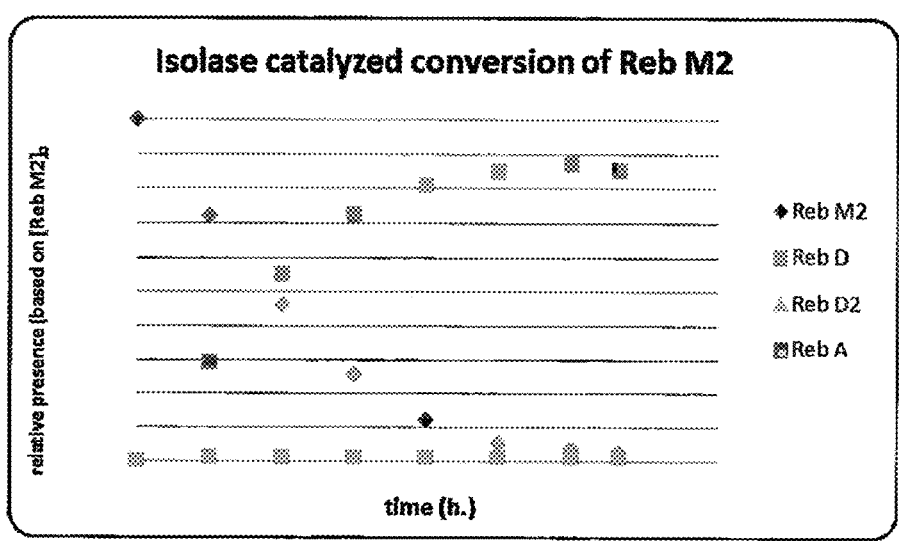
FIGS. 68A-68F show reaction profiles for Example 49.
Figure 68B:
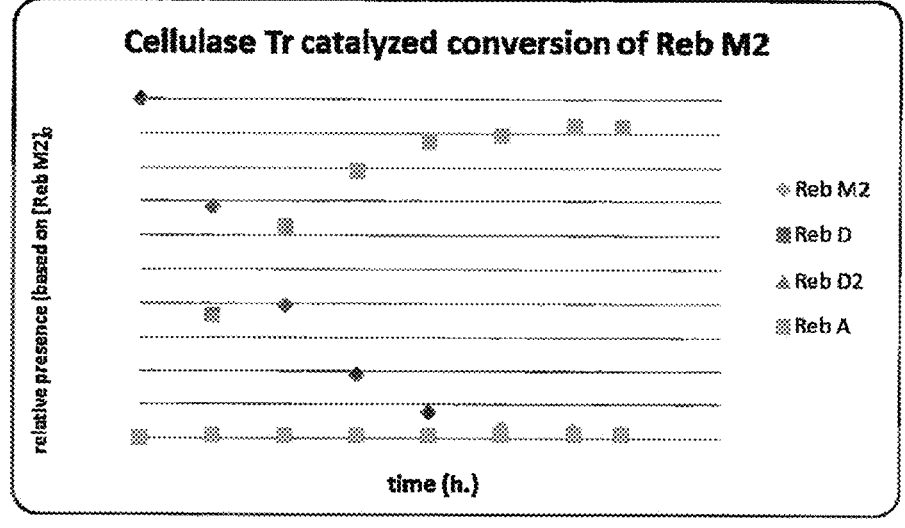
Figure 68C:
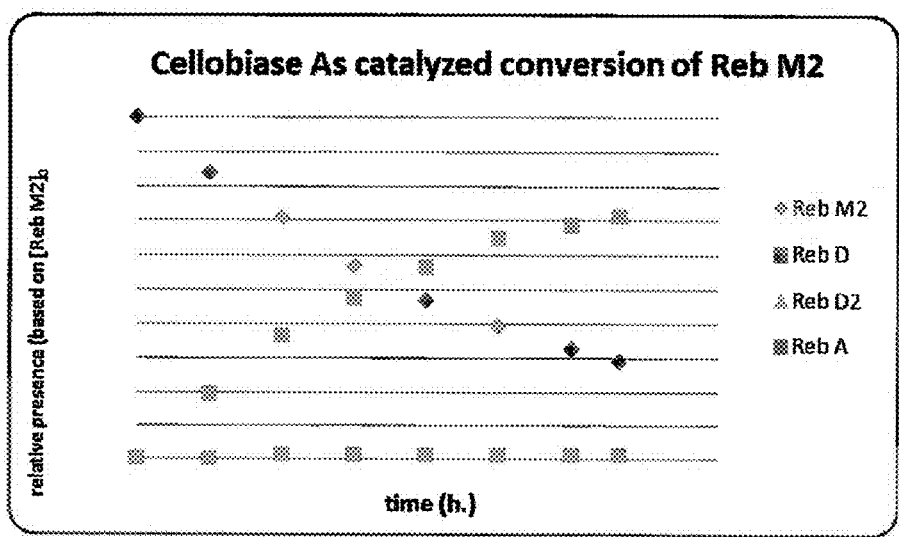
Figure 68D:
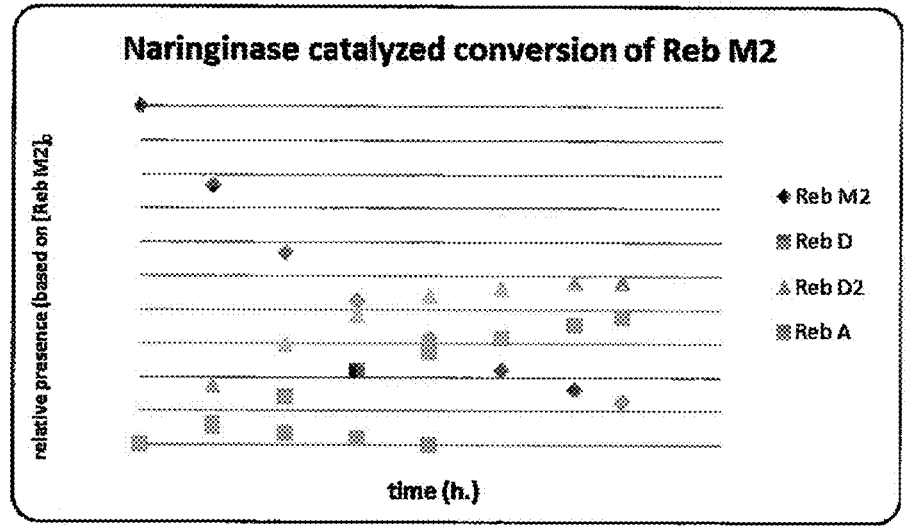
Figure 68E:
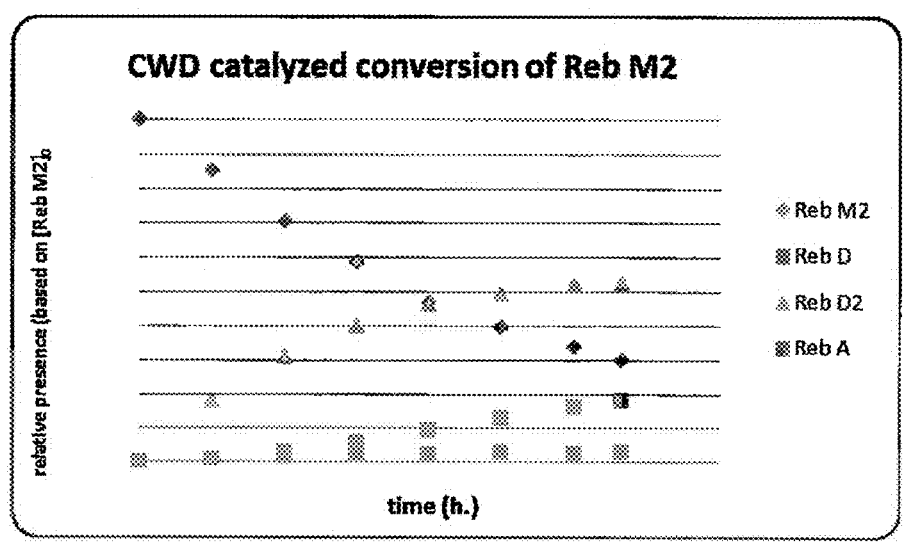
Figure 68F:
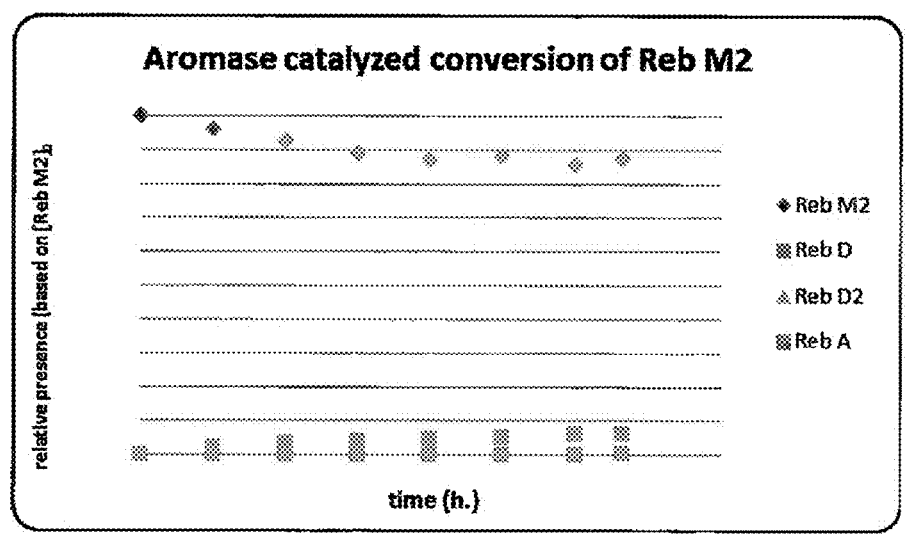

In similar manner the best clones of UGT76G1 directed evolution round 2 (UGT76G1-R2-B9 identified above as "Round2-Var66", see EXAMPLE 41) and round 3 (UGT76G1-R3-G3 identified above as "Round3-Var21", see EXAMPLE 44) and native UGT76G1 (see EXAMPLE 26) were tested for the conversion of Rebaudioside A to Rebaudioside I and the activities shown in FIG. 67b were determined.

Example 47

Isolation and Characterization of Reb I

Crude Reaction Sample. The sample, Lot Crude CB-2977-198, used for isolation, was prepared according to Example 46 with UGT76G1.

HPLC Analysis. Preliminary HPLC analyses of samples were performed using a Waters 2695 Alliance System with the following method: Phenomenex Synergi Hydro-RP, 4.6× 250 mm, 4 μm (p/n 00G-4375-E0); Column Temp: 55° C.; Mobile Phase A: 0.0284% $NH_4OAc$ and 0.0116% HOAc in water; Mobile Phase B: Acetonitrile (MeCN); Flow Rate: 1.0 mL/min; Injection volume: 10 μL. Detection was by UV (210 nm) and CAD Gradient:

| Time (min) | % A | % B |
|---|---|---|
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31-37 | 30 | 70 |
| 38 | 75 | 25 |

Isolation by HPLC. The purification was performed using a Waters Atlantis dC18 (30×100 mm, 5 μm, p/n 186001375) column with isocratic mobile phase conditions of 80:20 water/MeCN. Flow rate was maintained at 45 mL/min and injection load was 180 mg. Detector wavelength was set at 210 nm.

The analyses of fractions were performed using a Waters Atlantis dC18 (4.6×150 mm, 5 μm, p/n 186001342) column; Mobile Phase A: water; Mobile Phase B: MeCN; Flow Rate: 1 mL/min; Isocratic mobile phase conditions: 75:25 A/B for 30 min.

MS and MS/MS. MS and MS/MS data were generated with a Waters QT of Micro mass spectrometer equipped with an electrospray ionization source. The sample was analyzed by negative ESI. The sample was diluted to a concentration of 0.25 mg/mL with $H_2O$:MeCN (1:1) and introduced via flow injection for MS data acquisition. The sample was diluted further to 0.01 mg/mL to yield good s/n to tune for MS/MS and acquired by direct infusion. The collision energy was set to 60 V in order to acquire MS/MS data with increased fragment ion peaks due to the nature of the molecule NMR. The sample was prepared by dissolving ~1.0 mg in 180 μL of pyridine-$d_5$+TMS, and NMR data were acquired on a Bruker Avance 500 MHz instrument with either a 2.5 mm inverse probe or a 5 mm broad band probe. The 13C and HMBC NMR data were acquired at Rensselaer Polytechnic Institute using their Bruker Avance 600 MHz and 800 MHz instruments with 5 mm cryo-probe, respectively. The $^1$H and $^{13}$C NMR spectra were referenced to the TMS resonance ($\delta_H$ 0.00 ppm and $\delta_C$ 0.0 ppm).

Figure 28:
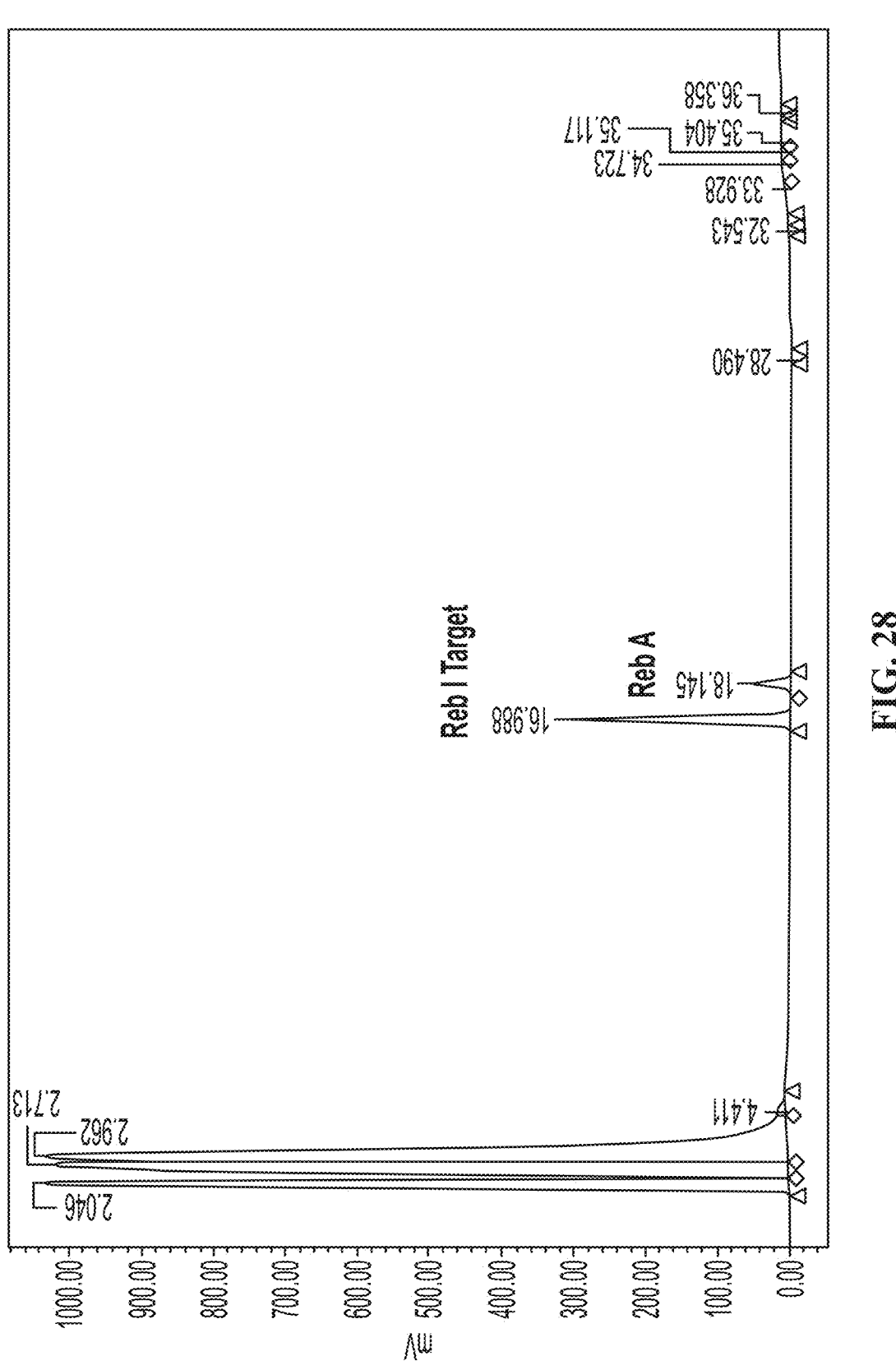
FIG. 28 shows an HPLC chromatogram for the analysis done in Example 47.

Isolation of Reb I was performed using a semi-synthetic steviol glycoside mixture, Lot number CB-2977-198. The material was analyzed by HPLC as described above. The Reb I peak was observed at a retention time ($t_R$) of approximately 17 min as shown in FIG. 28.

Results and Discussion

Figure 29:
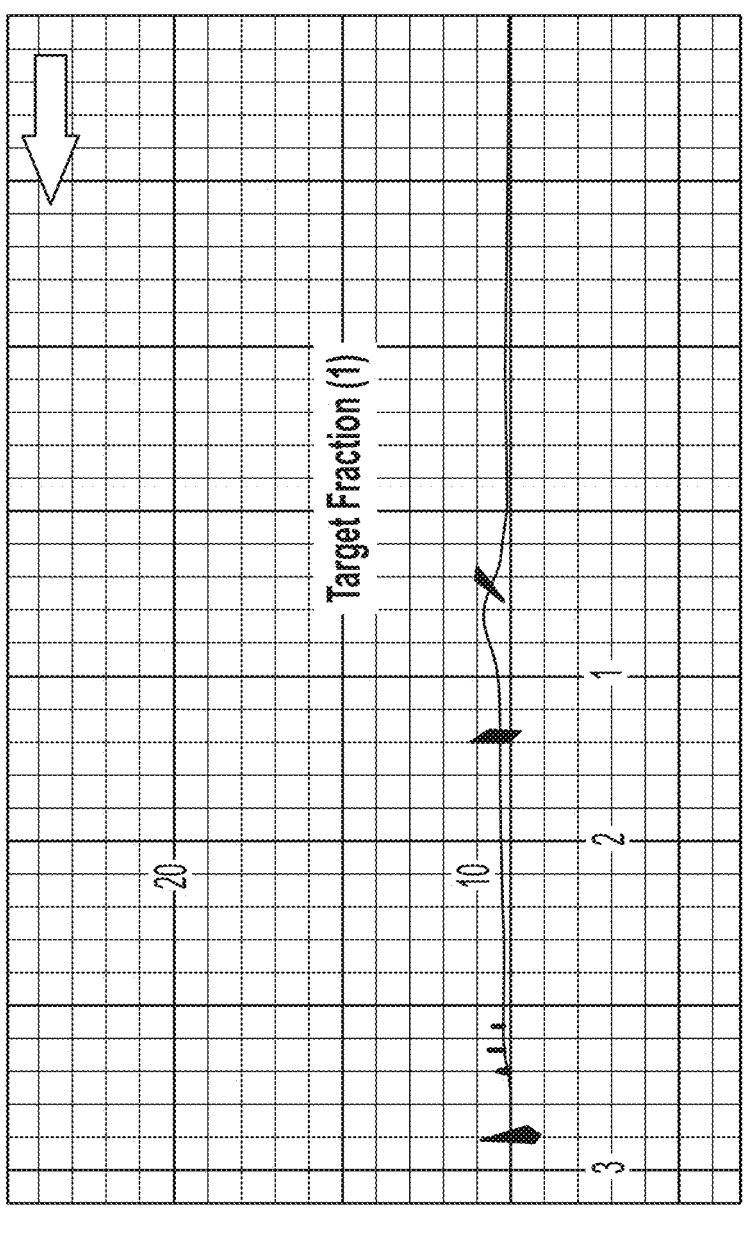
FIG. 29 shows an HPLC chromatogram for the analysis done in Example 47.
Figure 30:
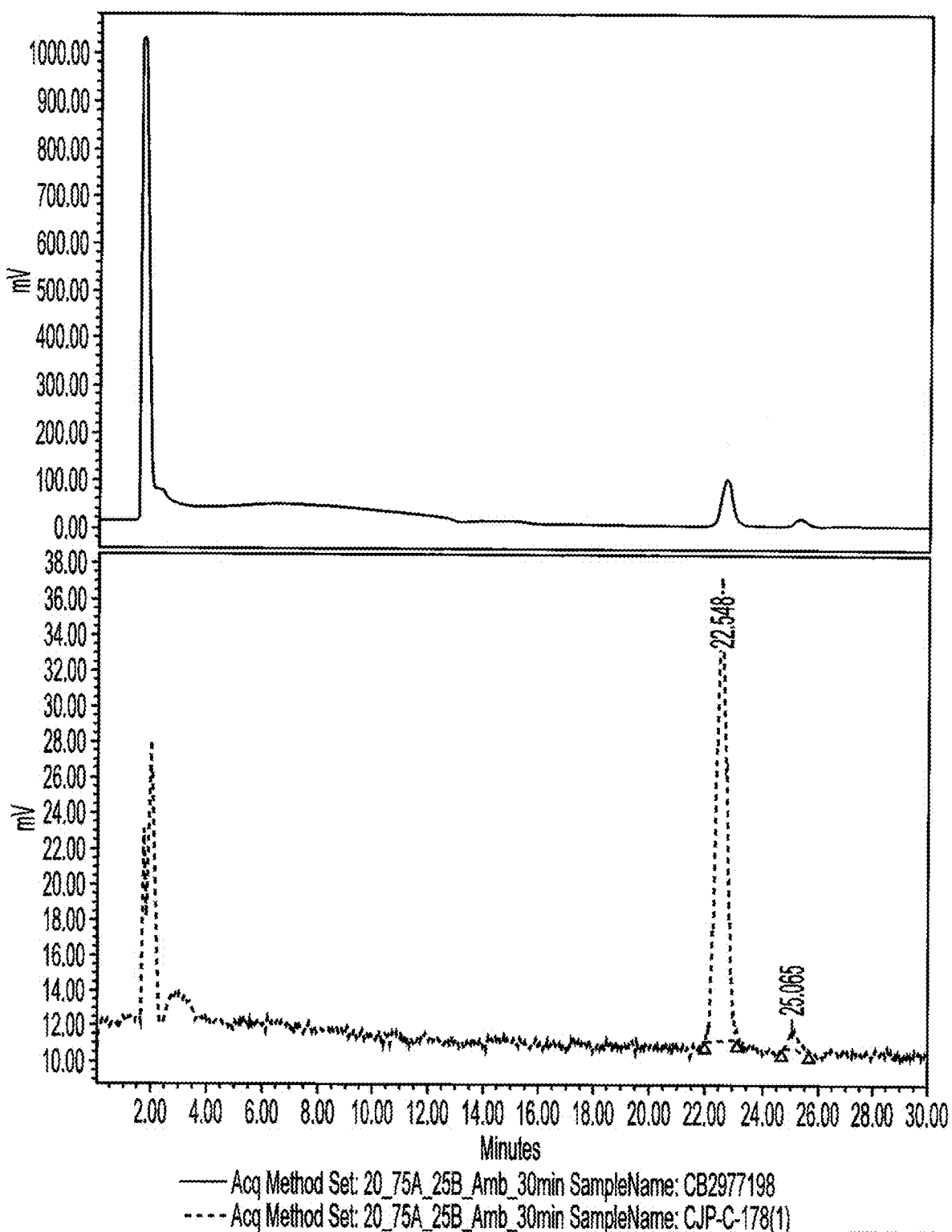
FIG. 30 shows an LC-CAD analysis done in Example 47.

The reb I peak was isolated from the reaction crude as described above and shown in FIG. 29. The isolated fraction was pooled and lyophilized. Purity of the final product was 91% as confirmed by LC-CAD using the method described above (FIG. 30). Approximately 1 mg of Reb I was provided for spectroscopic and spectrometric analyses.

Figure 31:
FIG. 31 shows an ESI-TOF mass spectrogram as described in Example 47.
Figure 32:
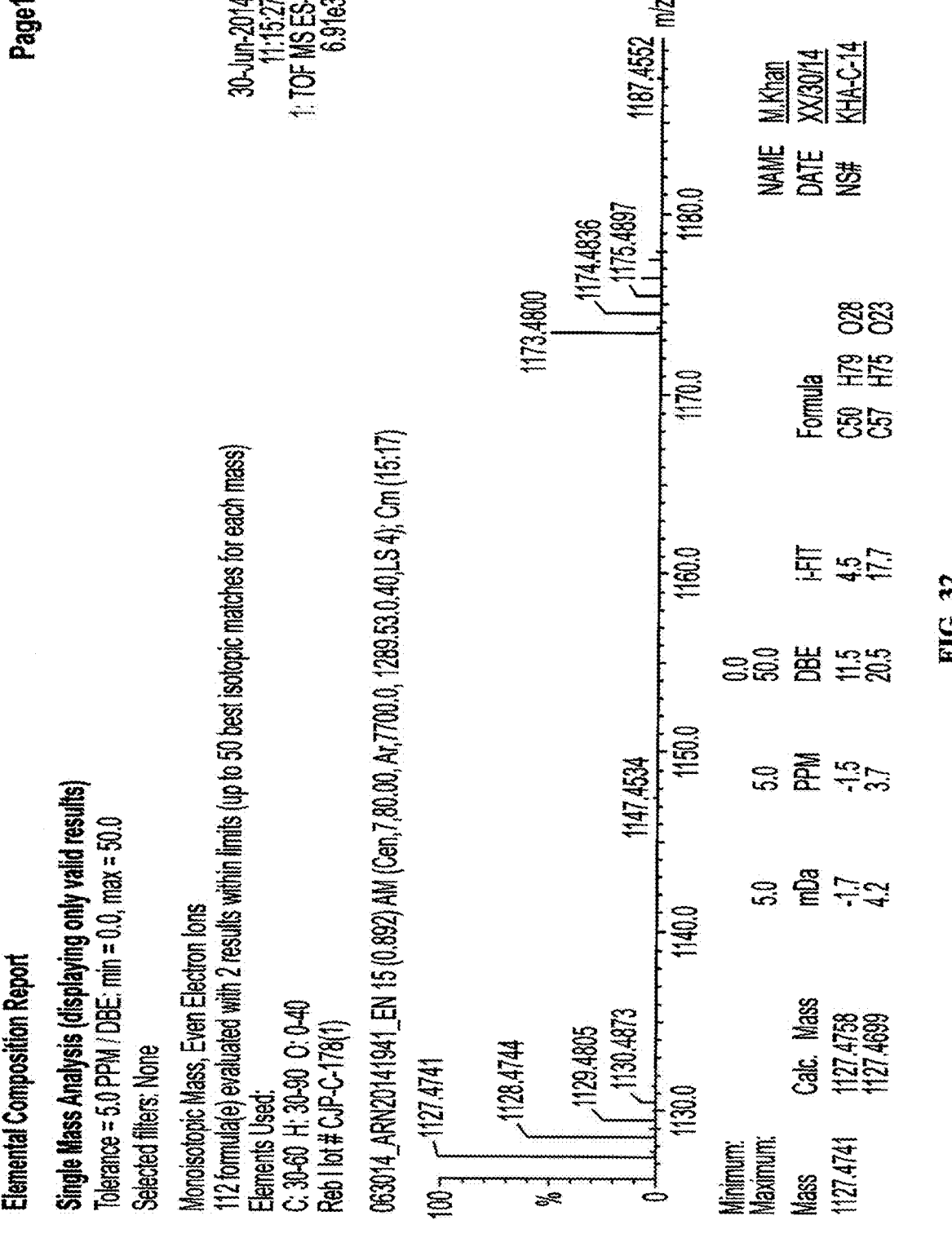
FIG. 32 shows a mass spectrogram as described in Example 47.

Mass Spectrometry. The ESI-TOF mass spectrum acquired by infusing a sample of reb I showed a [M-H]⁻ ion at m z 1127.4741 (FIG. 31). The mass of the [M-H]⁻ ion was in good agreement with the molecular formula $C_{50}H_{79}O_{28}$ (calcd for $C_{50}H_{79}O_{28}$: 1127.4758, error: −1.5 ppm) expected for reb I (FIG. 32). The MS data confirmed that reb I has a nominal mass of 1128 Daltons with the molecular formula, $C_{50}H_{80}O_{28}$.

Figure 33:
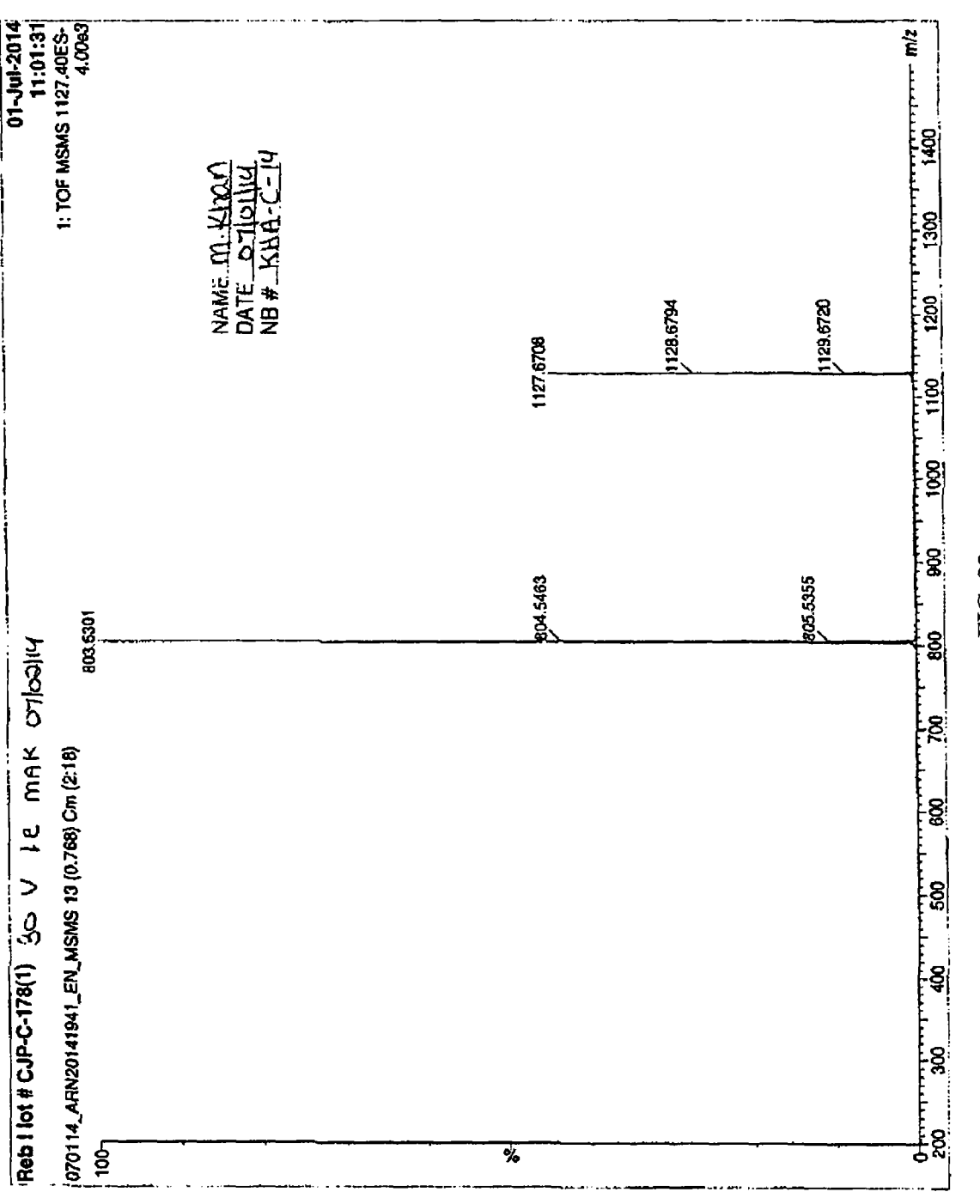
FIG. 33 shows an MS/MS spectrogram as described in Example 47.
Figure 34:
FIG. 34 shows an MS/MS spectrogram as described in Example 47.

The MS/MS spectrum of reb I, selecting the [M-H]⁻ ion at m z 1127.4 for fragmentation, indicated loss of two sugar units at m z 803.5301, however did not show additional fragmentation with collision energy of 30 V (FIG. 33). When higher collision energy was applied (60 V) (FIG. 34), the parent ion was not observed but sequential loss of three sugar units at m z 641.4488, 479.3897, and 317.3023 were observed from m z 803.5301

Figure 35A:
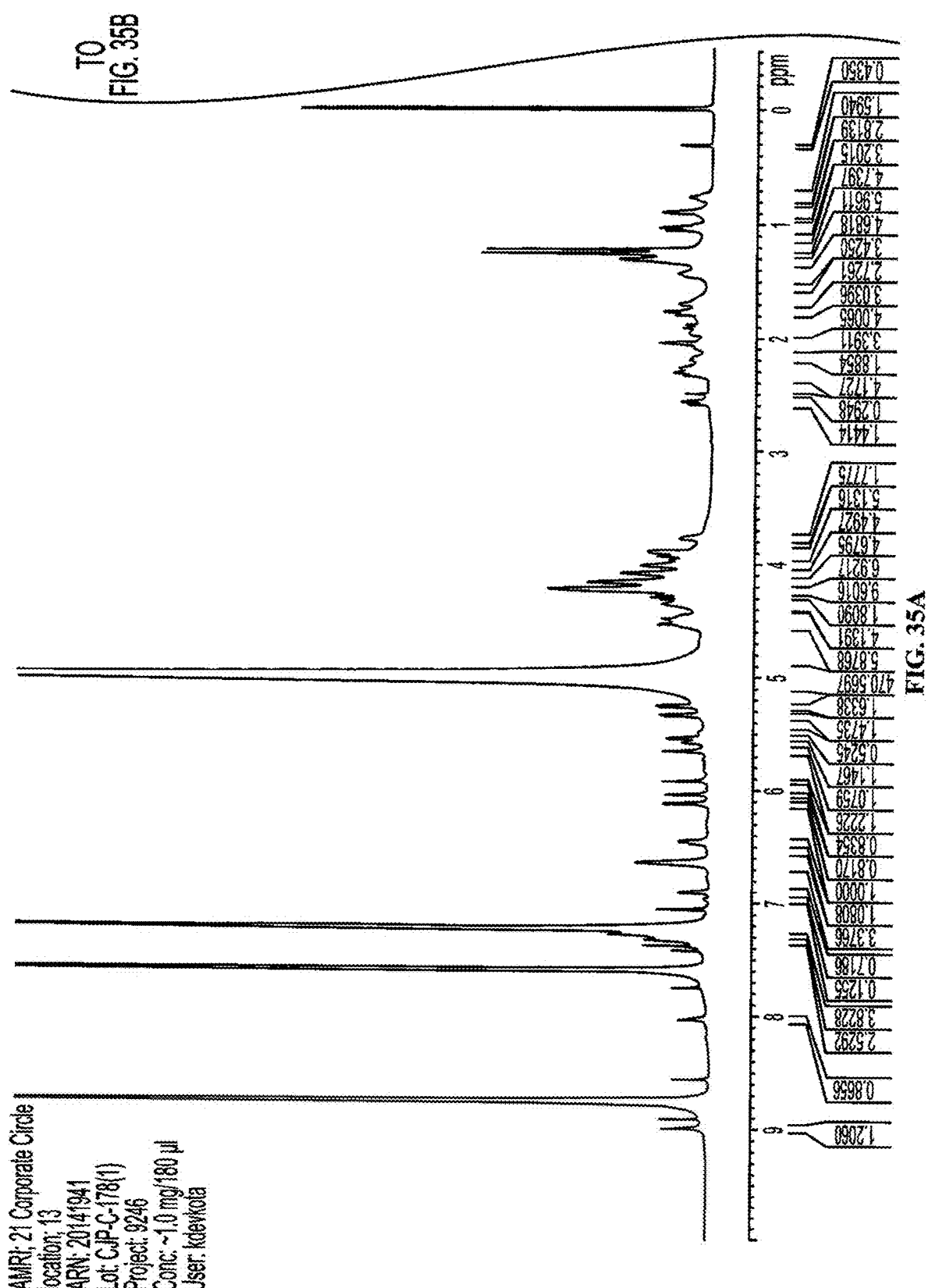
Figure 38A:
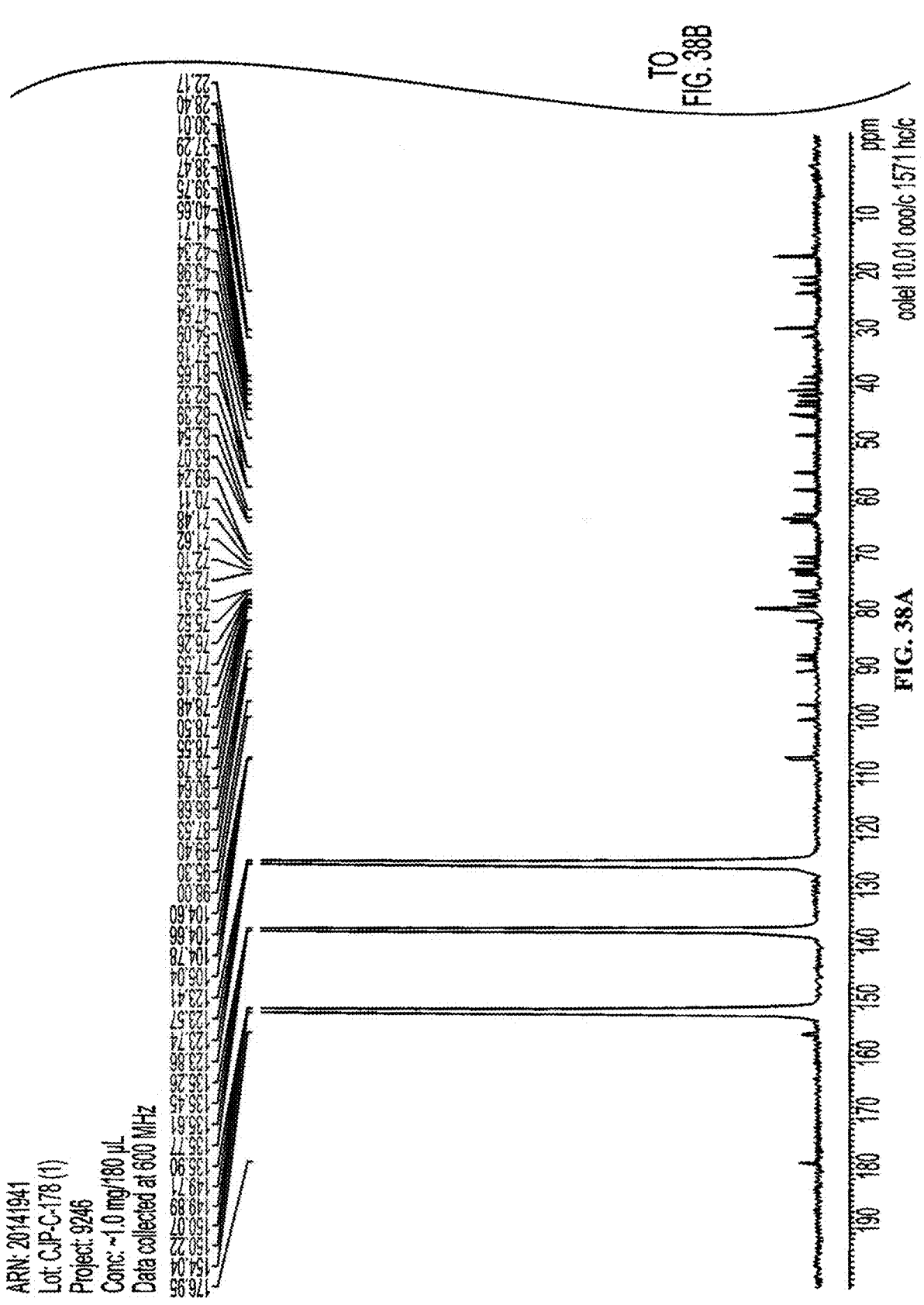
FIGS. 38A-38C show the results of $^{13}$C NMR as described in Example 47.
Figures 38A, 38B, 38C:
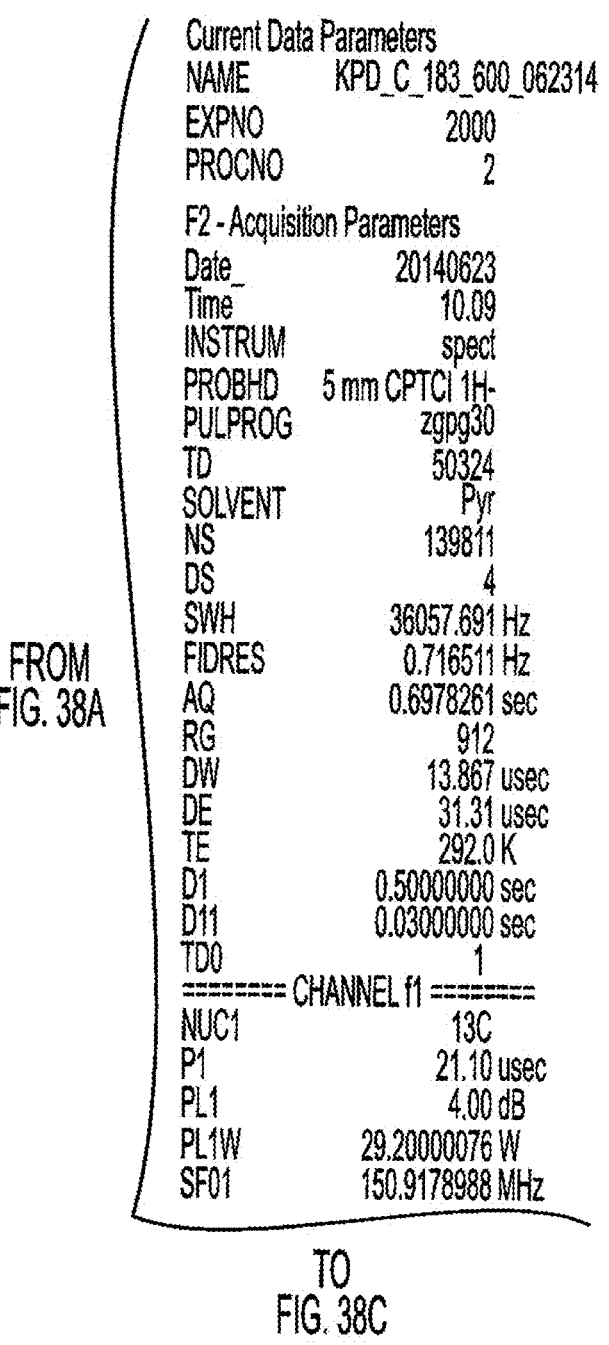
Figure 39A:
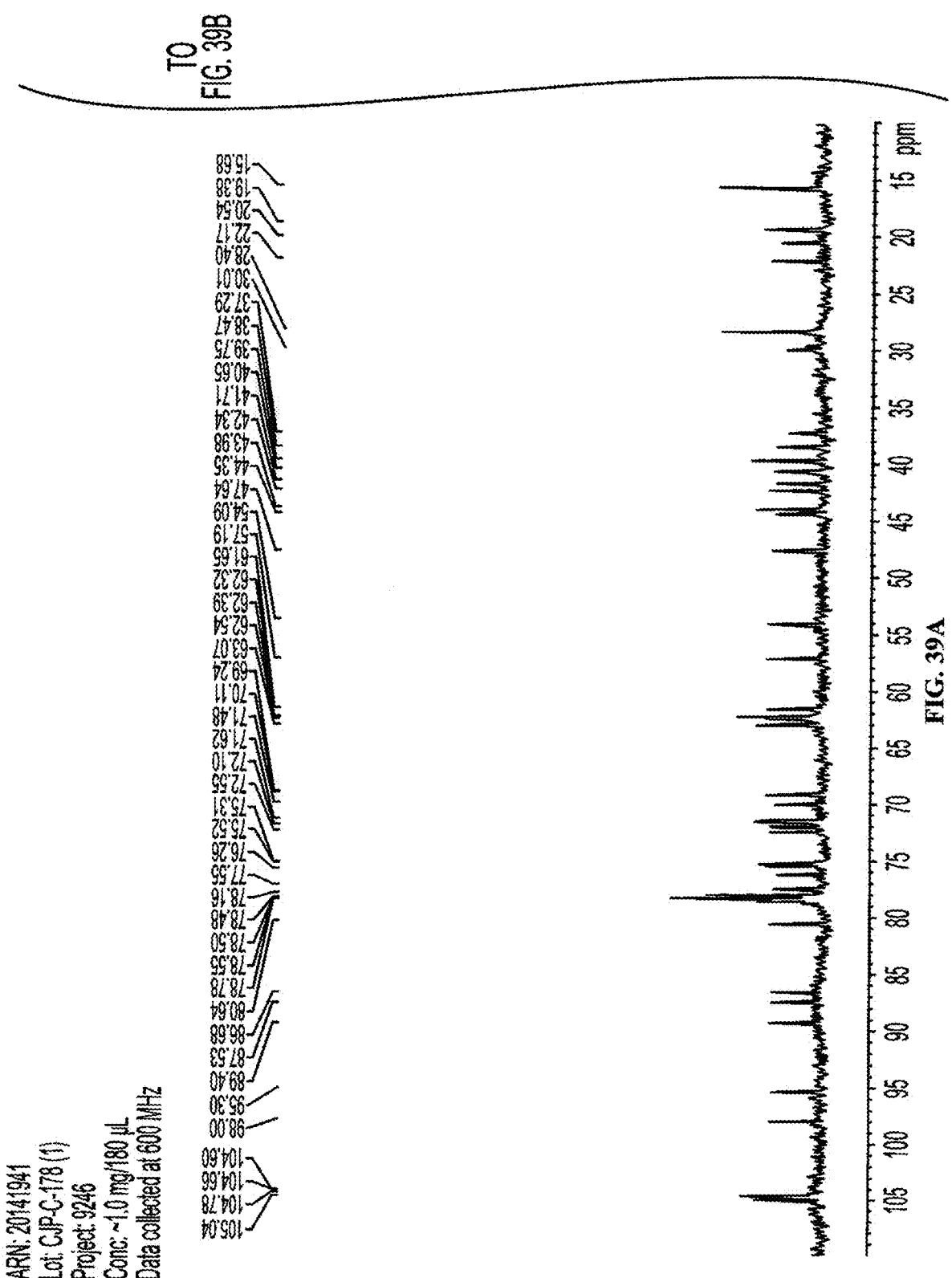
FIGS. 39A-39C show the results of $^{13}$C NMR as described in Example 47.
Figures 39A, 39B, 39C:
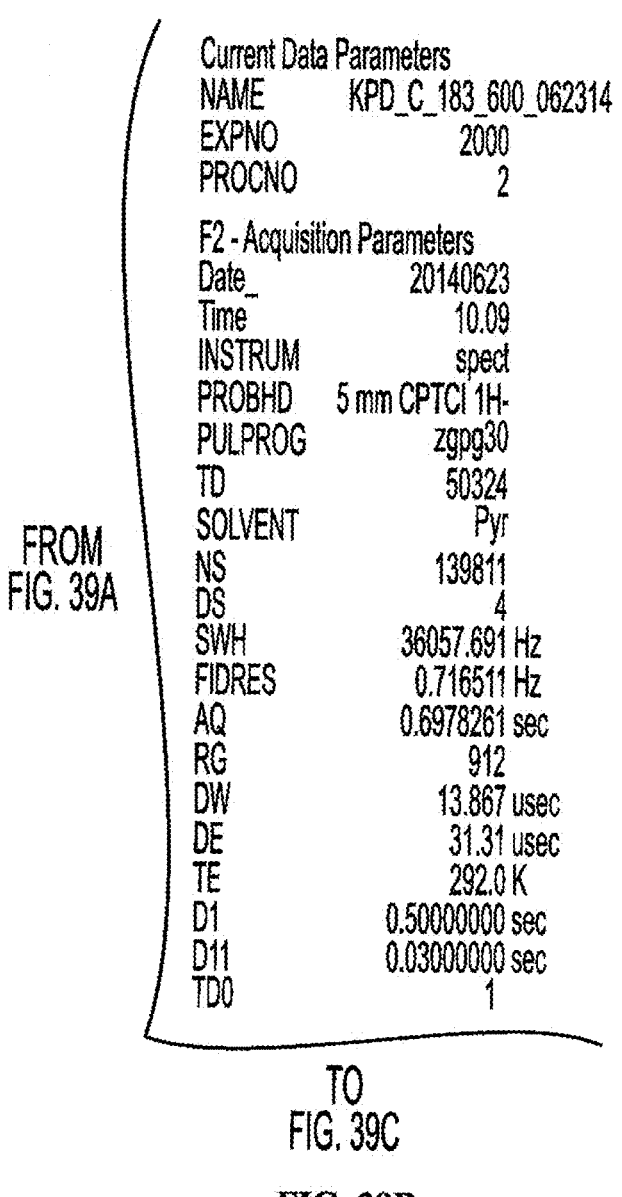
Figures 40A, 40B:
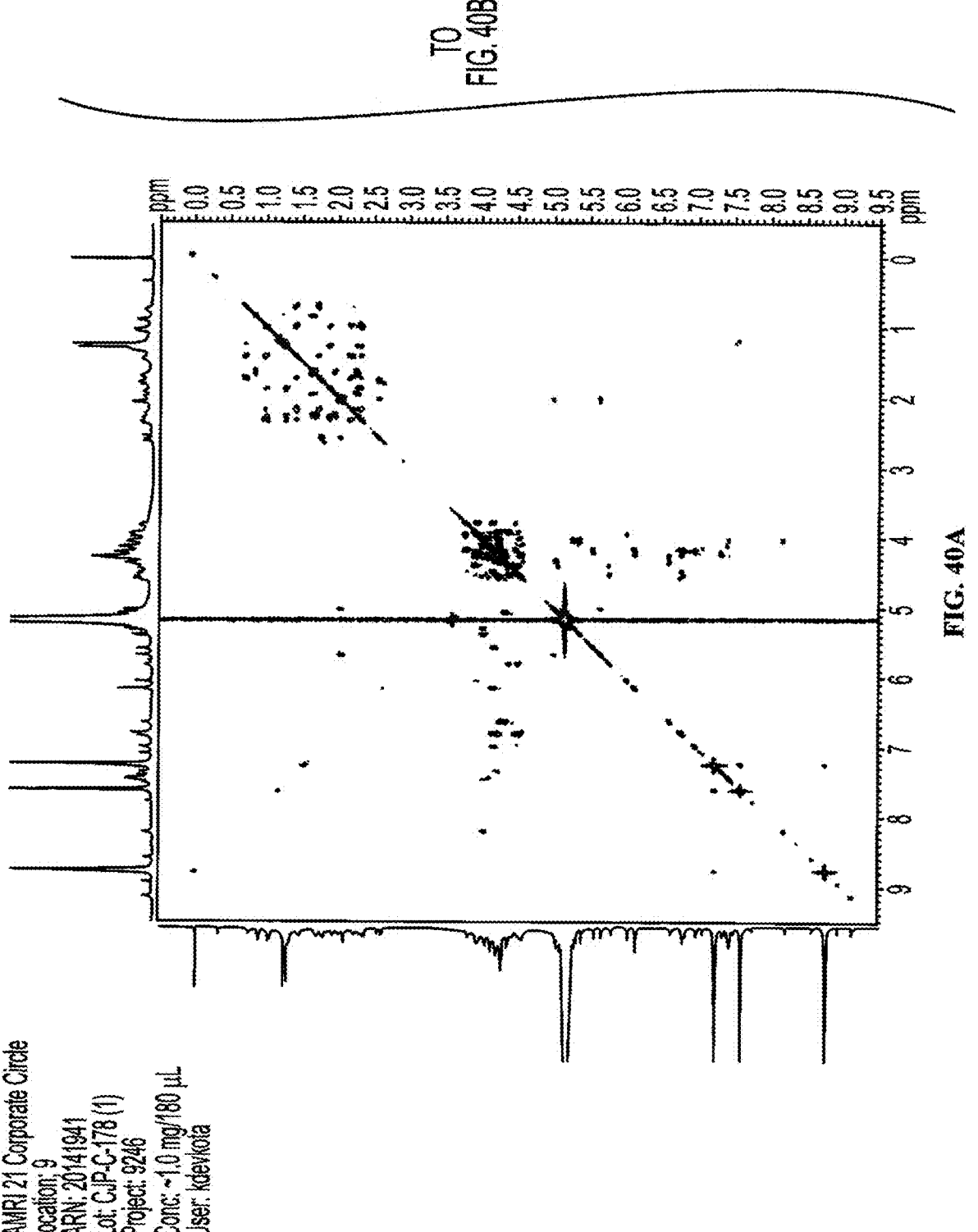
FIGS. 40A-40C show the results of $^1$H-$^1$H COSY as described in Example 47.
Figures 40A, 40B, 40C:
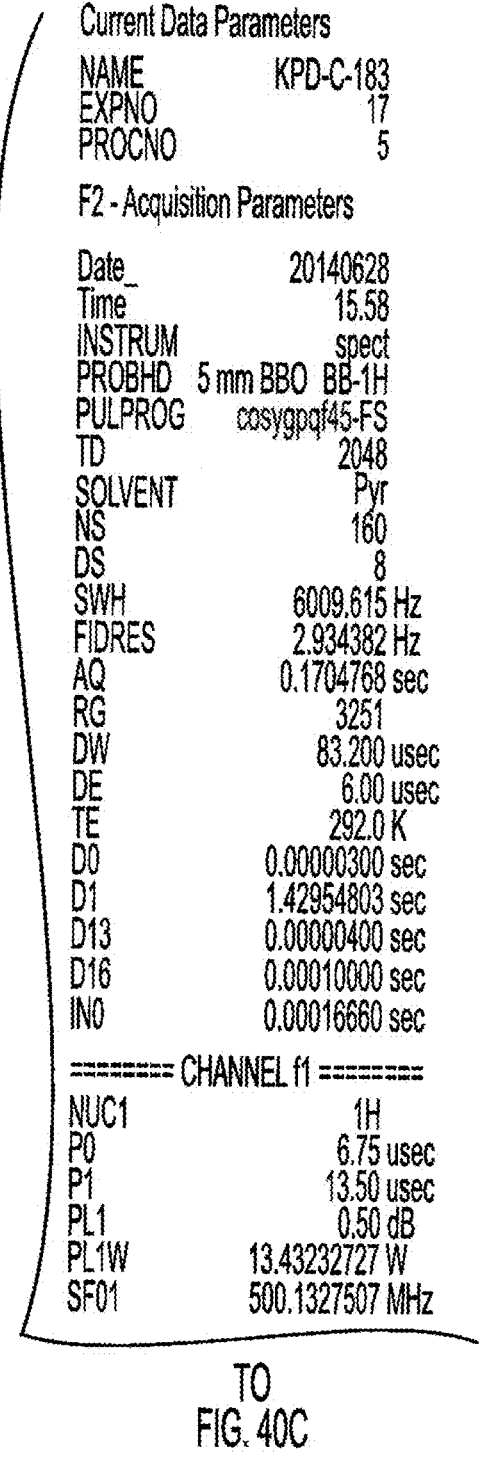
Figures 41A, 41B:
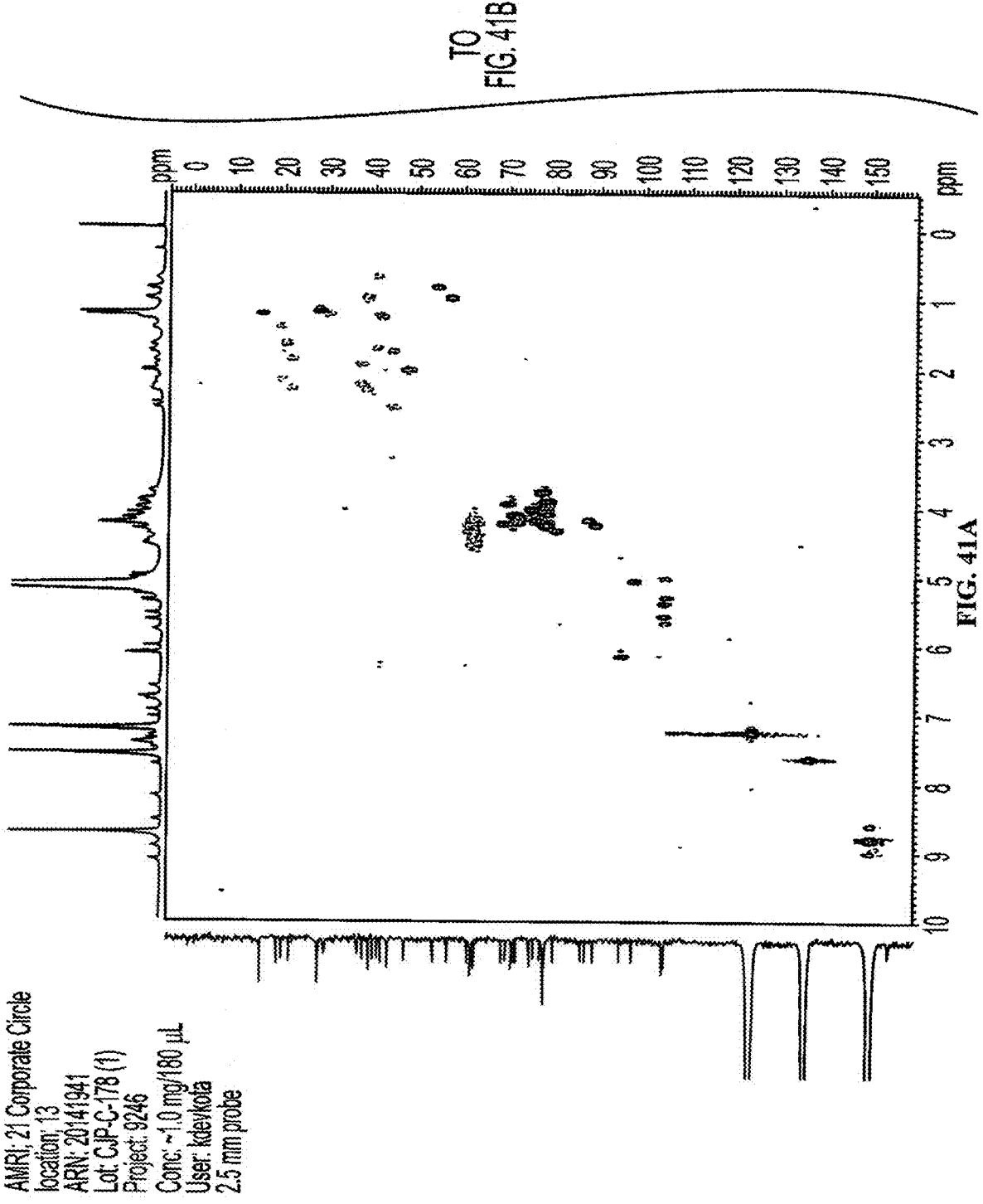
FIGS. 41A-41C show the results of HSQC-DEPT as described in Example 47.
Figures 41A, 41B, 41C:
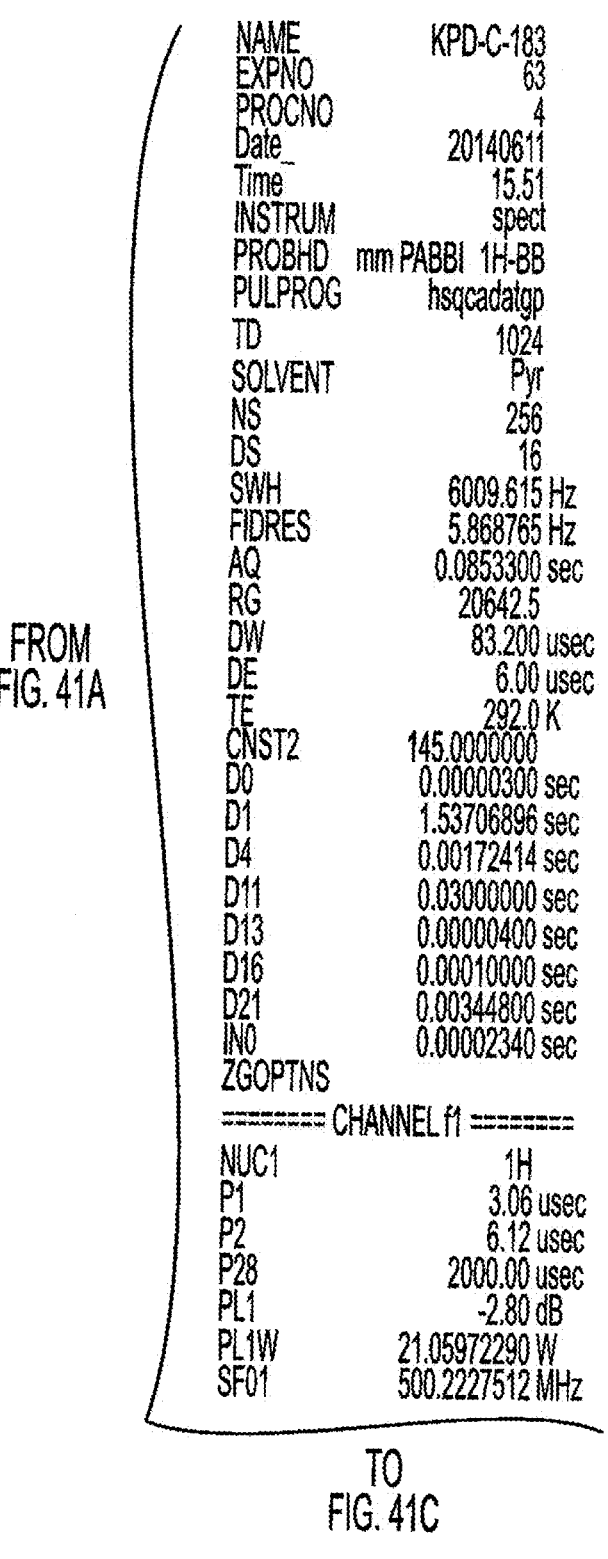
Figures 42A, 42B:
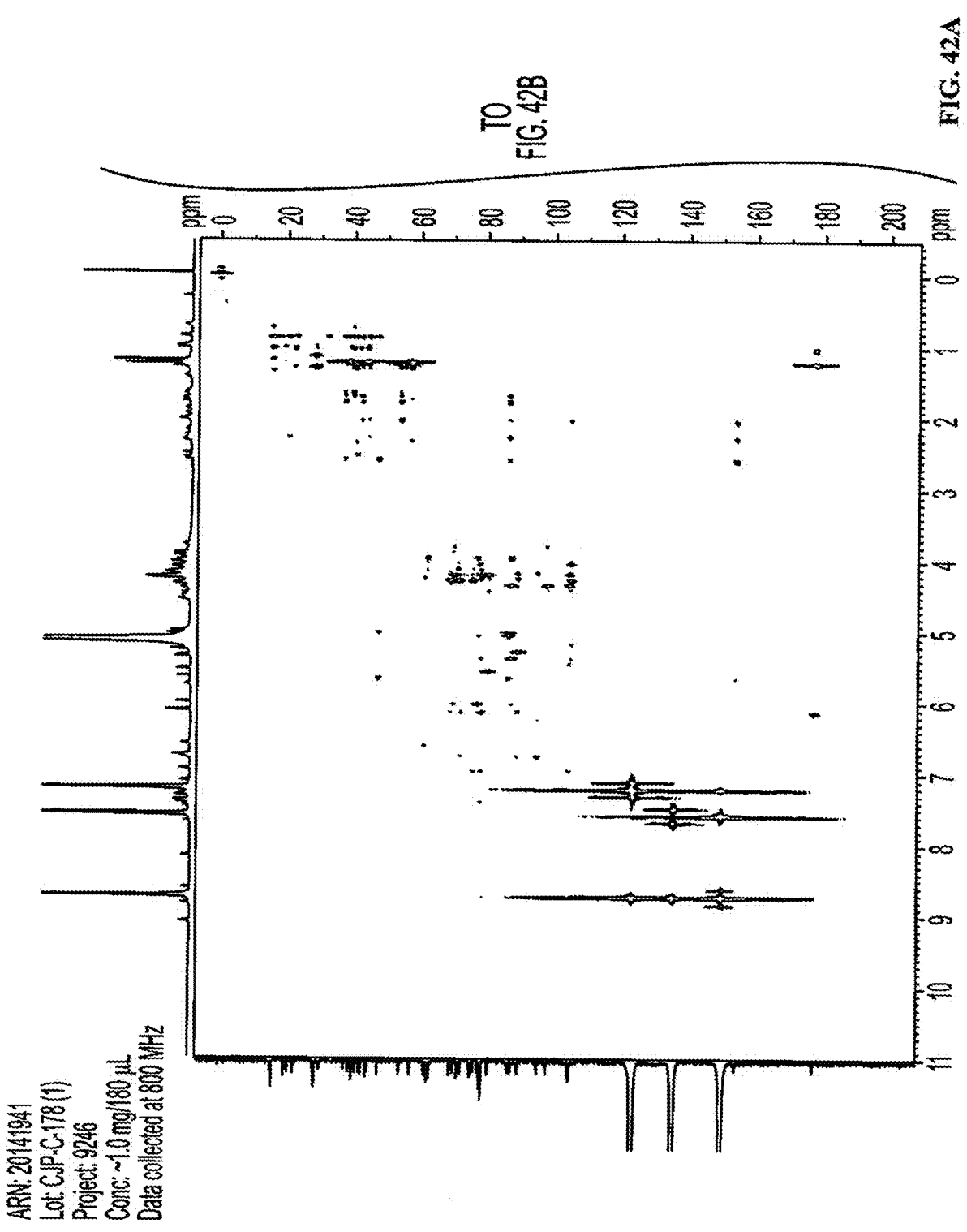
FIGS. 42A-42D show the results of HMBC as described in Example 47.
Figures 42A, 42C, 42D:
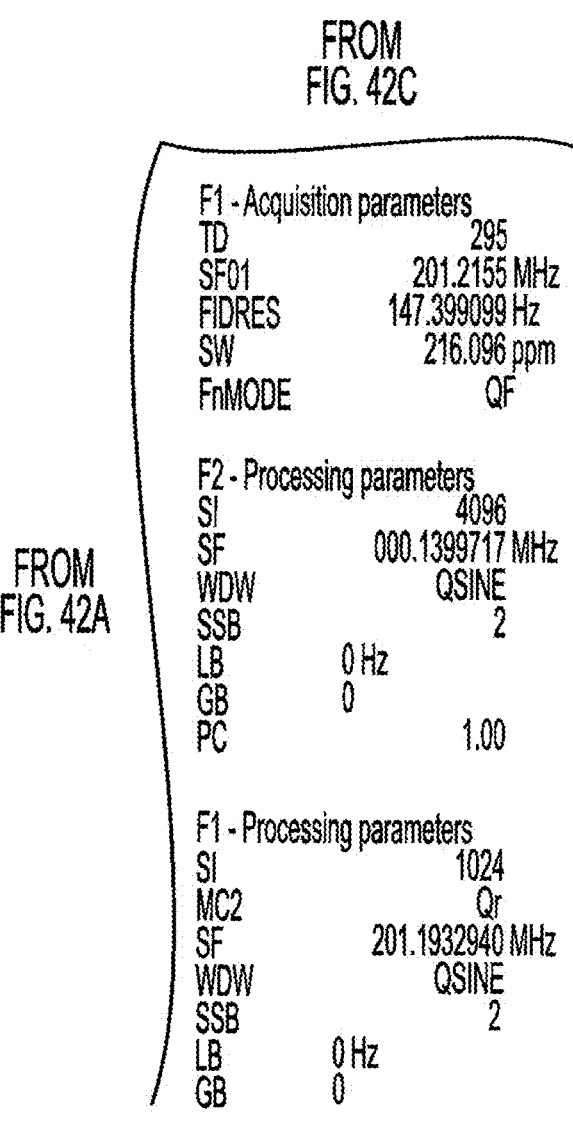
Figures 43A, 43B:
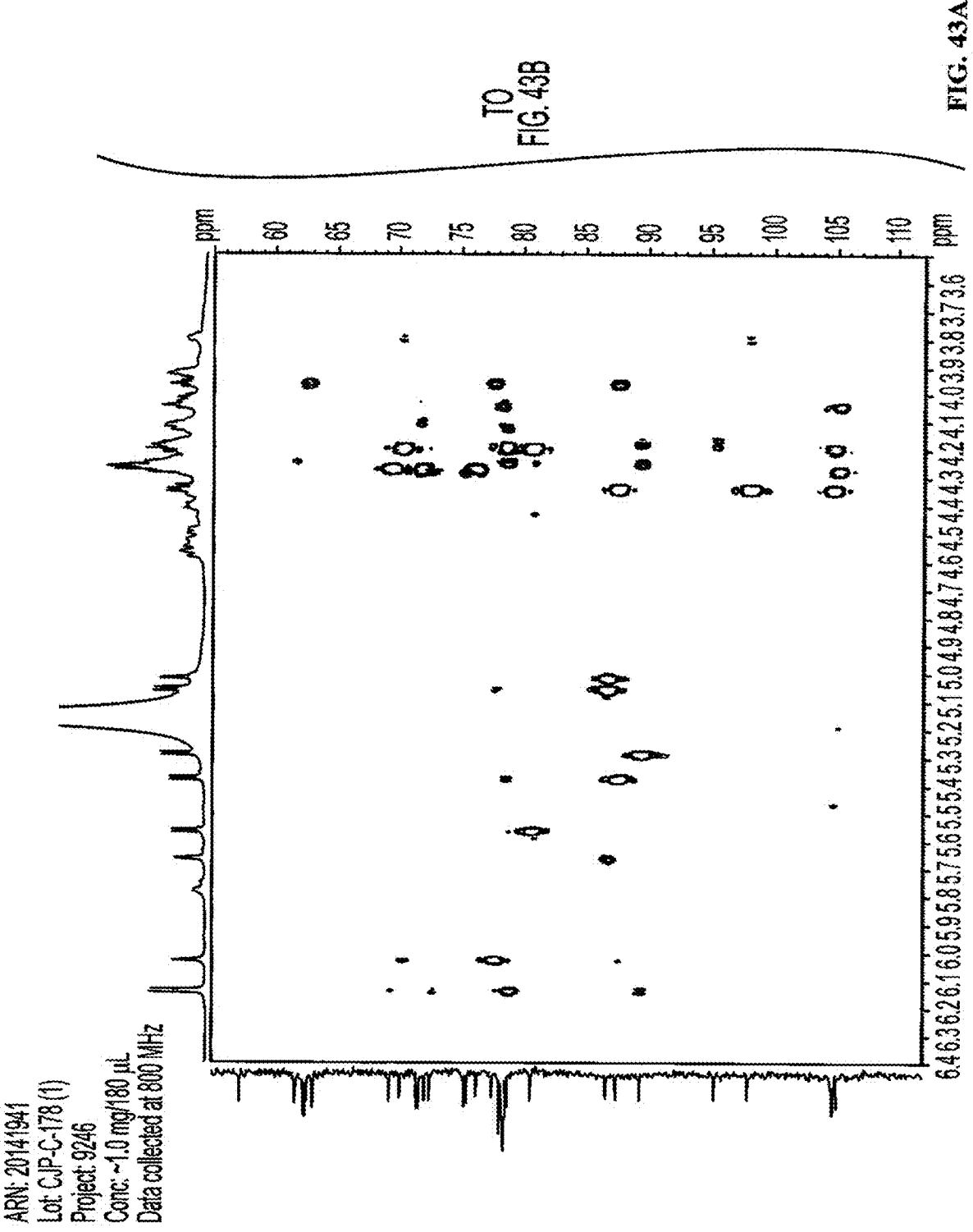
FIGS. 43A-43D show the results of HMBC as described in Example 47.
Figures 43A, 43C, 43D:
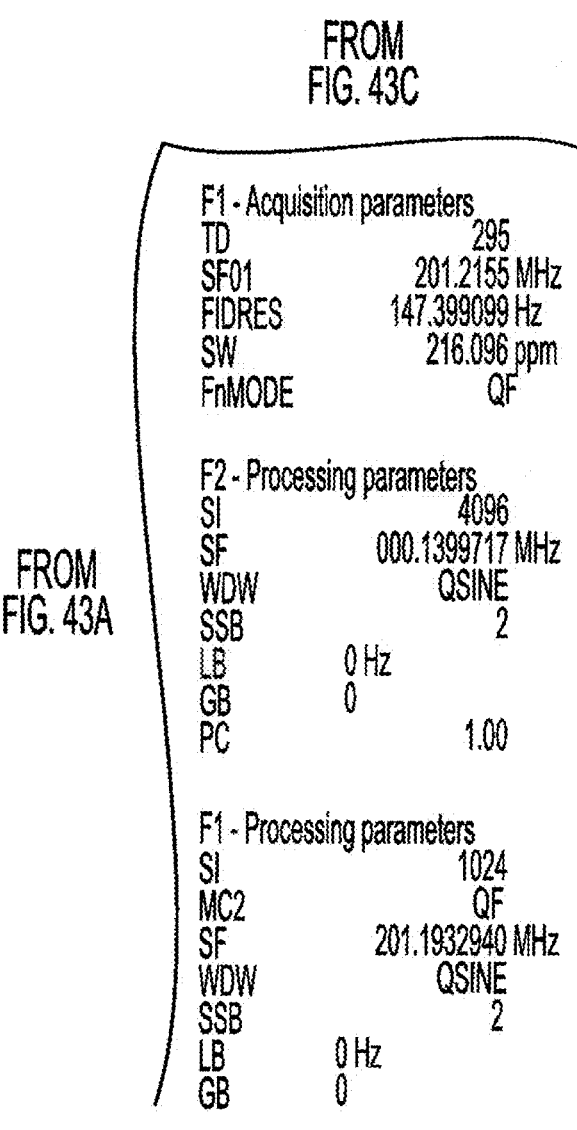
Figures 44A, 44B:
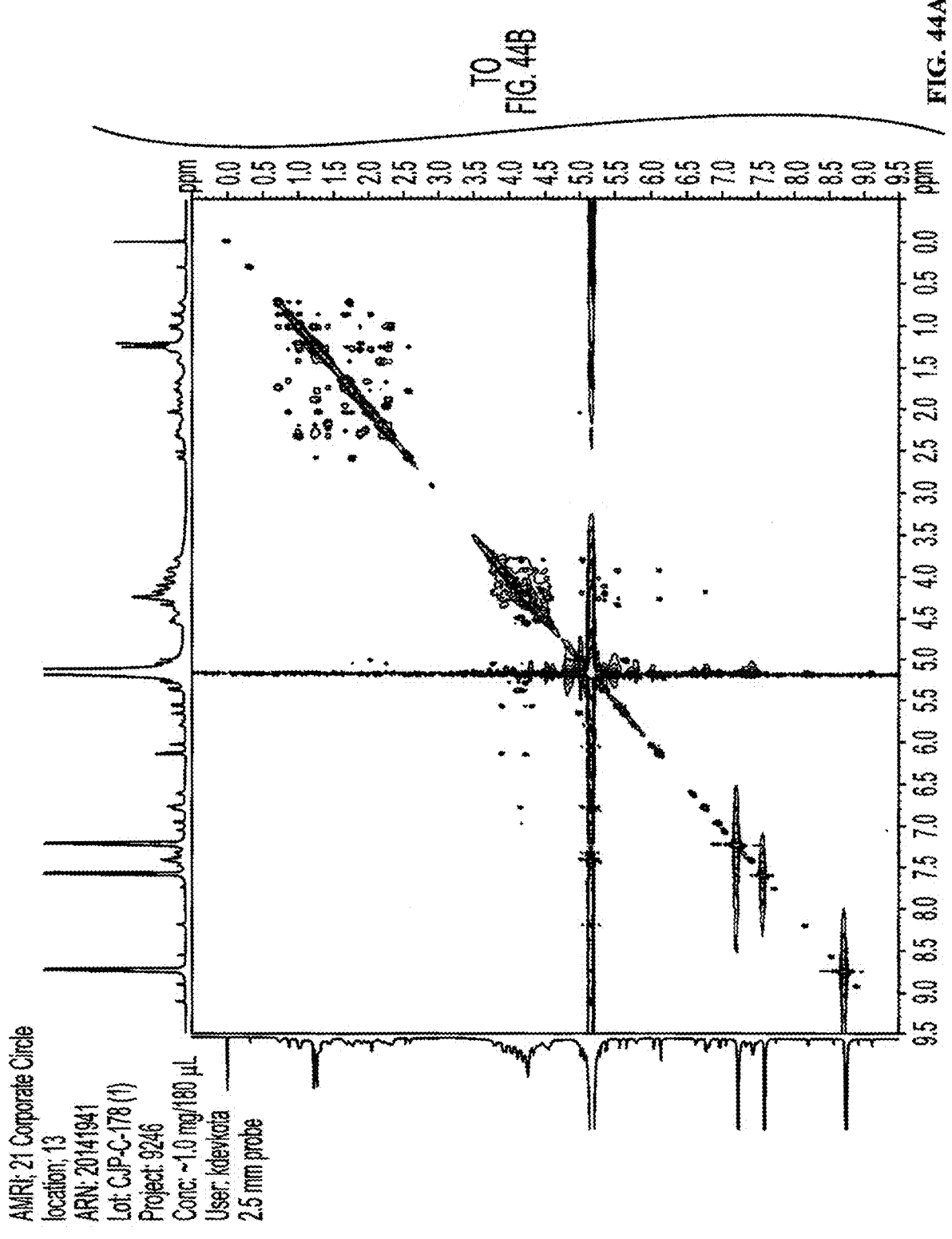
Figures 45A, 45B:
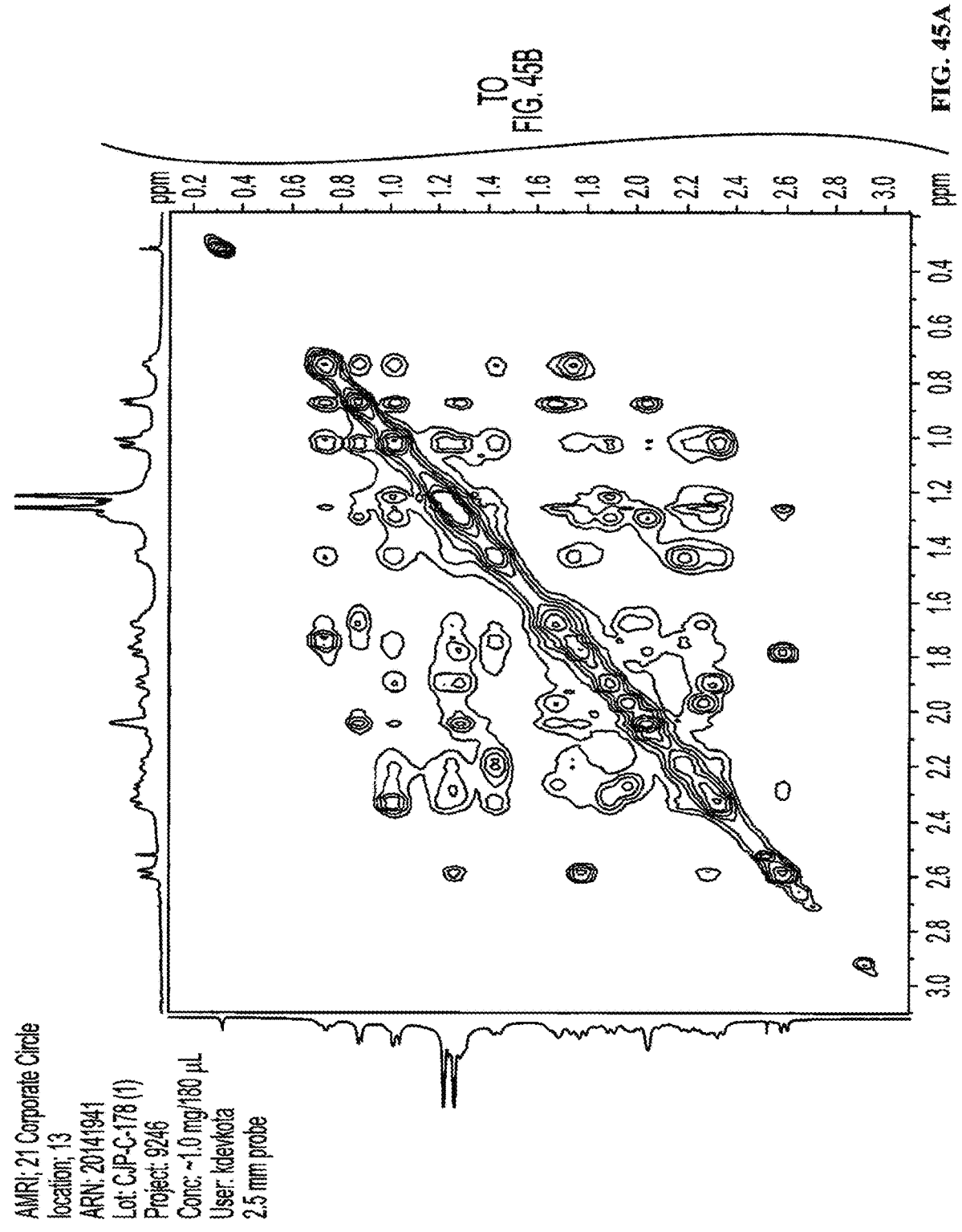

NMR Spectroscopy. A series of NMR experiments including $^1$H NMR (FIGS. 35-37), $^{13}$C NMR (FIGS. 38-39), $^1$H-$^1$H COSY (FIG. 40), HSQC-DEPT (FIG. 41), HMBC (FIGS. 42-43), NOESY (FIGS. 44-45), and 1D TOCSY (FIGS. 46-50) were performed to allow assignment of reb I.

Figures 36A, 36B:
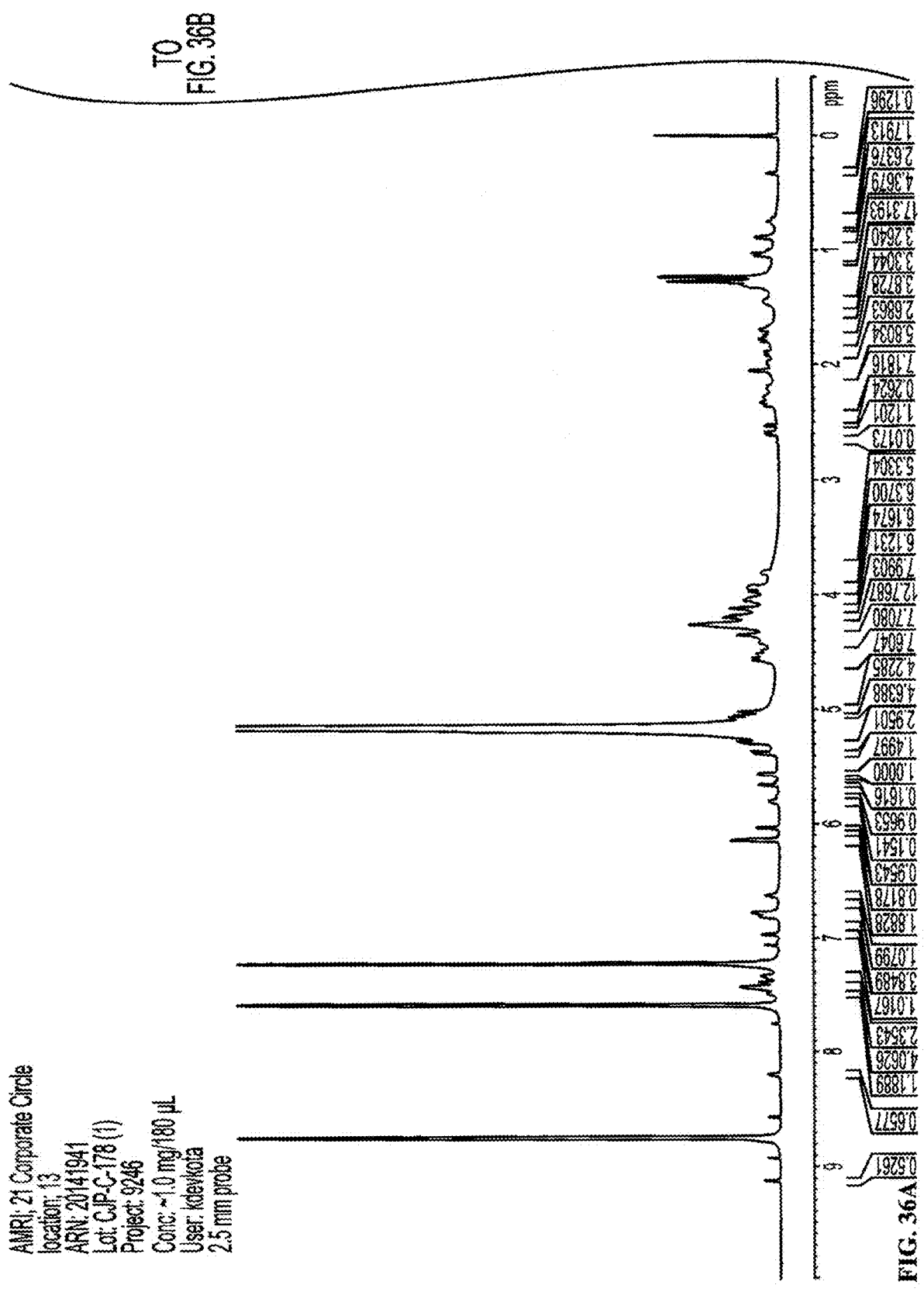
FIGS. 36A-36B show the results of $^1$H NMR as described in Example 47.
Figures 36A, 36B:
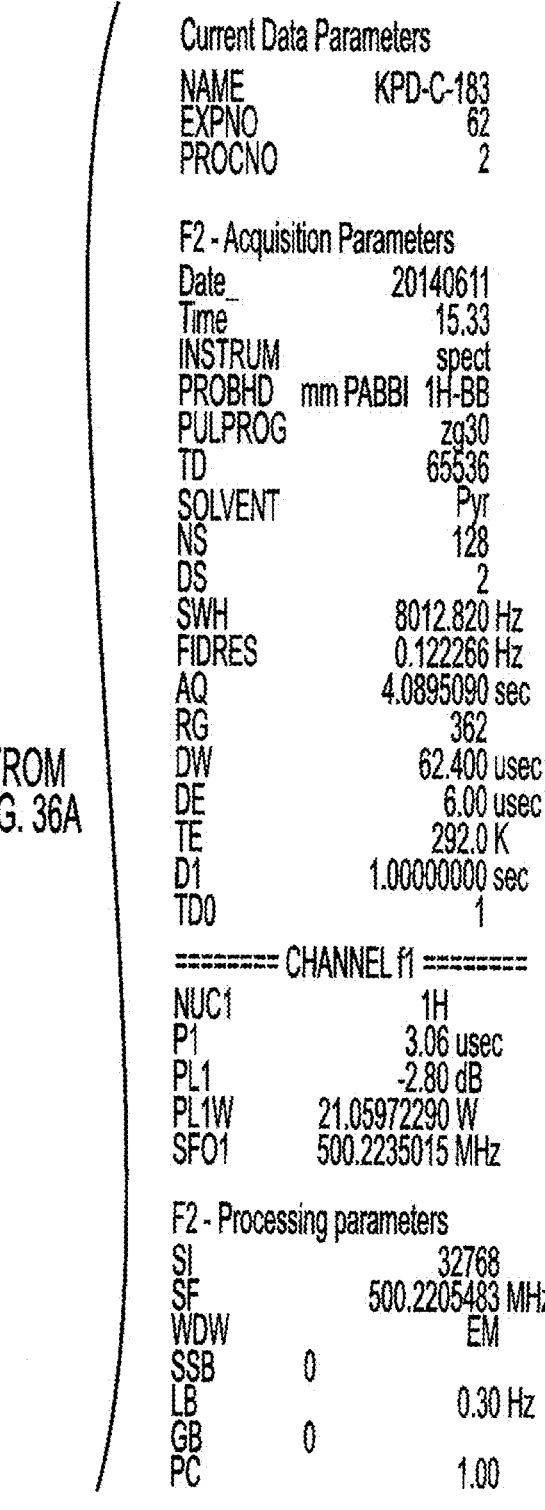
Figure 37A:
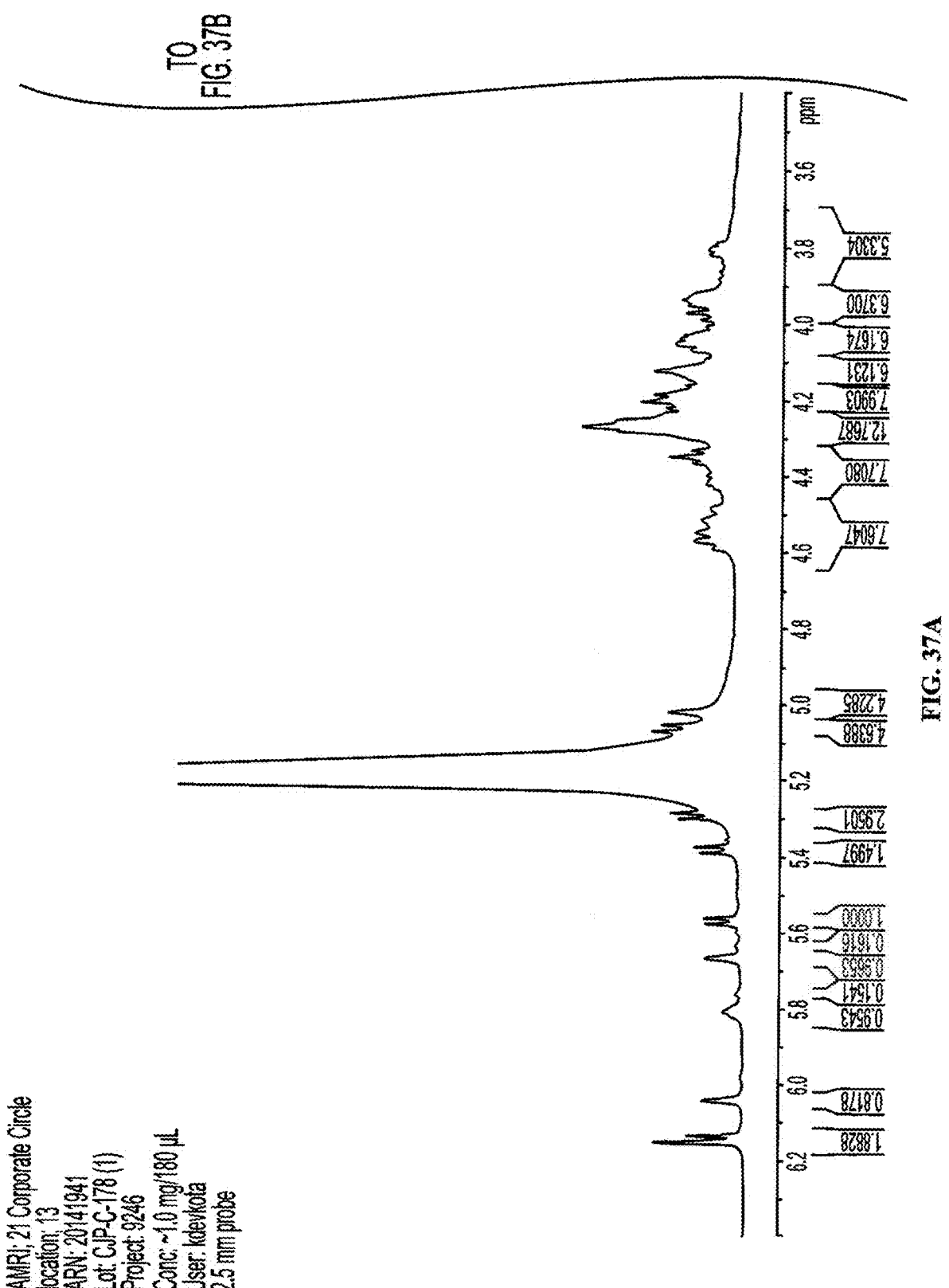
FIGS. 37A-37B show the results of $^1$H NMR as described in Example 47.
Figures 37A, 37B:
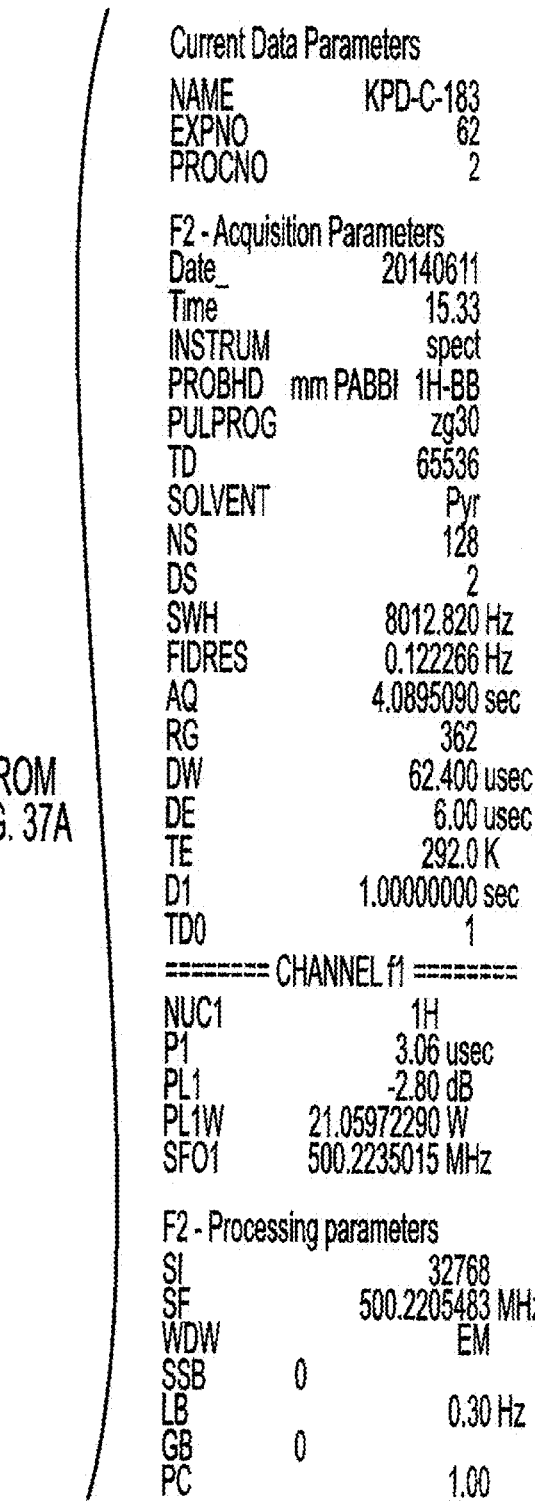

In the $^1$H NMR spectrum of reb I acquired at 300 K (FIG. 35), one of the anomeric protons was completely obscured by the water resonance. Therefore, $^1$H NMR spectrum of the sample was acquired at lower temperature (292 K), to shift out the water resonance, and at this temperature anomeric proton was sufficiently resolved (FIGS. 36-37). Thus, all other NMR data of reb I was acquired at 292 K.

The 1D and 2D NMR data indicated that the central core of the glycoside is a diterpene. An HMBC correlation from the methyl protons at $\delta_H$ 1.22 to the carbonyl at $\delta_C$ 176.9 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.5, 44.0, and 57.2 allowed assignment of C-3, C-4, and C-5. Analysis of the $^1$H-$^{13}$C HSQC-DEPT data indicated that the carbon at $\delta_C$ 38.5 was a methylene group and the carbon at $\delta_C$ 57.2 was a methine which were assigned as C-3 and C-5, respectively. This left the carbon at $\delta_C$ 44.0, which did not show a correlation in the HSQC-DEPT spectrum, to be assigned as the quaternary carbon, C-4. The $^1$H chemical shifts for C-3 ($\delta_H$ 1.02 and 2.35) and C-5 ($\delta_H$ 1.03) were assigned using the HSQC-DEPT data. A COSY correlation between one of the H-3 protons ($\delta_H$ 1.02) and a proton at $\delta_H$ 1.44 allowed assignment of one of the H-2 protons which in turn showed a correlation with a proton at $\delta_H$ 0.74 which was assigned to H-1. The remaining $^1$H and $^{13}$C chemical shifts for C-1 and C-2 were then assigned on the basis of additional COSY and HSQC-DEPT correlations and are summarized in the table below. $^1$H and $^{13}$C NMR (500 and 150 MHz, pyridine-$d_5$), assignments of the

| $^1$H and $^{13}$C NMR (500 and 150 MHz, pyridine-$d_5$), assignments of the Rebaudioside I aglycone. | | |
|---|---|---|
| Position | $^{13}$C | $^1$H |
| 1 | 40.7 | 0.74 t (11.6) |
|  |  | 1.75 m |
| 2 | 19.4 | 1.44 m |
|  |  | 2.20 m |
| 3 | 38.5 | 1.02 m |
|  |  | 2.35 m |
| 4 | 44.0 | — |
| 5 | 57.2 | 1.03 m |
| 6 | 22.2 | 1.90 m |
|  |  | 2.33 m |
| 7 | 41.7 | 1.29 m |
|  |  | 1.31 m |
| 8 | 42.3 | — |
| 9 | 54.1 | 0.88 d (6.3) |
| 10 | 39.8 | — |
| 11 | 20.5 | 1.67 m |
|  |  | 1.70 m |
| 12 | 37.3 | 1.98 m |
|  |  | 2.28 m |
| 13 | 86.7 | — |
| 14 | 44.3 | 1.78 m |
|  |  | 2.59 d (11.9) |

US 12,677,849 B2

95

-continued

| 1H and 13C NMR (500 and 150 MHz, pyridine-d5), assignments of the Rebaudioside I aglycone. | | |
|---|---|---|
| Position | 13C | 1H |
| 15 | 47.6 | 2.04 brs |
| 16 | 154.0 | — |
| 17 | 104.8 | 5.02 s |
| | | 5.67 s |
| 18 | 28.4 | 1.22 s |
| 19 | 176.9 | — |
| 20 | 15.7 | 1.26 s |

The other tertiary methyl singlet, observed at $\delta_H$ 1.26, showed HMBC correlations to C-1 and C-5 and was assigned as H-20. The methyl protons showed additional HMBC correlations to a quaternary carbon ($\delta_C$ 39.8) and a methine carbon ($\delta_C$ 54.1) which were assigned as C-10 and C-9, respectively. COSY correlations between H-5 ($\delta_H$ 1.03) and protons at $\delta_H$ 1.90 and 2.33 then allowed assignment of the H-6 protons which in turn showed correlations to protons at $\delta_H$ 1.29 and 1.31 which were assigned to H-7. The 13C chemical shifts for C-6 ($\delta_C$ 22.2) and C-7 ($\delta_C$ 41.7) were then determined from the HSQC-DEPT data. COSY correlations between H-9 ($\delta_H$ 0.88) and protons at $\delta_H$ 1.67 and 1.70 allowed assignment of the H-11 protons which in turn showed COSY correlations to protons at $\delta_H$ 1.98 and 2.28 which were assigned as the H-12 protons. The HSQC-DEPT data was then used to assign C-11 ($\delta_C$ 20.5) and C-12 ($\delta_C$ 37.3). The olefinic protons observed at $\delta_H$ 5.02 and 5.67 showed HMBC correlations to a quaternary carbon at $\delta_C$ 86.7 (C-13) and thus were assigned to H-17 ($\delta_C$ 104.8 via HSQC-DEPT). The methine proton H-9 showed HMBC correlations to carbons at $\delta_C$ 42.3, 44.3 and 47.6 which were assigned as C-8, C-14 and C-15, respectively. The 1H chemical shifts at C-14 ($\delta_H$ 1.78 and 2.59) and C-15 ($\delta_H$ 2.04) were assigned using the HSQC-DEPT data. Additional HMBC correlations from H-9 to C-11 and H-12 to C-9 further confirmed the assignments made above. HMBC correlations observed from H-14 to a quaternary carbon at $\delta_C$ 154.0 allowed the assignment of C-16 to complete the assignment of the central core.

Correlations observed in the NOESY spectrum were used to assign the relative stereochemistry of the central diterpene core. In the NOESY spectrum, NOE correlations were observed between H-14 and H-20 indicating that H-14 and H-20 are on the same face of the rings. Similarly, NOE correlations were observed between H-9 and H-5 as well as H-5 and H-18. NOE correlations between H-9 and H-14 were not observed. The NOESY data thus indicate that H-5, H-9 and H-18 were on the opposite face of the rings compared to H-14 and H-20 as presented in the figure below. These data thus indicate that the relative stereochemistry in the central core was retained during the glycosylation step.

Analysis of the 1H-13C HSQC-DEPT data for reb I confirmed the presence of five anomeric protons. All five anomeric protons were resolved in the spectra acquired at 292 K at $\delta_H$ 6.14 ($\delta_C$ 95.3), 5.57 ($\delta_C$ 104.6), 5.38 ($\delta_C$ 104.7), 5.29 ($\delta_C$ 105.0), and 5.06 ($\delta_C$ 98.0). Additionally, all five anomeric protons had large couplings (7.7 Hz-8.2 Hz) indicating that they had 0-configurations. The anomeric proton observed at $\delta_H$ 6.14 showed an HMBC correlation to C-19 which indicated that it corresponds to the anomeric proton of Glc$_I$. Similarly, the anomeric proton observed at $\delta_H$ 5.06 showed an HMBC correlation to C-13 allowing it to be assigned as the anomeric proton of Glc$_{II}$.

96

Figure 46:
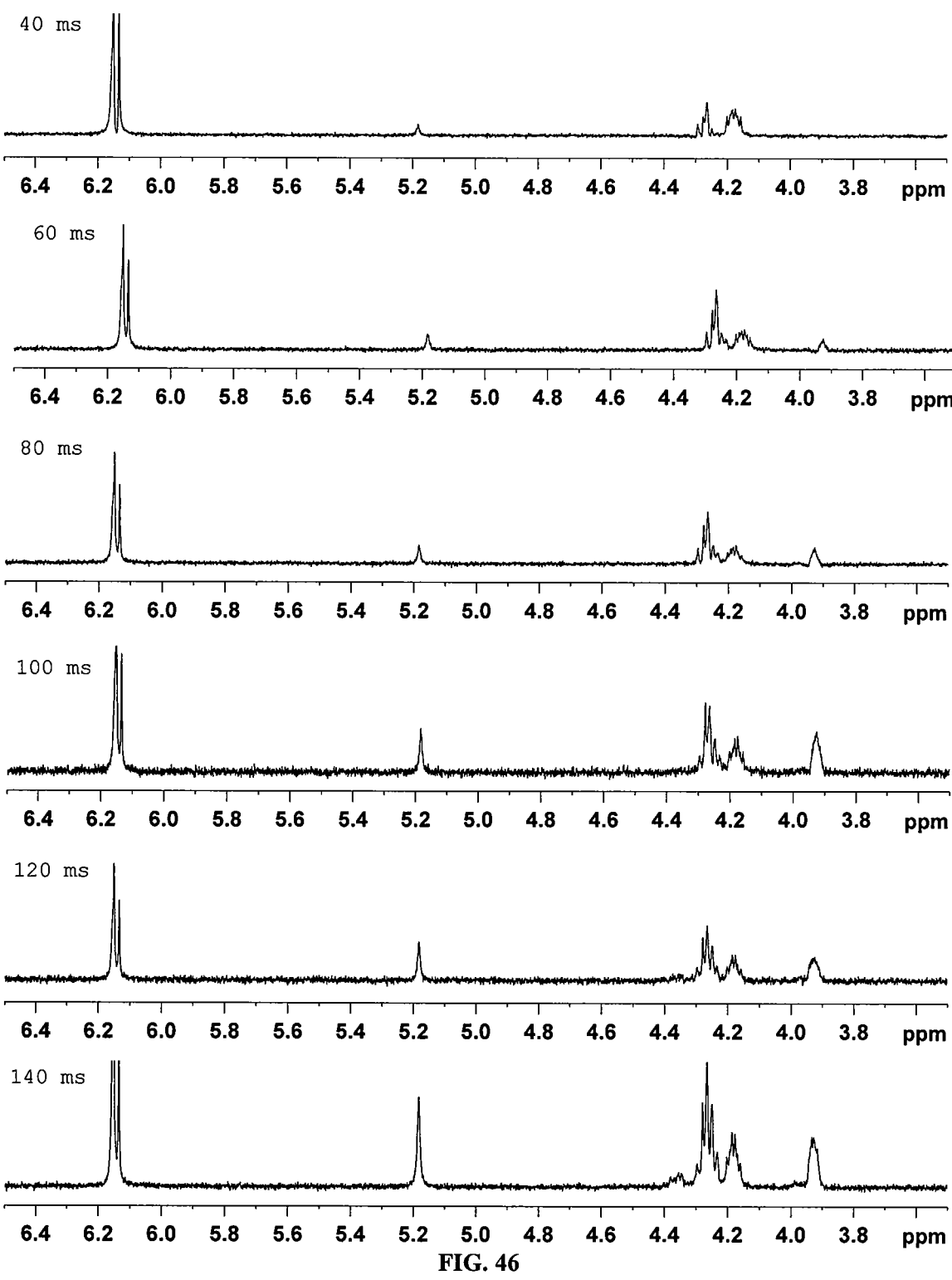
FIG. 46 shows the results of 1D TOCSY as described in Example 47.

The Glc$_I$ anomeric proton ($\delta_H$ 6.14) showed a COSY correlation to a proton at $\delta_H$ 4.18 which was assigned as Glc$_I$ H-2. Due to data overlap the COSY spectrum did not allow assignment of H-3 or H-4. Therefore, a series of 1D TOCSY experiments were performed using selective irradiation of the Glc$_I$ anomeric proton with several different mixing times (FIG. 46). In addition to confirming the assignment for Glc$_I$ H-2, the TOCSY data showed protons at $\delta_H$ 4.27, 4.25, and 3.93 which were assigned as H-3, H-4 and H-5, respectively. The proton observed at $\delta_H$ 4.37 in the TOCSY spectrum assigned to one of the Glc$_I$ H-6 protons. The other H-6 methylene proton at $\delta_H$ 4.27 was assigned based on COSY correlation from H-5 to $\delta_H$ 4.27. The 13C chemical shifts for Glc$_I$ C-2 ($\delta_C$ 72.5), C-3 (Sc 89.4), C-4 ($\delta_C$ 69.2), C-5 ($\delta_C$ 78.2-78.8) and C-6 ($\delta_C$ 61.7) were assigned using the HSQC-DEPT data. HMBC correlations from H-1 to C-3 and H-4 to C-6 further confirmed the assignments made above to complete the assignment of Glc$_I$.

Of the four remaining unassigned glucose moieties one was assigned as a substituent at C-3 of Glc$_I$ on the basis of HMBC correlations. The anomeric proton observed at $\delta_H$ 5.29 showed an HMBC correlation to Glc$_I$ C-3 and was assigned as the anomeric proton of Glc$_V$. The reciprocal HMBC correlation from Glc$_I$ H-3 to the anomeric carbon of Glc$_V$ was also observed.

A summary of the 1H and 13C chemical shifts for the glycoside at C-19 are shown in the following table:

| 1H and 13C NMR (500 and 150 MHz, pyridine-d5) assignments of Rebaudioside I C-19 glycoside. | | |
|---|---|---|
| Position | 13C | 1H |
| Glc$_I$-1 | 95.3 | 6.14 d (8.2) |
| Glc$_I$-2 | 72.5 | 4.18 m |
| Glc$_I$-3 | 89.4 | 4.27 m |
| Glc$_I$-4 | 69.2 | 4.25 m |
| Glc$_I$-5 | 78.2-78.8† | 3.93 m |
| Glc$_I$-6 | 61.7 | 4.27 m, 4.37 m |
| Glc$_V$-1 | 105.0 | 5.29 d (7.9) |
| Glc$_V$-2 | 75.3 or 75.5 | 4.04 m |
| Glc$_V$-3 | 78.2-78.6† | 4.27 m |
| Glc$_V$-4 | 71.5 or 71.6 | 4.12 m |
| Glc$_V$-5 | 78.5 or 78.6† | 4.05 m |
| Glc$_V$-6 | 62.3 or 62.4 | 4.26 m, 4.56 m |

†Five carbon resonances in the range of 78.2-78.8 (78.16, 78.47, 78.50, 78.55, and 78.77), hence chemical shift could not be unequivocally assigned.

A summary of key HMBC and COSY correlations used to assign the C-19 glycoside region are provided below.

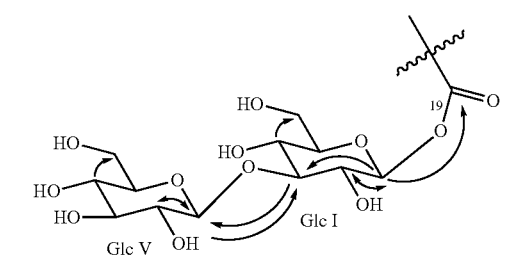

⌒ 1H-13C HMBC Correlations

⌒ 1H-1H COSY Correlations

Figure 47:
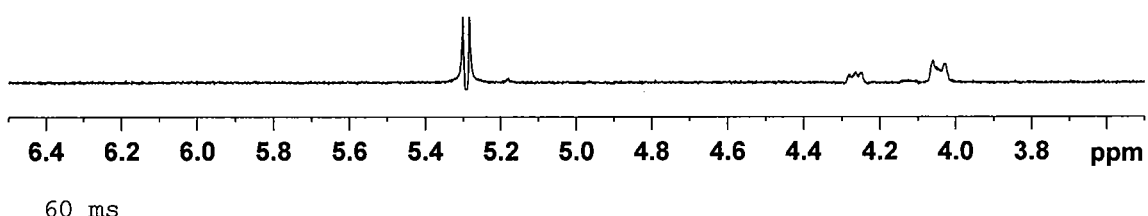
FIG. 47 shows the results of 1D TOCSY as described in Example 47.
Figure 47:
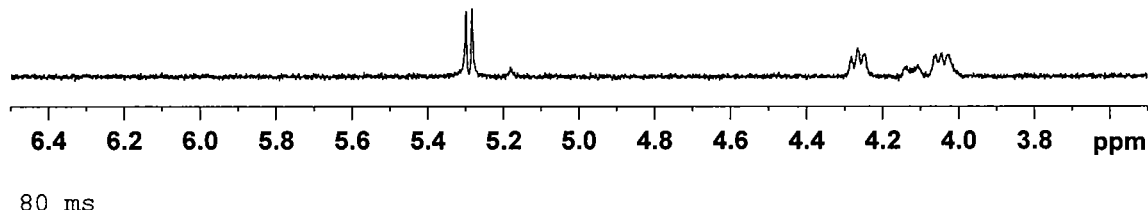
Figure 47:
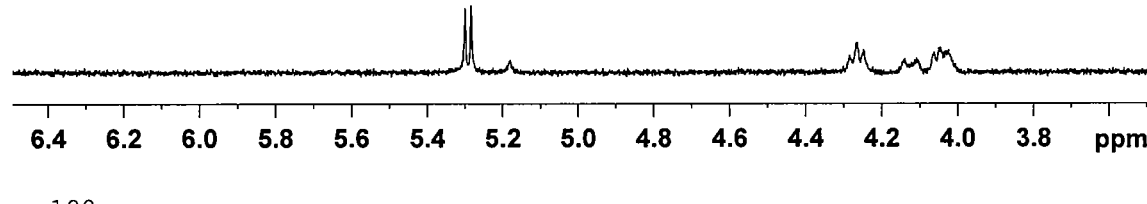
Figure 47:
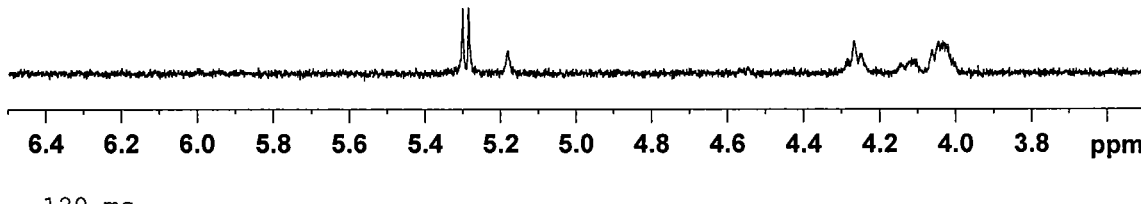
Figure 47:
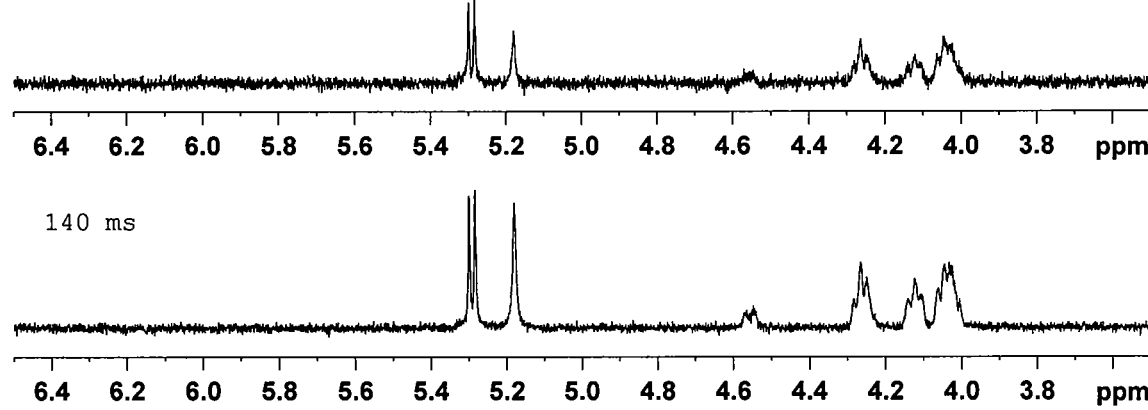

The anomeric proton of Glc$_V$ ($\delta_H$ 5.29) showed a COSY correlation with a proton at $\delta_H$ 4.04 which was assigned as Glc$_V$ H-2. Glc$_V$ C-2 ($\delta_C$ 75.3 or 75.5) was then assigned using the HSQC-DEPT data. Due to overlap in the data the COSY spectrum did not allow assignment of the remaining protons. Therefore, a series of 1D TOCSY experiments were performed using selective irradiation of the $Glc_V$ anomeric proton with several different mixing times (FIG. 47). In addition to confirming the assignments for $Glc_V$ H-2, the TOCSY data allowed assignment of $Glc_V$ H-3 ($\delta_H$ 4.27), H-4 ($\delta_H$ 4.12), and H-5 ($\delta_H$ 4.05). The proton observed at $\delta_H$ 4.56 in the TOCSY spectrum was assigned to one of the $Glc_V$ H-6 protons. The other H-6 methylene proton at $\delta_H$ 4.26 was assigned based on COSY correlation from H-5 to SH 4.26. The $^{13}$C chemical shifts for $Glc_V$ C-3 ($\delta_C$ 78.2-78.6), C-4 (Sc 71.5 or 71.6), C-5 ($\delta_C$ 78.5 or 78.6) and C-6 ($\delta_C$ 62.3 or 62.4) were assigned using the HSQC-DEPT data to complete the assignment of $Glc_V$.

Figure 48:
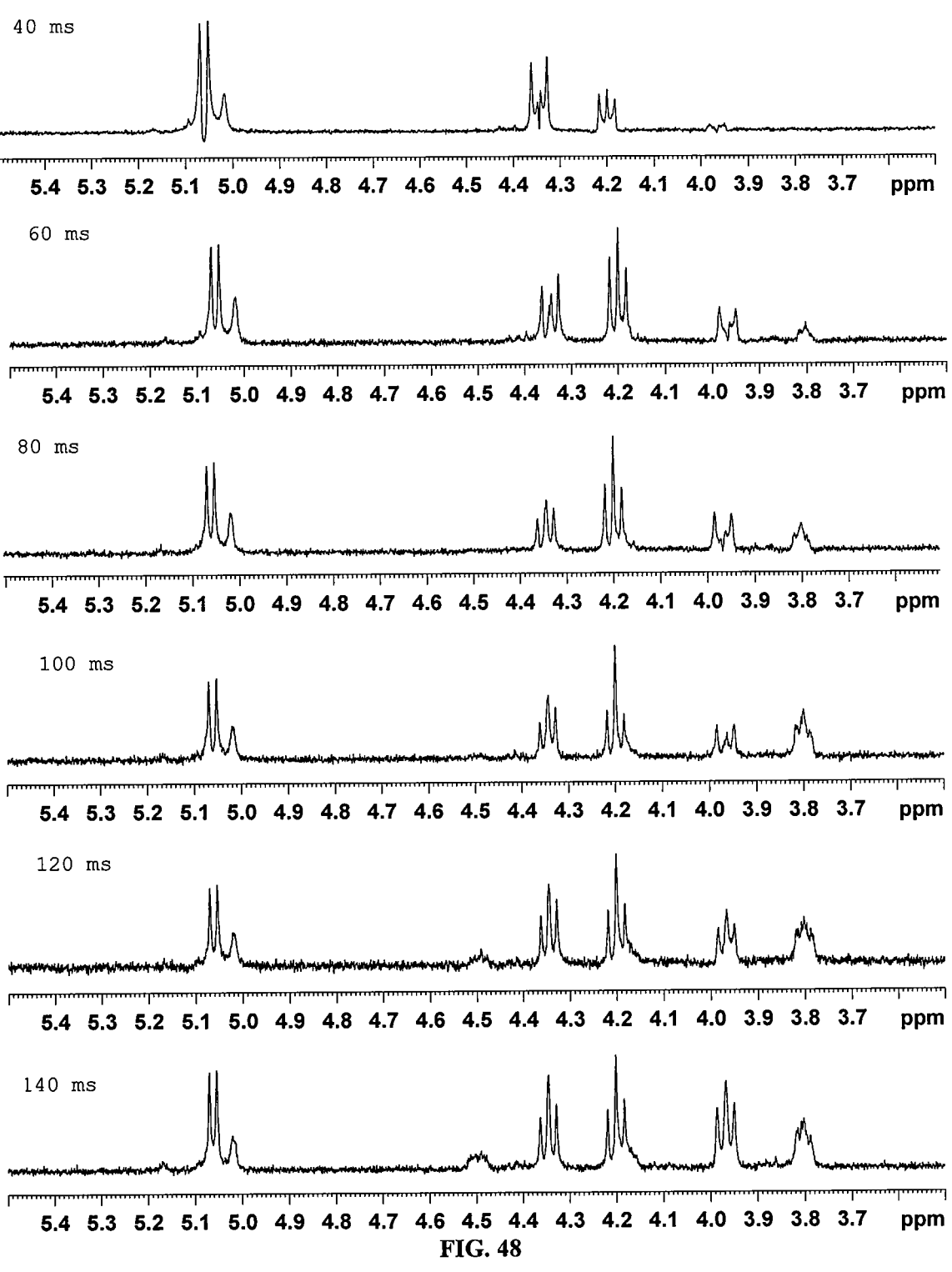
FIG. 48 shows the results of 1D TOCSY as described in Example 47.

Assignment of $Glc_{II}$ was carried out in a similar manner. The $Glc_{II}$ anomeric proton ($\delta_H$ 5.06) showed a COSY correlation to a proton at $\delta_H$ 4.34 which was assigned as $Glc_{II}$ H-2 and in turn showed a COSY correlation to a proton at $\delta_H$ 4.20 ($Glc_{II}$ H-3) which showed an additional correlation with a proton at $\delta_H$ 3.97 ($Glc_{II}$ H-4) which also showed a COSY correlation to a proton at $\delta_H$ 3.80 ($Glc_{II}$ H-5). H-5 showed additional COSY correlations to protons at $\delta_H$ 4.18 and 4.49 which were assigned to H-6. A series of 1D TOCSY experiments were also performed using selective irradiation of the $Glc_{II}$ anomeric proton with several different mixing times (FIG. 48). The TOCSY data confirmed the above proton assignments. Assignment of the $^{13}$C chemical shifts for $Glc_{II}$ C-2 ($\delta_C$ 80.2), C-3 ($\delta_C$ 87.5), C-4 ($\delta_C$ 70.1), C-5 ($\delta_C$ 77.6) and C-6 ($\delta_C$ 62.5) was based on HSQC-DEPT data. HMBC correlations from $Glc_{II}$ H-3 to C-2 and C-4 and also from $Glc_{II}$ H-4 to C-3, C-5 and C-6 confirmed the assignments made above to complete the assignment of $Glc_{II}$.

The remaining two unassigned glucose moieties were assigned as substituents at C-2 and C-3 of $Glc_{II}$ on the basis of HMBC correlations. The anomeric proton observed at $\delta_H$ 5.57 showed an HMBC correlation to $Glc_{II}$ C-2 and was assigned as the anomeric proton of $Glc_{III}$. The anomeric proton observed at $\delta_H$ 5.38 showed an HMBC correlation to $Glc_{II}$ C-3 and was assigned as the anomeric proton of $Glc_{IV}$. The reciprocal HMBC correlations from $Glc_{II}$ H-2 to the anomeric carbon of $Glc_{III}$ and from $Glc_{II}$ H-3 to the anomeric carbon of $Glc_{IV}$ were also observed.

Figure 49:
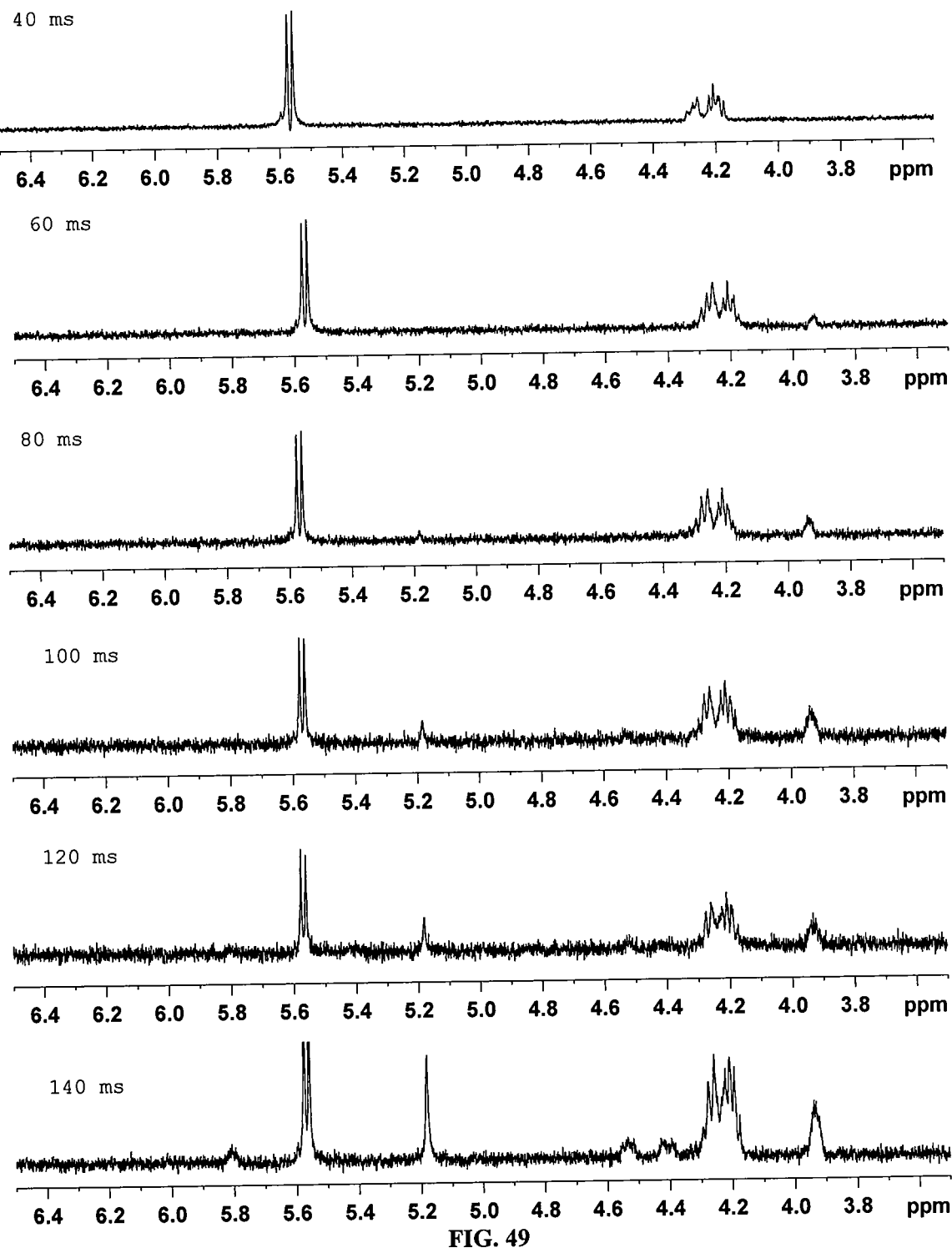
FIG. 49 shows the results of 1D TOCSY as described in Example 47.

The anomeric proton of $Glc_{III}$ ($\delta_H$ 5.57) showed a COSY correlation with a proton at $\delta_H$ 4.21 which was assigned as $Glc_{III}$ H-2. $Glc_{III}$ C-2 ($\delta_C$ 76.3) was then assigned using the HSQC-DEPT data. Due to data overlap the COSY spectrum did not allow assignment of the remaining protons. Therefore, a series of 1D TOCSY experiments were performed using selective irradiation of the $Glc_{III}$ anomeric proton with several different mixing times (FIG. 49). In addition to confirming the assignments for $Glc_{III}$ H-2, the TOCSY data allowed assignment of $Glc_{III}$ H-3 ($\delta_H$ 4.27), H-4 ($\delta_H$ 4.25) and H-5 ($\delta_H$ 3.94). The protons observed at $\delta_H$ 4.41 and SH 4.53 in the TOCSY spectrum were assigned as the $Glc_{III}$ H-6 protons. The $^{13}$C chemical shifts for C-3 ($\delta_C$ 78.2-78.6), C-4 ($\delta_C$ 72.1), C-5 ($\delta_C$ 78.2-78.8) and C-6 ($\delta_C$ 63.1) were assigned using the HSQC-DEPT data. HMBC correlations from H-5 to a carbon at $\delta_C$ 63.1 further confirmed the assignment of $Glc_{III}$ C-6 to complete the assignment of $Glc_{III}$.

Figure 50:
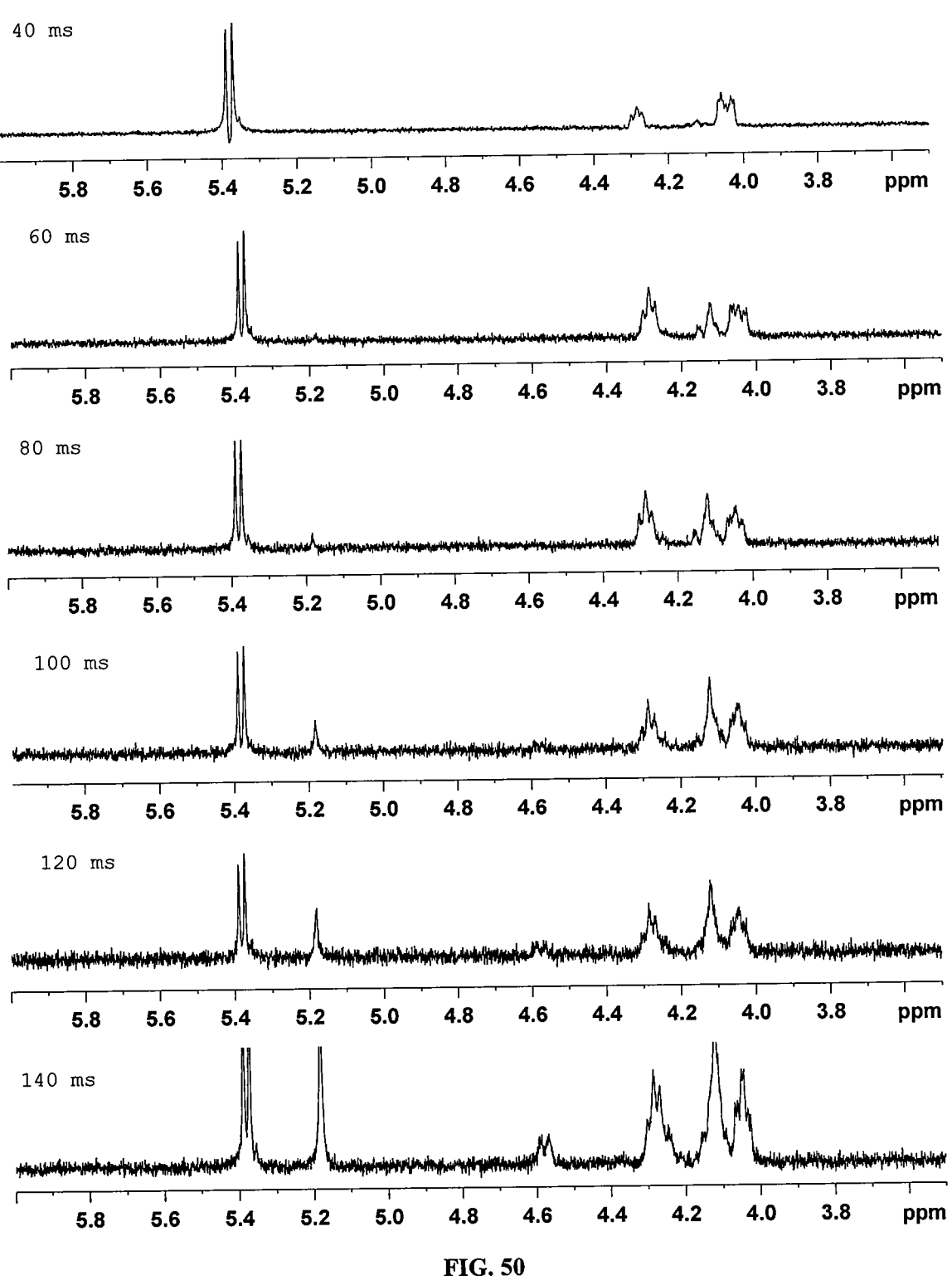
FIG. 50 shows the results of 1D TOCSY as described in Example 47.

The anomeric proton of $Glc_{IV}$ ($\delta_H$ 5.38) showed a COSY correlation with a proton at $\delta_H$ 4.01 which was assigned as $Glc_{IV}$ H-2. $Glc_{IV}$ C-2 ($\delta_C$ 75.3 or 75.5) was then assigned using the HSQC-DEPT data. Due to data overlap the COSY spectrum did not allow assignment of the remaining protons. Therefore a series of 1D TOCSY experiments were performed using selective irradiation of the $Glc_{IV}$ anomeric proton with several different mixing times (FIG. 50). In addition to confirming the assignments for $Glc_{IV}$ H-2, the 1D TOCSY data allowed assignment of H-3 ($\delta_H$ 4.28), H-4 ($\delta_H$ 4.11), H-5 ($\delta_H$ 4.13) and H-6 ($\delta_H$ 4.25 and 4.58). The proton at $\delta_H$ 4.25 also showed COSY correlation with SH 4.58 further confirmed that these protons belong to H-6. The $^{13}$C chemical shifts for C-3 ($\delta_C$ 78.2-78.6), C-4 ($\delta_C$ 72.1), C-5 ($\delta_C$ 78.2-78.6) and C-6 ($\delta_C$ 62.3 or 62.4) were assigned using the HSQC-DEPT data. HMBC correlations from H-4 to C-6 and H-5 to C-1 further confirmed the assignment of $Glc_{IV}$ C-6 to complete the assignment of $Glc_{IV}$.

A summary of the $^1$H and $^{13}$C chemical shifts for the glycoside at C-13 are found are shown below:

| $^1$H and $^{13}$C NMR (500 and 150 MHz, pyridine-$d_5$) assignments of the Rebaudioside I C-13 glycoside. | | |
|---|---|---|
| Position | $^{13}$C | $^1$H |
| $Glc_{II}$-1 | 98.0 | 5.06 d (7.9) |
| $Glc_{II}$-2 | 80.6 | 4.34 m |
| $Glc_{II}$-3 | 87.5 | 4.20 m |
| $Glc_{II}$-4 | 70.1 | 3.97 m |
| $Glc_{II}$-5 | 77.6 | 3.80 m |
| $Glc_{II}$-6 | 62.5 | 4.18 m, 4.49 m |
| $Glc_{III}$-1 | 104.6 | 5.57 d (7.7) |
| $Glc_{III}$-2 | 76.3 | 4.21 m |
| $Glc_{III}$-3 | 78.2-78.6† | 4.27 m |
| $Glc_{III}$-4 | 72.1 | 4.25 m |
| $Glc_{III}$-5 | 78.2-78.8† | 3.94 m |
| $Glc_{III}$-6 | 63.1 | 4.41 m, 4.53 m |
| $Glc_{IV}$-1 | 104.7 | 5.38 d (7.9) |
| $Glc_{IV}$-2 | 75.3 or 75.5 | 4.01 m |
| $Glc_{IV}$-3 | 78.2-78.6† | 4.28 m |
| $Glc_{IV}$-4 | 72.1 | 4.11 m |
| $Glc_{IV}$-5 | 78.2-78.6† | 4.13 m |
| $Glc_{IV}$-6 | 62.3 or 62.4 | 4.25 m, 4.58 m |

†Five carbon resonances in the range of 78.2-78.8 (78.16, 78.47, 78.50, 78.55, and 78.77), hence chemical shift could not be unequivocally assigned.

A summary of key HMBC and COSY correlations used to assign the C-13 glycoside region are provided below.

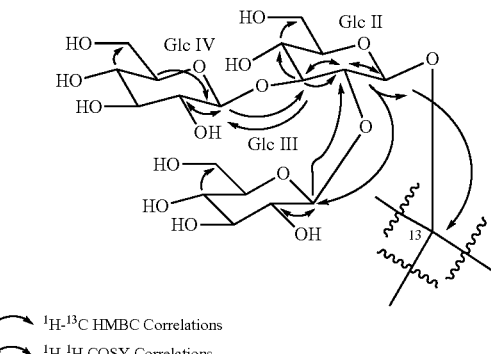

<span style="display:flex">↗ $^1$H-$^{13}$C HMBC Correlations</span>

<span style="display:flex">↗ $^1$H-$^1$H COSY Correlations</span>

NMR and MS analyses of rebaudioside I, reb I, allowed the full assignment of structure, shown below. The name of the chemical compound is (13-[(2-O-β-D-glucopyranosyl-3-O-β-D-glucopyranosyl)-β-D-glucopyranosyl)oxy] ent-kaur-16-en-19-oic acid-(3-O-β-D-glucopyranosyl)-β-D-glucopyranosyl) ester].

Example 48

Directed Evolution of UGTSL2 for the Conversion of Rebaudioside A to Rebaudioside D (Round 2)

Taking the native enzyme UGTSL2 (GI 460410132) as baseline, a list of 23 mutations was established containing different identified positive mutations for activity from the first round (EXAMPLE 45) and new mutations obtained by DNA2.0 ProteinGPS™ strategy. This list of mutations was subsequently used to design 46 variant genes that contained each 3 different mutations. After codon-optimized for expression in *E. coli* the genes were synthesized, subcloned in the pET30a+ plasmid and used for transformation of *E. coli* BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 μL aliquots were stored at –20° C. and at –80° C.

These storage aliquots of *E. coli* BL21(DE3) containing the pET30a+_UGTSL2var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 μL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysates were recovered by centrifugation.

In order to measure the activity of the variants for the transformation of Rebaudioside A to Rebaudioside D, 100 μL of fresh lysate was added to a solution of Rebaudioside A (final concentration 0.5 mM), $MgCl_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the initial rates after HPLC analysis (CAD detection) using the analytical method that was described above for the transformation of Rebaudioside A to Rebaudioside D.

In parallel for the most active clones, 100 μL of fresh lysate was added to a solution of Rebaudioside D (final concentration 0.5 mM), $MgCl_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the initial rates for Rebaudioside D conversion after HPLC analysis (CAD detection).

Apart from the new variants, both experiments were also performed with baseline clone, UGTSL2. The initial rates for the conversion of Rebaudioside A or Rebaudioside D for this baseline clone were defined as 100%.

Activity of each clone was defined as normalized activity compared to baseline clone UGTSL2 whereas specificity of each clone was expressed as the ratio between the initial rates for the conversion of Rebaudioside A and Rebaudioside D.

The normalized initial rate for the conversion of Rebaudioside A and the ratio between the initial rates for the conversion of Rebaudioside A and Rebaudioside D are depicted in the following table.

| Clone | Mutations* | Normalized initial rate for conversion of Rebaudioside A | Ratio between initial rates for the conversion of Rebaudioside A and Rebaudioside D |
|---|---|---|---|
| UGTSL2 | Baseline clone | 100% | 1.67 |
| Round2-var1 | UGTSL2 (Q27R_V270I_A285V) | 188% | 1.21 |
| Round2-var2 | UGTSL2 (F253Y_S255C_M354L) | 5% | Nd |
| Round2-var3 | UGTSL2_S255C_I352V_L393V | 28% | Nd |
| Round2-var4 | UGTSL2_R6H_N278G_T329I | 7% | Nd |
| Round2-var5 | UGTSL2_H247P_V270I_A285L | 75% | 1.27 |
| Round2-var6 | UGTSL2_I240L_T392A_L393V | 114% | 1.85 |
| Round2-var7 | UGTSL2_A285L_R312L_T392A | 135% | 1.66 |
| Round2-var8 | UGTSL2_Q27R_G387E_T392A | 164% | 1.65 |
| Round2-var9 | UGTSL2_Q27R_N278G_A341V | 178% | 3.13 |
| Round2-var10 | UGTSL2_I240L_A285L_N325S | 9% | Nd |

-continued

| Clone | Mutations* | Normalized initial rate for conversion of Rebaudioside A | Ratio between initial rates for the conversion of Rebaudioside A and Rebaudioside D |
|---|---|---|---|
| Round2-var11 | UGTSL2_S255C_S258T_N325S | 26% | Nd |
| Round2-var12 | UGTSL2_Q27R_N325S_I352V | 6% | Nd |
| Round2-var13 | UGTSL2_N325S_A341V_M354L | 116% | 1.89 |
| Round2-var14 | UGTSL2_S255C_A285V_T392A | 98% | 2.63 |
| Round2-var15 | UGTSL2_A285V_A341V_I352V | 26% | Nd |
| Round2-var16 | UGTSL2_F253Y_G387E_L393V | 88% | 1.69 |
| Round2-var17 | UGTSL2_V270I_T329I_L393V | 88% | 2.16 |
| Round2-var18 | UGTSL2_H247P_I333L_L393V | 197% | 1.75 |
| Round2-var19 | UGTSL2_L276A_R312L_N325S | 53% | 1.72 |
| Round2-var20 | UGTSL2_V270I_T329V_M354L | 30% | Nd |
| Round2-var21 | UGTSL2_A285V_I352V_G387E | 30% | Nd |
| Round2-var22 | UGTSL2_I240L_H247P_L276A | 76% | 2.00 |
| Round2-var23 | UGTSL2_A285V_R312L_T329I | 4% | Nd |
| Round2-var24 | UGTSL2_I240L_M354L_G387E | 8% | Nd |
| Round2-var25 | UGTSL2_N278G_R312L_I333L | 50% | 1.57 |
| Round2-var26 | UGTSL2_L276A_T329I_I352V | 0% | Nd |
| Round2-var27 | UGTSL2_L276A_T329V_G387E | 73% | Nd |
| Round2-var28 | UGTSL2_R6H_Q27R_L393V | 9% | Nd |
| Round2-var29 | UGTSL2_H247P_S258T_T329I | 129% | 1.21 |
| Round2-var30 | UGTSL2_N278G_N325S_T392A | 206% | 2.06 |
| Round2-var31 | UGTSL2_S255C_V270I_I333L | 81% | 2.87 |
| Round2-var32 | UGTSL2_R6H_H247P_A341V | 119% | 2.05 |
| Round2-var33 | UGTSL2_H247P_R312L_G387E | 67% | Nd |
| Round2-var34 | UGTSL2_R6H_I240L_T329V | 0% | Nd |
| Round2-var35 | UGTSL2_S258T_V270I_T392A | 146% | 1.71 |
| Round2-var36 | UGTSL2_F253Y_T329I_I333L | 76% | 1.69 |
| Round2-var37 | UGTSL2_S258T_A285V_A341V | 187% | 2.32 |
| Round2-var38 | UGTSL2_L276A_A285L_M354L | 12% | Nd |
| Round2-var39 | UGTSL2_Q27R_F253Y_T329V | 35% | Nd |
| Round2-var40 | UGTSL2_R6H_S258T_L276A | 36% | Nd |
| Round2-var41 | UGTSL2_S258T_N278G_M354L | 88% | 0.96 |
| Round2-var42 | UGTSL2_R6H_F253Y_A285L | 72% | 1.40 |
| Round2-var43 | UGTSL2_F253Y_R312L_I352V | 8% | Nd |
| Round2-var44 | UGTSL2_I240L_A285V_I333L | 43% | 1.06 |
| Round2-var45 | UGTSL2_S255C_N278G_T329V | 45% | 2.51 |

*Mutations are noted as follows: reference gene-original amino acid-position-new amino acid: For example the mutation of an isoleucine at position 240 to a Leucine for UGTSL2 is noted as UGTSL2 (I240L).
Nd means Not determined.

Modeling of these results allowed to obtain a ranking of the effect of each mutation.

The following mutations were determined as being beneficial for activity:

N325S, G387E, A285V, I333L, V270I, Q27R, N278G, L393V, S258T, A341V, H247P and T392A.

The following mutations were determined as being beneficial for an improved ratio between initial rate for the conversion of Rebaudioside A and Rebaudioside D:

V270I, T392A, T329V, L276A, L393V, A341V and S255C.

Example 49

Use of β-Glucosidases for the Conversion of Rebaudioside M2 to Rebaudioside D Different β-glucosidases were tested for the hydrolysis of Rebaudioside M2. The goal was to selectively hydrolyze the (1→6) glucoside bond in order to obtain Rebaudioside D. The desired general reaction scheme is as follows:

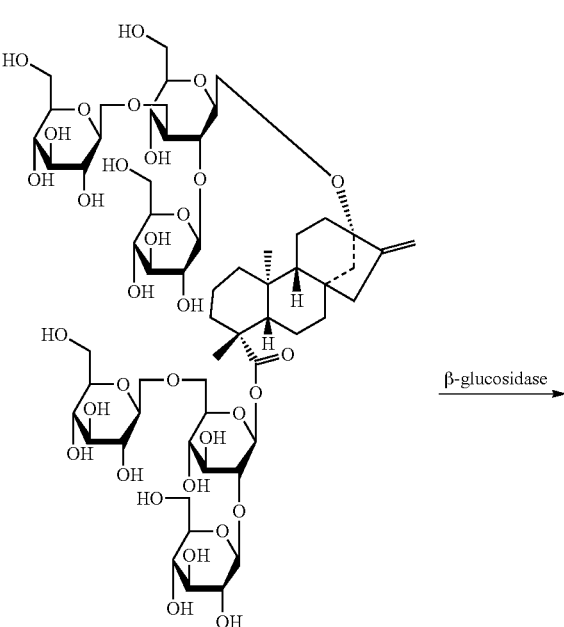

Rebaudioside M2

β-glucosidase

-continued

Rebaudioside D

First the selected β-glucosidases were tested on reference substrate 4-nitrophenyl-β-D-glucopyranoside to determine the activity. Based on the determined activities, the used quantities of enzyme were calculated as units for use in the hydrolysis of Rebaudioside M2.

The tested β-glucosidases are depicted in the following table:

| β-glucosidase | Manufacturer* | Activity enzyme using 4-nitrophenyl-β-D-glucopyranoside $(mmol \cdot min^{-1} \cdot mg^{-1})$ | Quantity of enzyme used (mg/mL of reaction mixture)/(U/mL) |
|---|---|---|---|
| Isolase | NEC | 0.29 | 1.50/0.44 |
| Aromase | Amano | 0.030 | 11.3/0.35 |
| Naringinase | Amano | 0.017 | 13.5/0.23 |
| Cellulase Tr (Celluclast ® 1.5L) | Novozyme | 0.026 | 20.4/0.53 |
| Cellobiase As (Novozyme 188) | Novozyme | 0.26 | 1.50/0.39 |
| CWD (Viscozyme ®L) | Novozyme | 0.0062 | 132/0.82 |

*Isolase (011410; National Enzyme Company, USA); Aromase (GLY0151441; Amano Enzyme, Japan); Naringinase (NAH0550102; Amano Enzyme, Japan), Cellulase from *Trichoderma reesei* ATCC 26921 (Sigma C2730); Cellobiase from *Aspergillus niger* (Sigma C6105); Viscozyme L (Sigma V2010)

The assay conditions were as follows:

Reactions were performed at 30° C. at a total volume of 10 mL containing 15 mM of sodium acetate buffer (pH 4.5) and 1 mM Rebaudioside M2. The reaction was started by the addition of enzyme.

625 µL of reaction mixture was sampled after 0, 0.5, 1, 1.5, 2, 2.5, 3 and 3.3 hrs and quenched with a mixture of 575 µL of 80% methanol and 50 µL of 2N $H_2SO_4$. The samples were analyzed by HPLC analysis (CAD detection) using the analytical method that was described above.

The reaction profiles of these reactions with different β-glucosidases are shown in FIGS. 68a-f.

It can be concluded that Naringinase and CWD catalyzed the formation of Rebaudioside D2 and Rebaudioside A which indicates a (1→2) bond glycolysis and (1→6) bond glycolysis respectively. These enzymes can be considered as non-selective for the conversion of Rebaudioside M2.

Isolase, Cellulase Tr and Cellobiase As possess a clear-cut selectivity for the conversion of Rebaudioside M2 to Rebaudioside D (hydrolysis of (1→6) glucoside bond), whereas Aromase possessed low overall activity for the conversion of Rebaudioside M2.

Example 50

Stability of Rebaudiosides in the Presence of Isolase, Cellulase Tr and Cellobiase as In order to assess the selectivity of Isolase, Cellulase Tr and Cellobiase As for Rebaudioside M2, Rebaudioside A, Rebaudioside D and Rebaudioside M were tested as substrates under the following conditions:

Reactions were performed over 24 h. at 30° C. at a total volume of 10 mL containing 15 mM of sodium acetate buffer (pH 4.5) and 1 mM of Rebaudioside A, Rebaudioside D or Rebaudioside M. The reaction was started by the addition of enzyme.

625 µL of reaction mixture was sampled after 0, 0.5, 1, 1.5, 2, 2.5, 3 and 3.3 hrs and quenched with a mixture of 575 µL of 80% methanol and 50 µL of 2N $H_2SO_4$. The samples were analyzed by HPLC.

Figure 69A:
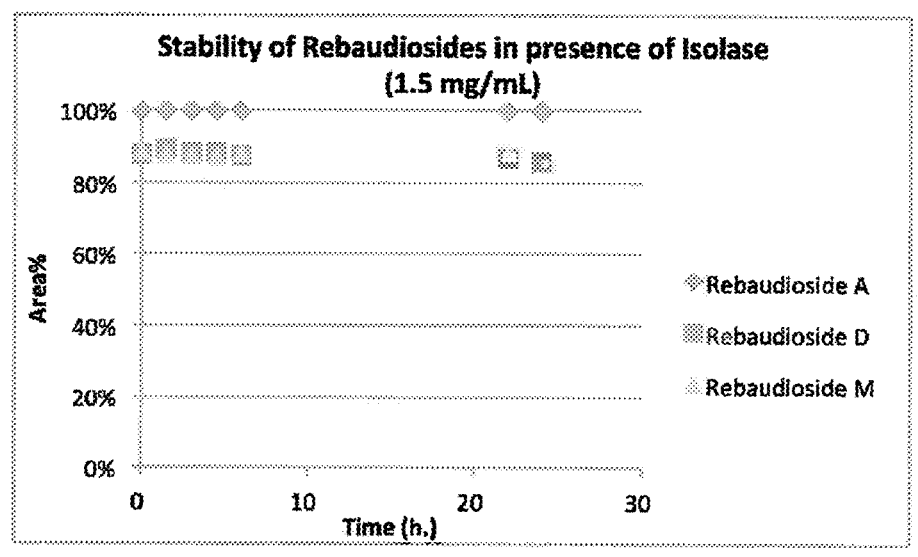
FIGS. 69A-69C show graphs showing the HPLC results for Example 50.
Figure 69B:
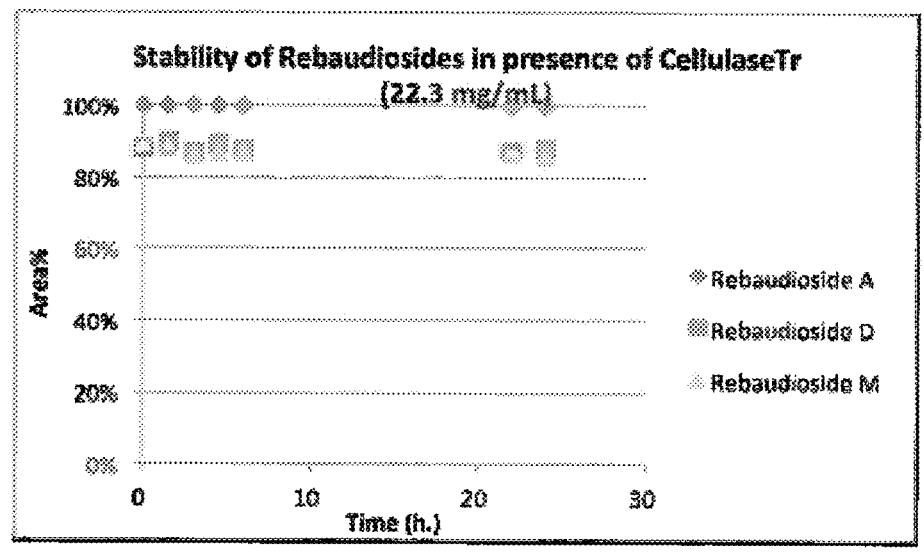
Figure 69C:
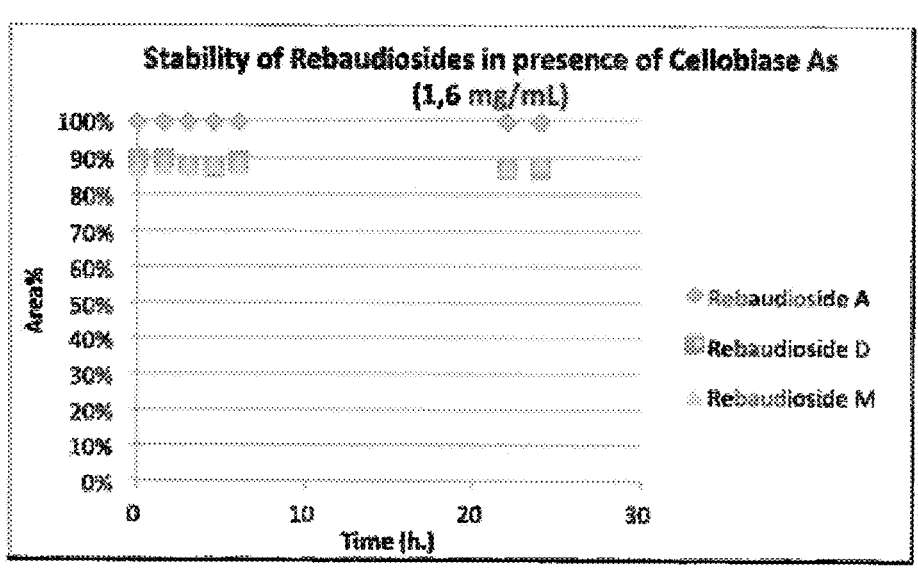
Figure 70A:
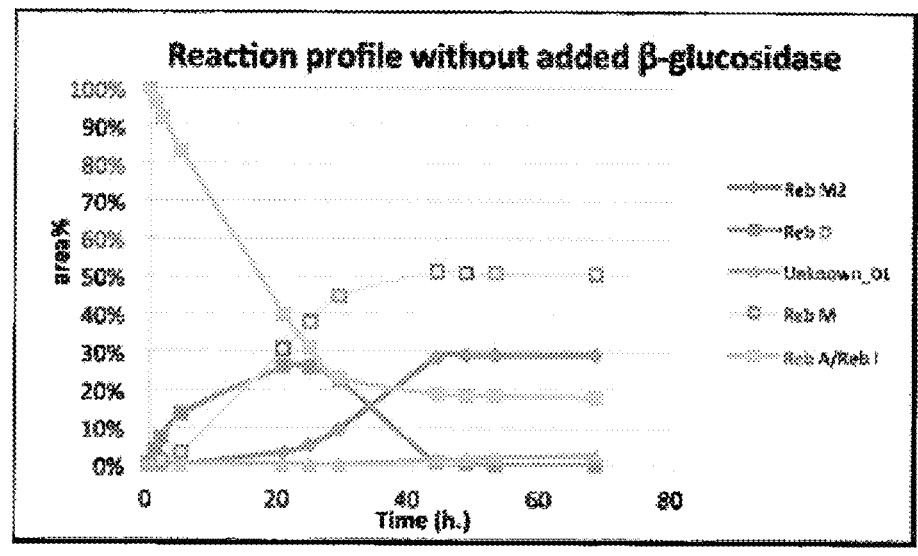
FIGS. 70A-70D show reaction profile graphs for Example 51.
Figure 70B:
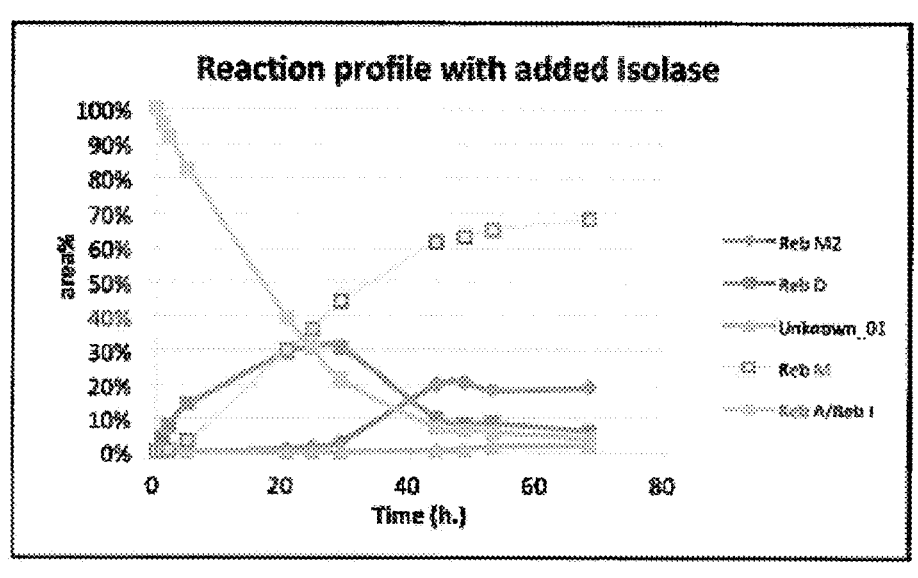
Figure 70C:
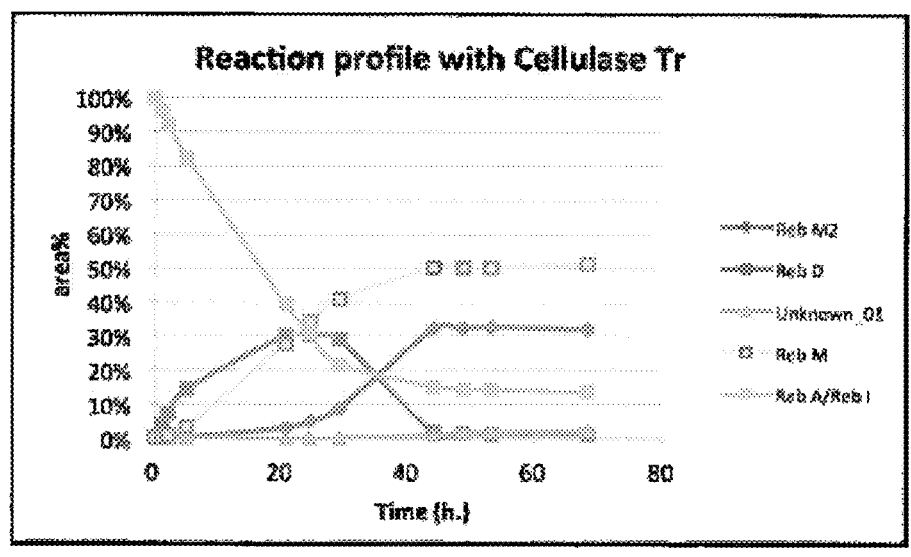
Figure 70D:
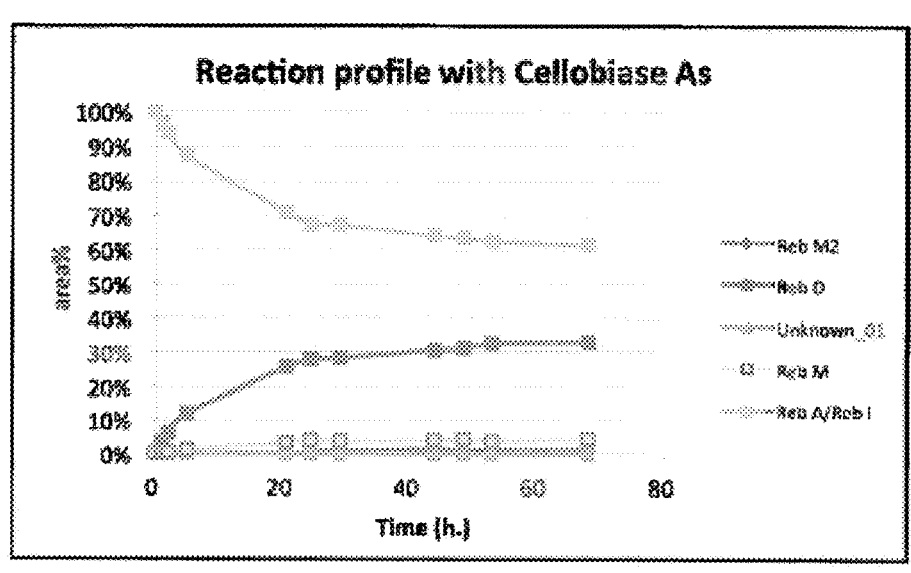

The results shown in FIGS. 69a-c were obtained. It can be observed that no significant conversion of Rebaudioside A, Rebaudioside D and Rebaudioside M can be observed in the presence of Isolase, Cellulase Tr and Cellobiase As.

Example 51

Four-Enzyme Reaction for the Conversion of Rebaudioside A to Rebaudioside M

The influence of adding Isolase, Cellulase Tr or Cellobiase As to the one-pot reaction of Rebaudioside A to Rebaudioside M with UGTSL2, UGT76G1-1R-F12 and AtSUS was studied. The following reaction conditions were used:

| Compound | Assay conc (mM) |
|---|---|
| Rebaudioside A | 2 |
| UDP | 0.25 |
| $MgCl_2$ | 3 |
| Phosphate buffer pH 7.0 | 50 |
| Sucrose | 100 |
| UGTSL2 lysate (2.1 U/mL) | 25 µL/mL (0.053 U/mL) |
| UGT76G1-R1-F12 lysate (2.5 U/mL) | 170 µL/mL (0.425 U/mL) |
| AtSUS (130 U/mL) | 25 µL/mL (3.25 U/mL) |
| Isolase | 0.3 mg/mL |
| Cellulase Tr | 0.3 mg/mL |
| Cellobiase As | 4.0 mg/mL |

The results for the experiments without and with added β-glucosidase are shown in FIGS. 70a-d. It can be seen that addition of Cellobiase As is blocking the reaction and that addition of Cellulase Tr does not have an influence on the reaction profile. However, addition of Isolase to the reaction mixture has a positive effect on the quantity of Rebaudioside M that is formed in the reaction. An increase of almost 20% is observed when Isolase is added. The Rebaudioside M2 content is approximately 10% lower and Rebaudioside I content is approximately 15% lower when Isolase is added to the reaction mixture compared to the reaction without added β-glucosidase.

Further improvement Reb M yield and reduction of Reb M2 and Reb I content can be achieved through optimization of the reaction parameters and amount of Isolase.

Example 52

Use of β-Glucosidases for the Conversion of Rebaudioside I to Rebaudioside A

Three β-glucosidases were tested for the hydrolysis of Rebaudioside I to Rebaudioside A. The goal was to selectively hydrolyze the (1→6) glucoside bond in order to obtain Rebaudioside D. The desired general reaction scheme is as follows:

Rebaudioside I

β-glucosidase

→

-continued

Rebaudioside A

The selected β-glucosidases were tested on reference substrate 4-nitrophenyl-β-D-glucopyranoside to determine the activity. Based on the determined activities, the used quantities of enzyme were calculated as units for use in the hydrolysis of Rebaudioside I. The tested β-glucosidases are depicted in the following table:

| β-glucosidase | Manufacturer* | Activity enzyme using 4-nitrophenyl-β-D-glucopyranoside $(mmol \cdot min^{-1} \cdot mg^{-1})$ | Quantity of enzyme used (mg/mL of reaction mixture)/(U/mL) |
|---|---|---|---|
| Isolase | NEC (011410) | 0.29 | 1.50/0.44 |
| Cellulase Tr (Celluclast ® 1.5L) | Novozymes* | 0.026 | 22.3/0.58 |
| Cellobiase As (Novozyme 188) | Novozymes* | 0.26 | 1.60/0.42 |

*Isolase (011410; National Enzyme Company, USA); Cellulase from *Trichoderma reesei* ATCC 26921 (Sigma C2730); Cellobiase from *Aspergillus niger* (Sigma C6105)

The assay conditions were as follows. Reactions were performed at 30° C. at a total volume of 2 mL containing 15 mM of sodium acetate buffer (pH 4.5) and 1 mM Rebaudioside I. The reaction was started by the addition of enzyme.

Figure 71:
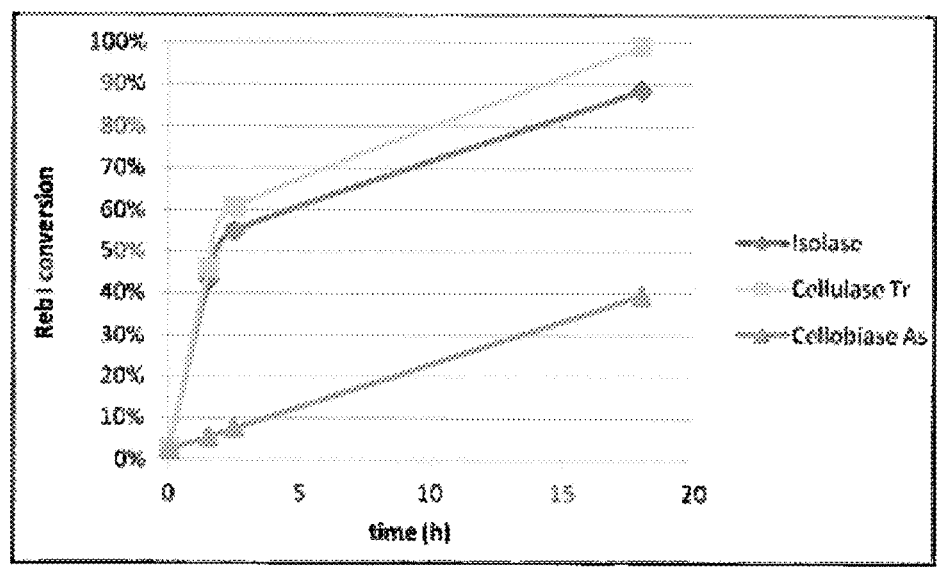
FIG. 71 shows a reaction profile graph for Example 52.

125 µL of reaction mixture was sampled after 0, 1.5, 2.5 and 18 h. and quenched with a mixture of 115 µL of 80% methanol and 10 µL of 2N $H_2SO_4$. The samples were analyzed by HPLC analysis (CAD detection) using the analytical method that was described above. The reaction profiles of the different β-glucosidases with Rebaudioside I are depicted in the graph shown in FIG. 71.

It can be observed that all three tested β-glucosidases converted Rebaudioside I. The sole product was Rebaudioside A.

Example 53

Directed Evolution of UGTSL2 for the Conversion of Rebaudioside A to Rebaudioside D (Round 3)

Taking the native enzyme UGTSL2 (GI 460410132) as baseline, a list of 13 mutations that were identified during round 2 (EXAMPLE 48) and another list of 12 new mutations that were obtained by DNA2.0 ProteinGPS™ strategy were prepared. This list of mutations was subsequently used to design 46 variant genes that contained each 1 to 8 different mutations. After codon-optimized for expression in *E. coli* the genes were synthesized, subcloned in the pET30a+ plasmid and used for transformation of *E. coli* BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of *E. coli* BL21(DE3) containing the pET30a+_UGTSL2var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysates were recovered by centrifugation.

In order to measure the activity of the variants for the transformation of Rebaudioside A to Rebaudioside D, 100 µL of fresh lysate was added to a solution of Rebaudioside A (final concentration 0.5 mM), $MgCl_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the initial rates after HPLC analysis (CAD detection) using the analytical method that was described above for the transformation of Rebaudioside A to Rebaudioside D.

In parallel 100 µL of fresh lysate was added to a solution of Rebaudioside D (final concentration 0.5 mM), $MgCl_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the initial rates for Rebaudioside D conversion after HPLC analysis (CAD detection).

Apart from the new variants for this round, both experiments were also performed with baseline clone, UGTSL2. The initial rates for the conversion of Rebaudioside A or Rebaudioside D for this baseline clone were defined as 100%.

Activity of each clone was defined as normalized activity compared to baseline clone UGTSL2 whereas specificity of each clone was expressed as the ratio between the initial rates for the conversion of Rebaudioside A and Rebaudioside D.

The normalized initial rate for the conversion of Rebaudioside A and the ratio between the initial rates for the conversion of Rebaudioside A and Rebaudioside D are depicted in the following table.

| Clone | Mutations* | Normalized initial rate for conversion of Rebaudioside A | Ratio between initial rates for the conversion of Rebaudioside A and Rebaudioside D |
|---|---|---|---|
| UGTSL2 | Baseline clone | 100% | 1.67 |
| Round3-var1 | UGTSL2_S255C_A285V_V349L_L393V | 13% | 1.86 |
| Round3-var2 | UGTSL2_N130G_S255C_N339G_T392A | 264% | 3.09 |
| Round3-var3 | UGTSL2_S255C_V270I_L276A_A285V | 10% | 4.50 |
| Round3-var4 | UGTSL2_S255C_A285I_T329V_H357Y_T392A | 70% | 4.87 |
| Round3-var5 | UGTSL2_S255C_A341V_T392A_I412M | 359% | 4.34 |
| Round3-var6 | UGTSL2_S255C_A285V_K301E_A341V_T392A_L393V | 104% | 4.34 |
| Round3-var7 | UGTSL2_S255C_L276A_K301E_T392A | 79% | 4.51 |
| Round3-var8 | UGTSL2_S255C_T392A_L393V_I412L | 46% | 2.12 |
| Round3-var9 | UGTSL2_F226V_S255C_V270I_T392A | 226% | 2.67 |
| Round3-var10 | UGTSL2_S255C_L276A_A285V_T329V_T392A_I412L | 5% | 8.57 |
| Round3-var11 | UGTSL2_S255C_H357Y_T392A_K408R | 0% | Nd |
| Round3-var12 | UGTSL2_S255C_V270I_A285V_A341V_T392A_I412L | 403% | 7.83 |
| Round3-var13 | UGTSL2_S255C_A285V_T329V_N339G_A341V_V349L_T392A | 0% | Nd |
| Round3-var14 | UGTSL2_N130G_A285V_A341V_T392A_K408R | 475% | 2.69 |
| Round3-var15 | UGTSL2_T329V | 122% | 2.62 |
| Round3-var16 | UGTSL2_P225L_F226V_S255C_A285V_T329V_T392A_L393V | 14% | 3.03 |
| Round3-var17 | UGTSL2_I203L_P225L_S255C_V349L_T392A | 0% | Nd |
| Round3-var18 | UGTSL2_V270I_A285I_K301E_T392A | 390% | 1.40 |

-continued

| Clone | Mutations* | Normalized initial rate for conversion of Rebaudioside A | Ratio between initial rates for the conversion of Rebaudioside A and Rebaudioside D |
|-------|-----------|---------|---------|
| Round3-var19 | UGTSL2_I203L_S255C_V270I_A285V_N339G_T392A_L393V | 12% | 1.81 |
| Round3-var20 | UGTSL2_N130G_S255C_L276A_A285I_T392A_L393V | 262% | 3.35 |
| Round3-var21 | UGTSL2_S255C_V270I_A285V_T329V_T392A_K408R_I412M | 67% | 3.33 |
| Round3-var22 | UGTSL2_I203L_F226V_S255C_L276A_A285V_T392A_I412M | 0% | Nd |
| Round3-var23 | UGTSL2_P225L_S255C_L276A_A285V_A341V_H357Y_T392A | 1% | Nd |
| Round3-var24 | UGTSL2_S258T_K408R | 58% | 3.12 |
| Round3-var25 | UGTSL2_F226V_H247P_S258T_A341V | 85% | 2.47 |
| Round3-var26 | UGTSL2_S258T_V270I_A341V_V349L | 5% | 1.74 |
| Round3-var27 | UGTSL2_S258T_L276A_A285V_K301E_A341V_L393V | 297% | 2.26 |
| Round3-var28 | UGTSL2_P225L_S258T_L276A_A341V | 22% | 1.08 |
| Round3-var29 | UGTSL2_S258T_L276A_N339G_A341V | 18% | 1.08 |
| Round3-var30 | UGTSL2_S258T_V270I_N278G_A285V_A341V_T392A | 313% | 2.29 |
| Round3-var31 | UGTSL2_F253Y_A341V_L393V | 105% | 3.88 |
| Round3-var32 | UGTSL2_N130G_S258T_N278G_A341V_H357Y | 13% | 1.66 |
| Round3-var33 | UGTSL2_H247P_S258T_N278G_A285V_A341V_L393V_K408R | 286% | 3.29 |
| Round3-var34 | UGTSL2_F253Y_S258T_V270I_L276A_A285I_A341V | 362% | 1.90 |
| Round3-var35 | UGTSL2_F253Y_S255C_S258T_A341V_T392A | 24% | 3.28 |
| Round3-var36 | UGTSL2_S255C_S258T_L276A_N278G_A285V_I333L_A341V | 121% | 3.36 |
| Round3-var37 | UGTSL2_F226V_S258T_I333L | 5% | 1.20 |
| Round3-var38 | UGTSL2_S255C_S258T_V270I_A285V_T329V | 139% | 2.59 |
| Round3-var39 | UGTSL2_S258T_L276A_A285V_H357Y_T392A | 94% | 1.98 |
| Round3-var40 | UGTSL2_S258T_N278G_K301E_T329V_A341V_I412L | 179% | 2.82 |
| Round3-var41 | UGTSL2_P225L_S258T_A285I_L393V_I412L | 1% | 0.59 |
| Round3-var42 | UGTSL2_I203L_N278G_A285V_I412M | 3% | 2.68 |
| Round3-var43 | UGTSL2_I203L_S258T_V270I_I333L_A341V_L393V | 44% | 6.27 |
| Round3-var44 | UGTSL2_S258T_A285V_T329V_N339G_A341V_V349L_T392A_L393V | 0% | Nd |
| Round3-var45 | UGTSL2_N130G_H247P_V270I_A285V_A341V_T392A | 869% | 2.69 |
| Round3-var46 | UGTSL2_S258T_A341V_T392A_I412M | 132% | 3.27 |

*Mutations are noted as follows: reference gene-original amino acid-position-new amino acid: For example the mutation of an isoleucine at position 240 to a Leucine for UGTSL2 is noted as UGTSL2 (I240L).
Nd means Not determined.

Modeling of these results allowed to obtain a ranking of the effect of each mutation. The following mutations were determined as being beneficial for activity:

N130G, H247P, F253Y, V270I, L276A, A285I, A285V, K301E, A341V, T392A, K408R, I412L.

The following mutations were determined as being beneficial for an improved ratio between initial rate for the conversion of Rebaudioside A and Rebaudioside D:

I203L, S255C, I333L, A341V, H357Y, L393V, K408R, I412L.

Example 54

One-Pot, Four-Enzyme Conversion of Rebaudioside A to Rebaudioside M 10 mL of a reaction mixture containing 5.0 mM of Rebaudioside A, 0.25 mM of UDP, 2 mM of MgCl$_2$, 100 mM of sucrose, 50 mM of potassium phosphate buffer pH 7.5, 2.5 U of UGTSL2-R3-D2 (UGTSL2-Round3-var12, see EXAMPLE 53), 25 U of UGT76G1-R3-G3 (UGT76G1-Round3-var21, see EXAMPLE 44), 25 U of AtSUS and 5 U of Isolase® was filtered through a 0.2 μm filter in a sterile flask. The resulting reaction mixture was gently shaken at 30° C. for 65 h.

Samples were taken under sterile conditions at regular intervals by taking 125 μL of reaction mixture and quenching it with 10 μL of 2 N H$_2$SO$_4$ and 765 μL of 50% methanol. After centrifugation, 200 μL of the supernatant was analyzed by HPLC.

Figure 72A:
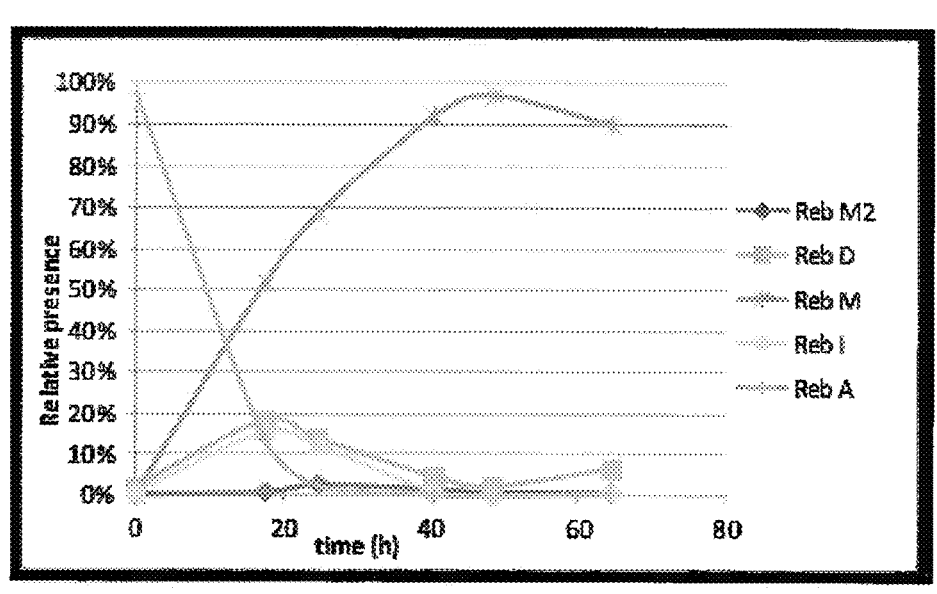
FIG. 72A shows a reaction profile graph for Example 54.
Figure 72B:
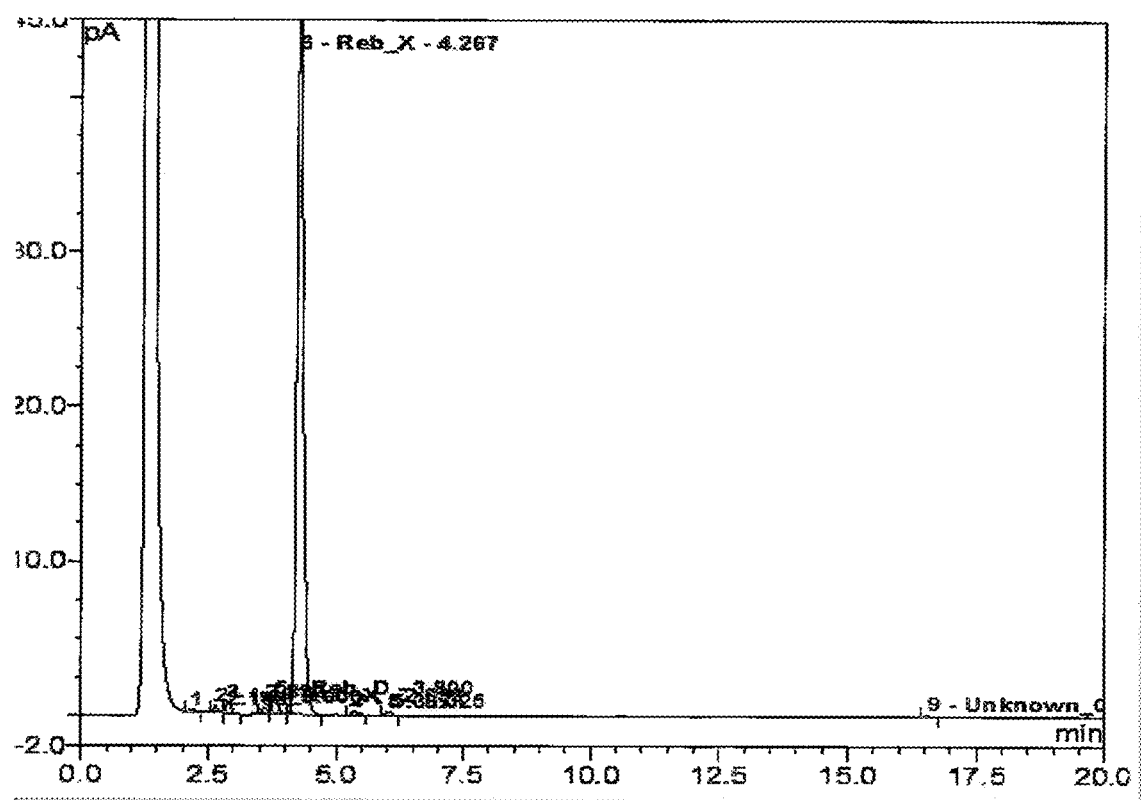
FIG. 72B shows an HPLC chromatogram showing the HPLC analysis for Example 54.

The reaction profile shown in FIG. 72a was obtained. The HPLC analysis after 48 h of reaction is shown in FIG. 72b.

Example 55

One-Pot, Four-Enzyme Conversion of Rebaudioside A to Rebaudioside M 10 mL of a reaction mixture containing 10.0 mM of Rebaudioside A, 0.50 mM of UDP, 3 mM of MgCl$_2$, 100 mM of sucrose, 50 mM of potassium phosphate buffer pH 7.5, 5.0 U of UGTSL2-R3-D2 (UGTSL2-Round3-var12, see EXAMPLE 53), 50 U of UGT76G1-R3-G3 (UGT76G1-Round3-var21, see EXAMPLE 44), 50 U of AtSUS and 10 U of Isolase® was filtered through a 0.2 μm filter in a sterile flask. The resulting reaction mixture was gently shaken at 30° C. for 66 h.

Samples were taken under sterile conditions at regular intervals by taking 125 μL of reaction mixture and quenching it with 10 μL of 2N H$_2$SO$_4$ and 765 μL of 50% methanol. After centrifugation, 200 μL of the supernatant was analyzed by HPLC.

Figure 73A:
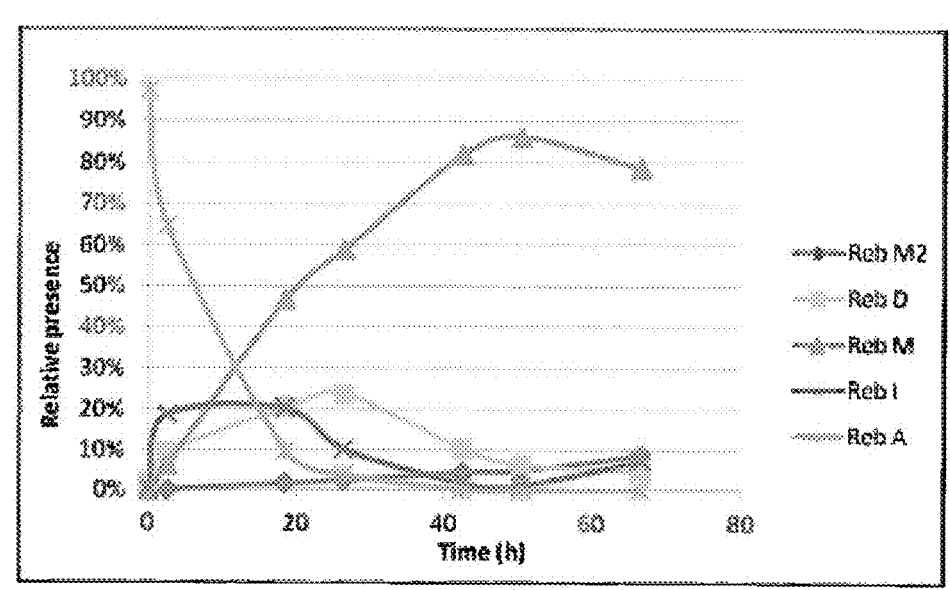
FIG. 73A shows a reaction profile graph for Example 55.
Figure 73B:
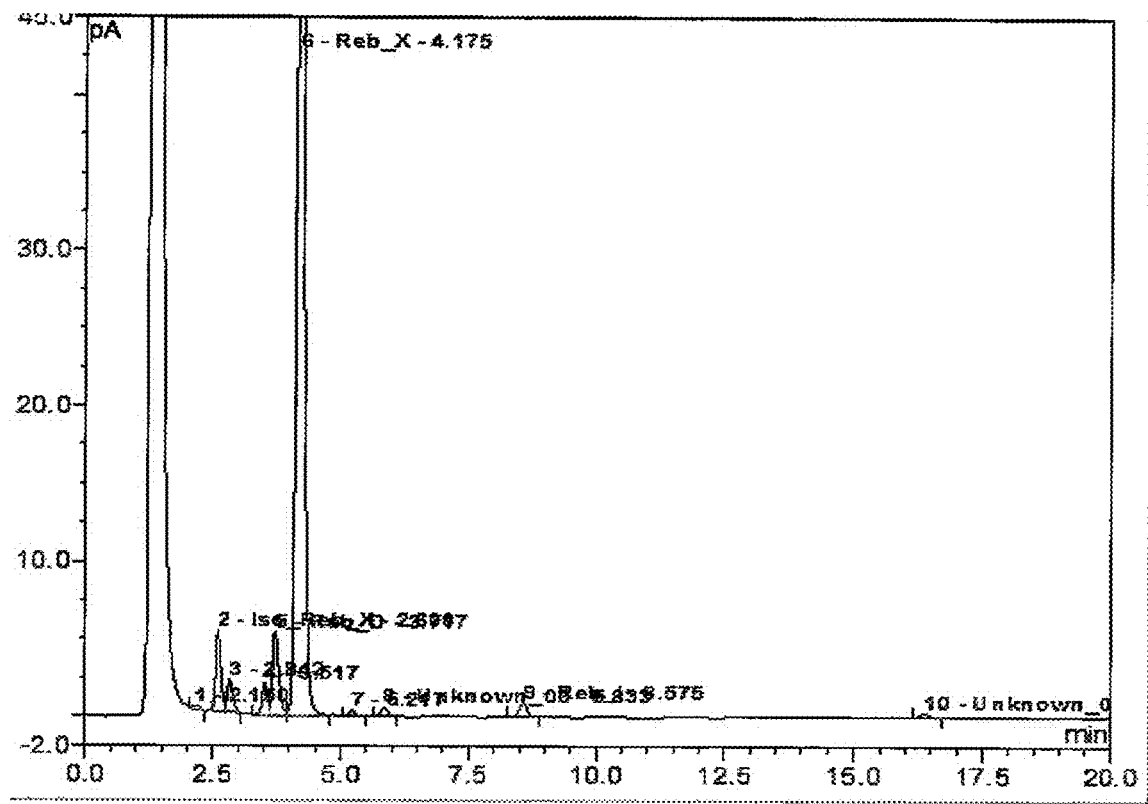
FIG. 73B shows an HPLC chromatogram showing the HPLC analysis for Example 55.

The reaction profile shown in FIG. 73a was obtained. The HPLC analysis after 48 h of reaction is shown in FIG. 73b.

Example 56

One-Pot, Four-Enzyme Conversion of Rebaudioside A to Rebaudioside M 50 mL of a reaction mixture containing 10.0 mM of Rebaudioside A, 0.5 mM of UDP, 4 mM of MgCl$_2$, 100 mM of sucrose, 50 mM of potassium phosphate buffer pH 7.5, 25 U of UGTSL2-R3-D2 (UGTSL2-Round3-var12, see EXAMPLE 53), 250 U of UGT76G1-R3-G3 (UGT76G1-Round3-var21, see EXAMPLE 44), 250 U of AtSUS and 50 U of Isolase® was filtered through a 0.2 μm filter in a sterile flask. The resulting reaction mixture was gently shaken at 35° C. for 95 hrs.

Samples were taken under sterile conditions at regular intervals by taking 125 µL of reaction mixture and quenching it with 10 µL of 2 N $H_2SO_4$ and 765 µL of 50% methanol. After centrifugation, 200 µL of the supernatant was analyzed by HPLC.

At the end of the reaction, the reaction mixture became a fine suspension. Filtration of the suspension and HPLC analysis of the residue and filtrate showed that the Reb M content in the filtrate was 79% and that the Reb M content in the solid was 97%.

Figure 74A:
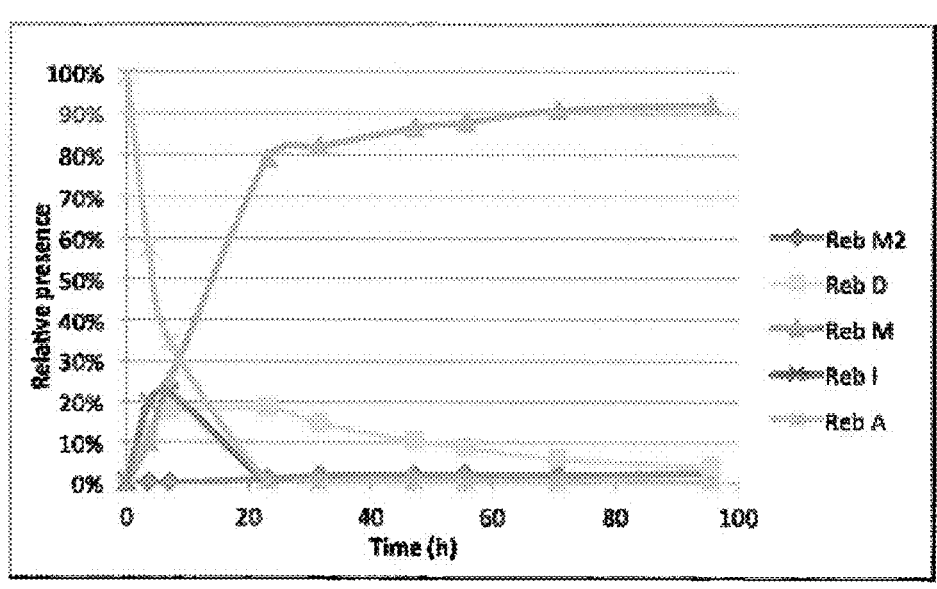
FIG. 74A shows a reaction profile graph for Example 56.
Figure 74B:
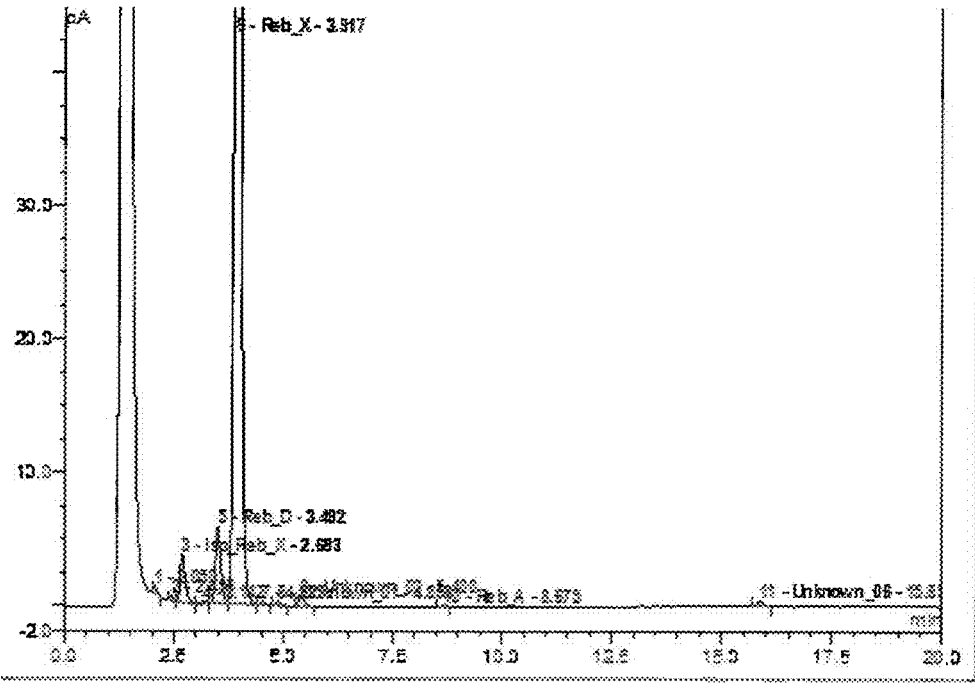
FIG. 74B shows an HPLC chromatogram showing the HPLC analysis for Example 56.

The reaction profile shown in FIG. 74*a* was obtained. The HPLC of the reaction mixture after 95 hrs is shown in FIG. 74*b*.

Example 57

One-Pot, Four-Enzyme Conversion of Rebaudioside A to Rebaudioside M (Addition of UGT76G1 and Isolase after 6.5 h)

A reaction mixture containing Rebaudioside A, UDP, MgCl₂, sucrose, potassium phosphate buffer pH 7.5, UGTSL2-R3-D2 (UGTSL2-Round3-var12, see EXAMPLE 53) and AtSUS was filtered through a 0.2 µm filter in a sterile flask. The resulting reaction mixture was gently shaken at 35° C. for 6.5 h. UGT76G1-R3-G3 (UGT76G1-Round3-var21, see EXAMPLE 44) and Isolase® were added and the reaction mixture was filtered through a 0.2 µm filter in a sterile flask and gently shaken for another 89 h at 35° C. The final volume of the reaction mixture was 50 mL and final concentrations of reagents and enzymes were as follows: 10.0 mM of Rebaudioside A, 0.5 mM of UDP, 4 mM of MgCl₂, 100 mM of sucrose, 50 mM of potassium phosphate buffer pH 7.5, 25 U of UGTSL2-R3-D2, 250 U of UGT76G1-R3-G3, 250 U of AtSUS and 50 U of Isolase®

Samples were taken under sterile conditions at regular intervals by taking 125 µL of reaction mixture and quenching it with 10 µL of 2 N $H_2SO_4$ and 765 µL of 50% methanol. After centrifugation, 200 µL of the supernatant was analyzed by HPLC.

Figure 75A:
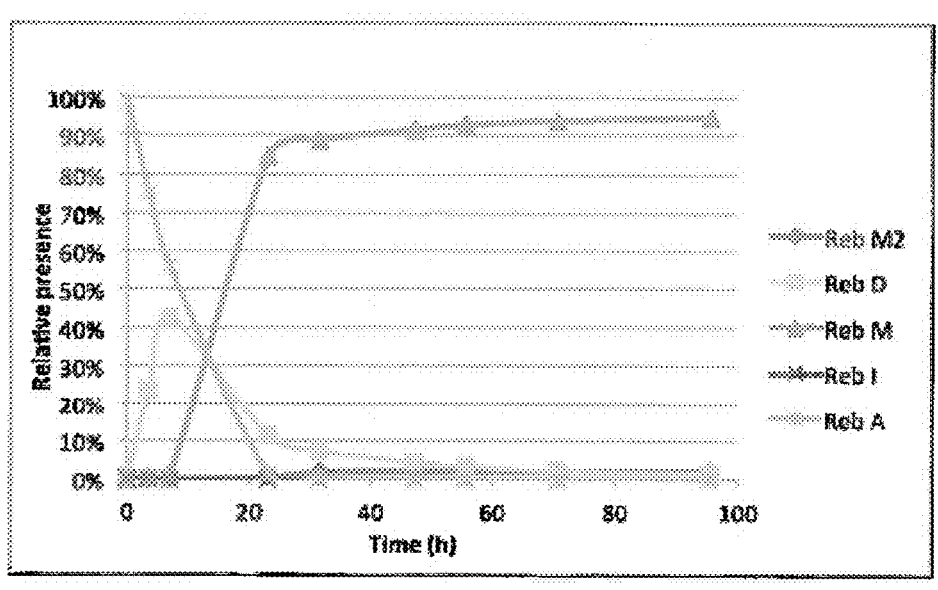
FIG. 75A shows a reaction profile graph for Example 57.
Figure 75B:
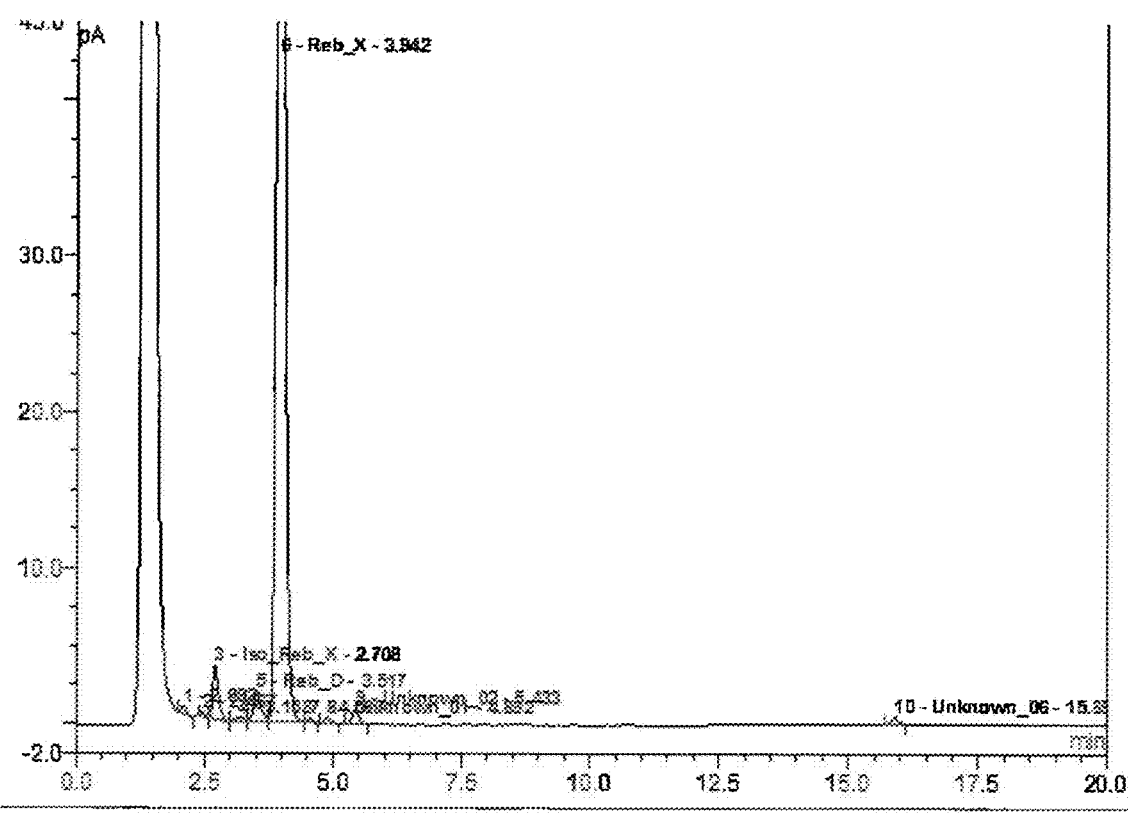
FIG. 75B shows an HPLC chromatogram showing the HPLC analysis for Example 57.

The reaction profile shown in FIG. 75*a* was obtained. The HPLC of the reaction mixture after 95 h is shown in FIG. 75*b*.

Example 58

One-Pot, Four-Enzyme Conversion of Rebaudioside A to Rebaudioside M (Addition of UGT76G1 and Isolase after 6.5 h)

A reaction mixture containing Rebaudioside A, UDP, MgCl₂, sucrose, potassium phosphate buffer pH 7.5, UGTSL2-R3-D2 (UGTSL2-Round3-var12, see EXAMPLE 53) and AtSUS was filtered through a 0.2 µm filter in a sterile flask. The resulting reaction mixture was gently shaken at 35° C. for 6.5 h. UGT76G1-R3-G3 (UGT76G1-Round3-var21, see EXAMPLE 44) and Isolase® were added and the reaction mixture was filtered through a 0.2 µm filter in a sterile flask and gently shaken for another 89 h at 35° C. The final volume of the reaction mixture was 50 mL and the final concentrations of reagents and enzymes were as follows: 10.0 mM of Rebaudioside A, 0.5 mM of UDP, 4 mM of MgCl₂, 100 mM of sucrose, 50 mM of potassium phosphate buffer pH 7.5, 25 U of UGTSL2-R3-D2, 250 U of UGT76G1-R3-G3, 250 U of AtSUS and 25 U of Isolase®. Samples were taken under sterile conditions at regular intervals by taking 125 µL of reaction mixture and quenching it with 10 µL of 2 N $H_2SO_4$ and 765 µL of 50% methanol. After centrifugation, 200 µL of the supernatant was analyzed by HPLC.

At the end of the reaction, the reaction mixture became a fine suspension. Filtration of the suspension and HPLC analysis of the residue and filtrate showed that the Reb M content in the filtrate was 81% and that the Reb M content in the solid was 98%.

Figure 76A:
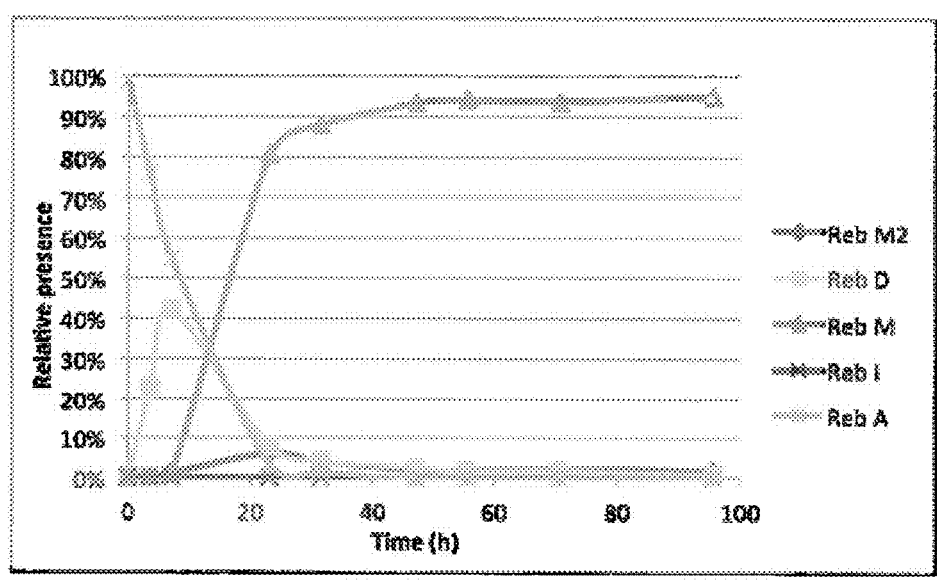
FIG. 76A shows a reaction profile graph for Example 58.
Figure 76B:
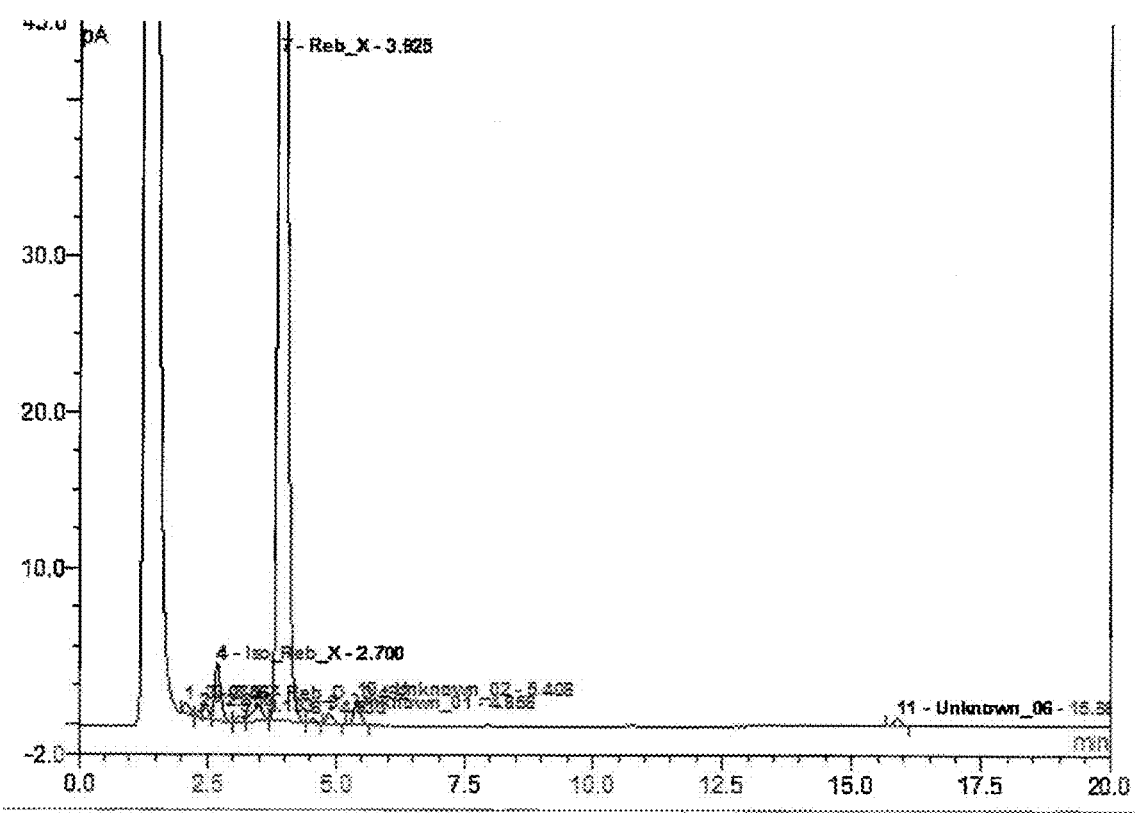
FIG. 76B shows an HPLC chromatogram showing the HPLC analysis for Example 58.

The reaction profile shown in FIG. 76*a* was obtained. The HPLC of the reaction mixture after 95 h is shown in FIG. 76*b*.

Example 59

Directed Evolution of UGTSL2 for the Conversion of Rebaudioside A to Rebaudioside D (Round 4)

The most active enzyme from the third round (see EXAMPLE 53) UGTSL2_round3-var45 was taken as starting point. The five best mutations for activity from round 3 were used to create a set of 10 variants containing each two of these mutations. After codon-optimized for expression in *E. coli* the genes were synthesized, subcloned in the pET30a+ plasmid and used for transformation of *E. coli* BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of *E. coli* BL21(DE3) containing the pET30a+_UGTSL2var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h. 3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysates were recovered by centrifugation. Lysates were diluted five-fold with water before activity testing.

In order to measure the activity of the variants for the transformation of Rebaudioside A to Rebaudioside D, 100 µL of fresh lysate was added to a solution of Rebaudioside A (final concentration 0.5 mM), MgCl₂ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the activities after HPLC analysis (CAD detection) using the analytical method that was described above for the transformation of Rebaudioside A to Rebaudioside D.

Selectivity of each clone was determined by measuring the amount of Rebaudioside M2 that was formed at 100% UDP-Glc conversion (defined as (2*[Reb M2]+[Reb D])/ ([Reb A]+[Reb D]+[Reb M2]).

In parallel the experiments were performed with baseline clone, UGTSL2-Round3-Var45. The initial rate for this baseline clone was defined as 100%. The relative initial rates and the amounts of Rebaudioside M2 that are formed at 100% UDP-Glc conversion for the round 4 clones are depicted in the following table:

| Clone | Mutations* | Normalized initial rate for conversion of Rebaudioside A | Rebaudioside M2 content at 100% UDP-Glc conversion |
|-------|-----------|------------------------------------------------------|--------------------------------------------------|
| Round3-var45 | UGTSL2 (N130G_H247P_V270I_A285V_A341V_T392A) | 100% | 15.80% |
| Round4-var1 | UGTSL2-Round3-var45 (K301E_V285I) | 96% | 15.90% |
| Round4-var2 | UGTSL2-Round3-var45 (K301E_I412L) | 90% | 15.30% |
| Round4-var3 | UGTSL2-Round3-var45 (K301E_L276A) | 135% | 16.80% |
| Round4-var4 | UGTSL2-Round3-var45 (K301E_K408R) | 90% | 14.90% |
| Round4-var5 | UGTSL2-Round3-var45 (V285I_I412L) | 77% | 15.60% |
| Round4-var6 | UGTSL2-Round3-var45 (V285I_L276A) | 124% | 16.60% |
| Round4-var7 | UGTSL2-Round3-var45 (V285I_K408R) | 98% | 16.50% |
| Round4-var8 | UGTSL2-Round3-var45 (I412L_L276A) | 88% | 15.10% |
| Round4-var9 | UGTSL2-Round3-var45 (I412L_K408R) | 82% | 15.00% |
| Round4-var10 | UGTSL2-Round3-var45 (L276A_K408R) | 93% | 15.40% |

*Mutations are noted as follows: reference gene-original amino acid-position-new amino acid: For example the mutation of an isoleucine at position 240 to a Leucine for UGTSL2 is noted as UGTSL2 (I240L).

Example 60

Directed Evolution of UGT76G1 for the Conversion of Rebaudioside D to Rebaudioside X (Round 4)

The most active clone from the third round of directed evolution of UGT76G1 (see EXAMPLE 44 round3_UGT76GTvar2T containing mutations: I46L_K303G_K393R) was chosen as baseline clone for round 4. The best identified mutations from round 3 (S119A, 274G, I295M, F314S and K334R) were used to create a set of 10 variants that contained each 2 of these mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of E. coli BL21(DE3) containing the pET30a+_UGT76G1var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 µL of fresh lysate that was added to a solution of Rebaudioside D (final concentration 0.5 mM), MgCl2 (final concentration 3 mM) and UDP-Glucose (final concentration 2.5 mM) in 50 mM phosphate buffer pH 7.2.

The reaction was allowed to run at 30° C. and samples were taken after 1, 2, 4, 6 and 22 h. to determine conversion and initial rate by HPLC (CAD detection) using the analytical method that was described above for the transformation of Rebaudioside D to Rebaudioside X. In parallel the experiments were performed with baseline clone, Round3-Var21. The conversion after 22 h. and initial rate for this baseline clone was defined as 100% and the normalized conversions and initial rates for the round 4 clones are depicted in the following table:

| Clone | Mutations* | Normalized conversion Reb D to Reb X after 22 h. | Normalized initial rate (0-4 h) |
|-------|-----------|-----------------------------------------------|--------------------------------|
| Round3-Var21 | UGT76G1 (S42A_F46L_Q266E_P272A_K303G_R334K_ G348P_L379G_K393R_I407V) | 100% | 100% |
| Round4-Var1 | Round3-Var21 (S119A_S274G) | 99.5% | 100% |
| Round4-Var2 | Round3-Var21 (S119A_I295M) | 95.4% | 93% |
| Round4-Var3 | Round3-Var21 (S119A_F314S) | 87.5% | 77% |
| Round4-Var4 | Round3-Var21 (S119A_K334R) | 94.0% | 81% |
| Round4-Var5 | Round3-Var21 (S274G_I295M) | 88.8% | 77% |
| Round4-Var6 | Round3-Var21 (S274G_F314S) | 86.7% | 75% |
| Round4-Var7 | Round3-Var21 (S274G_K334R) | 89.8% | 74% |
| Round4-Var8 | Round3-Var21 (I295M_F314S) | 84.3% | 72% |
| Round4-Var9 | Round3-Var21 (I295M_K334R) | 81.2% | 60% |
| Round4-Var10 | Round3-Var21 (F314S_K334R) | 85.6% | 74% |

*Mutations are noted as follows: reference gene-original amino acid-position-new amino acid: For example the mutation of Serine at position 119 to Alanine for variant 1 from the fourth round of directed evolution of UGT76G1 is noted as Round3-Var21 (S119A)

It is to be understood that the foregoing descriptions and specific embodiments have fully disclosed, illustrated and enabled the best mode of the invention and the principles thereof, and that modifications and additions may be made by those skilled in the art without departing from the spirit and scope of the invention, which is limited only by the scope of the appended claims.

The invention claimed is:

1. A method for producing a highly purified rebaudioside M composition, comprising the steps of:

(a) providing a starting composition comprising an organic compound with at least one carbon atom, wherein said starting composition is selected from the group consisting of steviolmonoside, steviolmonoside A, steviolbioside A, steviolbioside B, steviolbioside C, steviolbioside D, steviolbioside E, rubusoside, dulcoside A, dulcoside C, dulcoside D, stevioside A, stevioside B, stevioside C, stevioside G, stevioside H, rebaudioside B2, rebaudioside A4, rebaudioside C, rebaudioside C3, rebaudioside C4, rebaudioside C5, rebaudioside C6, rebaudioside E3, rebaudioside E4, rebaudioside E5, rebaudioside E6, rebaudioside E7, rebaudioside D5, rebaudioside D6, rebaudioside D7, rebaudioside D8, rebaudioside H2, rebaudioside H3, rebaudioside H4, rebaudioside H5, rebaudioside H6, rebaudioside K, rebaudioside N3, rebaudioside N4, rebaudioside N5, rebaudioside M3, polyols, and combinations thereof;

(b) providing a biocatalyst, the biocatalyst containing uridine diphosphate glycosyltransferases (UDP-glycosyltransferases), wherein the UDP-glycosyltransferase comprises an amino acid sequence selected from the group consisting of the amino acid sequence set forth in SEQ ID NO: 11 uridine diphosphate-glycosyltransferase 76G1 ("UGT76G1"), an amino acid sequence having at least 95% amino-acid sequence identity with the amino acid sequence set forth in SEQ ID NO: 11, the amino acid sequence set forth in SEQ ID NO: 9 uridine diphosphate-glycosyltransferase of *Solanum lycopersicum* origin ("UGTSL2") and an amino acid sequence having at least 95% amino-acid sequence identity with the amino acid sequence set forth in SEQ ID NO: 9, and further providing an enzyme with β-glucosidase activity from *Trichoderma reesei* or *Aspergillus niger;*

(c) contacting the UDP-glycosyltransferases and the enzyme with β-glucosidase activity with a medium comprising the starting composition to produce a composition comprising at least rebaudioside M; and (d) separating rebaudioside M from the medium to provide a highly purified rebaudioside M composition.

2. The method of claim 1, wherein rebaudioside M is separated from the medium using crystallization, separation by membranes, centrifugation, extraction, chromatographic separation or a combination of such methods.

3. The method of claim 1, wherein the highly purified rebaudioside M composition comprises rebaudioside M in an amount of at least 95% by weight on a dry weight basis.

4. The method of claim 1, further comprising providing an enzyme with β-glucosidase activity for hydrolysis of rebaudioside D2 or rebaudioside M2.

5. A highly purified rebaudioside M composition prepared according to the method of claim 1, (i) comprising the rebaudioside M content in an amount of at least 95% by weight on a dry weight basis, or (ii) wherein the rebaudioside M is polymorphic.

6. A consumable product comprising the highly purified rebaudioside M composition of claim 1, wherein the product is selected from the group consisting of a food, a beverage, a pharmaceutical composition, a tobacco product, a nutraceutical composition, an oral hygiene composition, and a cosmetic composition.

\* \* \* \* \*